US012807937B2

(12) United States Patent
Blazeck et al.

(10) Patent No.: US 12,807,937 B2
(45) Date of Patent: Nov. 24, 2026

(54) ENHANCED DIVERSIFYING BASE EDITORS FOR DIRECTED EVOLUTION

(71) Applicant: Georgia Tech Research Corporation, Atlanta, GA (US)

(72) Inventors: John James Blazeck, Atlanta, GA (US); Andrew Paul Cazier, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 588 days.

(21) Appl. No.: 18/512,405

(22) Filed: Nov. 17, 2023

(65) Prior Publication Data

US 2024/0167015 A1 May 23, 2024

Related U.S. Application Data

(60) Provisional application No. 63/384,131, filed on Nov. 17, 2022.

(51) Int. Cl.

*C12N 15/10* (2006.01)
*C12N 9/22* (2006.01)
*C12N 15/11* (2006.01)
*C12N 15/90* (2006.01)

(52) U.S. Cl.

CPC ........... *C12N 15/1058* (2013.01); *C12N 9/22* (2013.01); *C12N 15/1082* (2013.01); *C12N 15/11* (2013.01); *C12N 15/905* (2013.01); *C12N 2310/20* (2017.05); *C12N 2800/80* (2013.01)

(58) Field of Classification Search

CPC ........................................................ C12Q 1/68

See application file for complete search history.

(56) References Cited

U.S. PATENT DOCUMENTS

| | | | |
|---|---|---|---|
| 7,396,664 B2 | 7/2008 | Daly et al. | |
| 2012/0151613 A1 | 6/2012 | Wang et al. | |
| 2015/0044675 A1 | 2/2015 | Budzko et al. | |
| 2017/0183645 A1 | 6/2017 | Tran et al. | |
| 2022/0090043 A1 | 3/2022 | He et al. | |
| 2022/0290134 A1 * | 9/2022 | Jin ......................... | C12N 15/11 |

FOREIGN PATENT DOCUMENTS

| | | |
|---|---|---|
| WO | 2007025097 A2 | 3/2007 |
| WO | 2021155109 A1 | 8/2021 |

OTHER PUBLICATIONS

Ryan et al, Selection of chromosomal DNA libraries using a multiplex CRISPR system, eLife3:e03703, https://doi.org/10.7554/eLife.03703, Aug. 19, 2014.*

Altschul et al., "Basic local alignment search tool", Journal of Molecular Biology 215.3 (1990): 403-410.

Anand et al., "Cas9-mediated gene editing in *Saccharomyces cerevisiae*." Abstract (2017): 1-4.

Anzalone et al., "Genome editing with CRISPR-Cas nucleases, base editors, transposases and prime editors." Nature biotechnology 38.7 (2020): 824-844.

(Continued)

*Primary Examiner* — Yung-Sheng M Tsui

(74) *Attorney, Agent, or Firm* — Meunier Carlin & Curfman LLC

(57) ABSTRACT

The present disclosure relates gene editing systems, compositions, and methods of use to target proteins for directed evolution.

14 Claims, 31 Drawing Sheets

Specification includes a Sequence Listing.

(56) References Cited

OTHER PUBLICATIONS

Benatuil et al., "An improved yeast transformation method for the generation of very large human antibody libraries." Protein Engineering, Design & Selection 23.4 (2010): 155-159.
Boder et al., "Directed evolution of antibody fragments with monovalent femtomolar antigen-binding affinity." Proceedings of the National Academy of Sciences 97.20 (2000): 10701-10705.
Boder et al., "Engineering antibodies by yeast display." Archives of biochemistry and biophysics 526.2 (2012): 99-106.
Boder et al., "Optimal screening of surface-displayed polypeptide libraries." Biotechnology progress 14.1 (1998): 55-62.
Boder et al., "Yeast surface display for screening combinatorial polypeptide libraries." Nature biotechnology 15.6 (1997): 553-557.
Bushnell et al., "BBMerge-accurate paired shotgun read merging via overlap." PloS one 12.10 (2017): 1-10.
Chao et al., "Isolating and engineering human antibodies using yeast surface display." Nature protocols 1.2 (2006): 755-769.
Cheng et al., "Genome editor-directed in vivo library diversification." Cell chemical biology 28.8 (2021): 1109-1118.
Cravens et al., "Polymerase-guided base editing enables in vivo mutagenesis and rapid protein engineering." Nature Communications 12.1 (2021): 1579, 1-12.
Crook et al., "In vivo continuous evolution of genes and pathways in yeast." Nature communications 7.1 (2016): 13051, 1-14.
Després et al., "Perturbing proteomes at single residue resolution using base editing." Nature communications 11.1 (2020): 1871, 1-13.
Devilder et al., "Ex vivo evolution of human antibodies by CRISPR-X: from a naive B cell repertoire to affinity matured antibodies." BMC biotechnology 19 (2019): 1-13.
Di Noia et al., "Molecular mechanisms of antibody somatic hypermutation." Annu. Rev. Biochem. 76 (2007): 1-26.
Eriksen et al., "Directed evolution of a cellobiose utilization pathway in *Saccharomyces cerevisiae* by simultaneously engineering multiple proteins." Microbial cell factories 12 (2013): 1-11.
Finney-Manchester et al., "Harnessing mutagenic homologous recombination for targeted mutagenesis in vivo by TaGTEAM." Nucleic acids research 41.9 (2013): e99-e99, 1-10.
Flagfeldt et al., "Characterization of chromosomal integration sites for heterologous gene expression in *Saccharomyces cerevisiae*." Yeast 26.10 (2009): 545-551.
Geisberger et al., "The stability of AID and its function in class-switching are critically sensitive to the identity of its nuclear-export sequence." Proceedings of the National Academy of Sciences 106. 16 (2009): 6736-6741.
Gietz et al., "High-efficiency yeast transformation using the LiAc/SS carrier DNA/PEG method." Nature protocols 2.1 (2007): 30-35.
Hari et al., "Conformation-selective ATP-competitive inhibitors control regulatory interactions and noncatalytic functions of mitogen-activated protein kinases." Chemistry & biology 21.5 (2014): 628-635.
Hegemann et al., "Delete and repeat: a comprehensive toolkit for sequential gene knockout in the budding yeast *Saccharomyces cerevisiae*." Strain engineering: methods and protocols (2011): 188-206.
Hess et al., "Directed evolution using dCas9-targeted somatic hypermutation in mammalian cells." Nature methods 13.12 (2016): 1-57.
Hess et al., "Methods and applications of CRISPR-mediated base editing in eukaryotic genomes." Molecular cell 68.1 (2017): 26-43.
Horvath et al., "CRISPR/Cas, the immune system of bacteria and archaea." Science 327.5962 (2010): 165-170.
Hsu et al., "DNA targeting specificity of RNA-guided Cas9 nucleases." Nature biotechnology 31.9 (2013): 1-17.
Koblan et al., "Improving cytidine and adenine base editors by expression optimization and ancestral reconstruction." Nature biotechnology 36.9 (2018): 1-11.
Komor et al., "Programmable editing of a target base in genomic DNA without double-stranded DNA cleavage." Nature 533.7603 (2016): 1-25.
Konermann et al., "Genome-scale transcriptional activation by an engineered CRISPR-Cas9 complex." Nature 517 (2015): 1-37.
Krokan et al., "Uracil in DNA-occurrence, consequences and repair." Oncogene 21.58 (2002): 8935-8948.
Kurt et al., "CRISPR C-to-G base editors for inducing targeted DNA transversions in human cells." Nature biotechnology 39.1 (2021): 1-24.
Laughery et al., "R-loop formation by dCas9 is mutagenic in *Saccharomyces cerevisiae*." Nucleic acids research 47.5 (2019): 2389-2401.
Lee et al., "A highly characterized yeast toolkit for modular, multipart assembly." ACS synthetic biology 4.9 (2015): 975-986.
Li et al., "Targeted, random mutagenesis of plant genes with dual cytosine and adenine base editors." Nature biotechnology 38.7 (2020): 875-886.
Li, H., "A statistical framework for SNP calling, mutation discovery, association mapping and population genetical parameter estimation from sequencing data." Bioinformatics 27.21 (2011): 2987-2993.
Li, H., "Aligning sequence reads, clone sequences and assembly contigs with BWA-MEM." arXiv preprint arXiv:1303.3997 (2013): 1-3.
Lim et al., "Altering the RNA binding specificity of a translational repressor." Journal of Biological Chemistry 269.12 (1994): 9006-9010.
Lim et al., "Dual display of proteins on the yeast cell surface simplifies quantification of binding interactions and enzymatic bioconjugation reactions." Biotechnology journal 12.5 (2017): 1600696, 1-17.
Liu et al., "Intrinsic nucleotide preference of diversifying base editors guides antibody ex vivo affinity maturation." Cell Reports 25.4 (2018): 883-892.e1-e10.
Lu et al., "Development of therapeutic antibodies for the treatment of diseases." Journal of biomedical science 27 (2020): 1-30.
Ma et al., "Targeted AID-mediated mutagenesis (TAM) enables efficient genomic diversification in mammalian cells." Nature methods 13.12 (2016): 1029-1035.
Mali et al., "CAS9 transcriptional activators for target specificity screening and paired nickases for cooperative genome engineering." Nature biotechnology 31.9 (2013): 1-17.
Mayorov et al., "Expression of human AID in yeast induces mutations in context similar to the context of somatic hypermutation at GC pairs in immunoglobulin genes." BMC immunology 6 (2005): 1-12.
Michener et al., "High-throughput enzyme evolution in *Saccharomyces cerevisiae* using a synthetic RNA switch." Metabolic engineering 14.4 (2012): 306-316.
Midelfort et al., "Substantial energetic improvement with minimal structural perturbation in a high affinity mutant antibody." Journal of molecular biology 343.3 (2004): 685-701.
Nishida et al., "Targeted nucleotide editing using hybrid prokaryotic and vertebrate adaptive immune systems." Science 353.6305 (2016): aaf8729, 1-9.
Nishimasu et al., "Engineered CRISPR-Cas9 nuclease with expanded targeting space." Science 361.6408 (2018): 1-9.
Oh et al., "Multiplex evolution of antibody fragments utilizing a yeast surface display platform." ACS Synthetic Biology 9.8 (2020): A-F.
Owiti et al., "The etiology of uracil residues in the *Saccharomyces cerevisiae* genomic DNA." Current genetics 65 (2019): 393-399.
Pagès et al., "Mutational specificity and genetic control of replicative bypass of an abasic site in yeast." Proceedings of the National Academy of Sciences 105.4 (2008): 1170-1175.
Pan et al., "Random base editing for genome evolution in *Saccharomyces cerevisiae*." ACS Synthetic Biology 10.10 (2021): 2440-2446.
Pilzecker et al., "Mutating for good: DNA damage responses during somatic hypermutation." Frontiers in immunology 10 (2019): 439193, 1-13.

(56) References Cited

OTHER PUBLICATIONS

Potapov et al., "Comprehensive profiling of four base overhang ligation fidelity by T4 DNA ligase and application to DNA assembly." ACS synthetic biology 7.11 (2018): 2665-2674.
Qiao et al., "AID recognizes structured DNA for class switch recombination." Molecular cell 67.3 (2017): 360-373.e1-e4.
Rajpal et al., "A general method for greatly improving the affinity of antibodies by using combinatorial libraries." Proceedings of the National Academy of Sciences 102.24 (2005): 8466-8471.
Ravikumar et al., "Scalable, continuous evolution of genes at mutation rates above genomic error thresholds." Cell 175.7 (2018): 1945-1957.
Rees et al., "Base editing: precision chemistry on the genome and transcriptome of living cells." Nature reviews genetics 19.12 (2018): 1-41.
Roehner et al., "Double dutch: a tool for designing combinatorial libraries of biological systems." ACS Synthetic Biology 5.6 (2016): 507-517.
Romero et al., "Exploring protein fitness landscapes by directed evolution." Nature reviews Molecular cell biology 10.12 (2009): 1-25.
Swers et al., "Shuffled antibody libraries created by in vivo homologous recombination and yeast surface display." Nucleic acids research 32.3 (2004): e36-e36, 1-8.
Tan et al., "Expanding the genome-targeting scope and the site selectivity of high-precision base editors." Nature communications 11.1 (2020): 629, 1-11.
Tatusova et al., "BLAST 2 Sequences, a new tool for comparing protein and nucleotide sequences." FEMS microbiology letters 174.2 (1999): 247-250.
Taylor et al., "DNA deaminases induce break-associated mutation showers with implication of APOBEC3B and 3A in breast cancer kataegis." elife 2 (2013): e00534, 1-14.
Tou et al., "Targeted diversification in the *S. cerevisiae* genome with CRISPR-guided DNA polymerase I." ACS Synthetic Biology 9.7 (2020): A-F.
Tsien, R., "The green fluorescent protein." Annual review of biochemistry 67.1 (1998): 509-546.
Wang et al., "AID upmutants isolated using a high-throughput screen highlight the immunity/cancer balance limiting DNA deaminase activity." Nature structural & molecular biology 16.7 (2009): 1-24.
Wang et al., "sgBE: a structure-guided design of sgRNA architecture specifies base editing window and enables simultaneous conversion of cytosine and adenosine." Genome biology 21 (2020): 1-16.
Wellner et al., "Rapid generation of potent antibodies by autonomous hypermutation in yeast." Nature chemical biology 17.10 (2021): 1057-1064.
Young et al., "Iterative algorithm-guided design of massive strain libraries, applied to itaconic acid production in yeast." Metabolic engineering 48 (2018): 1-34.
Zalatan et al., "Engineering complex synthetic transcriptional programs with CRISPR RNA scaffolds." Cell 160.1 (2015): 339-350. S1-S5.
Zhang et al., "A gRNA-tRNA array for CRISPR-Cas9 based rapid multiplexed genome editing in *Saccharomyces cerevisiae*." Nature communications 10.1 (2019): 1-10.
Zhang et al., "Dual base editor catalyzes both cytosine and adenine base conversions in human cells." Nature biotechnology 38.7 (2020): 1-10.
Zhao et al., "Role of DNA polymerase η in the bypass of abasic sites in yeast cells." Nucleic acids research 32.13 (2004): 3984-3994.
Zheng et al., "Targeted mutagenesis: A sniper-like diversity generator in microbial engineering." Synthetic and Systems Biotechnology 2.2 (2017): 75-86.

* cited by examiner

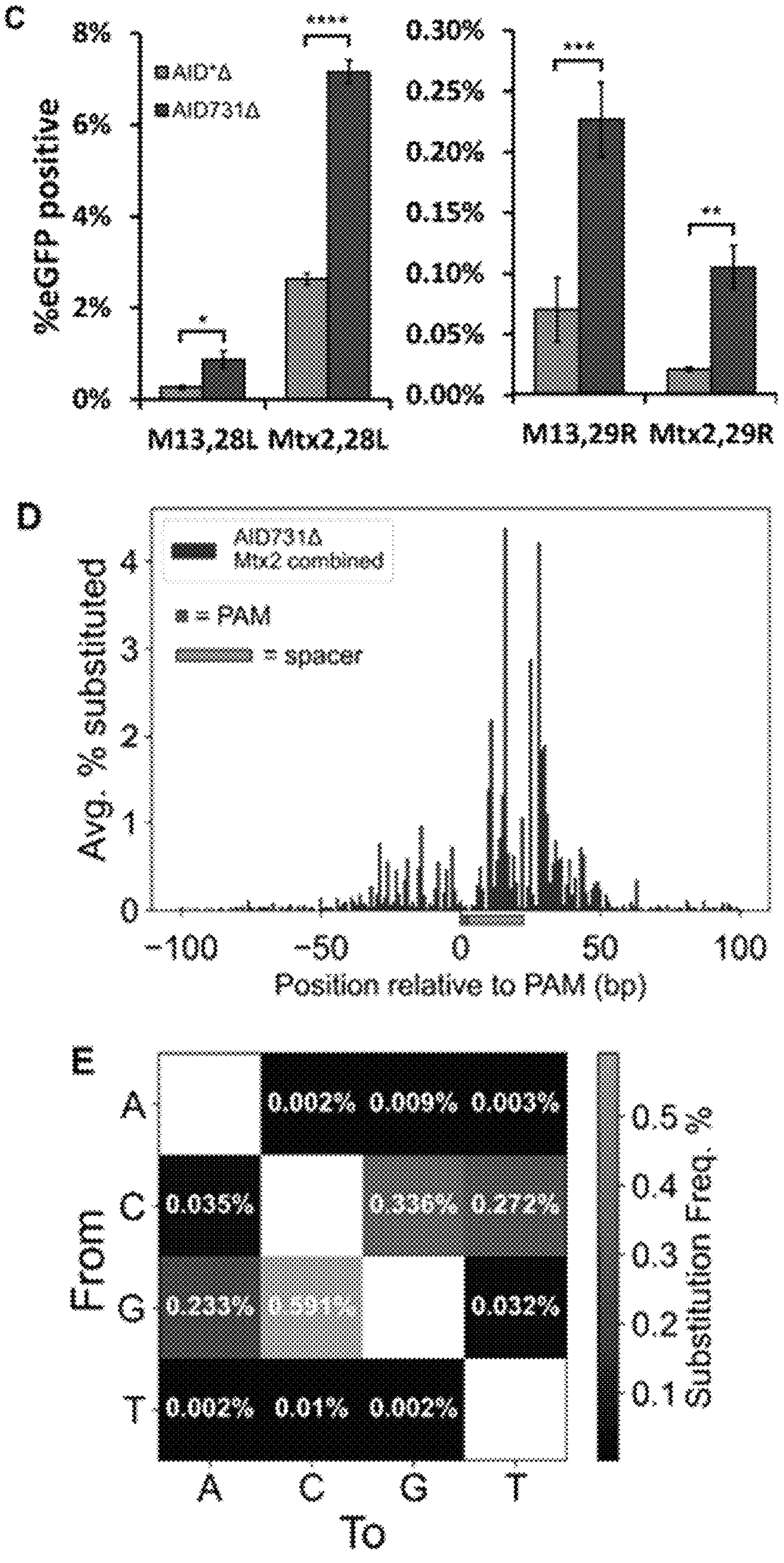
FIGS. 5C, 5D, and 5E

C
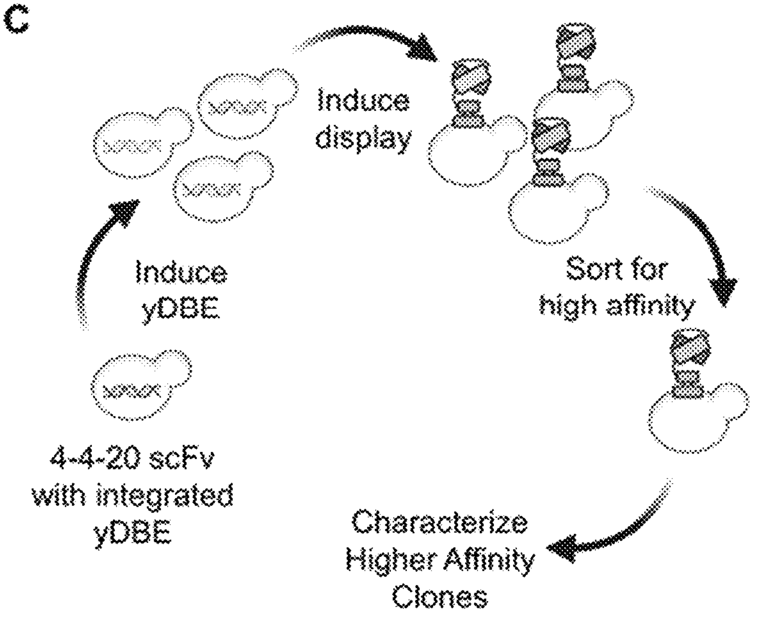
D
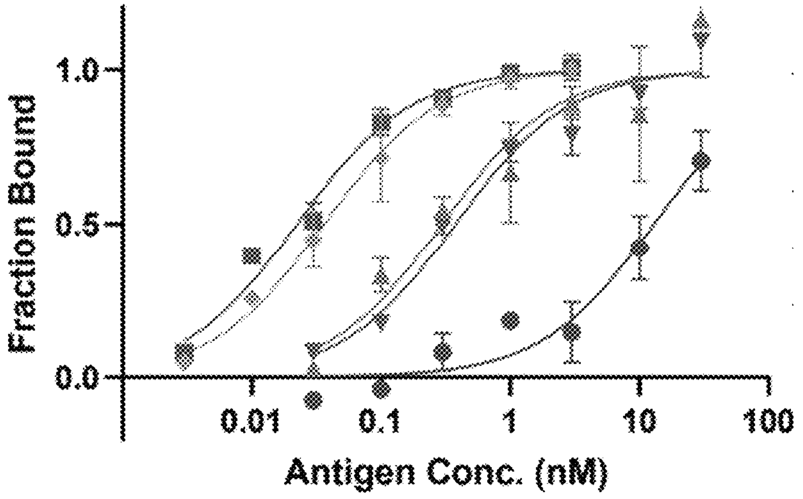
E
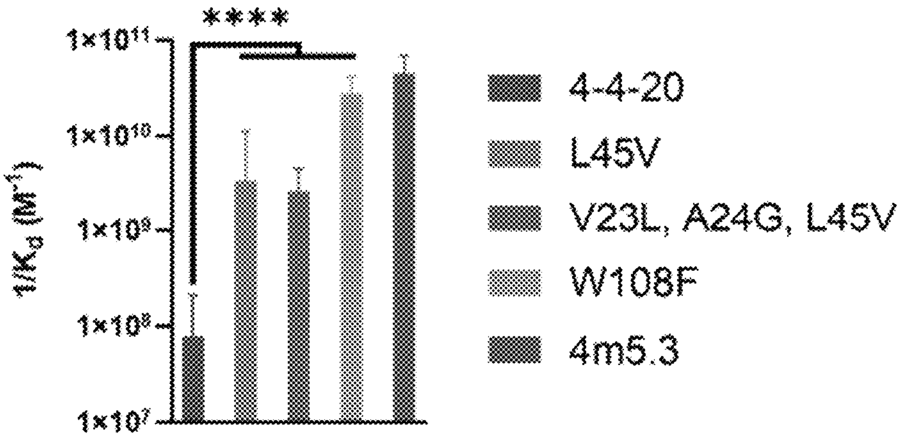
FIGS. 6C, 6D, and 6E

AID*Δ, M13-t22L

A

AVG 1.02%

B

AVG 1.47%

ENHANCED DIVERSIFYING BASE EDITORS FOR DIRECTED EVOLUTION

CROSS REFERENCE TO RELATED APPLICATIONS

This U.S. Nonprovisional Patent Application claims priority to, and the benefit of, U.S. Provisional Patent Application No. 63/384,131, filed Nov. 17, 2022, which is incorporated by reference herein in its entirety.

REFERENCE TO SEQUENCE LISTING

The sequence listing submitted on Nov. 17, 2023, as an .XML file entitled "10034-222US1_ST26.xml" created on Nov. 16, 2023, and having a file size of 315,191 bytes is hereby incorporated by reference pursuant to 37 C.F.R. § 1.52(e)(5).

FIELD

The present disclosure relates gene editing systems, compositions, and methods of use to target proteins for directed evolution.

BACKGROUND

Libraries have long been created through traditional mutagenesis techniques such as site-saturation mutagenesis and error-prone PCR. While these methods can introduce sufficient diversity, they require laborious cloning techniques and cannot be rapidly iterated. A faster strategy would be engineering yeast that can create the desired diversity in situ.

Given limitations of current laboratory techniques and methods in generating libraries, there is need to address the aforementioned problems mentioned above by engineering yeast to generate diverse libraries. The compositions, systems, and methods disclosed herein address these and other needs.

SUMMARY

The present disclosure provides CRISPR base editor systems and vectors for editing a gene. The present disclosure also provides methods of using the CRISPR base editor system.

In one aspect, disclosed herein is a gene editing system comprising a CRISPR base editor comprising a catalytically inactive nuclease, at least one guide RNA (gRNA), and a MS2 phage coat protein (MCP), wherein the MCP is operably linked to an activation-induced deaminase (AID), the at least one gRNA comprises at least one bacteriophage aptamer and at least one protospacer adjacent motif (PAM) sequence, and the gene editing system is coupled with a yeast display system to introduce a mutation into a target protein within a yeast cell.

In some embodiments, the gRNA binds a target nucleic acid encoding a target protein, or a fragment thereof. In some embodiments, the MCP binds the at least one bacteriophage aptamer of the gRNA. In some embodiments, the MCP comprises a nuclear localization signal (NLS). In some embodiments, the MCP comprises at least 90% sequence identity to SEQ ID NO: 41.

In some embodiments, the AID mutates the target nucleic acid encoding the target protein, or a fragment thereof. In some embodiments, the AID comprises SEQ ID NO: 43, SEQ ID NO: 45, SEQ ID NO: 47, SEQ ID NO: 49, SEQ ID NO: 51, or a variant thereof.

In some embodiments, the yeast cell expresses a mutant of the target protein. In some embodiments, the catalytically inactive nuclease comprises a dead Cas 9 (dCas9) or a dead Cas12 (dCas12). In some embodiments, the at least one bacteriophage aptamer comprises at least one MS2 aptamer. In some embodiments, the AID comprises a cytidine activation-induced deaminase or an adenine activation-induced deaminase. In some embodiments, the yeast display system or yeast cell comprises *Saccharomyces cerevisiae* (*S. cerevisiae*).

In one aspect, disclosed herein is an expression vector comprising one or more nucleic acid sequences encoding a CRISPR base editor, wherein the CRISPR base editor comprises a catalytically inactive nuclease, a MS2 phage coat protein (MCP), and an activation-induced deaminase (AID), wherein expression of the CRISPR base editor is under control of a yeast-derived promoter sequence and a yeast-derived terminator sequence.

In some embodiments, the expression vector further comprises a nucleic acid sequence encoding at least one guide RNA (gRNA). In some embodiments, the at least one gRNA comprises at least one bacteriophage aptamer and at least one protospacer adjacent motif (PAM) sequence.

In some embodiments, the one or more nucleic acid sequences encodes the MCP comprising at least 90% sequence identity to SEQ ID NO: 40. In some embodiments, the one or more nucleic acid sequences encodes the AID comprising SEQ ID NO: 42, SEQ ID NO: 44, SEQ ID NO: 46, SEQ ID NO: 48, SEQ ID NO: 50, or a variant thereof. In some embodiments, the catalytically inactive nuclease comprises a dead Cas 9 (dCas9) or a dead Cas12 (dCas12). In some embodiments, the one or more nucleic acid sequences encoding the catalytically inactive nuclease comprises at least 90% sequence identity to SEQ ID NO: 23.

In some embodiments, the at least one gRNA comprises SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or a variant thereof.

In some embodiments, the at least one PAM sequence comprises SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or a variant thereof.

In one aspect, disclosed herein is a method of treating or preventing a disease or disorder in a subject in need thereof, the method comprising identifying a target nucleic acid sequence encoding a target protein; incorporating into a yeast genome at least one expression vector comprising one or more nucleic acid sequences encoding the target nucleic acid sequence and a CRISPR base editor, wherein the CRISPR base editor comprises a catalytically inactive nuclease, at least one guide RNA (gRNA) comprising at least one bacteriophage aptamer and at least one protospacer adjacent motif (PAM) sequence, a MS2 phage coat protein (MCP), and an activation-induced deaminase (AID), and wherein expression of the CRISPR base editor is under control of a yeast-derived promoter sequence and a yeast-derived terminator sequence; inducing a mutation into the target protein, wherein the AID incorporates a mutation into the target nucleic acid sequence and the target nucleic acid is translated into the target protein, and wherein the mutation increases a function of the target protein relative to a wild-type control protein; expressing the target protein comprising the mutation in the yeast; isolating said target protein comprising the mutation; incorporating the target protein into a therapeutic composition; and administering the therapeutic composition to the subject.

BRIEF DESCRIPTION OF FIGURES

The accompanying figures, which are incorporated in and constitute a part of this specification, illustrate several aspects described below.

FIG. 2A shows a diagram of yDBE. MCP-AID, dCas9, and a MS2-loop-harboring gRNA together induce mutations near the targeted locus. FIG. 2B shows the outline of fluorescence shift assay for detecting DNA mutations induced by the base editor. The S65T mutation in wild-type GFP (wtGFP) shifts the fluorescence excitation peak, yielding fluorescence like enhanced GFP (eGFP). FIG. 2C shows the fluorescence shift assay results with initial base editor (strain AC001) and a nontargeting gRNA (NT1) or one of two targeting gRNAs (18L and t22L), all with M13 scaffolds. In C, bars represent mean±SD, n=3, ****$p<0.0001$. NT, not tested.

FIG. 4A shows the diagram of gRNA scaffold base pairing and possible positions for MS2 loop placement. Two examples drawn with MS2 loops are shown, M13 and Mtx2, but ten more variants were also constructed and tested. FIG. 4B shows the gene map showing the relative position of the S65 target site within wtGFP and the targeting location of three gRNA spacers sequences, 18L, t22L, and t74L. FIG. 4C shows the comparison of fluorescence shift assay activity using MCP-AID*Δ (strain AC001) and different gRNA scaffolds. Cells were induced for four days. Two separate sets of scaffolds were tested, each with three different spacer sequences. M13 and Mtx2 were assayed in both sets so that a comparison between sets could be made. In FIG. 4C, bars represent mean±SD, n=3, ns=not significant, $p<0.01$, *$p<0.001$, ****$p<0.0001$.

FIGS. 5A, 5B, 5C, 5D, 5E, and 5F show the target site tiling and high-throughput sequencing of yDBE. FIG. 5A shows the position of spacer sequences relative to fluorescence shift site (S65). The spacer number is a measure of how many bp the 3' end of the PAM is to the left (L) or right (R) of the target on the coding or template (t) strand. FIG. 5B shows the comparison of M13 and Mtx2 scaffolds with seven positional spacers in a fluorescence shift assay in strain AC001. Cells were induced for four days. FIG. 5C shows the comparison of M13 and Mtx2 scaffolds in a fluorescent shift assay with AID731Δ (strain AC0003) or the original, AID*Δ (strain AC001). Cells were induced for four days. FIG. 5D shows the combined high-throughput sequencing results using AID731Δ (strain AC0003) and Mtx2 scaffold with five separate spacer sequences, 81L, t22L, 28L, 29R, and t78R. The cells were induced for eight days. The plot gives the average substitution frequencies for each nucleotide position relative to the 3' end of the PAM in a ±100-bp window surrounding the targeted site. The orientation and binding position of the gRNA is depicted along the x-axis. The uncombined data is given in FIG. 11. FIG. 5E shows the heatmap detailing the nature of substitutions in a ±50-bp window centered on the PAM using the data highlighted in FIG. 5D. FIG. 5F further shows that combining two optimization strategies of AID variants and Mtx scaffolds results in improved based editing. In FIGS. 5B and 5C, bars represent mean±SD, n=3, ns=not significant, *$p<0.05$, $p<0.01$, *$p<0.001$, ****$p<0.0001$.

FIGS. 6A, 6B, 6C, 6D, and 6E show the yDBE-mediated diversification and isolation of an improved scFv. FIG. 6A shows the map of AGA2-4-4-20 locus with CDRs and gRNAs highlighted. Two sets of gRNAs were created, one designed for M13 and the other for Mtx2. FIG. 6B shows the schematic of multiplexing three gRNAs by designing a gRNA-tRNA cassette. After transcription, the gRNAs will be cleaved from the transcript as the cells process the tRNAs with native RNAses. FIG. 6C shows the process outline for improving antibody affinity using yDBE, yeast display, and FACS. FIG. 6D shows the antigen titration curves for wild-type 4-4-20, the three isolated mutants, and the ultra-high affinity 4m5.3 variant. FIG. 6E shows the plot of inverse $K_d$ for wild-type 4-4-20, the three isolated mutants, and the ultra-high affinity 4m5.3 variant. $K_d$ values were derived from best-fit lines shown in FIG. 6D. A higher value indicates stronger binding. In FIG. 6E, bars represent a 95% confidence interval. ****$p<0.0001$.

FIG. 7A shows the wtGFP contains an AGCT motif which is preferred by AID. Deamination and inaccurate repair can lead to the S65T mutation, which causes a shift in the excitation spectrum. FIG. 7B shows the control populations showing how wtGFP, eGFP, and No GFP have essentially no fluorescence overlap. FIG. 7C shows the FACS plot showing that a population of eGFP-positive cells is generated after 8 days of base editing using strain AC001 with t22L gRNA plasmid. Compare with FIG. 1C. FIG. 7D shows the FACS plot showing strain AC0003 after 4-day induction with two, separate gRNAs, M13-t22L or M13-18L. Compare with FIG. 2. FIG. 7E shows the FACS plot showing strain AC0003 after 4-day induction with two, separate gRNAs, M13-28L or Mtx2-28L. Compare with FIG. 4C. BP, band pass filter.

FIG. 8A shows the fluorescence shift assay with variants or alterations of MCP-AID*Δ after a 4-day induction. h.c.o=human codon optimized, alt.y.c.o=alternative yeast codon optimization. MCPz is a variant of MCP. Psbtdh3 is a strong, constitutive promoter from *Saccharomyces boulardii*. All other variants are controlled by the *S. cerevisiae* GAL2 promoter. NT1 is a nontargeting gRNA; t22L and 18L are targeting. FIG. 8B shows the fluorescence shift assay after 4-day induction with AID*Δ vs AID*A-RFA3. FIG. 8C shows the fluorescence shift assay after 4-day induction with AID731Δ and dCas9 (strain AC0003) or dCas9-RFA3 (strain AC0004). M13 scaffolds were used for all gRNAs. FIG. 8D shows the fusing AID directly to dCas9 (strain AC0005), vs recruiting AID with MCP (strain AC0003), did not improve the rate of mutation in a fluorescence shift assay when using an M13-28L gRNA. Cells were induced for 6d. In FIGS. 8A-8D, bars represent mean±SD, n=3, ns=not significant, *$p<0.05$, *$p<0.001$, **$p<0.0001$.

FIG. 14A shows a 1.5-fold improvement in equilibrium antigen binding. FIG. 14B shows the isolation of an scFv with higher equilibrium binding to FITC-dextran. Sequencing showed the variant had a W148L mutation, near HCDR2.

FIG. 15A shows the loop variants constructed and tested without any 1st loop modifications. FIGS. 15B and 15C show the eGFP fluorescence shift assay after 4-day induction.

FIG. 20A shows the standard yDBE with integrations at YPRCτ3Δ: dCas9 and MCP-AID. FIG. 20B shows the "Double-AID" yDBE with integrations at 1) YPRCτ3Δ: dCas9 and MCP-AID #1; and 2) GYP/NRT1: MCP-AID #2.

DETAILED DESCRIPTION

Figure 1:
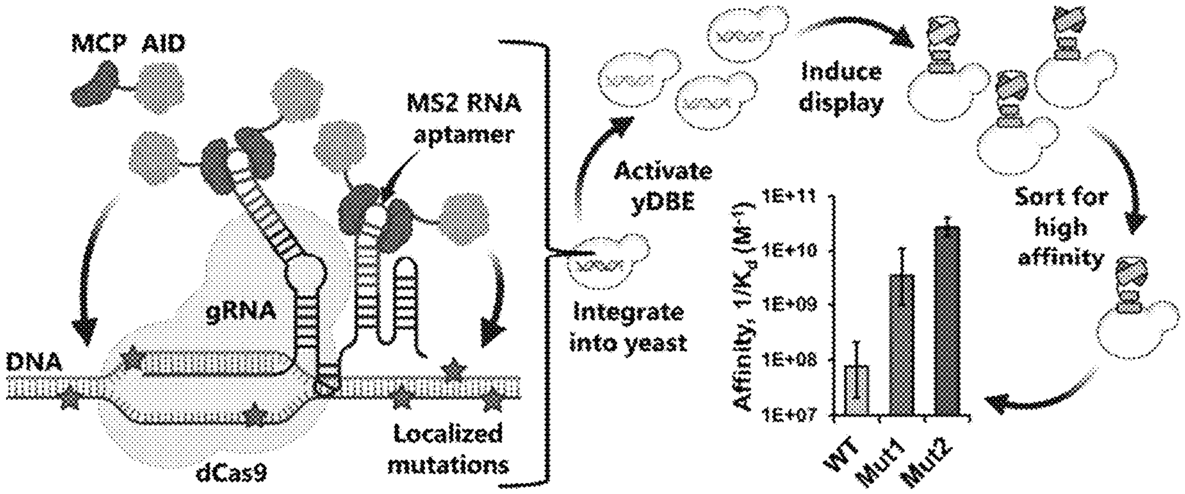
FIG. 1. shows a graphical representation of the CRISPR base editor system disclosed herein.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Reference will now be made in detail to the embodiments of the invention, examples of which are illustrated in the drawings and the examples. This invention may, however, be embodied in many different forms and should not be construed as limited to the embodiments set forth herein.

TERMINOLOGY

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

An "increase" can refer to any change that results in a greater amount of a symptom, disease, composition, condition, or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100%, or more, increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," means lowering of an event or characteristic (e.g., gene expression). It is understood that this is typically in relation to some standard or expected value, in other words it is relative, but that it is not always necessary for the standard or relative value to be referred to. For example, "reduces gene expression" means reducing or lowering the production of a gene product relative to a standard or a control.

The terms "treat," "treating," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the disclosure may be applied preventively, prophylactically, palliatively or remedially. Treatments are administered to a subject prior to onset (e.g., before obvious signs of disease), during early onset (e.g., upon initial signs and symptoms of disease), or after an established development of disease.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "enhance", "enhanced", "enhancement", "enhancing", and any grammatical variations thereof as used herein, refers to an act of intensifying, increasing, or further improving the quality, value, or extent of a biological function, composition, compound, cell, or tissue.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

"Composition" refers to any agent that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, a vector, polynucleotide, cells, salts, esters, amides, proagents, active metabolites, isomers, fragments, analogs, and the like. When the term "composition" is used, then, or when a particular composition is specifically identified, it is to be understood that the term includes the composition per se as well as pharmaceutically acceptable, pharmacologically active vector, polynucleotide, salts, esters, amides, proagents, conjugates, active metabolites, isomers, fragments, analogs, etc.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like.

"Consisting of" shall mean excluding more than trace elements of other ingredients and substantial method steps for administering the compositions provided and/or claimed in this disclosure. Embodiments defined by each of these transition terms are within the scope of this disclosure.

As used herein, "operably fused" or "operably linked" refers to two or more compositions or compounds being bound or linked together in such a way the optimizes the intended function. When bound or linked, these compositions or compounds can be linked covalently, electrostatic interaction, through hydrogen bonding, or any combinations thereof.

Reference also is made herein to peptides, polypeptides, proteins, and compositions comprising peptides, polypeptides, and proteins. As used herein, a polypeptide and/or protein is defined as a polymer of amino acids, typically of length≥100 amino acids (Garrett & Grisham, Biochemistry, 2nd edition, 1999, Brooks/Cole, 110). A peptide is defined as a short polymer of amino acids, of a length typically of 20 or less amino acids, and more typically of a length of 12 or less amino acids (Garrett & Grisham, Biochemistry, 2nd edition, 1999, Brooks/Cole, 110).

The peptides, polypeptides, and proteins disclosed herein may be modified to include mutations or non-amino acid moieties. Modifications may include but are not limited to carboxylation, PEGylation (e.g., N-terminal or C-terminal PEGylation via additional of polyethylene glycol), acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), glycosylation (e.g., the addition of a glycosyl group to either asparagine, hydroxylysine, serine, or threonine, resulting in a glycoprotein).

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods consider conservative amino acid substitutions. Such conservative substitutions generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length may be used to describe a length over which percentage identity may be measured.

Fusion proteins and fusion polynucleotides are also contemplated herein. A "fusion protein" refers to a protein formed by the fusion of at least one peptide, polypeptide, protein or variant thereof as disclosed herein to at least one molecule of a heterologous peptide, polypeptide, protein or variant thereof. The heterologous protein(s) may be fused at the N-terminus, the C-terminus, or both termini. A fusion protein comprises at least a fragment or variant of the heterologous protein(s) that are fused with one another, preferably by genetic fusion (i.e., the fusion protein is generated by translation of a nucleic acid in which a polynucleotide encoding all or a portion of a first heterologous protein is joined in-frame with a polynucleotide encoding all or a portion of a second heterologous protein). The heterologous protein(s), once part of the fusion protein, may each be referred to herein as a "portion", "region" or "moiety" of the fusion protein.

A fusion polynucleotide refers to the fusion of the nucleotide sequence of a first polynucleotide to the nucleotide sequence of a second heterologous polynucleotide (e.g., the 3' end of a first polynucleotide to a 5' end of the second polynucleotide). Where the first and second polynucleotides encode proteins, the fusion may be such that the encoded proteins are in-frame and results in a fusion protein. The first and second polynucleotide may be fused such that the first and second polynucleotide are operably linked (e.g., as a promoter and a gene expressed by the promoter as discussed below).

The term "variant" means a polypeptide derived from a parent polypeptide by one or more (several) alteration(s), i.e., a substitution, insertion, and/or deletion, at one or more (several) positions. A substitution means a replacement of an amino acid occupying a position with a different amino acid; a deletion means removal of an amino acid occupying a position; and an insertion nans adding 1 or more, such as 1, 2, 3, 4, 5, 6, 7, 8, 9 or 10, preferably 1-3 amino acids immediately adjacent an amino acid occupying a position. In relation to substitutions, 'immediately adjacent' may be to the N-side ('upstream') or C-side ('downstream') of the amino acid occupying a position ('the named amino acid'). Therefore, for an amino acid named/numbered 'X,' the insertion may be at position 'X+1' ('downstream' or at position 'X−1' ('upstream').

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In some embodiments a variant polypeptide may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length relative to a reference polypeptide.

A variant polypeptide may have substantially the same functional activity as a reference polypeptide. For example, a variant polypeptide may exhibit one or more biological activities associated with binding a ligand and/or binding DNA at a specific binding site.

A "nucleotide" is a compound consisting of a nucleoside, which consists of a nitrogenous base and a 5-carbon sugar, linked to a phosphate group forming the basic structural unit of nucleic acids, such as DNA or RNA. The four types of DNA nucleotides are adenine (A), cytosine (C), guanine (G), and thymine (T), each of which are bound together by a phosphodiester bond to form a nucleic acid molecule.

A "nucleic acid" is a chemical compound that serves as the primary information-carrying molecules in cells and make up the cellular genetic material. Nucleic acids comprise nucleotides, which are the monomers made of a 5-carbon sugar (usually ribose or deoxyribose), a phosphate group, and a nitrogenous base. A nucleic acid can also be a deoxyribonucleic acid (DNA) or a ribonucleic acid (RNA). A chimeric nucleic acid comprises two or more of the same kind of nucleic acid fused together to form one compound comprising genetic material.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Percent identity may be measured over the length of an entire defined polynucleotide sequence or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length may be used to describe a length over which percentage identity may be measured.

A "full length" polynucleotide sequence is one containing at least a translation initiation codon (e.g., methionine) followed by an open reading frame and a translation termination codon. A "full length" polynucleotide sequence encodes a "full length" polypeptide sequence.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In some embodiments a variant polynucleotide may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length relative to a reference polynucleotide.

A "promoter," as used herein, refers to a sequence in DNA that mediates the initiation of transcription by an RNApolymerase. Transcriptional promoters may comprise one or more of a number of different sequence elements as follows: 1) sequence elements present at the site of transcription initiation; 2) sequence elements present upstream of the transcription initiation site and; 3) sequence elements downstream of the transcription initiation site. The individual sequence elements function as sites on the DNA, where RNA polymerases and transcription factors facilitate positioning of RNA polymerases on the DNA bind.

"Expression" as used herein refers to the process by which information from a gene is used in the synthesis of a functional gene product that enables it to produce a peptide/protein end product, and ultimately affect a phenotype, as the final effect.

As used herein, the term "genetically modified" refers to a living cell, tissue, or organism whose genetic material has been altered using genetic engineering techniques. The genetical modification results in an alteration that does not occur naturally by mating and/or natural recombination. Modified genes can be transferred within the same species, across species (creating transgenic organisms), and across kingdoms. New, exogenous genes can be introduced, or endogenous genes can be enhanced, altered, or knocked out.

As used herein, the term, "deletion," also called gene deletion, deficiency, or deletion mutation, refers to part of a chromosome or a sequence of DNA being left out during DNA replication. Deletion, or gene deletions can cause any number of nucleotides to be deleted from a single base to an entire piece of chromosome.

Variants comprising deletions relative to a reference amino acid sequence or nucleotide sequence are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation or both of a reference polypeptide or a 5'-terminal or 3'-terminal truncation or both of a reference polynucleotide).

Variants comprising a fragment of a reference amino acid sequence or nucleotide sequence are contemplated herein. A "fragment" is a portion of an amino acid sequence or a nucleotide sequence which is identical in sequence to but shorter in length than the reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous nucleotides or contiguous amino acid residues of a reference polynucleotide or reference polypeptide, respectively. Fragments may be preferentially selected from certain regions of a molecule, for example the N-terminal region and/or the C-terminal region of a polypeptide or the 5'-terminal region and/or the 3' terminal region of a polynucleotide. The term "at least a fragment" encompasses the full-length polynucleotide or full length polypeptide.

Variants comprising insertions or additions relative to a reference sequence are contemplated herein. The words "insertion" and "addition" refer to changes in an amino acid or nucleotide sequence resulting in the addition of one or more amino acid residues or nucleotides. An insertion or addition may refer to 1, 2, 3, 4, 5, 10, 20, 30, 40, 50, 60, 70, 80, 90, 100, 150, or 200 amino acid residues or nucleotides.

As used herein, a "transcription terminator" or a "terminator" refers to a segment of a nucleic acid sequence that marks the end of gene in genomic DNA during the transcription process, or gene expression. This sequence mediates or signals the end of transcription by providing signaling nucleotides in newly synthesized RNA transcripts that trigger an RNA polymerase to release the DNA and newly synthesized RNA.

A "genome" refers to a complete set of genes or genetic material present within a cell, tissue, or organism. A genome can be nuclear (found within the cell nucleus) or mitochondrial (found with the cell mitochondria).

As used herein, a "mutation" refers to changing the structure of a gene, resulting in a variant form that may be transmitted to later generations. A mutation is caused by the alteration of single nucleotides in DNA, or the deletion, insertion, or rearrangement of larger sections of genes. A mutation can lead to the expression of a protein that has been changed physically or functionally leading to lethality, non-lethal dysfunction effects, or no effects.

"Recombinant" used in reference to a gene refers herein to a sequence of nucleic acids that are not naturally occurring in the genome of the bacterium. The non-naturally occurring sequence may include a recombination, substitution, deletion, or addition of one or more bases with respect to the nucleic acid sequence originally present in the natural genome of the bacterium.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"CRISPR" (Clustered Regularly Interspaced Short Palindromic Repeats) loci refers to certain genetic loci encoding components of DNA cleavage systems, for example, used by bacterial and archaeal cells to destroy foreign DNA (Horvath and Barrangou, 2010, Science 327: 167-170; WO2007025097, published 1 Mar. 2007). A CRISPR locus can consist of a CRISPR array, comprising short direct repeats (CRISPR repeats) separated by short variable DNA sequences (called spacers), which can be flanked by diverse Cas (CRISPR-associated) genes.

As used herein, an "effector" or "effector protein" is a protein that encompasses an activity including recognizing, binding to, and/or cleaving or nicking a polynucleotide target. An effector, or effector protein, may also be an endonuclease. The "effector complex" of a CRISPR system includes Cas proteins involved in crRNA and target recognition and binding. Some of the component Cas proteins may additionally comprise domains involved in target polynucleotide cleavage.

A nuclease is an enzyme capable of cleaving the phosphodiester bonds between nucleotides of nucleic acids. Nuclease can possess properties to cause double or single stranded breaks to target nucleic acids. Nucleases are commonly used in CRISPR technology to modify a host genome to express or inhibit a target gene.

The term "Cas protein" refers to a polypeptide encoded by a Cas (CRISPR-associated) gene. A Cas protein includes proteins encoded by a gene in a Cas locus and includes adaptation molecules as well as interference molecules. An interference molecule of a bacterial adaptive immunity complex includes endonucleases. A Cas endonuclease described herein comprises one or more nuclease domains. Contemplated herein are any Cas molecules that comprise a Rec3 clamp, as described below.

A Cas endonuclease may also include a multifunctional Cas endonuclease. The term "multifunctional Cas endonuclease" and "multifunctional Cas endonuclease polypeptide" are used interchangeably herein and includes reference to a single polypeptide that has Cas endonuclease functionality (comprising at least one protein domain that can act as a Cas endonuclease) and at least one other functionality, such as but not limited to, the functionality to form a complex (comprises at least a second protein domain that can form a complex with other proteins). In one aspect, the multifunctional Cas endonuclease comprises at least one additional protein domain relative (either internally, upstream (5'), downstream (3'), or both internally 5' and 3', or any combination thereof) to those domains typical of a Cas endonuclease.

As used herein, the term "guide polynucleotide", relates to a polynucleotide sequence that can form a complex with a Cas endonuclease, including the Cas endonuclease described herein, and enables the Cas endonuclease to recognize, optionally bind to, and optionally cleave a DNA target site. The guide polynucleotide sequence can be an RNA sequence, a DNA sequence, or a combination thereof (a RNA-DNA combination sequence).

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA).

The term "administer," "administering", or derivatives thereof refer to delivering a composition, substance, inhibitor, or medication to a subject or object by one or more the following routes: oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

Base Editor Systems

Clustered regularly interspaced short palindromic repeats (CRISPR) and CRISPR-associated system (CRISPR/-Cas9) is a popular tool for genome editing. As used herein, genome editing refers to the strategies and techniques for the targeted, specific modification of the genetic information (genome) of living organisms. Genome engineering is a very active field of research because of the wide range of applications, particularly in the areas of human health. For example, genome engineering can be used to alter (e.g., correct or inhibit) a gene carrying a harmful mutation or to explore the function of a gene. The present disclosure provides CRISPR base editor systems and vectors for editing a gene. The present disclosure also provides systems, vectors, and methods of using the CRISPR base editor system.

Base editing refers to a gene editing method to make targeted changes to a nucleic acid sequence. As an approach to genome editing, base editing uses components of CRISPR such as, for example gRNA and nucleases (i.e.: Cas endonucleases) together with other enzymes to directly introduce mutations into nucleic acid sequences. The difference between traditional CRISPR techniques and base editing techniques that incorporate CRISPR components is that base editing introduces mutations without making double-stranded DNA breaks. Thus, the present disclosure provides a base editor that introduces target nucleic acid mutations with minimal errors.

The present disclosure also provides systems, vectors, and methods utilizing directed evolution techniques to generate target proteins with optimal functions. "Directed evolution" refers to a method used in protein engineering that mimics the process of natural selection to steer proteins or nucleic acids towards user-defined objectives. Directed evolution comprises of subjecting a gene to iterative rounds of mutagenesis, selection, and amplification, to be performed in vivo such as for example in a prokaryotic species including, but not limited to yeast.

In one aspect, disclosed herein is a gene editing system comprising a CRISPR base editor comprising a catalytically inactive nuclease, at least one guide RNA (gRNA), and a MS2 phage coat protein (MCP), wherein the MCP is operably linked to an activation-induced deaminase (AID), the at least one gRNA comprises at least one bacteriophage aptamer and at least one protospacer adjacent motif (PAM) sequence, and the gene editing system is coupled with a yeast display system to introduce a mutation into a target protein within a yeast cell. As used herein, a "bacteriophage aptamer" refers to short, single-stranded nucleic acid sequences including, but not limited to DNA or RNA, derived from a bacteriophage virus. In general, aptamers comprise high affinity and specificity to interact with a desired target, such as for example the MCP protein. Further, a "bacteriophage" refers to a virus that infects and replicates within bacteria and archaea, but display minimal harmful effects in humans.

As used herein, a "yeast display" refers to a protein engineering technology wherein recombinant protein(s) are expressed in a yeast organism by incorporating a constructed nucleic acid sequence into the yeast genome. Following expression of the constructed nucleic acid sequence, the recombinant protein(s) are exposed on the yeast cell wall allowing for identification and/or isolation of said recombination.

In some embodiments, the gRNA binds a target nucleic acid encoding a target protein, or a fragment thereof. In some embodiments, the target protein comprises an antibody, or a fragment thereof. In some embodiments, the yeast display exposes an antibody, or a fragment thereof, on the cell wall surface. The term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

The term "antibody fragment" refers to a portion of a full-length antibody, generally the target binding or variable region. Examples of antibody fragments include Fab, Fab', $F(ab')_2$ and Fv fragments. The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI. As used herein, "functional fragment" with respect to antibodies, refers to Fv, F(ab) and $F(ab')_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules.

In some embodiments, the target protein includes, but is not limited to an enzyme, a structural protein, a contractile protein, a hormonal protein, a storage protein, a signaling protein, a transport protein, or fragments thereof.

In some embodiments, the MCP binds the at least one bacteriophage aptamer of the gRNA. In some embodiments, the MCP comprises a nuclear localization signal (NLS). In some embodiments, the MCP is operably fused to the NLS by a linker peptide. As used herein, a "NLS" refers to a short amino acid sequence that acts as a signal fragment that mediates the transport of proteins, either native or recombinant proteins, from the cytoplasm into the nucleus. In some embodiments, the NLS is a bipartite (BP) NLS. In some embodiments, the NLS is a monopartite (MP) NLS. The NLS can be located at the amino (N) terminus, the carboxy (C) terminus, or anywhere in between the N and C termini of the native or recombinant protein. Non-limiting examples of NLS include a simian virus 40 NLS, or mutants thereof, a cMYC NLS, or mutants thereof, and nucleoplasmin (Nuc) NLS, or mutants thereof.

In some embodiments, the MCP comprises at least 60% sequence identity to SEQ ID NO: 41. In some embodiments, the MCP comprises at least 70% sequence identity to SEQ ID NO: 41. In some embodiments, the MCP comprises at least 75% sequence identity to SEQ ID NO: 41. In some embodiments, the MCP comprises at least 80% sequence identity to SEQ ID NO: 41. In some embodiments, the MCP comprises at least 90% sequence identity to SEQ ID NO: 41. In some embodiments, the MCP comprises at least 95% sequence identity to SEQ ID NO: 41. In some embodiments, the MCP comprises at least 99% sequence identity to SEQ ID NO: 41. In some embodiments, the MCP comprises SEQ ID NO: 41.

In some embodiments, the AID mutates the target nucleic acid encoding the target protein, or a fragment thereof.

In some embodiments, the AID comprises at least 60% sequence identity to SEQ ID NO: 43. In some embodiments, the AID comprises at least 70% sequence identity to SEQ ID NO: 43. In some embodiments, the AID comprises at least 75% sequence identity to SEQ ID NO: 43. In some embodiments, the AID comprises at least 80% sequence identity to SEQ ID NO: 43. In some embodiments, the AID comprises at least 90% sequence identity to SEQ ID NO: 43. In some embodiments, the AID comprises at least 95% sequence identity to SEQ ID NO: 43. In some embodiments, the AID comprises at least 99% sequence identity to SEQ ID NO: 43. In some embodiments, the AID comprises SEQ ID NO: 43.

In some embodiments, the AID comprises at least 60% sequence identity to SEQ ID NO: 45. In some embodiments, the AID comprises at least 70% sequence identity to SEQ ID NO: 45. In some embodiments, the AID comprises at least 75% sequence identity to SEQ ID NO: 45. In some embodiments, the AID comprises at least 80% sequence identity to SEQ ID NO: 45. In some embodiments, the AID comprises at least 90% sequence identity to SEQ ID NO: 45. In some embodiments, the AID comprises at least 95% sequence identity to SEQ ID NO: 45. In some embodiments, the AID comprises at least 99% sequence identity to SEQ ID NO: 45. In some embodiments, the AID comprises SEQ ID NO: 45.

In some embodiments, the AID comprises at least 60% sequence identity to SEQ ID NO: 47. In some embodiments, the AID comprises at least 70% sequence identity to SEQ ID NO: 47. In some embodiments, the AID comprises at least 75% sequence identity to SEQ ID NO: 47. In some embodiments, the AID comprises at least 80% sequence identity to SEQ ID NO: 47. In some embodiments, the AID comprises at least 90% sequence identity to SEQ ID NO: 47. In some embodiments, the AID comprises at least 95% sequence identity to SEQ ID NO: 47. In some embodiments, the AID comprises at least 99% sequence identity to SEQ ID NO: 47. In some embodiments, the AID comprises SEQ ID NO: 47.

In some embodiments, the AID comprises at least 60% sequence identity to SEQ ID NO: 49. In some embodiments, the AID comprises at least 70% sequence identity to SEQ ID NO: 49. In some embodiments, the AID comprises at least 75% sequence identity to SEQ ID NO: 49. In some embodiments, the AID comprises at least 80% sequence identity to SEQ ID NO: 49. In some embodiments, the AID comprises at least 90% sequence identity to SEQ ID NO: 49. In some embodiments, the AID comprises at least 95% sequence identity to SEQ ID NO: 49. In some embodiments, the AID comprises at least 99% sequence identity to SEQ ID NO: 49. In some embodiments, the AID comprises SEQ ID NO: 49.

In some embodiments, the AID comprises at least 60% sequence identity to SEQ ID NO: 51. In some embodiments, the AID comprises at least 70% sequence identity to SEQ ID NO: 51. In some embodiments, the AID comprises at least 75% sequence identity to SEQ ID NO: 51. In some embodiments, the AID comprises at least 80% sequence identity to SEQ ID NO: 51. In some embodiments, the AID comprises at least 90% sequence identity to SEQ ID NO: 51. In some embodiments, the AID comprises at least 95% sequence identity to SEQ ID NO: 51. In some embodiments, the AID comprises at least 99% sequence identity to SEQ ID NO: 51. In some embodiments, the AID comprises SEQ ID NO: 51.

In some embodiments, the AID is a mutant AID. In some embodiments, the mutant AID comprises AID*Δ, AIDmono, AID*mono, AID731mono, AID731Δ, or AID dead. In some embodiments, the mutant AID comprises AID731Δ.

In some embodiments, an MCP of any preceding aspect fuses to an AID of any preceding aspect to form an MCP-AID fusion protein. In some embodiments, the CRISPR base editor system of any preceding aspect comprises one, two, three, or more MCP-AID fusion proteins.

In some embodiments, the yeast cell expresses a mutant of the target protein. The base editor of any preceding aspect, introduces mutations into the target protein to improve, increase, and/or enhance protein function. Thus, the base editor system introduces at least one substitution, insertion, deletion, frameshift mutation, or any combination thereof to improve, increase, and/or enhance protein function. The base editor of any preceding aspect can also introduce mutations into a defective protein, pathogenic protein, misfolded protein, or onco-protein (cancer-related) to render said protein dysfunctional.

The structure for Cas molecules was determined when bound in complex with a gRNA and double-stranded DNA target, in an active (DNA cleavage product state) and inactive (nonproductive state) conformation. This allowed for design of enzymes with different properties that facilitate better gene editing. The Cas nucleases disclosed herein have been mutated within the catalytic domains to be inactive, such that the Cas nuclease lacks endonuclease activity. In some embodiments, the catalytically inactive nuclease comprises a dead Cas 9 (dCas9) or a dead Cas12 (dCas12).

The coat protein (MCP) of the bacteriophage MS2 binds to specific stem-loop aptamers to regulate gene expression of viral genes. Herein, the MCP protein fused to the AID binds at least one MS2 aptamer, located with the gRNA, to introduce targeted mutations. In some embodiments, the at least one bacteriophage aptamer comprises at least one MS2 aptamer.

Activation-induced deaminases (AID) are enzymes that create mutations in nucleic acid sequences by deamination of cytosine (C) or adenine (A) bases. A non-limiting example of AID functions include AID enzymes changing a C:guanine (G) base pair into an uracil (U):G mismatch. Thus, during DNA replication, the host cell replication machinery recognizes the U base as a thymine (T), and hence the C:G is converted into a T:A base pair. In some embodiments, the AID comprises a cytidine activation-induced deaminase or an adenine activation-induced deaminase.

In some embodiments, the yeast display system or yeast cell is derived from any one organism including, but is not limited to *Saccharomyces cerevisiae* (*S. cerevisiae*), *Kluyveromyces lactis* (*K. lactis*), *Kluyverimyces marxianus*

(*K. marxianus*), *Scheffersomyces stipitis* (*S. stipites*), *Yarrowia lipolytica* (*Y. lipolytica*), *Hansenula polymorpha* (*H. polymorpha*), *Pichia pastoris* (*P. pastoris*), *Komagataella pastoris* (*K. pastoris*), *Ashbya gossypii* (*A. gossypii*), *Streptomyes noursei* (*S. noursei*), *Candida albicans* (*C. albicans*), and *Schizosaccharomyces pombe* (*S. pombe*).

Base Editor Vectors

In one aspect, disclosed herein is an expression vector comprising one or more nucleic acid sequences encoding a CRISPR base editor, wherein the CRISPR base editor comprises a catalytically inactive nuclease, a MS2 phage coat protein (MCP), and an activation-induced deaminase (AID), wherein expression of the CRISPR base editor is under control of a yeast-derived promoter sequence and a yeast-derived terminator sequence.

In some embodiments, the expression vector comprises a plasmid or a virus or viral vector. A plasmid or a viral vector can be capable of extrachromosomal replication or, optionally, can integrate into the host genome. As used herein, the term "integrated" used in reference to an expression vector (e.g., a plasmid or viral vector) means the expression vector, or a portion thereof, is incorporated (physically inserted or ligated) into the chromosomal DNA of a host cell. As used herein, a "viral vector" refers to a virus-like particle containing genetic material which can be introduced into a eukaryotic cell without causing substantial pathogenic effects to the eukaryotic cell. A wide range of viruses or viral vectors can be used for transduction but should be compatible with the cell type the virus or viral vector are transduced into (e.g., low toxicity, capability to enter cells). Suitable viruses and viral vectors include adenovirus, lentivirus, retrovirus, among others. In some embodiments, the expression vector encoding a chimeric polypeptide is a naked DNA or is comprised in a nanoparticle (e.g., liposomal vesicle, porous silicon nanoparticle, gold-DNA conjugate particle, polyethyleneimine polymer particle, cationic peptides, etc.).

In some embodiments, the one or more nucleic acid sequences encoding the CRISPR base editor system are separated and inserted into 1, 2, 3, or more expression vectors. In some embodiments, the one or more nucleic acid sequences encoding the CRISPR base editor system is inserted into a first expression vector and at least one guide RNA (gRNA) is inserted into a second expression vector.

In some embodiments, the yeast-derived promoter comprises a native yeast promoter or a mutated yeast promoter. In some embodiments, the yeast-derived promoter comprises a native yeast terminator or a mutated yeast terminator.

In some embodiments, the expression vector further comprises a nucleic acid sequence encoding at least one gRNA. In some embodiments, the at least one gRNA comprises at least one bacteriophage aptamer and at least one protospacer adjacent motif (PAM) sequence.

In some embodiments, the one or more nucleic acid sequences encodes the MCP comprising at least 60% sequence identity to SEQ ID NO: 40. In some embodiments, the one or more nucleic acid sequences encodes the MCP comprising at least 70% sequence identity to SEQ ID NO: 40. In some embodiments, the one or more nucleic acid sequences encodes the MCP comprising at least 75% sequence identity to SEQ ID NO: 40. In some embodiments, the one or more nucleic acid sequences encodes the MCP comprising at least 80% sequence identity to SEQ ID NO: 40. In some embodiments, the one or more nucleic acid sequences encodes the MCP comprising at least 90% sequence identity to SEQ ID NO: 40. In some embodiments, the one or more nucleic acid sequences encodes the MCP comprising at least 95% sequence identity to SEQ ID NO: 40. In some embodiments, the one or more nucleic acid sequences encodes the MCP comprising at least 99% sequence identity to SEQ ID NO: 40. In some embodiments, the one or more nucleic acid sequences encodes the MCP comprising SEQ ID NO: 40.

In some embodiments, the one or more nucleic acid sequences encodes the AID comprising at least 60% sequence identity to SEQ ID NO: 42. In some embodiments, the one or more nucleic acid sequences encodes the AID comprising at least 70% sequence identity to SEQ ID NO: 42. In some embodiments, the one or more nucleic acid sequences encodes the AID comprising at least 75% sequence identity to SEQ ID NO: 42. In some embodiments, the one or more nucleic acid sequences encodes the AID comprising at least 80% sequence identity to SEQ ID NO: 42. In some embodiments, the one or more nucleic acid sequences encodes the AID comprising at least 90% sequence identity to SEQ ID NO: 42. In some embodiments, the one or more nucleic acid sequences encodes the AID comprising at least 95% sequence identity to SEQ ID NO: 42. In some embodiments, the one or more nucleic acid sequences encodes the AID comprising at least 99% sequence identity to SEQ ID NO: 42. In some embodiments, the one or more nucleic acid sequences encoding the AID comprises SEQ ID NO: 42.

In some embodiments, the one or more nucleic acid sequences encodes the AID comprising at least 60% sequence identity to SEQ ID NO: 44. In some embodiments, the one or more nucleic acid sequences encodes the AID comprising at least 70% sequence identity to SEQ ID NO: 44. In some embodiments, the one or more nucleic acid sequences encodes the AID comprising at least 75% sequence identity to SEQ ID NO: 44. In some embodiments, the one or more nucleic acid sequences encodes the AID comprising at least 80% sequence identity to SEQ ID NO: 44. In some embodiments, the one or more nucleic acid sequences encodes the AID comprising at least 90% sequence identity to SEQ ID NO: 44. In some embodiments, the one or more nucleic acid sequences encodes the AID comprising at least 95% sequence identity to SEQ ID NO: 44. In some embodiments, the one or more nucleic acid sequences encodes the AID comprising at least 99% sequence identity to SEQ ID NO: 44. In some embodiments, the one or more nucleic acid sequences encoding the AID comprises SEQ ID NO: 44.

In some embodiments, the one or more nucleic acid sequences encodes the AID comprising at least 60% sequence identity to SEQ ID NO: 46. In some embodiments, the one or more nucleic acid sequences encodes the AID comprising at least 70% sequence identity to SEQ ID NO: 46. In some embodiments, the one or more nucleic acid sequences encodes the AID comprising at least 75% sequence identity to SEQ ID NO: 46. In some embodiments, the one or more nucleic acid sequences encodes the AID comprising at least 80% sequence identity to SEQ ID NO: 46. In some embodiments, the one or more nucleic acid sequences encodes the AID comprising at least 90% sequence identity to SEQ ID NO: 46. In some embodiments, the one or more nucleic acid sequences encodes the AID comprising at least 95% sequence identity to SEQ ID NO: 46. In some embodiments, the one or more nucleic acid sequences encodes the AID comprising at least 99% sequence identity to SEQ ID NO: 46. In some embodiments, the one or more nucleic acid sequences encoding the AID comprises SEQ ID NO: 46.

In some embodiments, the one or more nucleic acid sequences encodes the AID comprising at least 60% sequence identity to SEQ ID NO: 48. In some embodiments, the one or more nucleic acid sequences encodes the AID comprising at least 70% sequence identity to SEQ ID NO: 48. In some embodiments, the one or more nucleic acid sequences encodes the AID comprising at least 75% sequence identity to SEQ ID NO: 48. In some embodiments, the one or more nucleic acid sequences encodes the AID comprising at least 80% sequence identity to SEQ ID NO: 48. In some embodiments, the one or more nucleic acid sequences encodes the AID comprising at least 90% sequence identity to SEQ ID NO: 48. In some embodiments, the one or more nucleic acid sequences encodes the AID comprising at least 95% sequence identity to SEQ ID NO: 48. In some embodiments, the one or more nucleic acid sequences encodes the AID comprising at least 99% sequence identity to SEQ ID NO: 48. In some embodiments, the one or more nucleic acid sequences encoding the AID comprises SEQ ID NO: 48.

In some embodiments, the one or more nucleic acid sequences encodes the AID comprising at least 60% sequence identity to SEQ ID NO: 50. In some embodiments, the one or more nucleic acid sequences encodes the AID comprising at least 70% sequence identity to SEQ ID NO: 50. In some embodiments, the one or more nucleic acid sequences encodes the AID comprising at least 75% sequence identity to SEQ ID NO: 50. In some embodiments, the one or more nucleic acid sequences encodes the AID comprising at least 80% sequence identity to SEQ ID NO: 50. In some embodiments, the one or more nucleic acid sequences encodes the AID comprising at least 90% sequence identity to SEQ ID NO: 50. In some embodiments, the one or more nucleic acid sequences encodes the AID comprising at least 95% sequence identity to SEQ ID NO: 50. In some embodiments, the one or more nucleic acid sequences encodes the AID comprising at least 99% sequence identity to SEQ ID NO: 50. In some embodiments, the one or more nucleic acid sequences encoding the AID comprises SEQ ID NO: 50.

In some embodiments, the one or more nucleic acids encoding the catalytically inactive nuclease comprises a dead Cas 9 (dCas9) or a dead Cas12 (dCas12). In some embodiments, the one or more nucleic acid sequences encoding the catalytically inactive nuclease comprises at least 60% sequence identity to SEQ ID NO: 23. In some embodiments, the one or more nucleic acid sequences encoding the catalytically inactive nuclease comprises at least 70% sequence identity to SEQ ID NO: 23. In some embodiments, the one or more nucleic acid sequences encoding the catalytically inactive nuclease comprises at least 75% sequence identity to SEQ ID NO: 23. In some embodiments, the one or more nucleic acid sequences encoding the catalytically inactive nuclease comprises at least 80% sequence identity to SEQ ID NO: 23. In some embodiments, the one or more nucleic acid sequences encoding the catalytically inactive nuclease comprises at least 90% sequence identity to SEQ ID NO: 23. In some embodiments, the one or more nucleic acid sequences encoding the catalytically inactive nuclease comprises at least 95% sequence identity to SEQ ID NO: 23. In some embodiments, the one or more nucleic acid sequences encoding the catalytically inactive nuclease comprises at least 99% sequence identity to SEQ ID NO: 23. In some embodiments, the one or more nucleic acid sequences encoding the catalytically inactive nuclease comprises SEQ ID NO: 23.

In some embodiments, the at least one gRNA comprises SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, or a variant thereof.

In some embodiments, the at least one gRNA comprises a m1,3tx2 gRNA. In some embodiments, the m1,3tx2 gRNA comprises at least 60% sequence identity to SEQ ID NO: 12. In some embodiments, the m1,3tx2 gRNA comprises at least 70% sequence identity to SEQ ID NO: 12. In some embodiments, the m1,3tx2 gRNA comprises at least 75% sequence identity to SEQ ID NO: 12. In some embodiments, the m1,3tx2 gRNA comprises at least 80% sequence identity to SEQ ID NO: 12. In some embodiments, the m1,3tx2 gRNA comprises at least 90% sequence identity to SEQ ID NO: 12. In some embodiments, the m1,3tx2 gRNA comprises at least 95% sequence identity to SEQ ID NO: 12. In some embodiments, the m1,3tx2 gRNA comprises at least 99% sequence identity to SEQ ID NO: 12. In some embodiments, the m1,3tx2 gRNA comprises SEQ ID NO: 12.

In some embodiments, the at least one PAM sequence comprises SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or a variant thereof.

In some embodiments, the expression vector of any preceding aspect is a component of a therapeutic composition further comprising a pharmaceutically acceptable carrier. As herein, a "pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, New Jersey), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

Methods of Mutating a Protein

In one aspect, disclosed herein is a method of mutating a target protein using a CRISPR base editor system expressed in a yeast, the method comprising identifying a target nucleic acid sequence encoding a target protein; incorporating into a yeast genome at least one expression vector comprising one or more nucleic acid sequences encoding the target nucleic acid sequence and a CRISPR base editor, wherein the CRISPR base editor comprises a catalytically inactive nuclease, at least one guide RNA (gRNA) comprising at least one bacteriophage aptamer and at least one protospacer adjacent motif (PAM) sequence, a MS2 phage coat protein (MCP), and an activation-induced deaminase (AID), and wherein expression of the CRISPR base editor is under control of a yeast-derived promoter sequence and a yeast-derived terminator sequence; inducing a mutation into the target protein, wherein the AID incorporates a mutation into the target nucleic acid sequence and the target nucleic acid is translated into the target protein, and wherein the mutation increases a function of the target protein relative to a wild-type control protein; expressing the target protein comprising the mutation in the yeast; and isolating said target protein comprising the mutation.

In one aspect, disclosed herein is a method of mutating a target protein using a CRISPR base editor system expressed in a yeast, the method comprising identifying a target nucleic acid sequence encoding a target protein; incorporating into a yeast genome at least one expression vector comprising one or more nucleic acid sequences encoding the target nucleic acid sequence and a CRISPR base editor, wherein the CRISPR base editor comprises a catalytically inactive nuclease, at least one guide RNA (gRNA) comprising at least one bacteriophage aptamer and at least one protospacer adjacent motif (PAM) sequence, a MS2 phage coat protein (MCP), and an activation-induced deaminase (AID), and wherein expression of the CRISPR base editor is under control of a yeast-derived promoter sequence and a yeast-derived terminator sequence; and inducing a mutation into the target protein, wherein the AID incorporates a mutation into the target nucleic acid sequence and the target nucleic acid is translated into the target protein, and wherein the mutation increases a function of the target protein relative to a wild-type control protein.

In one aspect, disclosed herein is a method of mutating a target protein using a CRISPR base editor system expressed in a yeast, the method comprising identifying a target nucleic acid sequence encoding a target protein; incorporating into a yeast genome at least one expression vector comprising one or more nucleic acid sequences encoding the target nucleic acid sequence and a CRISPR base editor, wherein the CRISPR base editor comprises a catalytically inactive nuclease, at least one guide RNA (gRNA) comprising at least one bacteriophage aptamer and at least one protospacer adjacent motif (PAM) sequence, a MS2 phage coat protein (MCP), and an activation-induced deaminase (AID), and wherein expression of the CRISPR base editor is under control of a yeast-derived promoter sequence and a yeast-derived terminator sequence; inducing a mutation into the target protein, wherein the AID incorporates a mutation into the target nucleic acid sequence and the target nucleic acid is translated into the target protein, and wherein the mutation increases a function of the target protein relative to a wild-type control protein; and expressing the target protein comprising the mutation in the yeast.

In some embodiments, the method of mutating a protein comprises the CRISPR base editor system of any preceding aspect or the expression vector of any preceding aspect.

In some embodiments, the method of mutating a protein comprises the gRNA binding a target nucleic acid encoding a target protein, or a fragment thereof. In some embodiments, the method of mutating a protein comprises the MCP binding the at least one bacteriophage aptamer of the gRNA.

In some embodiments, the at least one bacteriophage aptamer comprises an MS2 aptamer. In some embodiments, the MCP comprises an NLS.

In some embodiments, the method of mutating a protein comprises the AID mutating the target nucleic acid encoding the target protein, or a fragment thereof. In some embodiments, the method of mutating a protein comprises an AID731Δ mutant.

In some embodiments, the method of mutating a protein comprises the gRNA and PAM sequence of any preceding aspect.

In some embodiments, the method of mutating a protein comprises a yeast cell that expresses a mutant of the target protein. In some embodiments, the mutant of the target protein comprises an antibody, an enzyme, a structural protein, a contractile protein, a hormonal protein, a storage protein, a signaling protein, a transport protein, or fragments thereof.

In some embodiments, the method of mutating a protein comprises a dead Cas 9 (dCas9) or a dead Cas12 (dCas12). In some embodiments, the method of mutating a protein comprises a cytidine activation-induced deaminase or an adenine activation-induced deaminase.

In some embodiments, the method of mutating a protein comprises a yeast display for expressing the mutant of the target protein. In some embodiments, the yeast display comprises *Saccharomyces cerevisiae* (*S. cerevisiae*).

Methods of Treating and/or Preventing Diseases or Disorders

In one aspect, disclosed herein is a method of treating or preventing a disease or disorder in a subject in need thereof, the method comprising identifying a target nucleic acid sequence encoding a target protein; incorporating into a yeast genome at least one expression vector comprising one or more nucleic acid sequences encoding the target nucleic acid sequence and a CRISPR base editor, wherein the CRISPR base editor comprises a catalytically inactive nuclease, at least one guide RNA (gRNA) comprising at least one bacteriophage aptamer and at least one protospacer adjacent motif (PAM) sequence, a MS2 phage coat protein (MCP), and an activation-induced deaminase (AID), and wherein expression of the CRISPR base editor is under control of a yeast-derived promoter sequence and a yeast-derived terminator sequence; inducing a mutation into the target protein, wherein the AID incorporates a mutation into the target nucleic acid sequence and the target nucleic acid is translated into the target protein, and wherein the mutation increases a function of the target protein relative to a wild-type control protein; expressing the target protein comprising the mutation in the yeast; isolating said target protein comprising the mutation; incorporating the target protein into a therapeutic composition; and administering the therapeutic composition to the subject.

In some embodiments, the method of treating or preventing a disease or disorder comprises the CRISPR base editor system of any preceding aspect or the expression vector of any preceding aspect.

In some embodiments, the method of treating or preventing a disease or disorder comprises the gRNA binding a target nucleic acid encoding a target protein, or a fragment thereof. In some embodiments, the method of treating or preventing a disease or disorder comprises the MCP binding the at least one bacteriophage aptamer of the gRNA. In some embodiments, the at least one bacteriophage aptamer comprises an MS2 aptamer. In some embodiments, the MCP comprises an NLS.

In some embodiments, the method of treating or preventing a disease or disorder comprises the AID mutating the target nucleic acid encoding the target protein, or a fragment thereof. In some embodiments, the method of treating or preventing a disease or disorder comprises an AID731Δ mutant.

In some embodiments, the method of treating or preventing a disease or disorder comprises the gRNA and PAM sequence of any preceding aspect.

In some embodiments, the method of treating or preventing a disease or disorder comprises a yeast cell that expresses a mutant of the target protein. In some embodiments, the mutant of the target protein comprises an antibody, an enzyme, a structural protein, a contractile protein, a hormonal protein, a storage protein, a signaling protein, a transport protein, or fragments thereof.

In some embodiments, the method of treating or preventing a disease or disorder comprises a dead Cas 9 (dCas9) or a dead Cas12 (dCas12). In some embodiments, the method of treating or preventing a disease or disorder comprises a cytidine activation-induced deaminase or an adenine activation-induced deaminase.

In some embodiments, the method of treating or preventing a disease or disorder comprises a yeast display for expressing the mutant of the target protein. In some embodiments, the yeast display comprises *Saccharomyces cerevisiae* (*S. cerevisiae*).

In some embodiments, the CRISPR base editor system of any preceding aspect or the expression vector of any preceding aspect is a component of a therapeutic composition further comprises a pharmaceutically acceptable carrier of any preceding aspect.

The therapeutic composition may be administered in such amounts, time, and route deemed necessary in order to achieve the desired result. The exact amount of the therapeutic composition will vary from subject to subject, depending on the species, age, and general condition of the subject, the severity of the disease, the particular therapeutic composition, its mode of administration, its mode of activity, and the like. The therapeutic composition is preferably formulated in dosage unit form for ease of administration and uniformity of dosage. It will be understood, however, that the total daily usage of the therapeutic composition will be decided by the attending physician within the scope of sound medical judgment. The specific therapeutically effective dose level for any particular subject will depend upon a variety of factors including the disease(s) being treated and the severity of the symptoms; the activity of the therapeutic composition employed; the specific therapeutic composition employed; the age, body weight, general health, sex and diet of the patient; the time of administration, route of administration, and rate of excretion of the specific therapeutic composition employed; the duration of the treatment; drugs used in combination or coincidental with the specific therapeutic composition employed; and like factors well known in the medical arts.

The therapeutic composition may be administered by any route. In some embodiments, the therapeutic composition is administered via a variety of routes, including oral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the therapeutic composition (e.g., its stability in the environment of the subject's body), the condition of the subject (e.g., whether the subject is able to tolerate administration), etc.

The exact amount of therapeutic composition required to achieve a therapeutically or prophylactically effective amount will vary from subject to subject, depending on species, age, and general condition of a subject, severity of the side effects, identity of the particular compound(s), mode of administration, and the like. The amount to be administered to, for example, a child or an adolescent can be determined by a medical practitioner or person skilled in the art and can be lower or the same as that administered to an adult.

In one aspect, disclosed herein is therapeutic composition of any preceding aspect and a pharmaceutically acceptable carrier selected from an excipient, a diluent, a salt, a buffer, a stabilizer, a lipid, an emulsion, a nanoparticle, and a cream. One or more active agents (e.g. CRISPR base editor systems) can be administered in the "native" form or, if desired in the form of salts, esters, amides, prodrugs, or a derivative that is pharmacologically suitable. Salts, esters, amides, prodrugs, and other derivatives of the active agents can be prepared using standards procedures known to those skilled in the art of synthetic organic chemistry and described, for example, by March (1992) *Advanced Organic Chemistry; Reactions, Mechanisms, and Structure,* $4^{th}$ Ed. N.Y. Wiley-Interscience.

In some embodiments, the therapeutic composition is administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more times. In some embodiments, the therapeutic composition is administered daily. In some embodiments, the therapeutic composition is administered every day, every 2 days, every 3 days, every 4 days, every 5 days, every 6 days, every 7 days, or more. In some embodiments, the therapeutic composition is administered every week, every 2 weeks, every 3 weeks, every 4 weeks, or more. In some embodiments, the therapeutic composition is administered every month, every 2 months, every 3 months, every 4 months, every 5 months, every 6 months, every 7 months, every 8 months, every 9 months, every 10 months, every 11 months, every 12 months, or more. In some embodiments, the therapeutic composition is administered every year, every 2 years, every 3 years, every 4 years, every 5 years, or more.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are set forth below to illustrate the compositions, devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: A Rapid Antibody Enhancement Platform in *Saccharomyces cerevisiae* Using an Improved, Diversifying CRISPR Base Editor The yeast *Saccharomyces cerevisiae* is commonly used to interrogate and screen protein variants and to perform directed evolution studies to develop proteins with enhanced features. While several techniques have been described that help enable the use of yeast for directed evolution, there remains a need to increase their speed and ease of use. Herein, yDBE, a yeast diversifying base editor, is presented that functions in vivo and employs a CRISPR-dCas9-directed cytidine deaminase base editor to diversify DNA in a targeted, rapid, and high-breadth manner. To develop yDBE, the mutation rate of an initial base editor is enhanced by employing improved deaminase variants and characterizing several scaffolded guide constructs. The ability of the yDBE platform to improve the affinity of a displayed antibody scFv, rapidly generating diversified libraries and isolating improved binders via cell sorting is demonstrated. By performing high-throughput sequencing analysis of the high-activity yDBE, it enables a mutation rate of $2.13\times10^{-4}$ substitutions/bp/generation over a window of 100 bp. As yDBE functions entirely in vivo and can be easily programmed to diversify nearly any such window of DNA, it is a powerful tool for facilitating a variety of directed evolution experiments.

Directed evolution via DNA mutagenesis and screening of the resultant protein libraries is an essential strategy for improving protein function. The yeast *Saccharomyces cerevisiae* is frequently used for directed evolution experiments because it grows rapidly, has well developed genetic tools, can carry out eukaryotic posttranslational modifications, and can be engineered to display proteins or protein fragments tethered to the cell surface. The majority of directed evolution programs in yeast utilize mutant libraries created through traditional, in vitro mutagenesis techniques such as site-saturation mutagenesis or error-prone PCR. While these methods introduce sufficient diversity, they require laborious in vitro cloning procedures that slow the iterative process of directed evolution.

To circumvent these issues, a number of methods have been developed to continuously generate genetic diversity within a cell. Within yeast specifically, tet-directed DNA glycosylases (TaGTEAM), CRISPR-targeted error-prone DNA polymerases (EvolvR), a T7-polymerase-guided cytidine deaminase (TRIDENT), retrotransposon cycling with an error-prone reverse transcription step (ICE), and error-prone orthogonal DNA polymerases contained on cytoplasmic plasmids (OrthoRep and AHEAD) enable DNA mutation in vivo. These systems, with the exception of EvolvR, are unable to target multiple sequence regions and require a targeted gene to be first inserted in a predefined location. The rate of DNA diversification, as measured by substitutions per basepair per generation (s.p.b), can vary widely in these systems. As an example, OrthoRep, which reports a mutation rate of $1\times10^{-5}$ s.p.b., in some cases took up to 13 passages, or up to 90 generations, to evolve a desired resistance phenotype. The highest reported mutation rate attained by these yeast-based systems is $1\times10^{-3}$ s.p.b. using TRIDENT.

CRISPR base editors mediate in situ DNA mutation in a targeted manner by employing programmable DNA binding proteins, such as dCas9, to target cytidine or adenine deaminases to specific DNA sequences. In this way, nucleotide deaminases are directed to a specific locus that bears homology to a 20-bp spacer sequence within a CRISPR guide RNA (gRNA), resulting in DNA mutations near the targeted site. The deaminase can be fused directly to the dCas9 protein or recruited through a secondary protein-protein or protein-RNA interaction, for instance, by incorporating MS2 aptamer sequences into a gRNA scaffold and taking advantage of the high affinity interaction between the MS2 phage coat protein (MCP) and MS2 aptamers. In yeast specifically, CRISPR base editors have been employed to perturb essential genes using dCas9 fusions of *Petromyzon marinus* CDA1 or human APOBEC3A deaminases. Cytidine deaminases transform cytosine to uracil in ssDNA, and because uracil is recognized as DNA damage, it is often repaired inaccurately, leading to permanent DNA mutations. Possible outcomes of cytosine deamination to uracil include 1) replacement with thymine as the DNA undergoes replication, 2) excision and replacement with any nucleotide through base excision repair, or 3) mismatch repair, especially when one strand of DNA is nicked, causing mutations at or near the uracil. In this way, a variety of substitutions can occur at or near the deaminated cytosine.

Many CRISPR base editor engineering efforts have increased the precision and specificity of DNA mutagenesis to enable their application in gene editing technologies, for instance, for clinical application in which only one specific DNA base pair mutation is desired or allowable. To give two specific examples, a uracil glycosylase inhibitor domain or a uracil DNA glycosylase can be incorporated into a base editor to help reinforce C-to-T or C-to-G mutations, respectively. In contrast, diversifying base editors (DBEs), are designed to generate a high mutational load via a variety of substitutions in the vicinity of their target site with applications in directed evolution. For instance, the CRISPR-X technique utilized a human activation-induced cytidine deaminase (AID)-MCP fusion protein to mutate DNA in mammalian cells and recapitulate aspects of antibody affinity maturation. AID is the catalytic deaminase enzyme that mediates somatic hypermutation of antibody sequences, i.e., their mutation, in B cells.

Antibody therapeutics have seen tremendous growth over the past decade and are used to treat a variety of diseases, including viral infections, autoimmune disorders, and cancer. Due to its ability to grow rapidly to high densities and surface-present libraries of antibody variants, *S. cerevisiae* has become a popular platform for therapeutic antibody interrogation. A recently described in vivo continuous evolution platform for the isolation of high affinity nanobodies in yeast, AHEAD, demonstrates the remarkable potential of combining in situ DNA diversification with yeast protein display.[17] Surprisingly, to the best of one's knowledge, DBEs have not been designed or employed for use in yeast.

In this work, a yeast DBE (yDBE) was created and then improved. The yDBE also established that it effectively mediated targeted DNA diversification of both an enzyme and an antibody fragment. Using a fluorescence shift assay of GFP enzyme variants, the initial mutagenesis capability of the yDBE was improved by (1) identifying a highly active AID variant from a panel of previously described or novel AID upmutants, (2) adjusting the number and placement of MS2 aptamers housed within the gRNA scaffold to find complementary scaffolds with high activity and unique targeting profiles, and (3) increasing the versatility of the yDBE platform to promote multi-loci targeting using rapidly-assembled, tRNA-gRNA cassettes. The yDBE platform was demonstrated to be utilized to improve the affinity of an anti-fluorescein scFv by over 100-fold through in situ DNA diversification coupled with yeast display. This work demonstrates the first development of a diversifying base-editor system for targeted and rapid DNA diversification in yeast. Furthermore, this is the first instance in which the human AID enzyme has been employed for CRISPR base editing in yeast. Lastly, yDBE enables a mutation rate of $2.13\times10^{-4}$ s.p.b. over a window of 100 bp, approaching prior best-in-class in vivo mutagenesis studies.

Results and Discussion:

Development of an initial CRISPR diversifying base editor for yeast (yDBE). A programmable, yeast-based diversifying base editor strain was developed for preliminary testing by genomically integrating codon-optimized MCP-AID*Δ and dCas9 proteins. When coupled with a gRNA encoding MS2 aptamer loops, FIG. 2A outlines how the yDBE enabled targeted DNA mutation in yeast, mimicking the capabilities and design of the CRISPR-X platform developed in mammalian cells. MCP forms dimers when binding MS2 aptamers, allowing multiple AID*Δ proteins to be recruited to the targeted site. AID*Δ is a more active mutant of human activation-induced cytidine deaminase (Table 3). dCas9 and MCP-AID*Δ were placed under the control of galactose-inducible promoters, pGAL1 and pGAL2, respectively. Wild-type GFP (wtGFP) was also genomically integrated at a separate locus, with the constitutive Ptdh3 promoter driving its expression. The integration sites (YORWΔ22 and YPRCτ3) were utilized that are known to afford robust transgene expression. Lastly, scaffolded gRNAs were expressed on a plasmid that was transformed into the yeast after the base editor integration. The initial system used gRNAs with an M13 scaffold in which two MS2 loops were incorporated in the scaffold in the first and third loop of the gRNA as will be described further below.

A fluorescence shift-based assay was used to determine if the initial yDBE platform introduces targeted mutations into the wtGFP enzyme. Compared to wtGFP, enhanced GFP (eGFP) has an S65T mutation that shifts the excitation spectra peak from 405 nm to 488 nm (FIG. 2B). AID prefers to deaminate cytidines within a WRCY nucleotide motif, especially the palindromic AGCT. As the S65 amino acid in wtGFP is part of an AGCT nucleotide motif, targeting this region with an AID-based base editor results in wtGFP→eGFP mutations over time, allowing sensitive detection of base editor activity via flow cytometry and the use of fluorescence shift percentage as a correlate for the overall base editor mutation rate (FIG. 7). Using the initial yDBE system targeted by either of two different M13 scaffolded gRNAs, a small fraction of yeast cells was generated, <0.05%, that displayed eGFP's excitation after two days induction (FIG. 2C). Furthermore, the DNA from cells within the eGFP population were sequenced to verify the presence of the expected S65T mutation, confirming yDBE function. The fluorescence at 2, 4, and 8 days was measured and it was observed that mutations accumulated roughly linearly over time (FIG. 2C), approaching 0.5% eGFP+ cells. GFP-targeting gRNAs are named as follows: nucleotide distance from the S65 target site to the 3' end of the gRNA PAM (NGG-3'), L or R for left or right in the direction of the GFP open reading frame, and either a "t" for gRNAs that target dCas9 to bind to the template strand or no additional symbol for the coding strand.

As a prior study revealed that dCas9 alone can result in mutations in a targeted locus, the present disclosure verified that AID was required to induce the S65T mutation by determining that a modified yDBE strain harboring a catalytically inactive mutant (AIDdead) did not result in any eGFP+ cells after a 4-day induction (FIG. 2C). Similarly, the initial yDBE did not result in accumulation of eGFP+ cells when used with a nontargeting gRNA, NT1 (FIG. 2C).

Figure 8A:
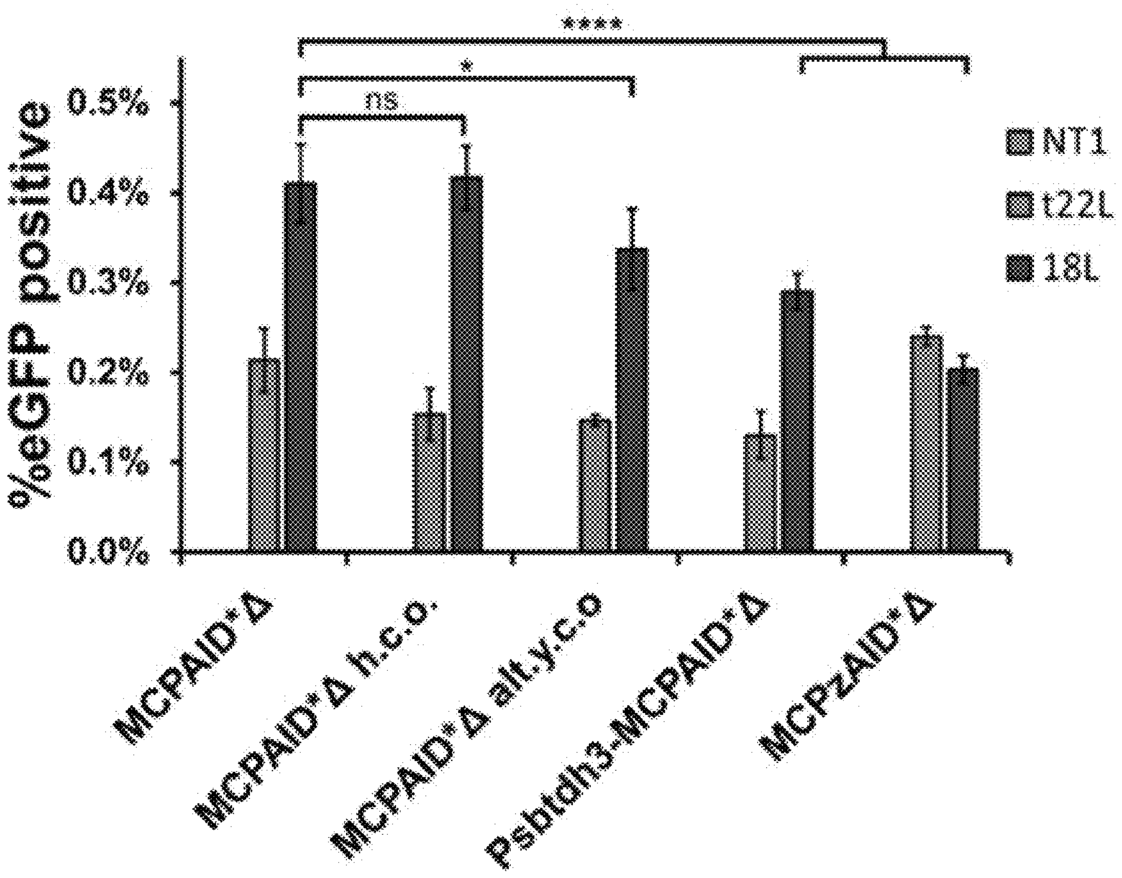
FIGS. 8A, 8B, 8C, and 8D show the fluorescence shift assay results after modifying yDBE components.
Figure 8B:
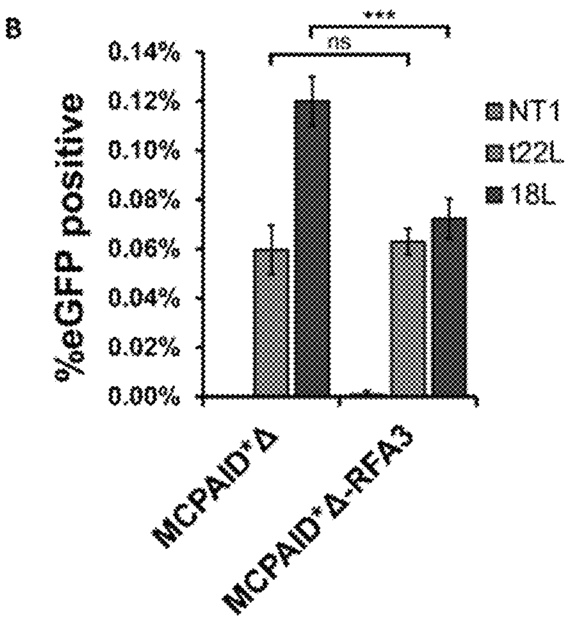
Figure 8C:
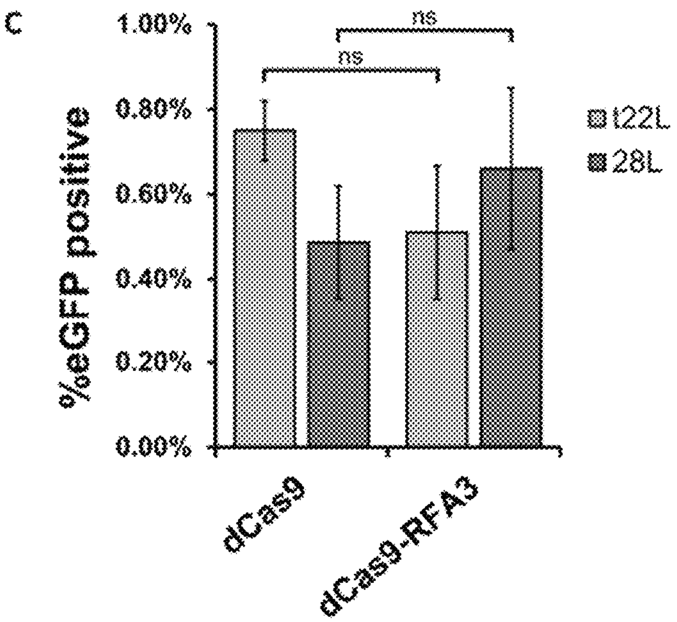
Figure 8D:
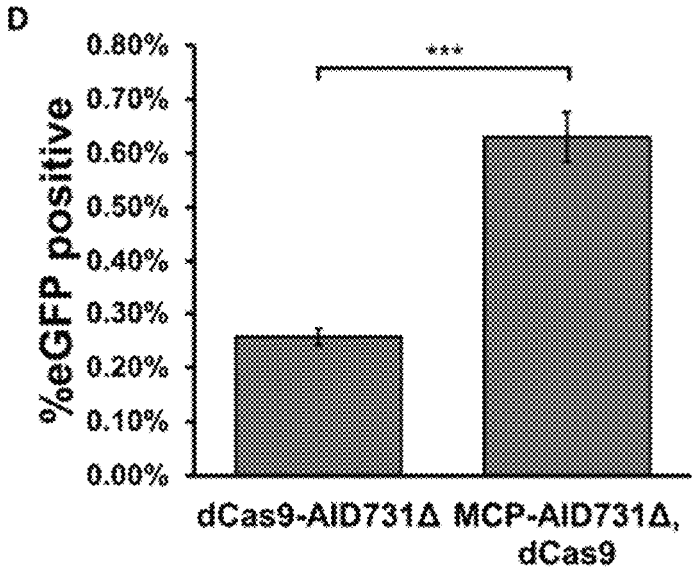

Employing higher activity AID variants to enhance yDBE mutation rate. After confirming the functionality of a yDBE, its activity was improved through two main strategies: 1) improving the activity or expression of the deaminase and 2) optimizing the location of the MS2 aptamers within the gRNA scaffold. In the first strategy, several methods were explored to increase the expression of AID*Δ and thereby increase base editing activity. It was found that 1) altering the codon optimization, 2) changing the GAL2 promoter to a strong, orthologous, constitutive promoter, or 3) using an altered MCP variant either did not change or decreased the activity relative to the initial base editor (FIG. 8A). Next, base editor variants were made that included the yeast ssDNA binding protein RFA3, a subunit of the replication factor A (RPA) complex. Fusing RFA3 to rat APOBEC1 (a cytidine deaminase related to AID) has been shown to increase the rate of genome-wide mutations. RFA3 was fused to the C-terminus of MCP-AID*Δ or directly to dCas9 and performed fluorescence shift assays but again did not detect an increase in eGFP mutations (FIGS. 8B and 8C). Finally, it was also confirmed that employing MS2 aptamer scaffolded gRNAs to recruit MCP-AID to a dCas9-targeted DNA locus outperforms a direct dCas9-AID fusion protein in the fluorescence shift assay (FIG. 8D). While it is possible that the gRNA used for this comparison favored the MS2-based system, previous work in mammalian cells has also shown that base editors that use MCP-MS2 recruitment induce broader mutations compared to direct dCas9-deaminase fusions. Therefore, additional strategies were pursued to enhance the MS2-based system.

Figure 3:
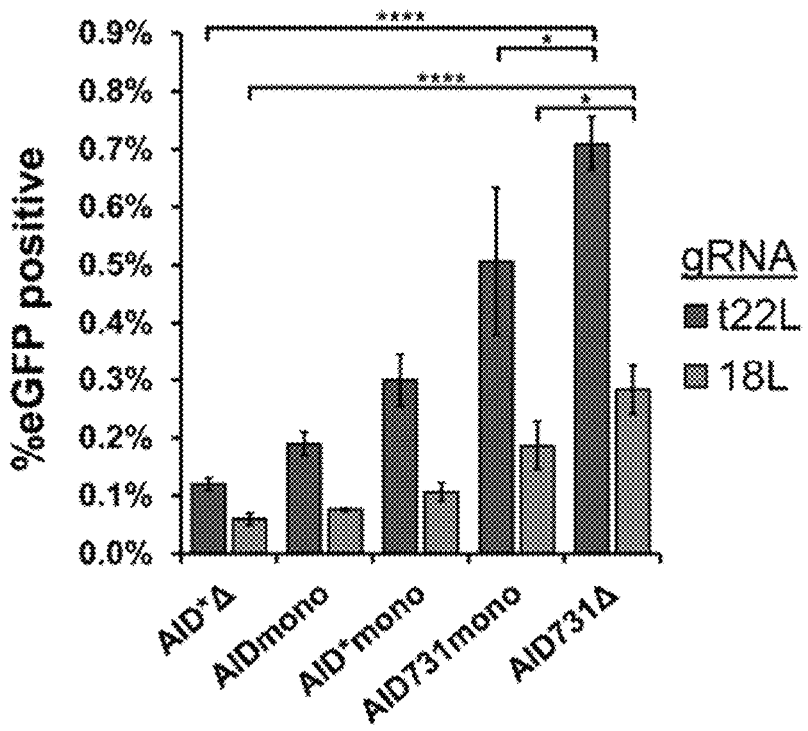
FIG. 3 shows employing higher activity AID variants to enhance yDBE mutation rate. Mutants of AID fused to MCP were tested in a fluorescence shift assay with two targeting gRNAs (18L and t22L) with an M13 scaffold. Cells were induced for 24 hours. Bars represent mean±SD, n=3, *$p<0.05$ and ****$p<0.0001$.

As attempts to alter expression or fuse mutation-enhancing factors to yDBE failed to noticeably improve its function, it was next investigated if engineered AID variants with higher catalytic activity might improve yDBE-mediated mutation rates. AID*Δ has a premature stop codon (195*) to remove its final three residues that can mediate nuclear export. All the tested variants also lack this nuclear export signal. AID*Δ, which contains three coding mutations, K10 E, T82I, and E156G, was isolated from previous work that measured global mutation rates of AID variants in *E. coli*. Interestingly, a related variant was reported to have more than 5-fold activity relative to the K10E, T82I, E156G mutant. This variant, referred to as "Mut7.3.1," contains 9 coding mutations, including the 3 coding mutations found in AID*Δ, though it still retained a nuclear export signal (Table 3). Separate AID engineering efforts have also generated a variant dubbed AIDmono that showed higher activity as a base editor. To determine if use of an enhanced AID variant could improve the mutational rate, the Mut7.3.1 (AID731Δ) and AIDmono variants were fused to MCP, as well as combined mutations from AID*Δ, Mut7.3.1, and AIDmono into novel variants: AID*mono and AID731mono (Table 3). The activity was tested in comparison to the initial yDBE in the context of two targeting (18L, and t22L) and one nontargeting (NT1) gRNAs (FIG. 3). Promisingly, the best performing variant, AID731Δ, had at least a 5-fold increase in activity in mutation rate, as assessed by eGFP fluorescence shift, relative to AID*Δ. The improvement was consistent for both the 18L and t22L gRNA targeting sequences, which target different DNA strands (coding versus template) at differential distances from the nucleotides that encode the initial S65 residue. After only one day of yDBE induction with the 18L gRNA, 0.71% of cells harboring the AID731Δ yDBE were positive for the eGFP mutation compared to 0.12% of AID*Δ cells.

Varying MS2 aptamer placement. As a second strategy to increase yDBE mutational rate, it was sought to determine the ideal location and number of MS2 aptamers within the gRNA framework. Previous studies have characterized the impact of different MS2 aptamer locations in gRNAs, typically in mammalian cell hosts. As the effect of MS2 aptamers placement within gRNAs has not been characterized previously in yeast nor in the context of DBEs, a comprehensive set of gRNA/MS2 aptamer designs were analyzed using the initial yDBE that employed AID*Δ.

gRNAs that complex with the SpCas9 protein contain four loops (FIG. 4A), of which three (loops 1, 3, and 4) support insertion of an MS2 aptamer sequence, i.e., an MS2 loop. MS2 loops can also be appended to the "tail" or 3' end of the gRNA. In the nomenclature herein, MS2 loop insertion into natural gRNA loops is denoted by the loop number, while inclusion on the gRNA tail is denoted by a 't.' A tandem repeat of the MS2 loop on the gRNA tail, denoted with 'tx2,' has been described previously and was also tested by itself and in combination with other MS2 insertions.

Figures 4A, 4B:
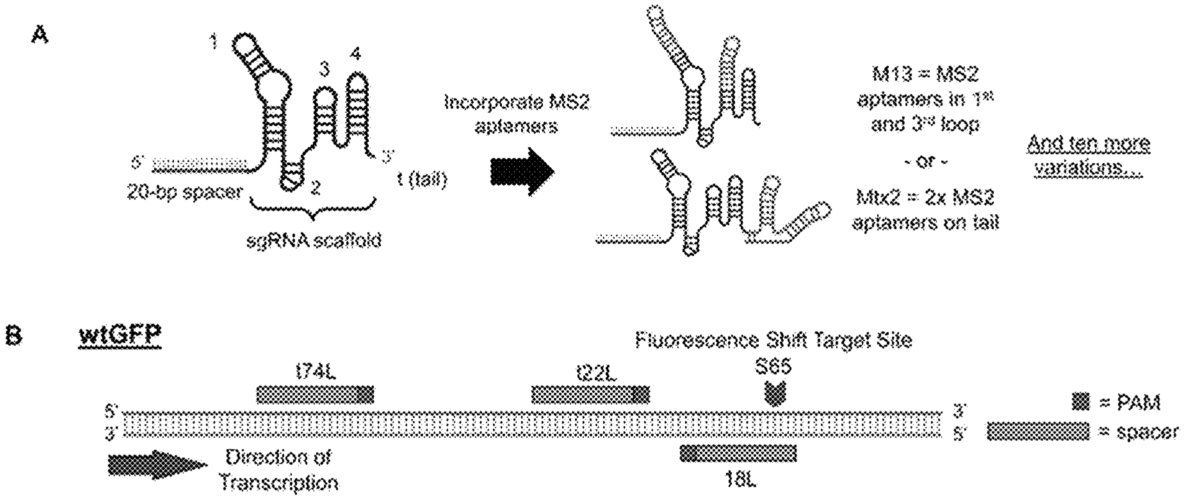
FIGS. 4A, 4B, and 4C show varying MS2 aptamer placement to increase diversification.
Figure 4C:
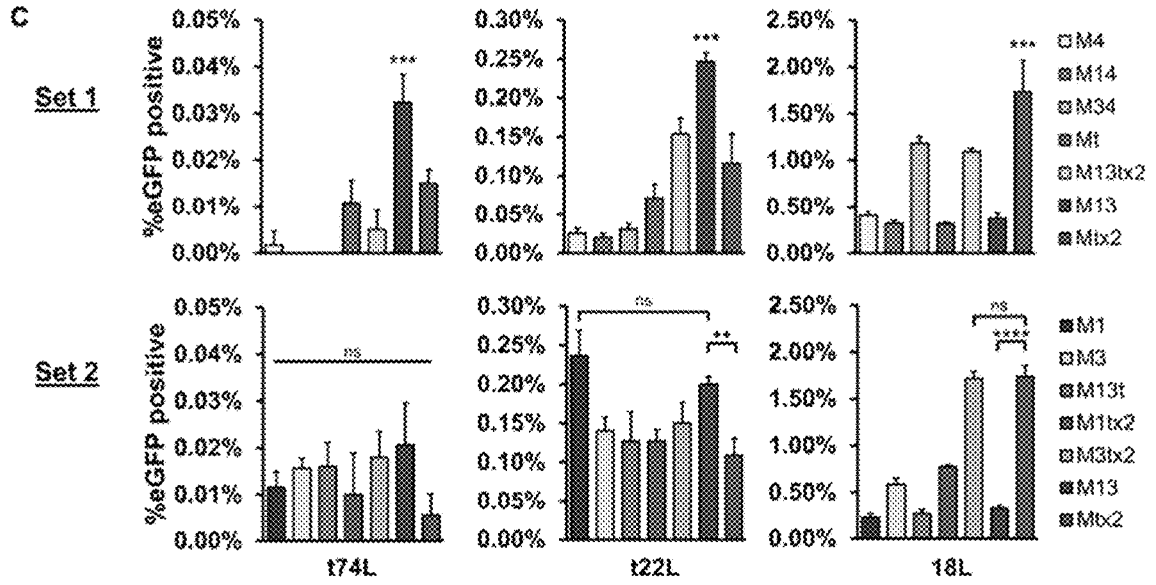
Figure 9:
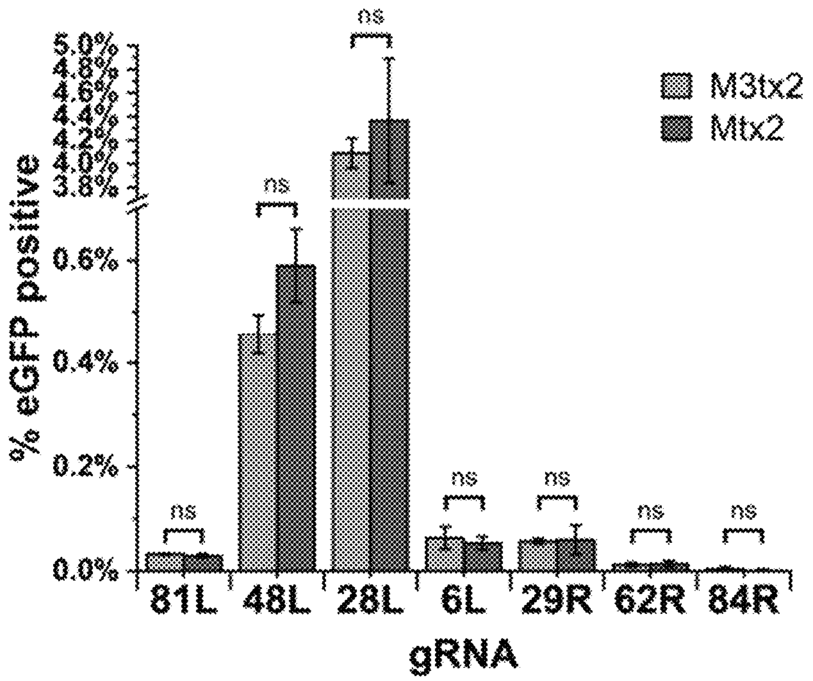
FIG. 9 shows the fluorescent shift assay gRNA tiling experiment comparing Mtx2 and M3tx2. Fluorescence shift assay after 4-day induction comparing M3tx2 and Mtx2 scaffolds with 7 positional spacers with AID*Δ (Strain AC001). Bars represent mean±SD, n=3, ns=not significant.
Figure 10A:
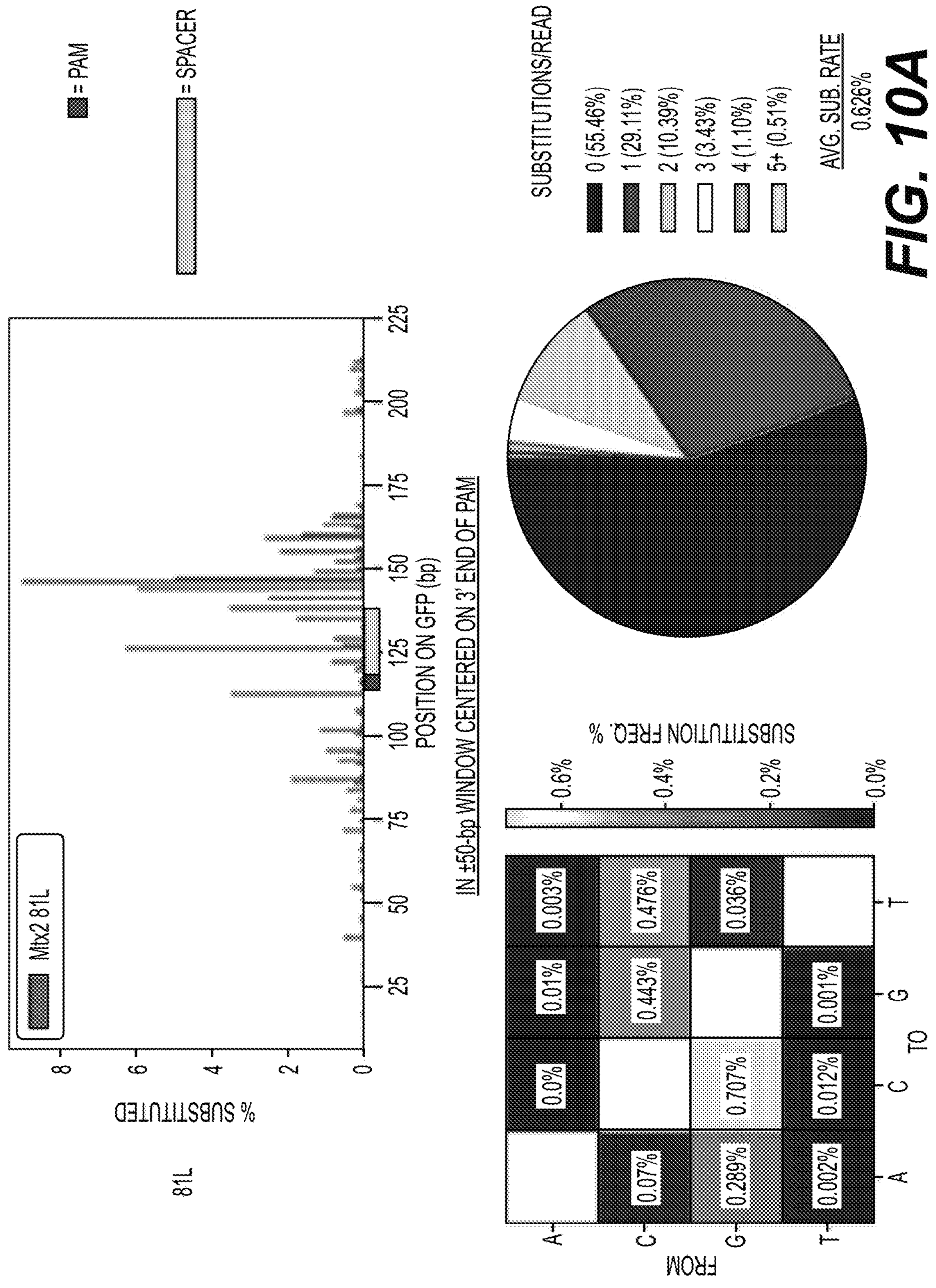
FIGS. 10A, 10B, 10C, 10D, and 10E show the high-throughput sequencing results for five separate, GFP-targeting Mtx2 gRNAs. DNA was extracted, amplified, and sequenced after 8-day yDBE induction in strain AC0003. For each gRNA, a substitution distribution plot, substitution heatmap, and substitution-per-read pie chart were generated. The substitution distribution plot shows the per-nucleotide rate of substitutions in a ±100-bp window. The relative position and orientation of the gRNA is shown along the x-axis. The substitution heatmap shows the average rate at which each possible substitution type was detected in a ±50-bp window. The pie chart shows how many substitutions were detected in a ±50-bp window per sequencing read. Lastly, the average mutation rate in a ±50-bp window is given on the right.
Figure 10B:
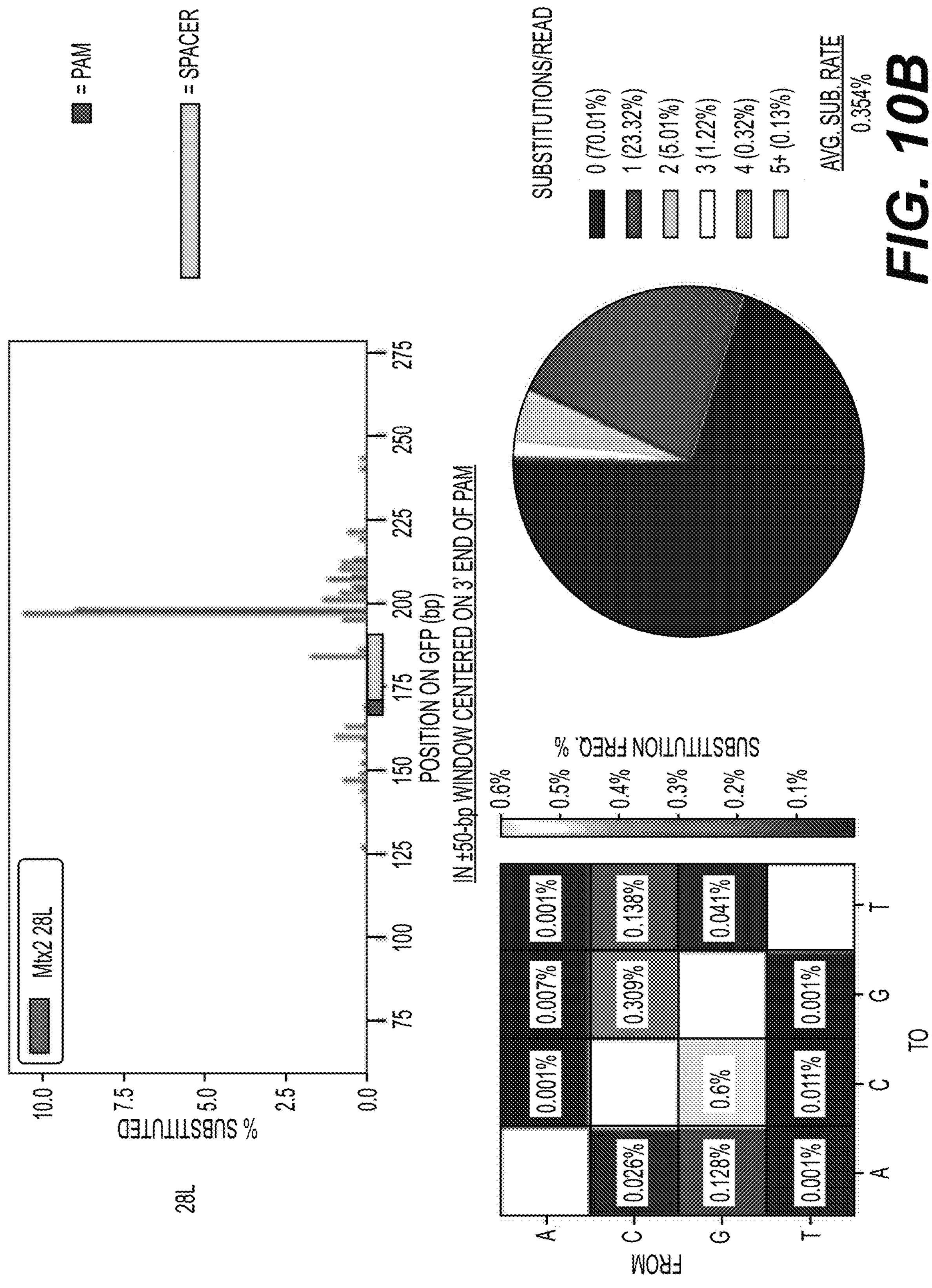
Figure 10C:
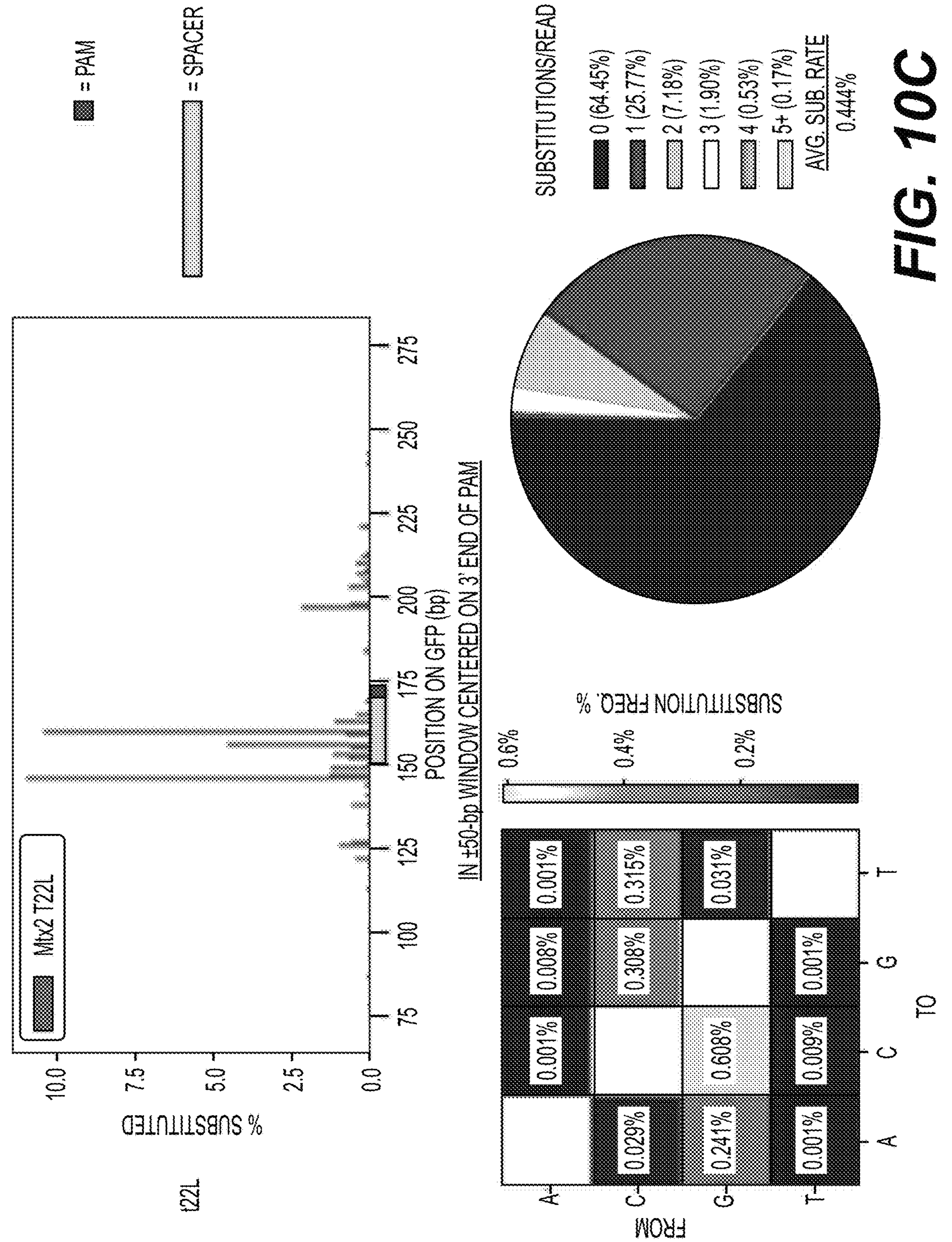
Figure 10D:
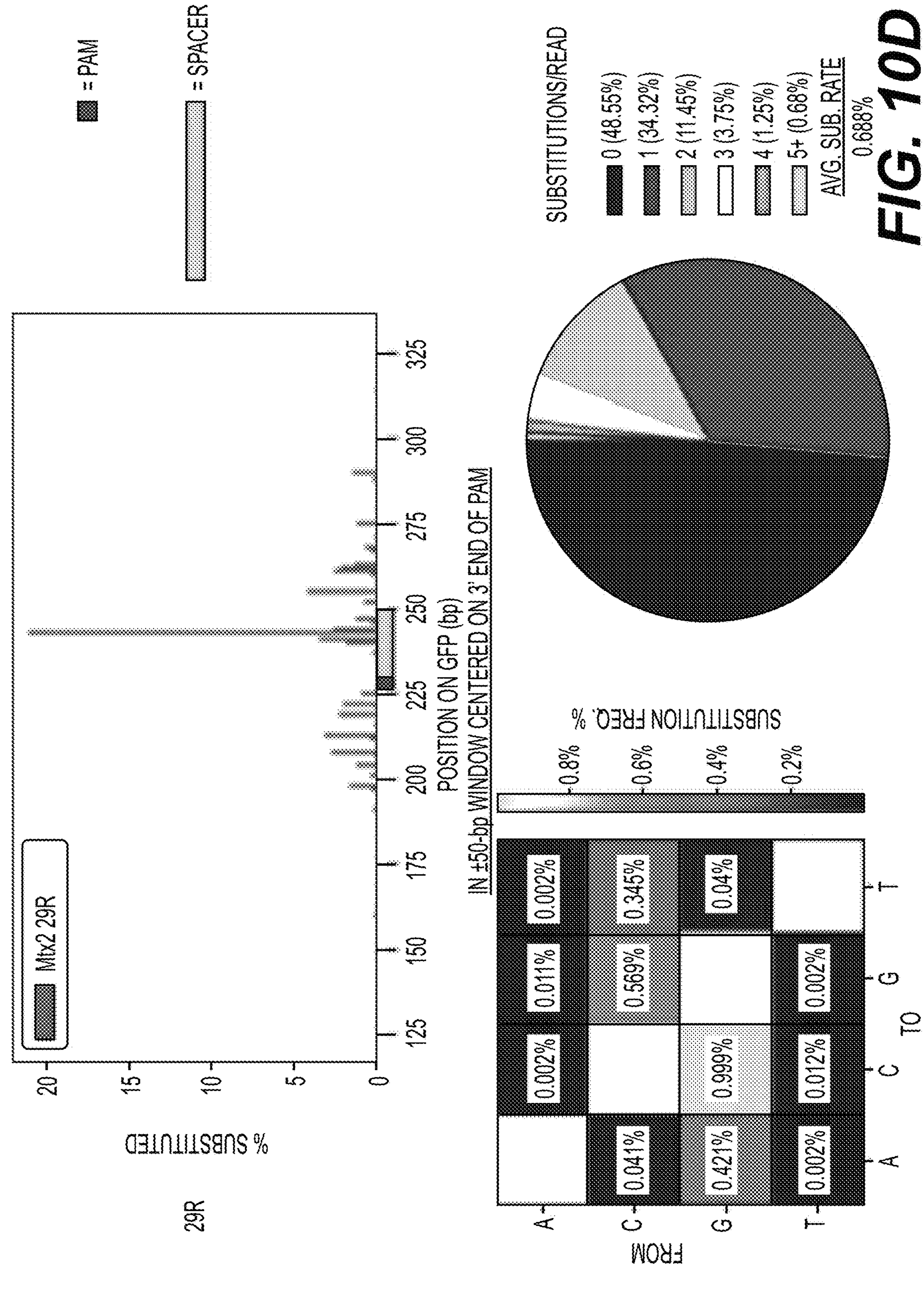
Figure 10E:
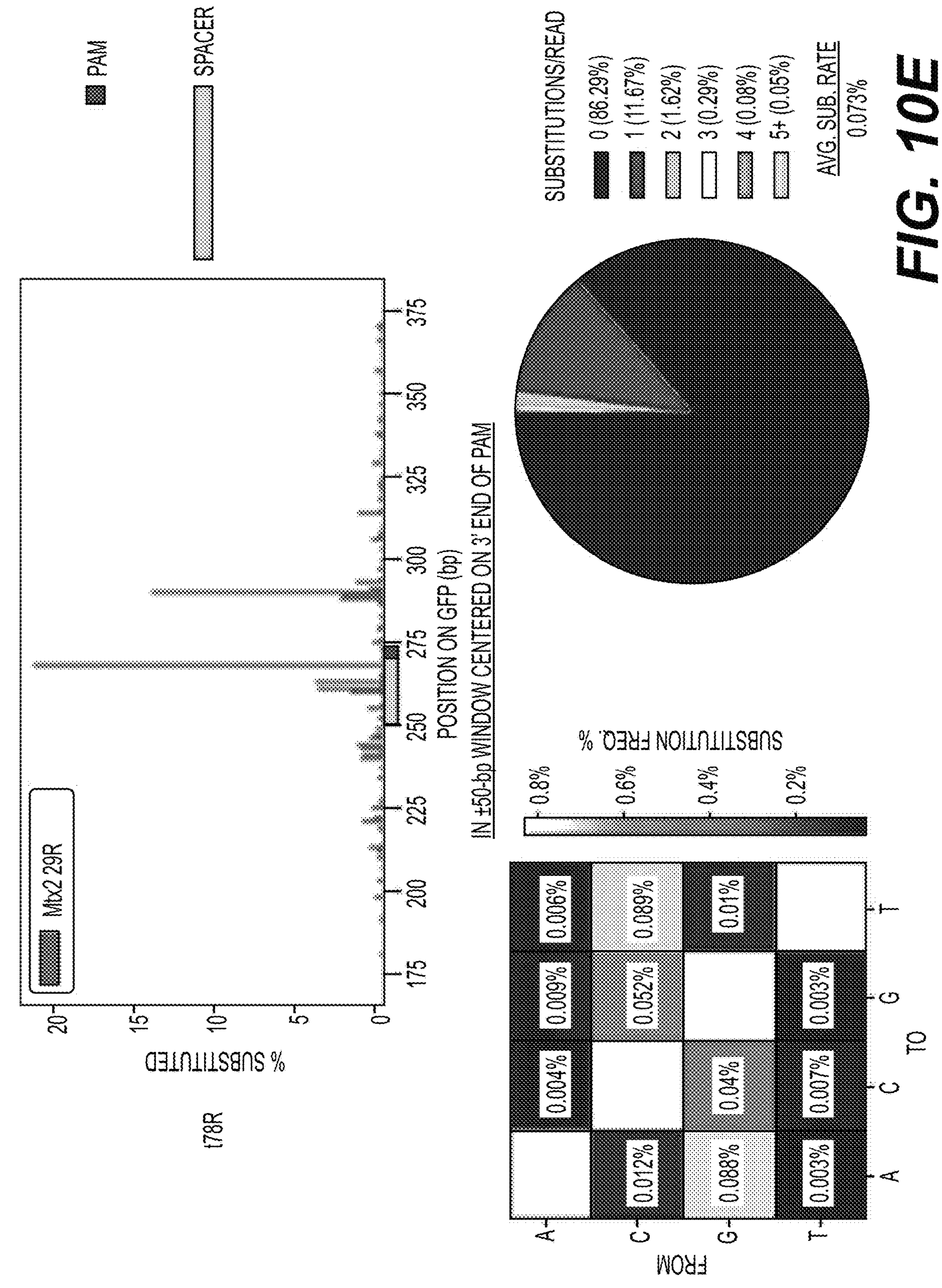

In total, 11 different scaffolded gRNA constructs were constructed and tested, dubbed M1, M3, M4, M14, M34, Mt, Mtx2, M1tx2, M3tx2, M13t, M13tx2, and compared them to the starting configuration, M13. Across two experiments, the mutational capacity bestowed by each MS2 loop configuration was assessed in the yDBE system using in fluorescence shift assays, and each MS2 loop configuration was tested in the context of three gRNA spacer sequences to ensure effects were not gRNA dependent (FIGS. 4B and 4C). Two configurations, M13 and Mtx2, were repeated in both experiments to allow qualitative comparison between the sets. The M13 and Mtx2 configurations were selected for further analysis due to their superior performance with the t22L/t74L and 18L gRNAs, respectively. While M3tx2 had a signal comparable to Mtx2, additional tests with alternative spacer sequences did not demonstrate significant improvement (FIG. 9). The Mtx2 configuration and 18L gRNA combination improved EGFP+ mutation occurrence fivefold compared to the initial M13 configuration used in yDBE.

Figures 5A, 5B:
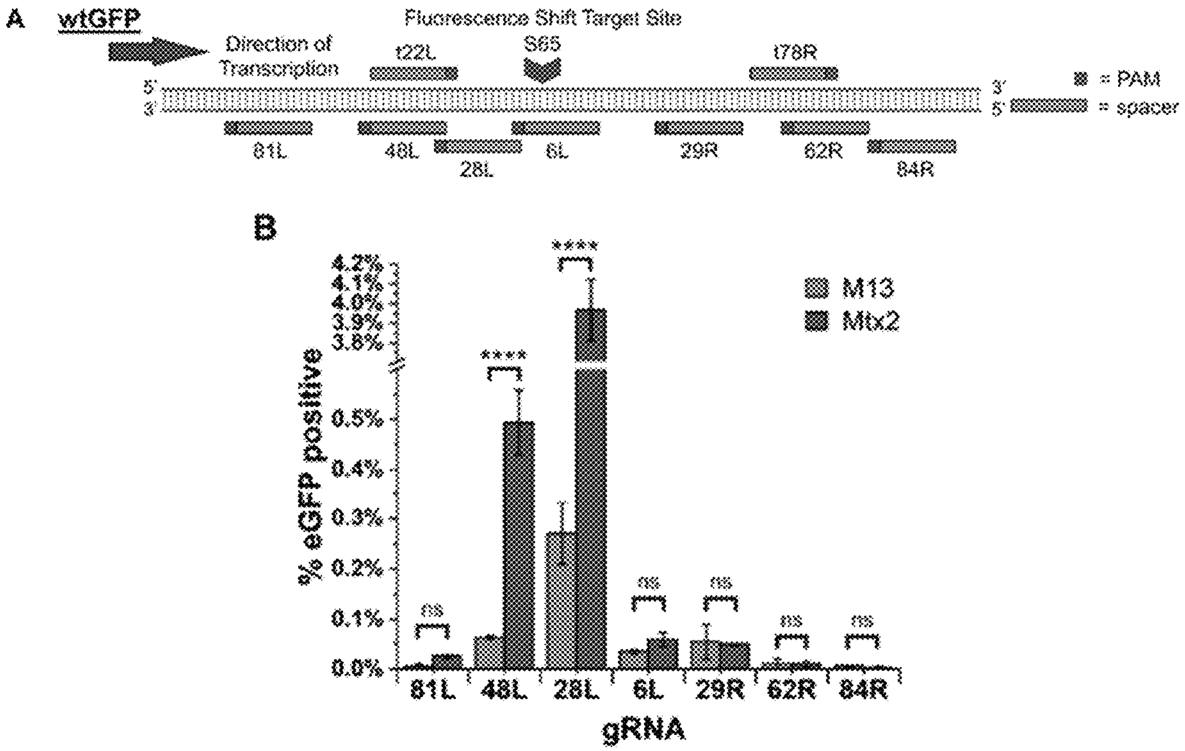

It was next sought to understand the mutagenic window afforded by the M13 and Mtx2 loop configurations, as a larger nucleotide range in which mutations occur is beneficial for a DBE. Previous work in mammalian cells showed that, while mutations could be detected −50 to +50 bp relative to the CRISPR PAM and the direction of transcription, the highest rate of mutation was seen from +20 to +40 bp, independent of the DNA strand being targeted. The mutational window was approximated to allow the M13 and Mtx2 loop configurations by using seven distinct gRNAs targeted (i.e., were complementary to) across the breadth of the coding strand of wtGFP (FIG. 5A). The 3' end of the PAMs of the gRNA spacer sequences ranged from −81 bp (Left, or L) to +84 bp (Right, or R) relative to the site of the desired mutation at S65T. Both the M13 and Mtx2 scaffolds, the mutation rate was highest when using the 28L gRNA (FIG. 5B), and the mutation rates were reduced substantially for the most distant gRNAs. As the Mtx2 scaffolded design significantly outperformed M13 when aimed to the left of the target site, affording by far the highest mutation rates detected, it was proceeded to further characterize the combination of the AID731Δ variant and the Mtx2 scaffold.

Figure 11:
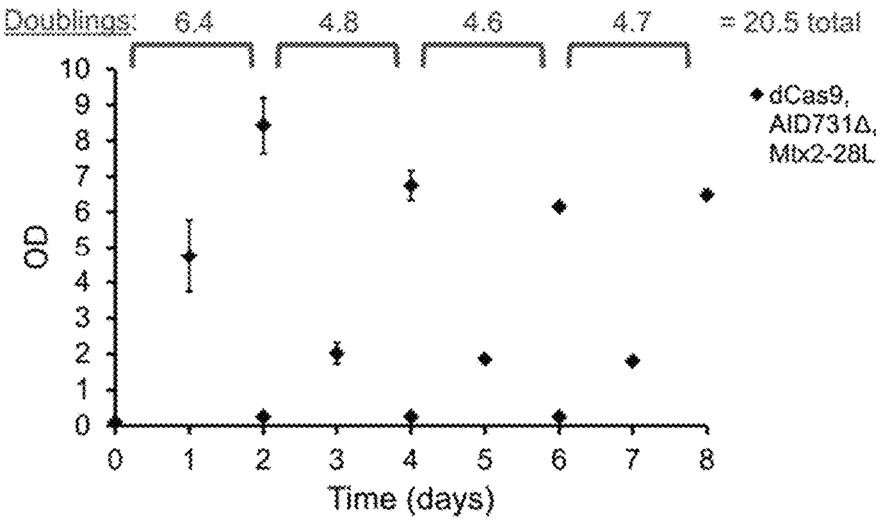
FIG. 11 shows the growth rate of yDBE yeast. Representative optical density (OD) measurements during 8-day galactose induction of strain AC003 with Mtx2-28L plasmid. At time zero, the cells began at an OD of 0.1. Every two days, they were passaged with fresh SD-Trp media and diluted to an OD of 0.2. Bars represent mean±SD, n=3.

Combining AID731Δ and Mtx2 scaffold. By combining the Mtx2 scaffold with AID731Δ, a rate of wtGFP to eGFP fluorescence shift was achieved of over 7% with gRNA 28L after 4 days of induction, representing an improvement over the original CRISPR-X (AID*Δ and M13 gRNA scaffold) construct performance in yeast of 26-fold (FIG. 5C). When using a gRNA that is less favorable to the Mtx2 scaffold, 29R, the improvement was still 1.5-fold. To precisely quantify the mutational rate afforded by the yDBE platform, as well as to begin to understand this gRNA target site preference, high-throughput amplicon sequencing of wtGFP pooled DNA mutagenized by the Mtx2 scaffold and AID731Δ variant was performed. More specifically, wtGFP with the AID731Δ-Mtx2 yDBE was targeted for eight days to allow mutations to accumulate, then extracted genomic DNA, amplified the GFP locus, and sequenced it with an Illumina MiSeq instrument. To better generalize the conclusions, five, separate GFP-targeting gRNAs were used at a variety of locations, with two targeting the template strand (t22L and t78R) and three targeting the coding strand (81L, 28L, and 29R). The gRNAs each performed at varying levels, with the use of t78R resulting in the fewest mutations and 29R resulting in the most (FIGS. 10A, 10B, 10C, 10D, and 10E). The results were combined into a single plot using the 3' end of the PAM as a reference point. Note that the data for the gRNAs that target the template strand were flipped due to the opposite directionality of the PAM. When combined, a clear mutation profile emerged with substitutions appearing throughout a window that spanned approximately ±50 bp relative to the PAM (FIG. 5D). In this window, the average rate of substitutions for the five Mtx2 gRNAs with the AID731Δ yDBE was $4.4\times10^{-3}$ substitutions/bp. As approximately 20.5 yeast doublings (generations) occurred during the 8-day yDBE induction (FIG. 11), the overall average rate of mutation is calculated to be $2.13\times10^{-4}$ s.p.b. across a 100-nucleotide window centered slightly 5' of the PAM and encompassing the gRNA targeting site. The rate of mutations at S65 for 28L and 29R correlated well with what was seen in the fluorescence shift assay (FIGS. 5C and 10). Nearly all the substitutions occurred at CG pairs (FIG. 5E), which is consistent with cytidine deaminase activity. The frequency of indels was extremely low, with the highest rates at any position reaching only 0.005% in the ±50-bp window. With the 29R gRNA, over 50% of reads had at least one mutation, and over 17% had two or more mutations (FIGS. 10A, 10B, 10C, 10D, and 10E). These results confirm that the enhanced yDBE was introducing a sufficient variety and magnitude of mutations to create screening libraries for directed evolution.

Improving antibody affinity via yDBE in situ DNA diversification and surface display. It was next aimed to demonstrate the capabilities of yDBE by using it to improve the affinity of an antibody. 4-4-20, a single-chain variable fragment (scFv) that binds fluorescein, was integrated into the genome of yDBE-expression yeast strains. Because they demonstrated differential activity in gRNA-spacer selection, both M13 and Mtx2 MS2 loop configurations, both in concert with the AID731Δ variant, were used in parallel, directed evolution trials.

Figures 6A, 6B:
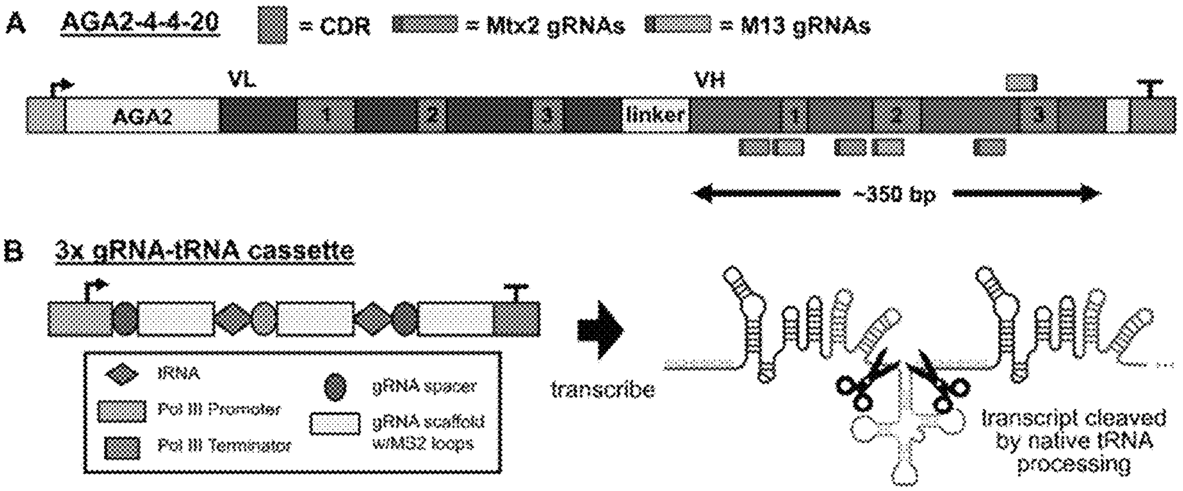
Figure 7A:
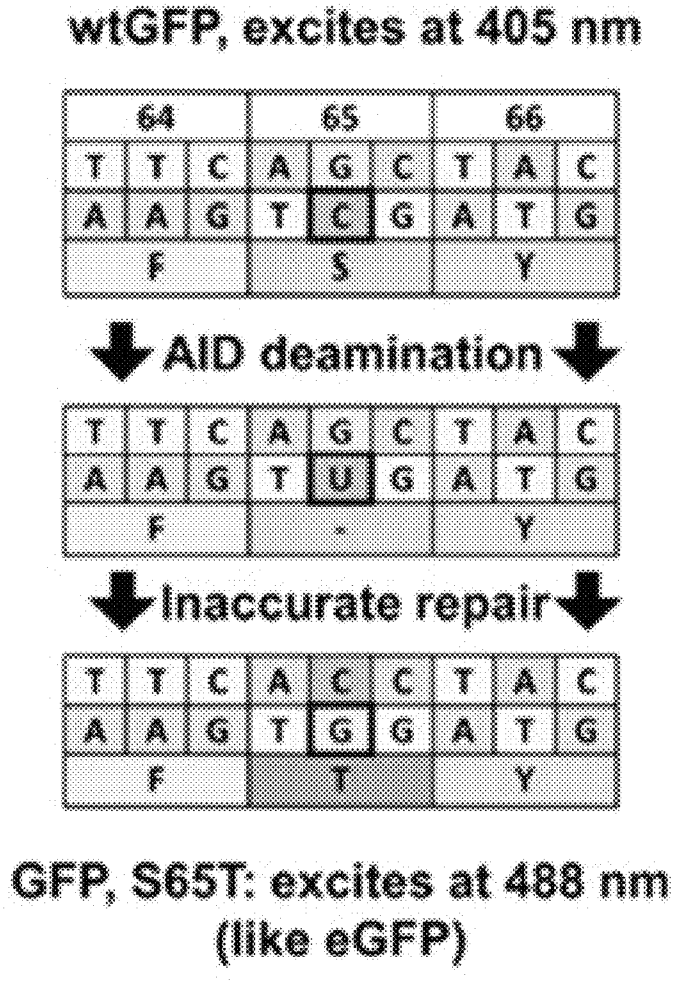
FIGS. 7A, 7B, 7C, 7D, and 7E show the description of fluorescence shift assay and representative FACS plots.
Figure 7B:
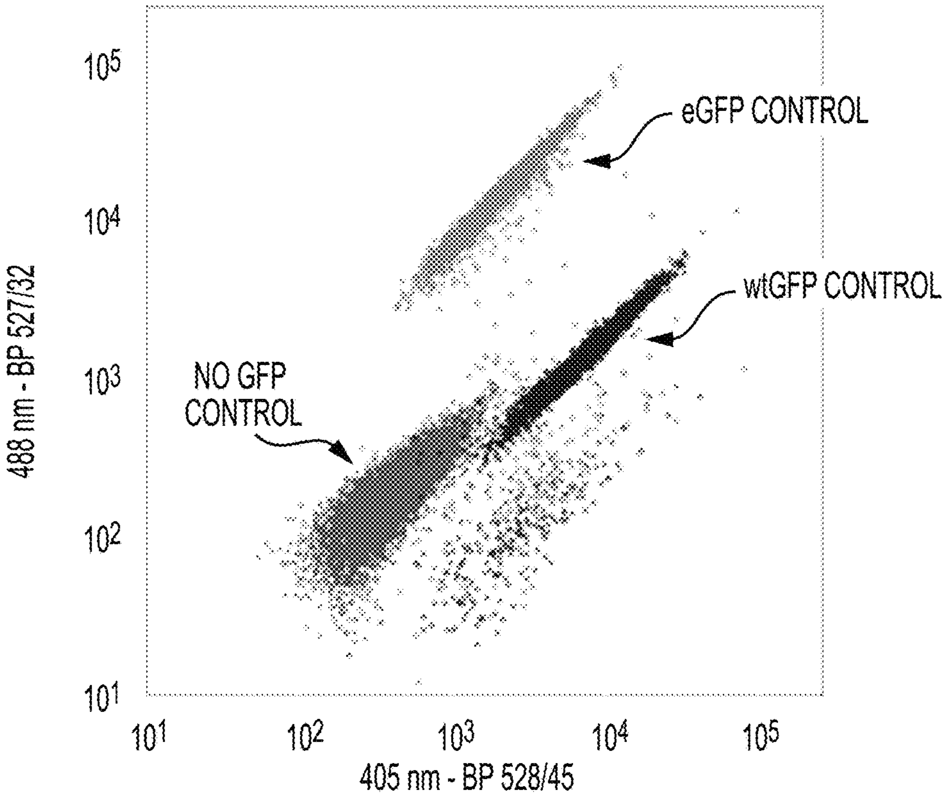
Figure 7C:
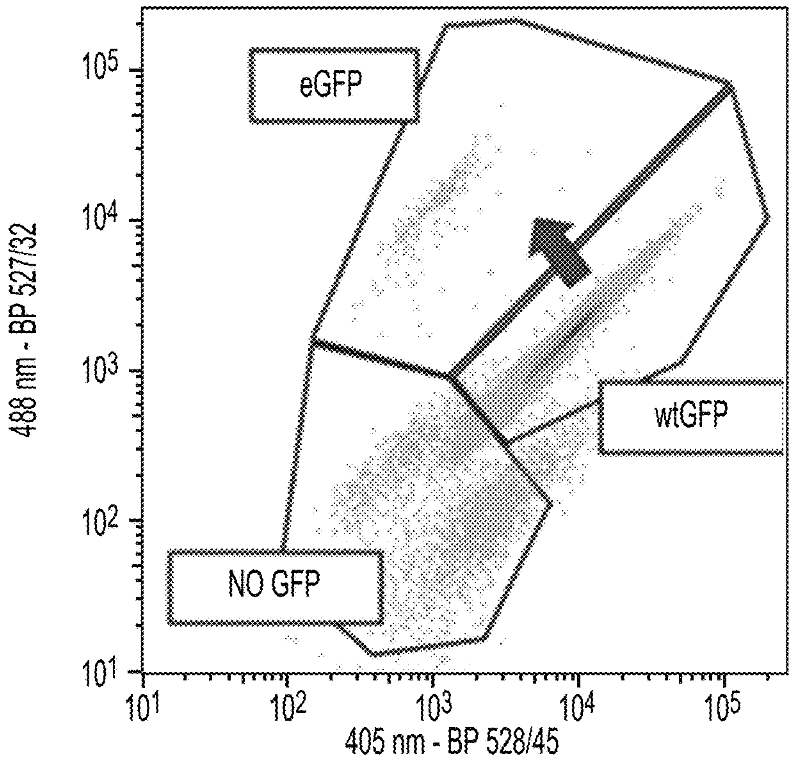
Figure 7D:
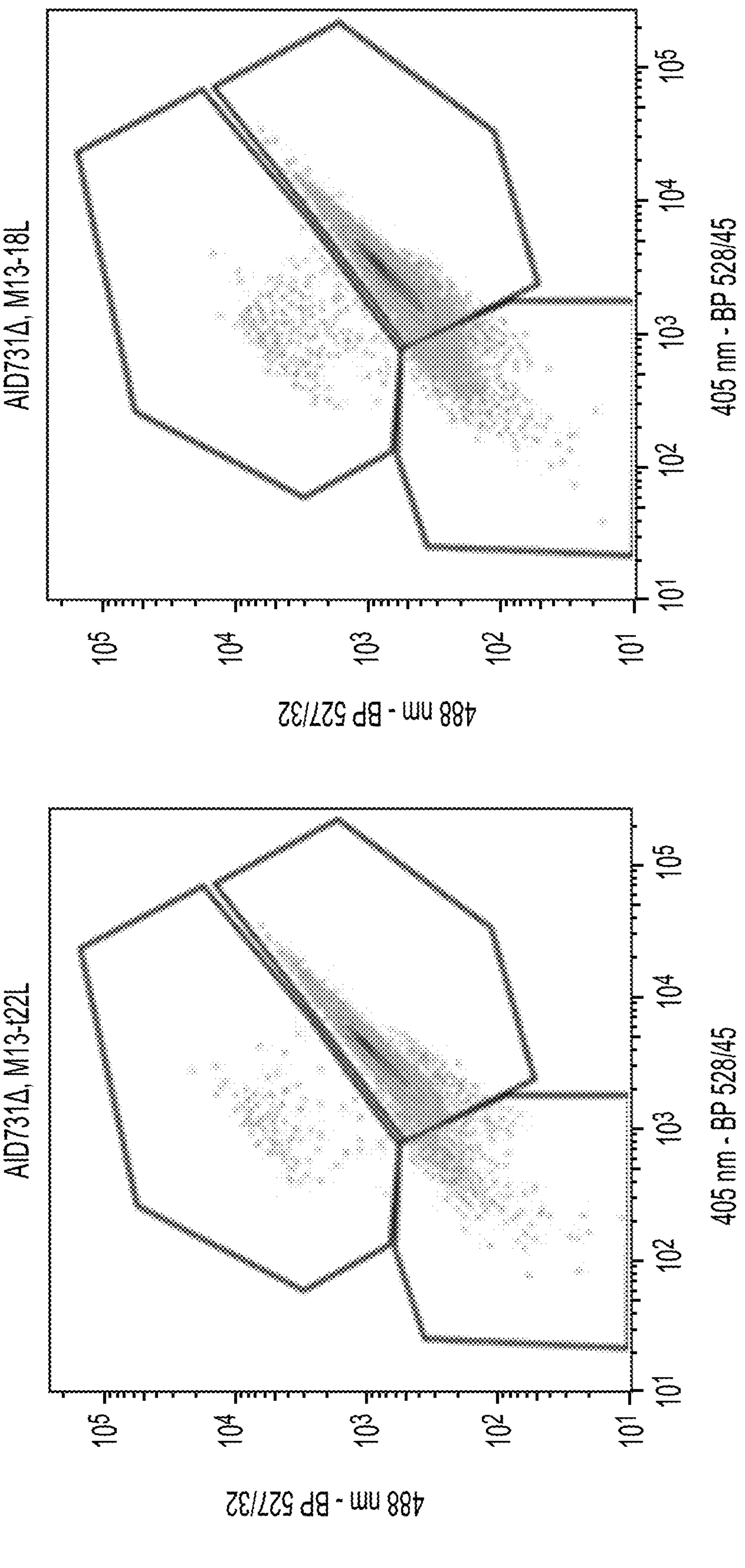
Figure 7E:
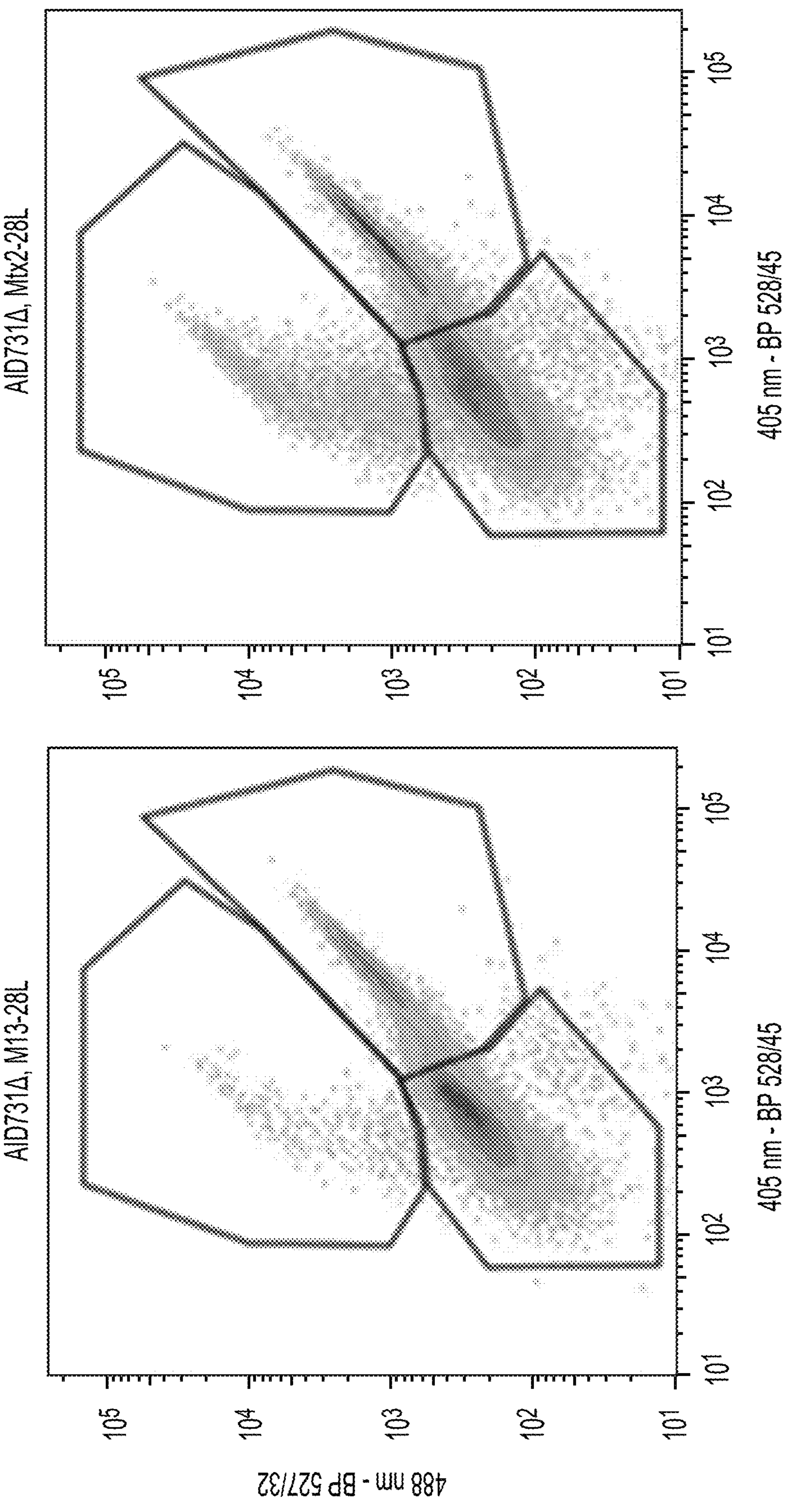

An scFv is comprised of a $V_H$ and $V_L$ segment, each approximately 345 bp in length (FIG. 6A). Therefore, it would not be possible to reach a high level of mutagenesis over the entirety of 4-4-20's DNA sequence using a single targeting gRNA with the yDBE, which can diversify across a region of ~100 nucleotides. Complementarity determining regions (CDRs) within antibody heavy chains are particularly important for affinity, making it ideal if the in situ DNA diversification rate could be maximized within the three $V_H$ CDRs of 4-4-20. To enable this function, three gRNAs were co-expressed as gRNA-tRNA arrays, allowing for multiple DNA sequence targeting. Two separate, 3× gRNA-tRNA cassettes were created to target the $V_H$ CDRs—one using M13 scaffolds and one Mtx2 (FIG. 6B). Based on the results from the fluorescence shift assays and high-throughput sequencing, the coding strand ~20 bp upstream (relative to the direction of transcription) of each CDR was targeted for the Mtx2 configuration. For the M13 configuration, the coding strand was targeted more directly on each CDR, except for CDR3 where the template strand was targeted due to a lack of a suitable PAM site on the coding strand.

Figure 12:
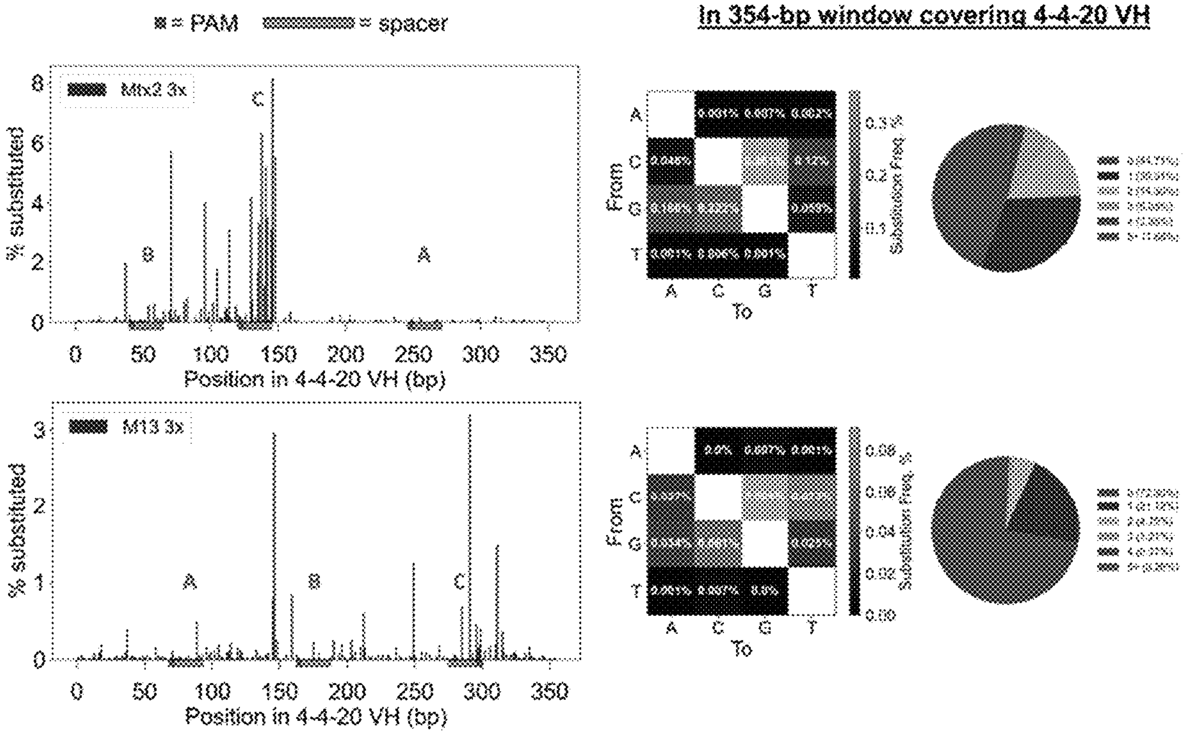
FIG. 12 shows the high-throughput amplicon sequencing results of 4-4-20 $V_H$. DNA was extracted and amplified after 8-day yDBE induction in strain AC301 with a 3× gRNA-tRNA cassette using Mtx2 (top) or M13 (bottom) scaffolds. The substitution distribution plots show the per-nucleotide rate of substitutions in a 354-bp window covering the entire $V_H$ of 4-4-20. The approximate position and orientation of each gRNA is shown along the x-axis, and the position of each gRNA within the 3× cassette (A, B, then C) is shown on the plot. The substitution heatmap shows the average rate at which each possible substitution type was detected within the 354-bp window. The pie chart shows how many substitutions were detected in the 354-bp window per sequencing read.
Figure 13:
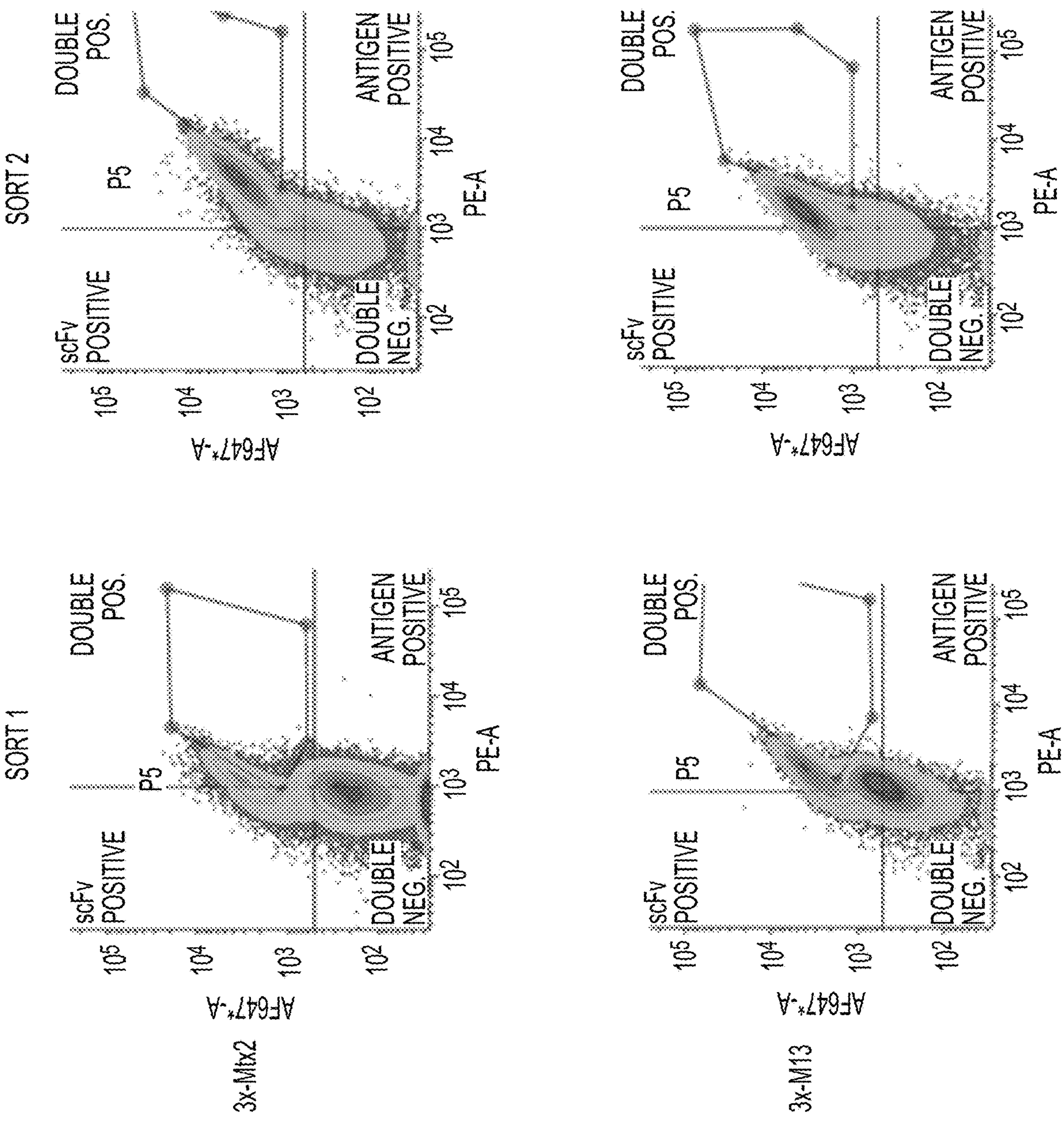
FIG. 13 shows the FACS plots of 4-4-20 mutant sorting. FACS plots showing yeast display of 4-4-20 prior to each of four sequential sorts to select for high-affinity antibodies. Anti-c-myc with AF647 measures scFv expression (y-axis) while the antigen binding is measured with streptavidin-PE (x-axis) following a competitive stain to discriminate the best binders. Prior to Sort 1, AC301 yeast were induced to base edit for 8 days with a 3× gRNA-tRNA cassette with M13 or Mtx2 scaffolds.
Figure 13:
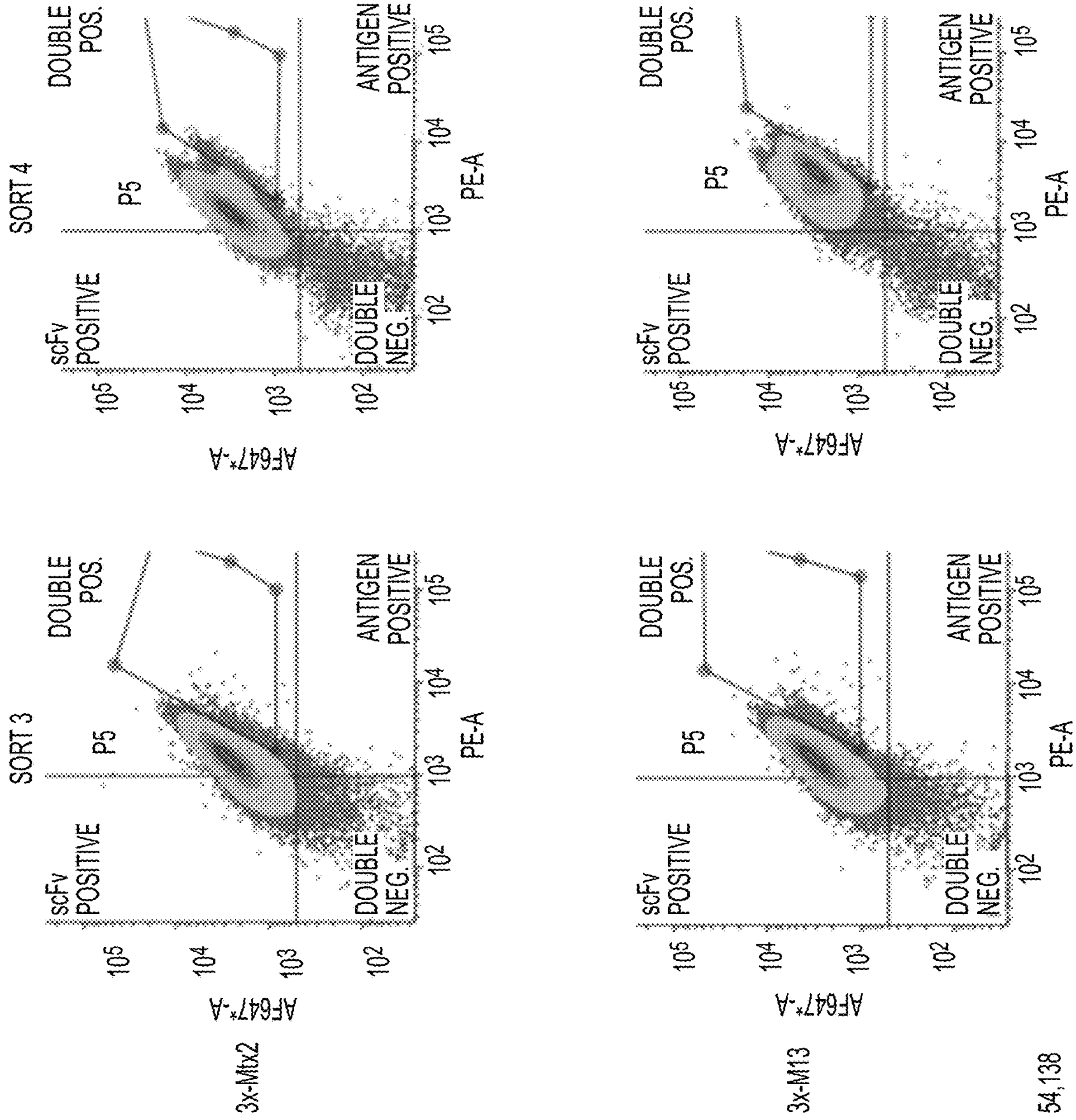

Eight days were allowed in total for yDBE-mediated in situ antibody diversification to occur, with passages every 2 days (FIG. 6C). After induction, amplicons from the yeast were submitted for high-throughput sequencing, which showed substitutions spread across the $V_H$ of 4-4-20 for both M13 and Mtx2 gRNA cassettes, though the rate per gRNA appeared lower based on the 1× gRNA targeting of GFP (FIG. 12). The rate of substitutions was overall higher for the Mtx2 cassette, but since the cassettes use different spacers, this comparison should be approached with caution. It also should be noted that 4-4-20 has a substantially lower GC content compared to the mammalian codon-optimized GFP that was used (46% vs 61%) which may explain the decrease in base editing capability. After scFv mutant library creation, cells were sorted four times using a competitive stain in which aminofluorescein is used to compete with fluorescein in the 4-4-20 scFv, leading to better antibody discrimination than equilibrium staining (FIG. 13). Following primary staining with biotinylated fluorescein and the competitive aminofluorescein stain, the cells were stained with streptavidin-PE and AlexaFluor647 anti-c-myc antibody. Therefore, antigen binding was indicated by PE signal, whereas AlexaFluor647 showed the relative expression of scFv on the cell surface, allowing assessment of the antigen binding capability of scFv-positive cells.

After the final round of sorting, cells were plated and individual colonies picked to assess their affinity through yeast display. For the yDBEs using both the M13 and Mtx2 scaffolds, it was found that several mutant scFvs had a substantial increase in affinity over wild-type 4-4-20. Sequencing of single scFvs showed mutations in each CDR of the heavy chain, near or overlapping the spacers selected (Table 1). The nucleotide substitutions all occurred at C or G residues, consistent with AID activity and high-throughput sequencing results. Interestingly, certain mutants, such as L45V, were isolated from both the M13 and Mtx2 sorts, demonstrating convergence between the two libraries despite having different gRNA spacer sequences. Three mutants were selected for further characterization: W108F isolated from the yeast using the M13 scaffold design, and L45V and V23L, A24G, L45V from the yeast harboring Mtx2 scaffolded yDBE, where residue numbering refers to the position within the $V_H$. These three variants were amplified from genomic DNA and re-cloned into EBY100 to ensure that examination of the scFv mutations in isolation. Using flow cytometry, each scFv's $K_d$ value was calculated for fluorescein by titrating a broad range of concentrations (FIG. 6D). The W108F variant had a large, 358-fold improvement over the 4-4-20 antibody (FIG. 6E and Table 4). By the screen, this is approaching the $K_d$ of the high affinity, previously described 4m5.3 mutant. Interestingly, while the L45V variant has not been described previously, mutating the W108 residue has been shown to be productive for enhancing affinity, however the W108F mutation specifically did not stand out. In addition, affinity-enhancing mutations near multiple CDRs of the 4-4-20 scFv were isolated from a single library, showing successful targeting of multiple DNA loci simultaneously using yDBE in single cells. As the L45V and V23L, A24G, L45V mutants also had improvement in affinity at 43-fold and 34-fold, respectively (FIG. 6E), the ability to rapidly improve an antibody sequence using multiple yDBE designs was demonstrated by successfully isolating a variety of enhanced 4-4-20 variants.

Conclusion:

Herein, the mutational rate of yDBE, a CRISPR diversifying base editor for in situ diversification of DNA in yeast, was designed and enhanced. Using fluorescence shift-based assays, two major components of the base editor were improved and characterized. First, the yDBE mutagenesis rate was universally improved 5-fold by surveying previously described and creating entirely new AID mutants with enhanced activity, particularly AID731Δ. Second, the mutational capability of a variety of gRNA/MS2 scaffold architectures was assessed and two, M13 and Mtx2, were identified which support high rates of mutagenesis but have unique targeting preferences. In addition, by mutating either wtGFP or the 4-4-20 scFv using distinct gRNA regions, yDBE is demonstrated to be reprogrammed to rapidly target new DNA sequences. Using high-throughput sequencing, a variety of mutations occurring on both sides of the targeted spacer region were confirmed, with the majority of mutations occurring within a 100-nucleotide window centered near the PAM. The combined Mtx2 mutation profile created through high-throughput sequencing showed a concentration of substitutions in the gRNA-binding region, especially at the 5' end of where the spacer binds. dCas9 is relatively tolerant to single or sometimes even double mismatches in these areas, and for this reason the base editor continues operating despite the mounting mutations.

The enhanced yDBE, employing the novel mutant AID731Δ in concert with the Mtx2 scaffold design, is estimated to have a mutation rate of $2.13\times10^4$ s.p.b. over a region of 100 nucleotides, which is comparable to previously described in situ mutagenesis platforms for yeast. Because of its ability to readily substitute C residues in both strands into any other nucleotide, the base editor can make a variety of mutations in many DNA sequences. There was a preference for C-to-G substitutions using yDBE which contrasts with results in CRISPR-X, carried out in mammalian cells, that showed a preference for C-to-T substitutions. This is likely due to the preference yeast have to insert a cytosine across from an abasic site during the translesion synthesis step of base excision repair. Indeed, Target-AID, a precise base editor employed in yeast, similarly found a high ratio of C-to-G substitutions in targeted poly-C regions and identified polymerase 9 as the most likely cause. Similarly, AID* (the triple mutant of wild-type AID) overexpression in yeast causes many C-to-G mutations, which required active base excision repair proteins UNG1 and REV1. In general, a higher mutation rate was observed when using gRNAs that targeted the coding strand. Targeting this strand with dCas9 alone has been shown to be mutagenic in yeast through R-loop formation in the transcribed strand, which exposes it to background deaminase activity. It has been contemplated that this R-loop formation allows more access for the MCP-AID component of yDBE, leading to higher mutation rates.

One limitation of previous yDBE is the difficulty in universally mutating single, large genes >1,000 bp in length. While other systems such as OrthoRep and TRIDENT excel in this use case,[16,14] they require placing genes adjacent to specific promoters, and these systems are unable to target multiple targets nor endogenous targets. Therefore, to further expand the targeting breadth of yDBE, the present disclosure implements a multiplexing gRNA expression cassette methodology by interspacing gRNAs with a tRNA. Interestingly, for both the M13 and Mtx2 gRNAs, the first gRNA of the cassette had the fewest substitutions near its target site, while the last gRNA had the most. This contradicts previous work with Cas9 gene knockout assays that found that the efficiency of the gRNAs generally decreased along the cassette. Targeting additional templates with new sets of spacers elucidates any effect array position has on gRNA efficiency. Another potential limitation of previous yDBE is the difficulty in targeting regions low in GC content. The high-throughput sequencing performed herein determined that only 1.3% of mutations occurred at A or T bases when applying the base editor. A way to overcome this is combining cytidine base editors with adenine base editors. Such a strategy has already been shown in CRISPR base editors in mammalian cells and plants and in a T7-RNAP-driven system (TRIDENT) in yeast.

The base editor demonstrated that by targeting exogenous genes (wtGFP and 4-4-20 scFv), it is equally suitable for targeting endogenous genes. For this reason, the yDBE platform can be extended to a wide variety of directed evolution tasks. For instance, since the yDBE system is amenable to multiplexing, it aids in the evolution of more complex phenotypes such as resistance to stress and optimization of metabolic pathways by enabling the mutation of multiple, distant loci simultaneously. Lastly, because the yDBE system uses AID, the mutagenic component driving somatic hypermutation in B cells, it is engineered to better recapitulate the mutational profile of affinity matured antibodies compared to other in vivo mutagenesis systems. For at least these reasons, the abilities of the systems disclosed herein improve antibody affinity.

Methods:

Media, culture, and base strains. NEB 10-beta *E. coli* (New England Biolabs) were used to amplify plasmid constructs for molecular cloning. *E. coli* were cultured in 5 mL of LB broth (Teknova) at 37 °C overnight with agitation. LB was supplemented with 34 μg/mL chloramphenicol (Sigma Aldrich) or 100 μg/mL ampicillin (Sigma Aldrich) antibiotic for selection.

All yeast strains developed in this work are derived from strain EBY100 ($Leu^-$, $Trp^-$; ATCC MYA-4941), which is designed for yeast display. When harboring a plasmid, yeast were cultured in 2 mL of synthetic glucose (dextrose) or galactose-Trp media (SD-Trp, or SG-Trp), comprised of 0.74 g/L complete supplemental media-TRP (CSM-TRP, Sunrise Science), 0.67 g/L yeast nitrogen base (YNB, BD), and 20 g/L of glucose (Fisher Scientific) or galactose sugar (Sigma-Aldrich). In instances using selections for the Leu2 gene, CSM-TRP was replaced with 0.47 g/L CSM-LEU (Sunrise Science). When no selection was applied, YPD media, 10 g/L yeast extract (Thermofisher), 20 g/L peptone (Thermofisher), and 20 g/L glucose, was used. As needed, YPD was supplemented with 100 μg/mL nourseothricin (Gold Biotechnology) for NAT gene selection. For yeast display of antibody fragments, SD-Trp or SG-Trp media was further buffered to pH 6.25 by adding 5.4 g/L $Na_2HPO_4$ and 8.56 $NaH_2PO_4 \cdot H_2O$. Yeast were grown at 30 °C with agitation. For both yeast and *E. coli*, solid media plates were made with the addition of 20 g/L of agar (Fisher Scientific).

General Cloning Procedures

Polymerase chain reaction (PCR) was carried out using KOD Hot Start DNA polymerase (Sigma-Aldrich). Custom DNA oligomers were synthesized by Eurofins Genomics. All oligomers/primers are listed in Supplemental Table S3. Gibson Assembly was carried out using a master mix containing Taq Ligase (Enzymatics), Phusion polymerase (New England Biolabs), and T5 Exonuclease (New England Biolabs). 100 ng of linearized backbone was combined with a 2× molar excess of PCR inserts in a 5 μL volume. 15 μL of master mix was then added, and the reaction was run on a thermocycler at 50 °C for one hour.

Golden Gate Assembly was carried out using a modification of previously described protocols. When annealing complementary oligos, compatible primers were combined at 25 μM in a 20-μ L volume and held at 97 °C for 5 min, then ramped down to 20 °C over the course of 35 minutes. In a 20-μ L reaction, 100 ng of base plasmid, 0.25 pmol annealed oligos (or a 2× molar excess of insert when assembling gRNA-tRNA cassettes or HR plasmids), 2 μL of T4 Ligase 10× Buffer, 0.4 μL of T4 Ligase (New England Biolabs), and 1 μL of BsaI-HFv2 (New England Biolabs) were combined. The following temperature profile was followed for the reaction: Step 1, 37 °C for 30 min; Step 2, 37 °C for 10 min; Step 3, 16 °C for 5 min; Step 4, repeat steps 2 and 3 for 30 cycles; Step 5, 37 °C for 30 min; Step 6, 60 °C for 5 min; Step 7, 80 °C for 5 min; Step 8, 4 °C hold. After assembly, the reaction mixture was dialyzed against ultrapure water and then transformed via electroporation into *E. coli* using standard electroporator protocols and then plated on solid media. Transformants were cultured overnight, and plasmids were extracted using a Qiaprep Spin Miniprep Kit (Qiagen). Plasmids were confirmed via both restriction enzyme digest check and Sanger sequencing.

Cloning Yeast Diversifying Base Editor (yDBE) Constructs

The amino acid sequence for MCP-AID*Δ was codon optimized for expression in yeast and synthesized by Twist Bioscience. MCP (MS2 phage coat protein) contains the N55K mutation and AID*Δ is an engineered version of human AID with the following amino acid mutations: K10E, T82I, E156G, 195*. MCP and AID*Δ are connected by a $(GGGGS)^4$ linker and SV40 nuclear localization sequence. The dCas9 construct was derived from plasmid bRA77 (Addgene plasmid #100953) and includes a yeast-codon-optimized Cas9 from *Streptococcus pyogenes* with a triple, C-terminal, SV40 nuclear localization sequence. The PCR and Gibson Assembly was used to introduce the necessary mutations (D10A, H840A) to make nuclease dead Cas9 (dCas9).

Both dCas9 and MCP-AID*Δ were first placed into base "EMY" constructs using Gibson Assembly. Promoters and terminators were then added to each sequence and cloned with Golden Gate Assembly into a backbone that is compatible with yeast homologous recombination (HR). Base EMY plasmids containing verified yeast promoters, terminators, and backbones (both HR-ready and 2p expression plasmid sets) were compatible with Golden Gate cloning. MCP-AID*Δ was placed under control of the *S. cerevisiae* GAL2 promoter, while dCas9 was placed under control of the GAL1 promoter. Both the GAL1 and GAL2 promoters are strongly induced in galactose media.

The 4-4-20 scFv fused to AGA2 was taken from plasmid pCT302 (Addgene plasmid #41845) and placed in an HR vector. 4-4-20 is expressed under control of the pGAL1 promoter. Mammalian-codon-optimized wild-type GFP (wtGFP) was created from an eGFP expression vector, pcDNA3-eGFP-LIC (Addgene plasmid #40768). Mutations L64F and T65S (reverting eGFP to wtGFP) were introduced using Gibson Assembly. Note that wtGFP still contains an H231L mutation and valine insertion at the "1a" position relative to *Aequorea victoria* GFP, but neither mutation affects the excitation/emission spectra. wtGFP was placed into a base EMY vector, and Golden Gate Assembly was used to place it in an HR vector along with a strong, constitutive promoter (pTDH3).

The sequence for AIDdead was synthesized as a linear fragment by Twist Bioscience, inserted into an EMY base vector using Gibson Assembly, and then placed into an HR vector using Golden Gate. Alternate codon optimizations of AID were synthesized by Twist Bioscience, amplified and cloned using a similar pipeline to AIDdead. Mutants AID731Δ, AIDmono, AID*mono, and AID731mono were created by amplifying fragments of AIDdead or AID*Δ with custom primers to introduce the desired mutations, then inserting the amplicons into an HR vector using Gibson Assembly. A complete list of mutations from the wildtype AID sequence can be found in Table 3. For strains including RFA3, the RFA3 coding sequence was amplified from yeast genomic DNA and then fused to the C-terminus of AID*Δ or dCas9 and placed in an EMY backbone using Gibson Assembly followed by Golden Gate Assembly to place into an HR backbone. A similar strategy was used to fuse AID731Δ to the C-terminus of dCas9 in an EMY backbone to create dCas9-AID731Δ. An alternate sequence for MCP, dubbed MCPz, was synthesized by Twist Bioscience and then fused to AID*Δ and directly cloned into an HR backbone using Gibson Assembly. All AID mutants were placed under the pGAL2 promoter to allow comparison to the original construct. dCas9-RFA3 and dCas9-AID731Δ were under the control of the pGAL1 promoter.

gRNA plasmid cloning. For single targeting gRNA plasmids, a Golden-Gate-compatible base plasmid was first constructed using Gibson Assembly. Four gRNA scaffolds were synthesized by Twist Bioscience: No MS2, M13, M4, and Mtx2. Each of these were cloned into a 2p, Trp-selection plasmid, pY120, using Gibson Assembly creating pY120g-NoMS2, pY120g-M13, pY120g-M4, and pY120g-Mtx2, respectively. Each plasmid consists of a strong, yeast, RNA polymerase III pSNR52 promoter, a blank gap region flanked by BsaI cut sites, the gRNA scaffold variant, and a tSUP4 terminator. Using these first four plasmids, all the remaining gRNA scaffold variants were made using PCR and Gibson Assembly of partial scaffold fragments (M1, M14, M3tx2, etc.; Table 6). To construct true targeting cassettes, e.g., to mutate wtGFP by targeting distinct DNA sequences within the gene as described below, the blank gap region was routinely replaced by a 20-bp spacer sequence using annealed oligos and Golden Gate Assembly. A full list of spacer sequences can be found in Table 7.

For 3× gRNA-tRNA cassettes, the assembly strategy of GTR-CRISPR was generally followed. First a base plasmid was made to attach the M13 or Mtx2 scaffold gRNA with yeast $tRNA^{GLY}$ (GCC). Gibson Assembly was used to join the tRNA to the C-terminal end of the gRNA scaffold in a pUC19 base vector, creating pUC19-M13-tRNAGly and pUC19-Mtx2-tRNAGly. At the C-terminal end of the gRNA scaffold, the tRNAs were separated by a short 'AAACAA' nucleotide linker. Custom primers were used to perform two separate PCRs that would add the desired spacer sequences along with BsaI recognition sites that would reveal customized 4-bp gates when digested. Golden gates were checked for compatibility using a custom python script and a dataset that measured gate fidelity in the presence of T4 Ligase. The two PCRs were combined with their matching pY120g-M13 or pY120g-Mtx2 base plasmids in a Golden Gate Assembly to produce a 3× gRNA-tRNA cassette.

Yeast strain engineering. The Ura3 selection marker, along with the adjacent pGAL1-AGA1 construct, were removed by plating on 5-FOA to create strain EBY101 (Table 2), which was sequence confirmed following gDNA extraction and then used as a base for all fluorescence shift assay and high-throughput sequencing tests. Linear fragments to be used for integration were amplified using PCR. For simultaneous integrations, each linear fragment had 50-60 base pairs of homology to the adjacent fragments (e.g., HR1 has homology to HR2 and HR2 has homology to HR3, etc.). Linear fragments were integrated using the high-efficiency, lithium acetate transformation method, and integration loci were selected based off prior work showing sites that yield robust gene expression. For an initial strain construction step and demonstration of yDBE activity via mutation of wtGFP (shift assay described below), the wtGFP was inserted at YORWΔ22 along with the NAT (nourseothricin resistance) gene (EBY101-wtGFP). The base editor gene expression constructs (e.g., MCP-AID*Δ and dCas9) along with a Leu marker gene were integrated simultaneously at YPRCτ3 (AC001). AIDdead was integrated in a similar manner (AC0002). These integrations, along with all those described below, were confirmed by PCR of extracted genomic DNA. Finally, gRNA plasmids were transformed into desired strains using the same lithium acetate transformation protocol used for integrations.

To test MCP-AID mutants, three preliminary strains were created that had an integrated wtGFP at YORWΔ22 and an integrated dCas9 and gRNA expression cassette (either 18L, t22L, or NT1 gRNA targeting sequences) at YPRCτ3 (strains AC201-203). Then, for each MCP-AID variant, linear expression constructs were amplified and integrated at the YPRCΔ15 locus with TRP selection in strains AC201-203. For brevity, the resultant strains are excluded from Table 2. For further analysis, MCP-AID731Δ and dCas9 were later integrated at YPRCτ3 (AC003), which facilitated comparisons to AC001 with a larger set of gRNAs expressed on plasmids. dCas9-RFA3 with AID731Δ or dCas9-AID731Δ were integrated at YPRCτ3 (AC004 and AC005, respectively), followed by gRNA plasmid transformation, for comparison with AC003.

For creation of strains for yeast display studies and mutation of an scFv, an AGA2-4-4-20 expression construct was inserted at YORWΔ22 along with the NAT gene in EBY100. The optimized base editor (MCP-AID731Δ and dCas9) was then integrated at YPRCτ3 (AC301). Lastly, the M13 and Mtx2 3× gRNA-tRNA plasmids were transformed into this strain. To confirm the binding profile of 4-4-20 variants, 4-4-20 mutant strains were created by first making an integration-compatible vector using Gibson Assembly, then amplifying a linear AGA2-4-4-20 (mutant) fragment using PCR and integrating the construct into otherwise unmodified strain EBY100.

wtGFP-eGFP fluorescence shift assay. For the wtGFP-eGFP fluorescence shift assay, yeast were picked from a plate into 2 mL SD-Trp at 30 °C with shaking. After overnight growth, the cells were induced by diluting the cells down to an OD of 0.25 in 2 mL SG-Trp media. Cells were then cultured for the specified time (1-8 days). For inductions longer than 2 days, cultures were passaged in fresh SG-Trp media every 2 days, with initial OD set at 0.25. After induction of yDBEs in galactose, $1\times10^7$ cells were rinsed with phosphate buffered saline (PBS) and analyzed using a FACSMelody flow cytometer (BD). Flow cytometry data analysis was performed using FlowJo.

High-throughput sequencing of mutated genomic yeast DNA. To induce mutations prior to high throughput sequencing, AC003 yeast with pY120g-Mtx2-28L were cultured for 8 days in SG-Trp media. The cells were diluted every 2 days in fresh media down to an OD of 0.25. Genomic DNA was collected using the Yeastar Genomic DNA Kit (Zymo Research). The wtGFP locus was amplified by PCR with primers that added sequencing adapters, and DNA concentrations were measured using the Qubit fluorimetry system. DNA was sent to Genewiz for EZ-Amplicon sequencing (PE250 MiSeq, Illumina), generating 100,000+ reads per run. The paired reads were first merged together using BBMerge and then aligned to the reference using bwa mem. Then, variant calls were compiled together using samtools mpileup. To remove background signal from the analysis, DNA from EBY101-wtGFP with plasmid pY120 (which lacks all base editor components) was also sequenced. The cells were similarly cultured for 8 days, and the amplified DNA was prepared similar to the base editor strains. Before the final substitution frequency analysis, the background signal from EBY101-wtGFP was subtracted from the signal collected from the base editor strain, and negative values were set to zero. DNA from the $V_H$ of 4-4-20 was prepared and sequenced similarly to GFP DNA.

A custom Python script was used to calculate and visualize the average substitution and insertion/deletion rate over a user-specified window. First, the substitution rate was calculated on a per-nucleotide basis using the file generated by mpileup. The rate is the number of reads with a mismatch from the reference nucleotide divided by the number of total reads that aligned to that nucleotide, excluding insertions or deletions. These per-nucleotide rates could then be averaged across a window to give an overall substitution rate. Additional custom Python scripts were used to plot the frequency of mutations at each base (distribution plots) and map the frequency of each type of substitution (heatmaps). The number of substitutions per read was calculated and visualized using a custom Python script that processed the MD:Z tag from the bam file produced during the bwa mem alignment step. All Python scripts are available upon request.

Yeast display and sorting. To induce mutations prior to staining and sorting, yeast were cultured for 8 days in SG-Trp. The cells were diluted every 2 days in fresh media down to an OD of 0.25. Cells were induced to display by first growing in buffered SD-Trp media overnight then diluting the cells to OD 0.5 in buffered SG-Trp and culturing for 24 hours.

Due to the relatively high starting affinity of 4-4-20 for fluorescein, the scFvs were screened using a competitive assay.[6] $2\times10^7$ cells were first rinsed with PBSF (PBS with 0.1% BSA) and stained with 1 μM biotinylated fluorescein (Biotium) for 60 minutes in a volume of 200 μL. Cells were rinsed again with PBSF then stained with aminofluorescein (Thermo Scientific), a non-fluorescent competitor. Cells were then placed on ice and then rinsed with ice-cold PBSF and scFv expression was stained for using an anti-c-myc antibody conjugated to AF647 (Cell Signaling Technologies) at 8 μg/mL. The presence of remaining scFv-bound biotinylated fluorescein was visualized using streptavidin-PE (Invitrogen) at 10 μg/mL. The secondary stain was performed on ice in the dark for 30 minutes. The cells were then rinsed and sorted using a FACSMelody instrument. The sorted cells were collected in SD-Trp media and allowed to recover for 1-2 days. This process was repeated four times, each time using a more stringent gate during FACS. After the fourth sort, the cells were plated on synthetic, -TRP plates and allowed to grow for 2 days.

Single yeast colonies were picked and compared against strain EBY100-4420. Clones which had a substantial increase in antigen binding in a competitive stain relative to EBY100-4420 were selected for further characterization. From these mutants, the 4-4-20 scFv gene was extracted using a nested colony PCR and Sanger sequenced. To verify that affinity improvements were definitively and solely from mutations in the 4-4-20 sequence, the mutant sequences were copied using PCR, cloned into an HR backbone, and integrated into an unmodified strain background as described above.

Titration of antibody affinity. An antigen titration was used to measure the affinity of 4-4-20 and its variants. Cells were first cultured and induced to display scFv as described above. $1\times10^5$ cells were rinsed then stained in 500 μL PBSF with antigen concentrations ranging from 0.3 pM to 30 nM of biotinylated fluorescein for 3 hours at room temperature. For antigen concentrations 0.1 nM and 0.03 nM, $1\times10^4$ displaying cells were mixed with $1\times10^5$ of non-displaying cells to both ensure that antigen quantities were never limiting and there were still sufficient cells to form a pellet. For the lowest two concentrations, 3 pM and 0.01 nM, $1\times10^5$ cells were used but the volume was increased to 40 mL and 14 mL respectively to prevent limiting antigen quantities. After primary staining, cells were placed on ice, rinsed with ice-cold PBSF, and then stained with secondary reagents (streptavidin-PE and anti-c-myc-AF647) in 30 μL for 30 minutes on ice. Cells were then rinsed and analyzed on a FACSMelody flow cytometer. Data was normalized and best-fit lines were calculated using a nonlinear regression in Graphpad Prism.

Statistics. All the fluorescence shift assays and the antigen titration were performed in biological triplicate (n=3). All reported error bars represent one standard deviation, except where otherwise noted. To calculate p-values, a multiple comparison test using Tukey's range method was done using Graphpad Prism. For comparisons of the dissociation constants generated by the best-fit curves of the antigen titrations, an extra-sum-of-squares F test was done in Graphpad Prism.

Example 2: Enhanced Diversifying Base Editors for Directed Evolution in *Saccharomyces cerevisiae*

The yeast *Saccharomyces cerevisiae* is commonly used to screen protein variants to interrogate and improve their structure and performance. While there are many techniques to carry out directed evolution in yeast, there is still a need to improve their speed and ease of use. Herein, an optimized and integrated CRISPR diversifying base editor for use in yeast and demonstrate its ability to rapidly improve the affinity of an antibody through yeast display. The base editor mutation rate up was enhanced to 27-fold by characterizing an improved deaminase variant and by optimizing the structure of the CRISPR guide RNAs. The optimized diversifying base editor was applied to generate a library of anti-fluorescein scFv variants and a higher affinity mutate was isolated via FACS sorting. The diversifying base editor is a powerful tool for facilitating not only antibody affinity maturation, but any directed evolution experiments, and are able to attain a rate of in situ mutations of $1\times10^4$ mutations/ bp/generation, roughly 10-fold higher than the previously reported highest rate of in situ mutations. In general, the names *S. cerevisiae* and yeast are used interchangeably.

Libraries have long been created through traditional mutagenesis techniques such as site-saturation mutagenesis and error-prone PCR. While these methods can introduce sufficient diversity, they require laborious cloning techniques and cannot be rapidly iterated. A faster strategy is engineering yeast that can create the desired diversity in situ. To this end, a number of methods have been developed to generate genetic diversity within a cell. However, they generally result in low mutation rates, untargeted mutations, an inability to quickly re-target the mutagenesis system, and/or require upstream efforts of molecular cloning with non-traditional vector systems. For example, OrthoRep, which is a method for error-prone PCR integrated within a yeast cell, took up to 13 passages, or up to 90 generations, to evolve a desired resistance phenotype. This represents a substantial time investment to introduce diversity. The present disclosure describes development of a technique that exceeds the reported Orthorep mutation rate of $1\times10^{-5}$ mutations/bp/generation by 10-fold.

Figure 2A:
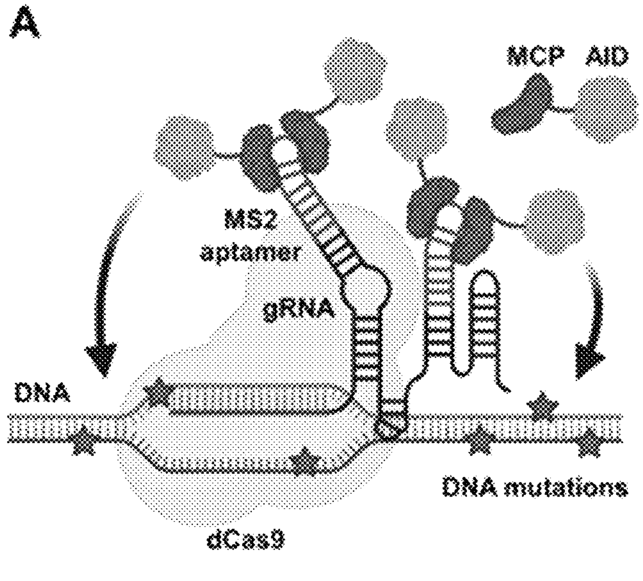
FIGS. 2A, 2B, and 2C show the development of an initial CRISPR diversifying base editor for yeast (yDBE).
Figure 2B:
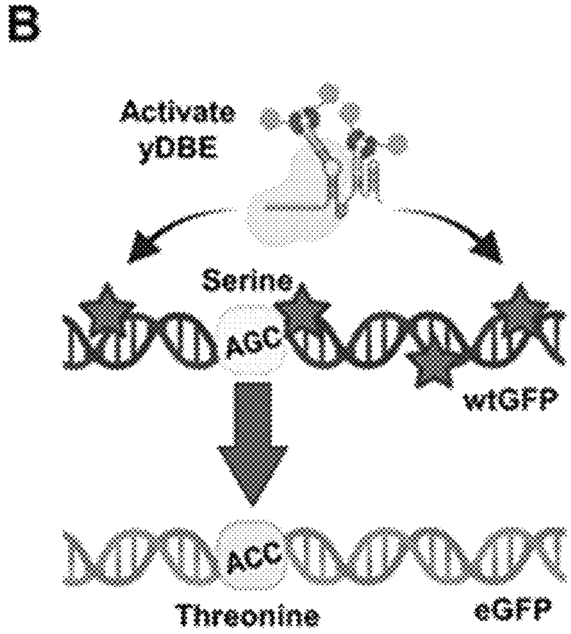
Figure 2C:
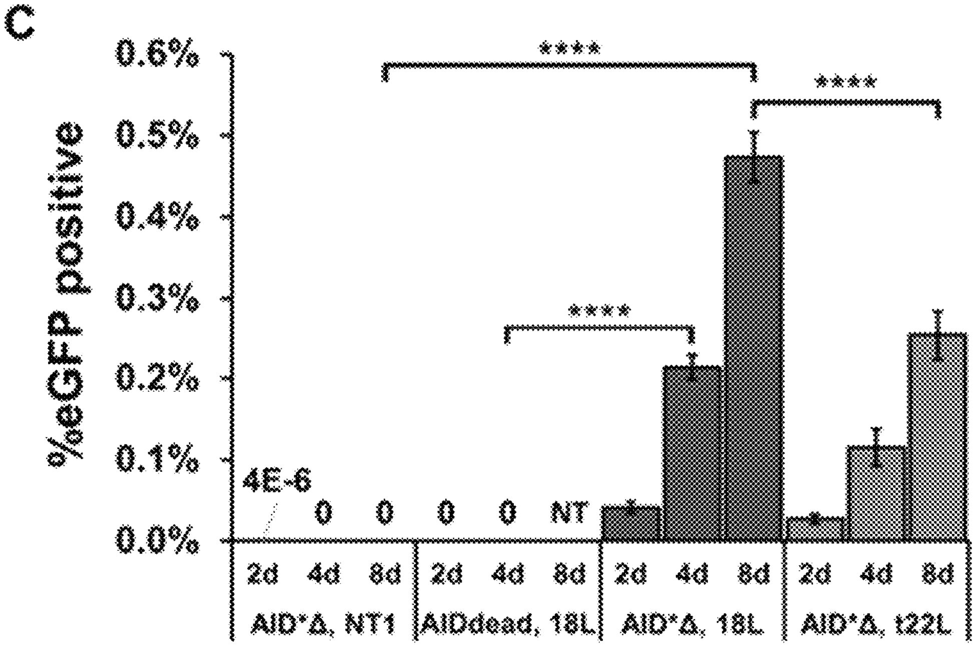

CRISPR base editors demonstrate great applications, which in general combine CRISPR DNA binding proteins such as Cas9 and Cas12 with cytidine or adenine deaminases (FIG. 2A). Catalytically inactive nucleases (e.g., dCas9) or nickases (e.g., nCas9) are directed to a specific locus within a genome that bears homology to a 20-bp spacer sequence within a CRISPR guide RNA (gRNA). The deaminase can be fused directly to the CRISPR protein or can be recruited via a secondary protein-protein or protein-RNA interaction, such as fusing the deaminase to the MS2 phage coat protein (MCP) and inserting an MS2 aptamer into the gRNA sequence, where MCP's high affinity for MS2 aptamers results in the deaminase recruitment. In general, regardless of their technique of construction, CRISPR base editors suffer from very low mutation rates, in part because prior efforts have focused on allowing only very precise mutations to occur, instead of promoting broad mutation as done with the diversifying base editor systems disclosed herein. Base editors are able to target a specific region of DNA very well and can generate mutations in situ. However, diversifying base editor systems have never, to date, been developed for use in *Saccharomyces cerevisiae*, despite this organisms prior use for other in situ mutation platforms.

The present disclosure provides a developed diversifying base editor system in yeast for use with the human activation-induced cytidine deaminase (AID), which is the enzyme responsible for somatic hypermutation of antibody DNA region in developing B-cell lymphocytes, which are the type of human immune cell that creates and produces antibodies. It stands to reason that using AID to mutagenize antibodies in yeast in the context of a diversifying CRISPR base editor leads to affinity maturation that most closely resembles that which occurs in human B cells.

Antibody therapeutics have seen tremendous growth over the past decade. This versatile drug platform has been used to treat a variety of diseases, including viral infections, autoimmune disorders, and cancer. The yeast *Saccharomyces cerevisiae* has become a popular platform for antibody interrogation. Yeast can be engineered to display antibody fragments on their cell surface, allowing for quick characterization of the antibody through flow cytometry and other techniques. Yeast also grow rapidly and to high densities, making them ideal for screening large libraries of antibody variants up to $10^{10}$ in size. Generating mutant libraries is useful for altering the characteristics of a candidate antibody therapeutic, most often to improve the affinity.

A dCas9 CRISPR diversifying base editor has been optimized for use in yeast that generates in situ mutations in a targeted but broad manner at high rates and that is further compatible with yeast display. The diversifying base editor was optimized in two critical ways using a fluorescent screen. First, by testing a variety of AID enzymes, both previously described and novel, a highly active variant was identified that improved mutation rates. Second, the location of MS2 aptamer loops was optimized within the gRNA scaffold to further maximize in situ mutation rate and increase the breadth of mutation across a small region of the genome. Third, the versatility of the platform was increased using rapidly-assembled, tRNA-gRNA cassettes. This system was applied to improve the affinity of an anti-fluorescein antibody scFV using yeast display. While CRISPR base editors have been used previously in yeast, the present disclosure demonstrates for the first time they can been applied for diversification and directed evolution, i.e., this is the first demonstration of a diversifying base editor in yeast, and it is fully compatible with high throughput screens like yeast display of antibodies. Three new methods of increasing the mutational rate and breadth are also demonstrated. These include (1) using an AID variant with high catalytic activity to increase mutation rate, (2) optimizing the placement and number of MS2 aptamer loops with the gRNA to increase both mutation rate and mutation breadth (i.e., how far away from the gRNA target site that mutations can still occur), and (3) utilizing rapidly-assembled, tRNA-gRNA cassettes to enable targeting multiple DNA regions with the diversifying base editor, again improving its breadth of mutation. Finally, this is the first demonstration of human AID being used for CRISPR base editing in yeast. The enhanced diversifying base editor is fully compatible with high throughput screens like yeast display of antibodies, and is the first demonstration of human AID being used for CRISPR base editing in yeast.

This CRISPR-based diversifying base editing platform for yeast has general utility for high throughput in situ targetable mutation generation that can be applied towards the rapid and directed evolution of desired cellular phenotypes and protein characteristics. Because a single yeast strain that has been engineered to express the dCas9 protein and MCP-AID fusion protein can be easily engineered to create mutations in a user-defined manner via expression of an easily introduced gRNA, this platform can allow for evolution of any native or heterologous DNA sequence with ease. This platform can also allow for continuous in vivo directed evolution and for retargeting the diversifying base editing system towards new DNA regions of interest by introducing new targeting gRNAs at any time. This platform can also allow for simultaneous evolution of multiple DNA regions at a time by expressing several gRNAs simultaneously, as described with the gRNA-tRNA arrays.

Characterization of an initial CRISPR diversifying base editor in yeast. A base editing strain was created for preliminary testing by integrating dCas9 in the yeast genome as well as a fusion protein consisting of the MCP (MS2-binding protein) and a variant of AID called AID*Δ. dCas9 expression was controlled by a galactose-inducible promoter: Pgal1, and MCP-AID* A expression was similarly controlled by Pgal2. The fluorescent protein, wtGFP, was also integrated into the yeast genome at a separate site and was under the control of a constitutive promoter, pTDH3. For these two genome integration sites, the genomic sites YORWΔ22 and YPRCτ3 were selected because said sites are noncoding loci with high transgene expression. A fluorescence-based assay was then used that could detect mutations to characterize the base editor's ability to generate in situ mutations. Relative to "wild-type" GFP (wtGFP), enhanced GFP (eGFP) has a mutation at S65T which causes a shift in the excitation spectra peak from 405 nm to 488 nm (FIGS. 2B and 2C. The excitation spectra shift can be easily detected using FACS. AID prefers to deaminate cytidines within a WRCY motif, especially the palindromic AGCT. S65 in wtGFP is part of an AGCT motif, making the shift assay especially sensitive to base editor activity.

By targeting this locus within wtGFP with the base editor by expression a MS2-containing gRNA with homology to DNA near this site, the base editor creates S65T mutations in situ over time in yeast, and the fraction of cells with eGFP-like fluorescence were able to be used as a correlate for base editor mutation rate. As described below, high-throughput sequencing confirmed that a higher rate of eGFP-like fluorescence correlates with a higher rate of mutation at all proximal bases, showing that this assay can also detect breadth of mutation rate for a diversifying based editor.

The initial base editor (MCP-AID*Δ and dCas9) was applied and cells with a shifted excitation were produced (FIG. 2D). Sequencing confirmed that cells within the eGFP population possessed the intended S65T mutation. The fluorescence was measured at 2, 4, and 8 days and the mutations accumulated roughly linearly over time. Previous work has shown that dCas9 alone can increase the mutation rate in a targeted locus. To verify that AID was required to induce the S65T mutation, two negative controls: an MCP-AIDdead base editor strain and a nontargeting gRNA, NT1, were tested. For both strains, the mutation rate dropped below the sensitivity of the assay, confirming that the fluorescence shift is caused only with an active AID enzyme and a properly targeted dCas9. This suite of demonstrations represents a new technology in that it is the first time that a diversifying base editor has been described in yeast and the first time that AID has been used to mutate DNA in yeast as part of CRISPR base editing system.

Enhancing CRISPR diversifying base editor mutation rate by varying AID variant. It was sought to improve the mutation rate afforded by the AID-based CRISPR diversifying base editor through two main strategies: 1) improving the activity of the deaminase and 2) optimizing the location of the ms2 aptamers within the gRNA scaffold.

To determine if utilizing alternative AID variants improved the mutation rate bestowed by the CRISPR based editor system in yeast, a few previously described mutants of AID were assessed for their activity in the present platform (when fused to MCP and coexpressed with dCas9). Some of the mutations described in prior work were combined into novel variants not previously reported, mainly AID*mono and AID731mono (Table 3). As a secondary strategy, AID variants were also made that included the yeast ssDNA binding protein RFA3, a subunit of the replication factor A (RPA) complex. Previous work has shown that fusing RFA3 to AID leads to an increase in the rate of genome-wide mutations. A fluorescence shift assay was performed on all variants. The best performing variant, AID731Δ, had a roughly 5-fold increase in activity in base editing relative to AID*Δ, as measured by increased eGFP fluorescence that corresponded to a DNA S65T mutation, without any discernible impact to growth (FIG. 3 and Table 3).

Enhancing CRISPR diversifying base editor mutation rate and breadth by optimizing ms2 aptamer placement with the gRNA scaffold (FIG. 4A). The placement of ms2 aptamers was also optimized within the gRNA framework to increase mutation rate and breadth. Previous studies have characterized a number of ms2 aptamer locations in spCas9 gRNAs. However, these studies were largely performed in mammalian cells, and never in the context of a diversifying base editor, and to the best of one's knowledge, ms2 aptamers within gRNAs have not been characterized previously in yeast. Therefore, a comprehensive set of gRNA/ms2 aptamer designs were analyzed in yeast. Two sets of gRNA scaffold variants were assessed with fluorescence shift assays (FIG. 4C). Three gRNA targeting sequences were used to assure the effect was not gRNA dependent (FIG. 4B). It was determined that having two aptamers placed on the 3' end of the gRNA (2× MS2 tail, or mtx2) had the highest average rate of mutation across the three gRNA targeting sequences.

In addition, it was ideal to expand the mutagenic window, i.e., the breadth of mutation, to allow more thorough mutation introduction across a wider range of DNA via the diversifying base editor. Previous work in mammalian cells estimated that, while mutations could be detected −50 to +50 bp relative to the tip of the targeting gRNA binding region and the direction of transcription, the highest rate of mutation was seen from +20 to +40 bp. This window was independent of the strand that was being targeted. The mutational window of the base editor was approximated using a set of seven positional gRNAs which targeted the template strand of wtGFP and spanned from −81 bp to +84 bp relative to the site of the desired mutation at S65T (FIG. 5A). The mtx2 ms2 aptamer arrangement performed best in terms of allowing a high mutation rate when targeted near the site of interest or farther away from the site of interest, although it was found that mutation rates dropped off substantially when using the most distant gRNAs (FIGS. 5B and 9).

Figure 5F:
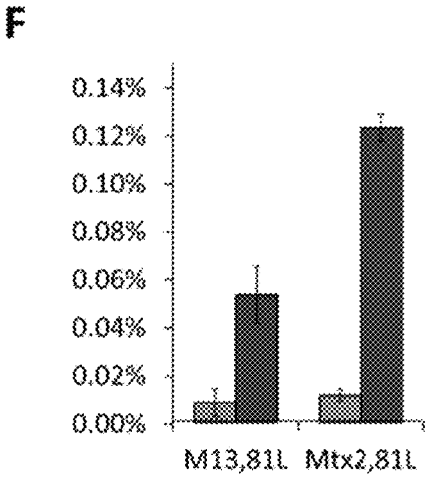

By combining the best gRNA scaffold (mtx2) with the best AID (AID731Δ) variant, a rate of wtGFP to eGFP fluorescence shift of over 7% after 4 days was achieved, representing an improvement over the original construct performance of 26-fold (FIGS. 5C and 5F).

Enhancing CRISPR diversifying base editor mutation breadth by expressing several gRNAs in a gRNA-tRNA array and the optimized diversifying base editor's application towards improving affinity of an antibody-derived protein. 4-4-20, a mouse-derived single-chain variable fragment (scFv) that binds fluorescein, was selected as the model antibody for yeast display and in vivo targeted evolution with the enhanced diversifying base editor. The scFv was integrated into the yeast genome, and the base editor integrated at a separate genomic locus. Finally, gRNAs expressed on plasmids were used to target the scFv. The optimal mtx2 scaffold and AID731Δ base editor was used.

An scFv is comprised of a $V_H$ and $V_L$ segment, each approximately 340 bp in length. Given this size, it is not possible to reach a high level of mutagenesis over this window using a single gRNA. Ideally, each complementarity determining region (CDR) of the scFv could be targeted with a separate gRNA to maximize the rate of mutation in these important regions. This requires a great mutational breadth from the CRISPR diversifying based editor. It was determined that a mechanism that employs gRNA processing using interspersed tRNAs in array is used to allow for simultaneous coexpression of several gRNAs to allow for a greater breadth of mutation rate. A golden gate assembly method, similar to that described by a tool called GTR-CRISPR, was used to create 3× and 6× gRNA-tRNA cassettes (i.e., cassettes with three different targeting gRNAs or 6 different targeting gRNAs) that target the $V_H$ CDRs or the $V_H$ and $V_L$ CDRs, respectively, of the 4-4-20 scFv (FIG. 6A).

The base editor was induced in galactose media for eight days with the 3 or 6 gRNAs (or a 1 gRNA test as a control) to generate a large library of scFv mutants. Cells were passaged every 2 days. Deep sequencing showed that mutations were localized around each CDR, with a peak in mutations roughly 20 basepairs downstream of the targeting gRNA PAM. The yeast was further sorted that were displaying the scFv for their improved binding to the scFv's target, fluorescein. The cells were stained with biotinylated fluorescein and AlexaFluor647 anti-c-myc antibody. The cells were sorted 3 times, each time recovering only the top 1-2% of scFv-positive cells based on their antigen binding.

Figure 14A:
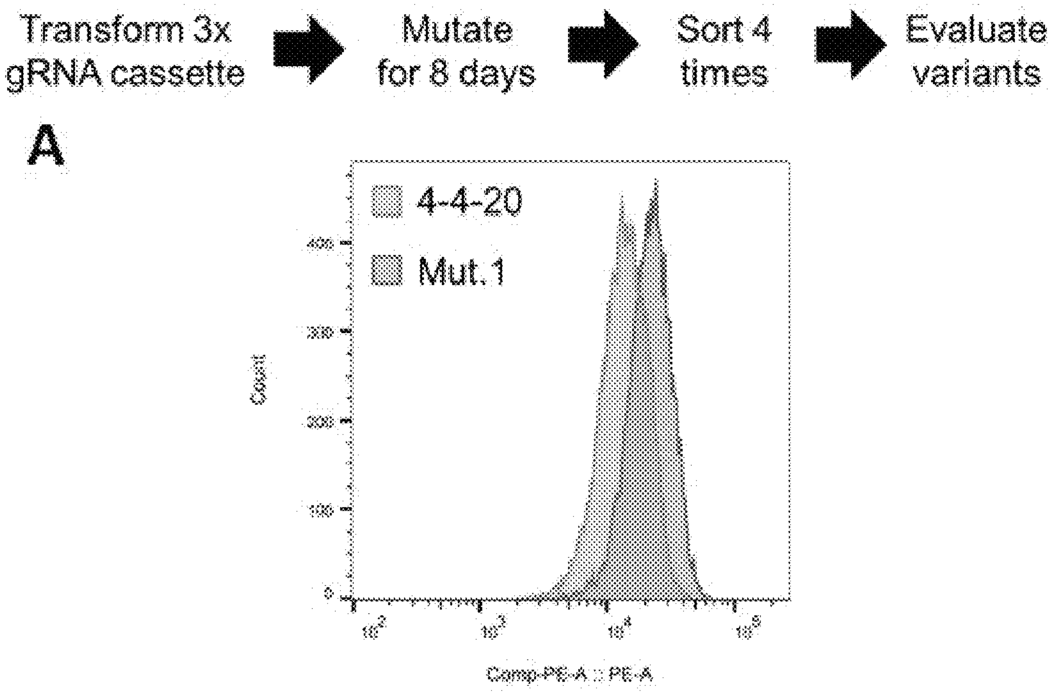
FIGS. 14A and 14B show improved scFV antigen binding when integrating dCas9, MCP-AIDv5, and 4-4-20 into the yeast genome.
Figure 14B:
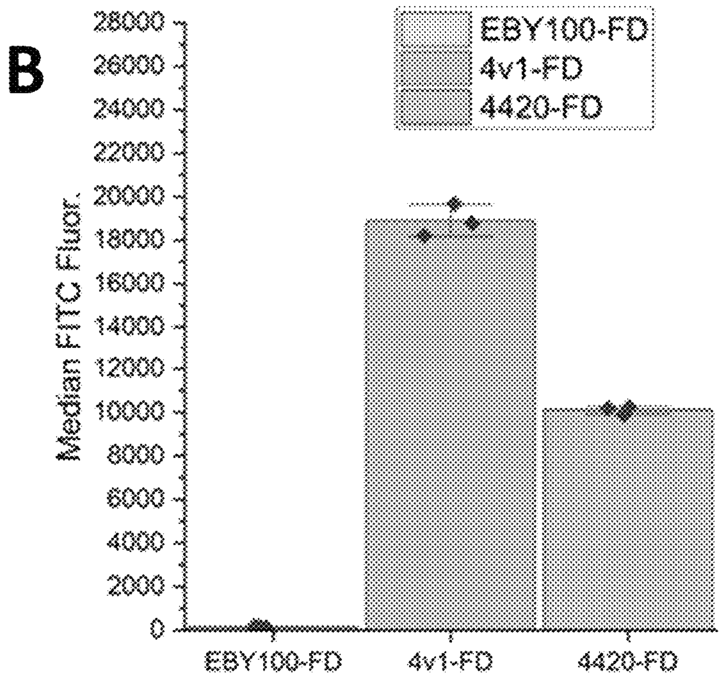
Figure 15A:
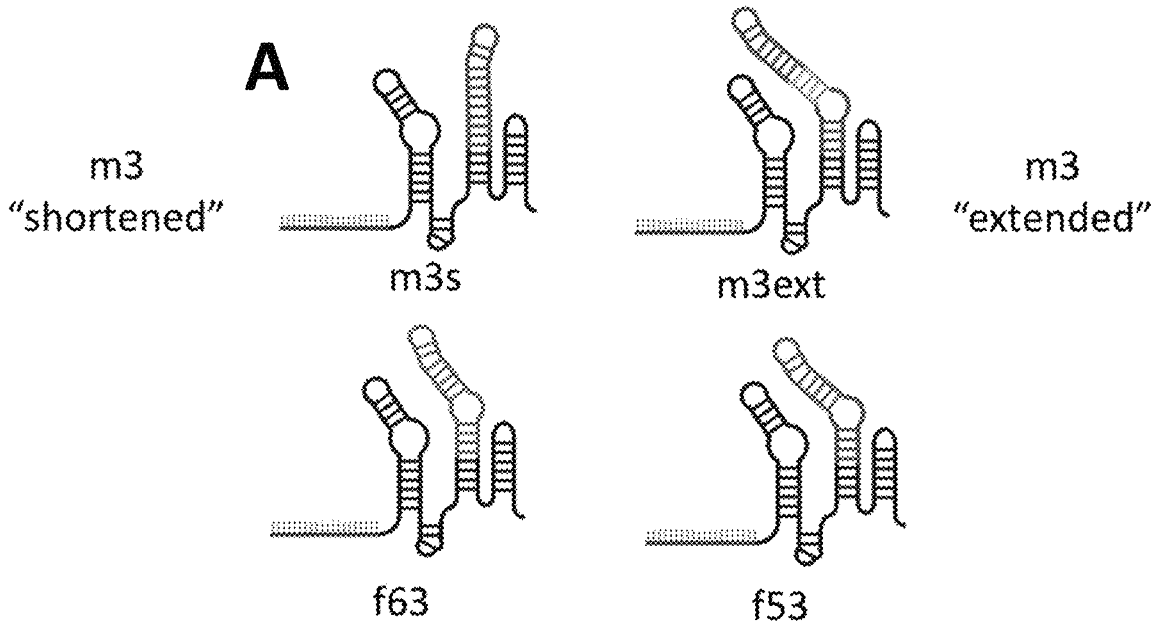
FIGS. 15A, 15B, and 15C show additional modifications made to the gRNA scaffolds.
Figures 15B, 15C:
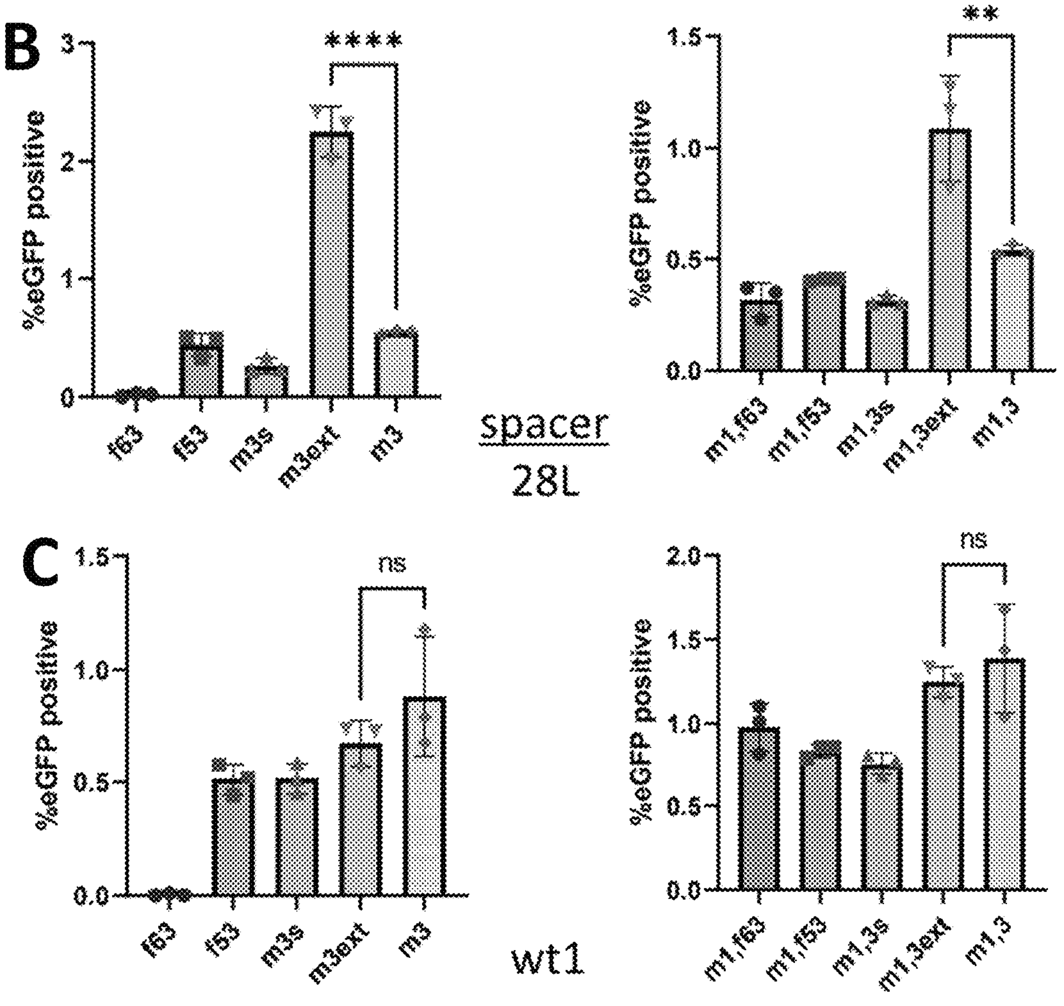
Figure 16:
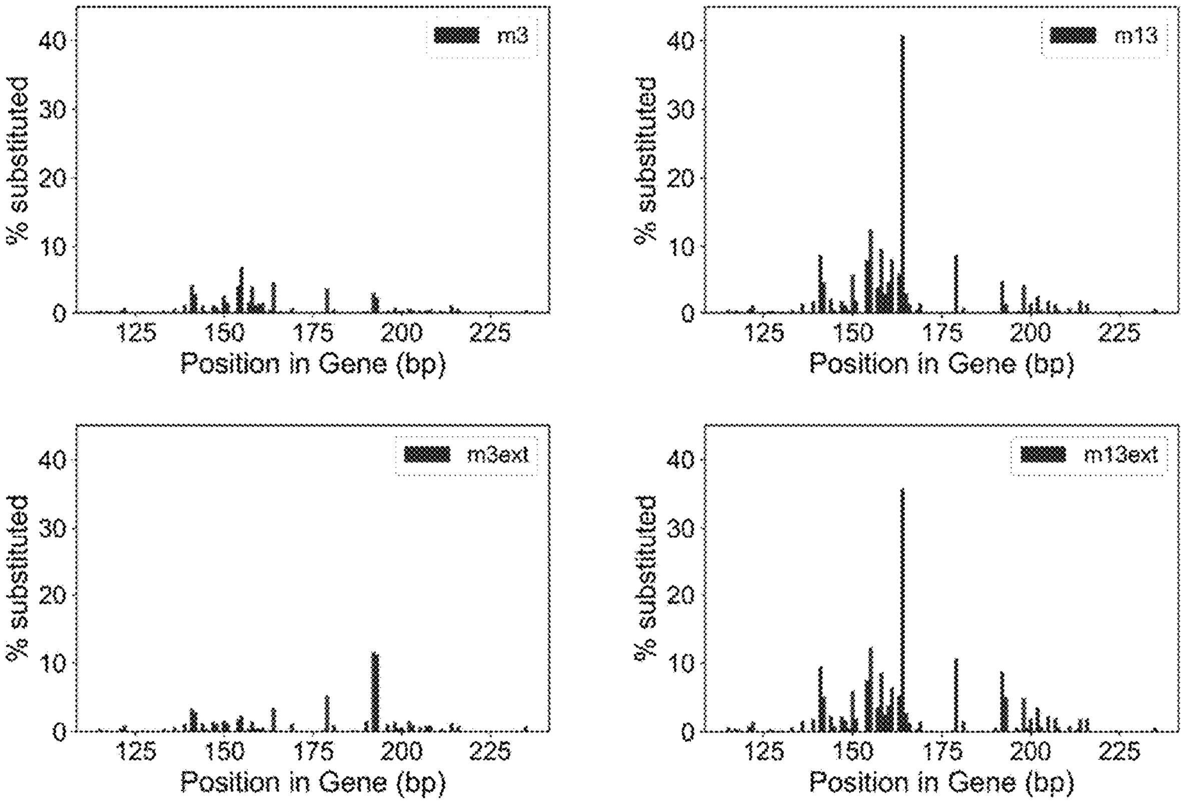
FIG. 16 shows that an extended MS2 loop sequence in the sgRNA appears to cause more mutations that the corresponding control length MS2 loop sequence when analyzed with high-throughput sequencing after an 8-day induction with 28L spacer.
Figure 17A:
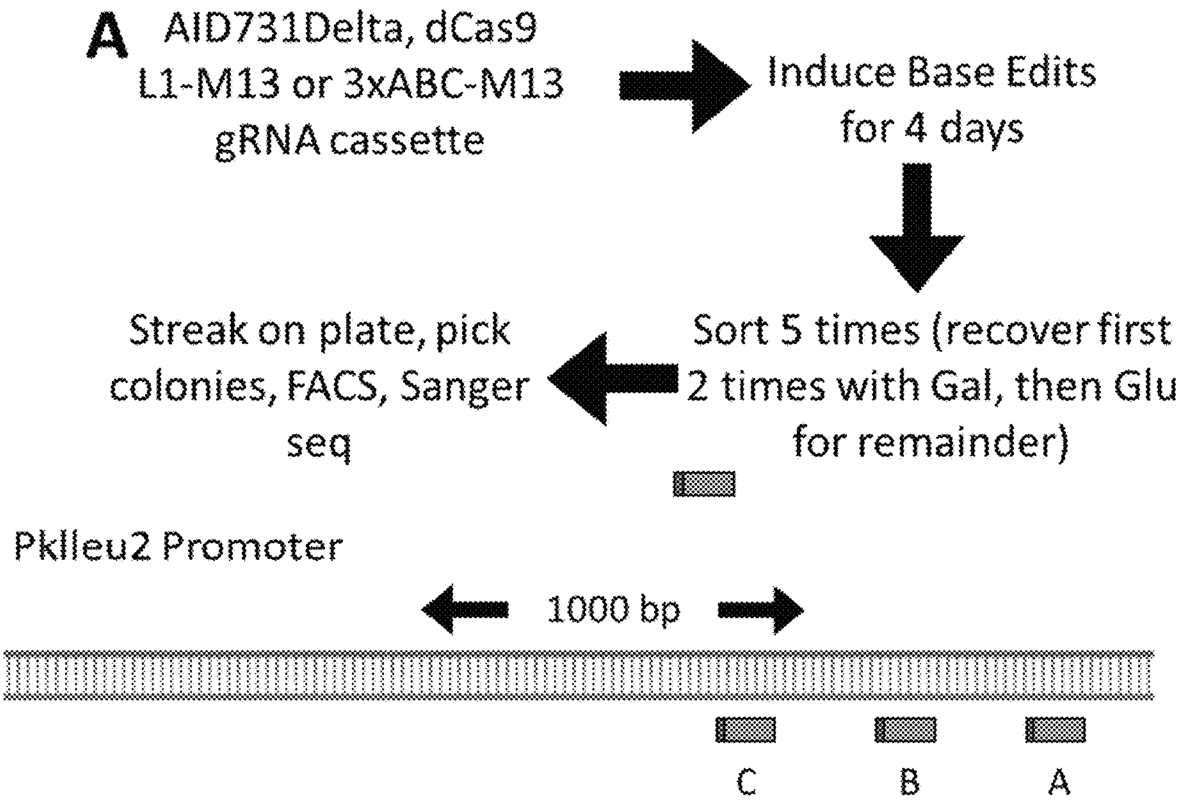
FIGS. 17A and 17B show promoter engineering using yeast diversifying base editor (yDBE) system to create Pklleu2 mutants that increase gene expression relative to the wildtype Pklleu2 promoter sequence, including L1-3, 3x-6, 3x-7, and 3x-8.
Figure 17B:
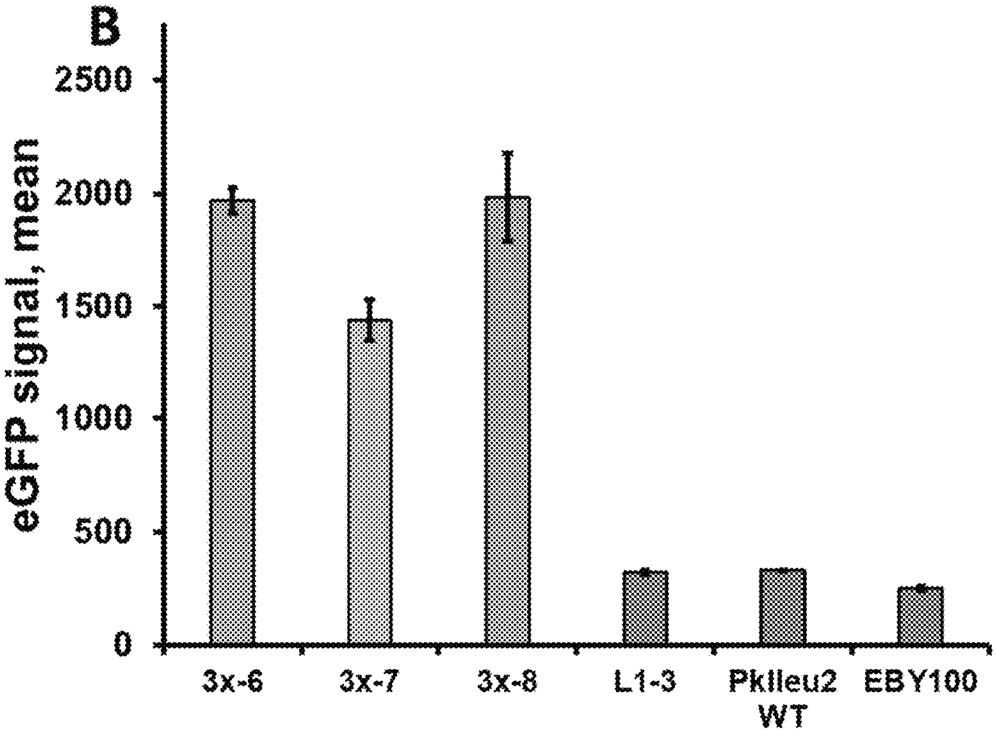
Figures 18A, 18B:
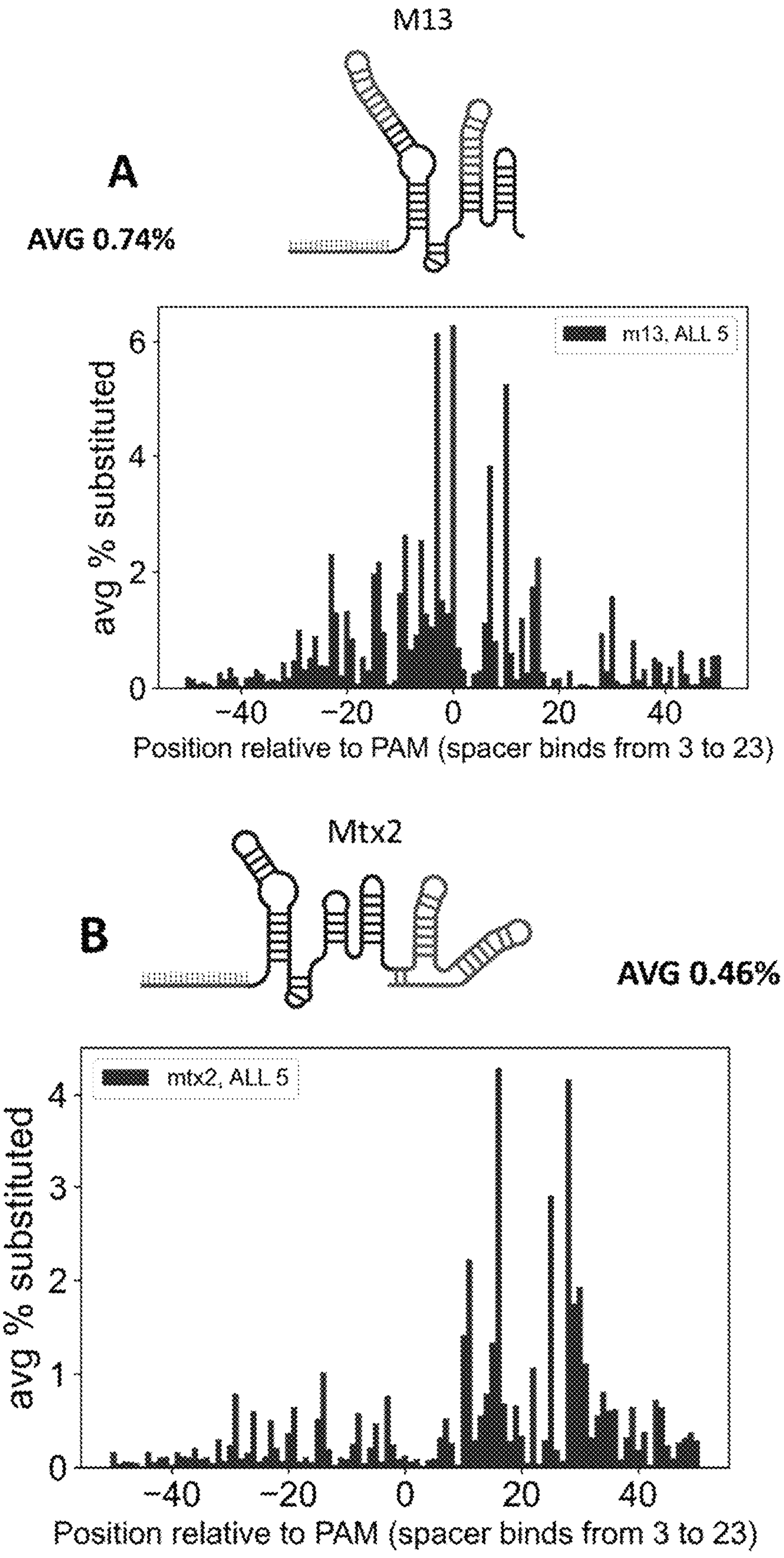
FIGS. 18A and 18B show that the M13 gRNA is superior to Mtx2, on average, in terms of mutation rate bestowed, as gauged by high-throughput amplicon sequencing, though the distributions of mutations are unique.
Figure 19A:
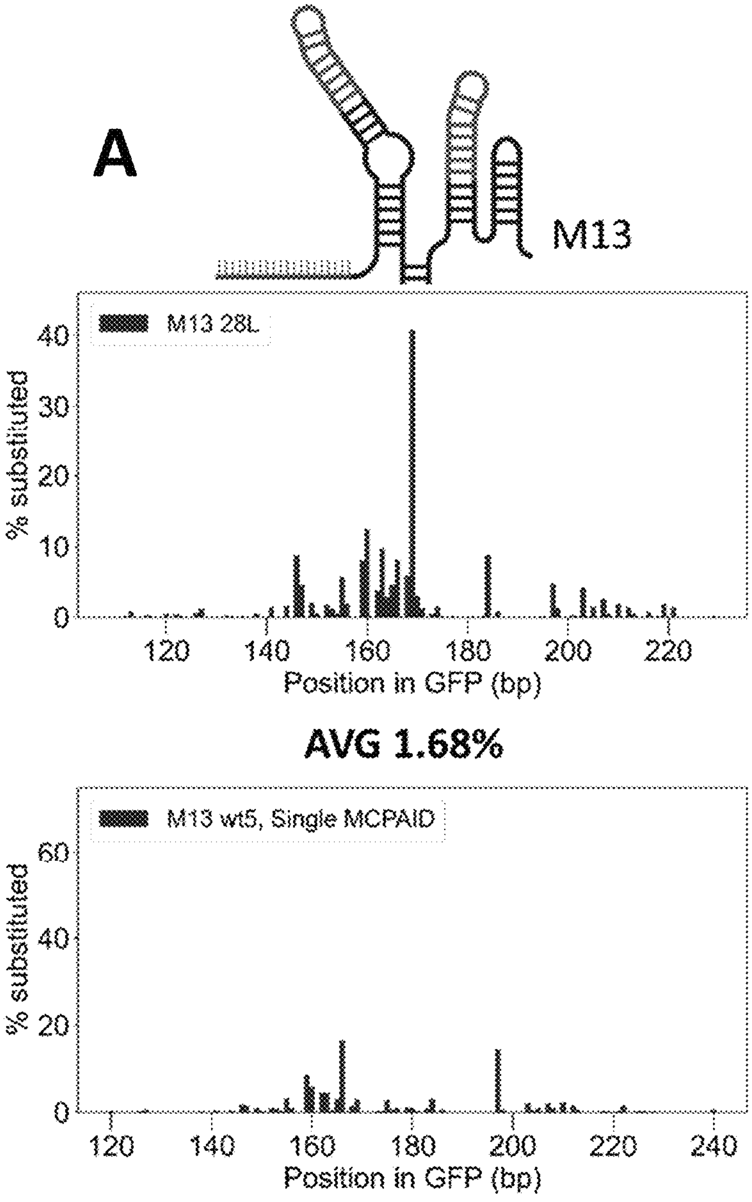
FIGS. 19A and 19B show that the M13tx2 gRNA is superior to M13 in terms of mutation rate bestowed, as gauged by high-throughput amplicon sequencing.
Figure 19B:
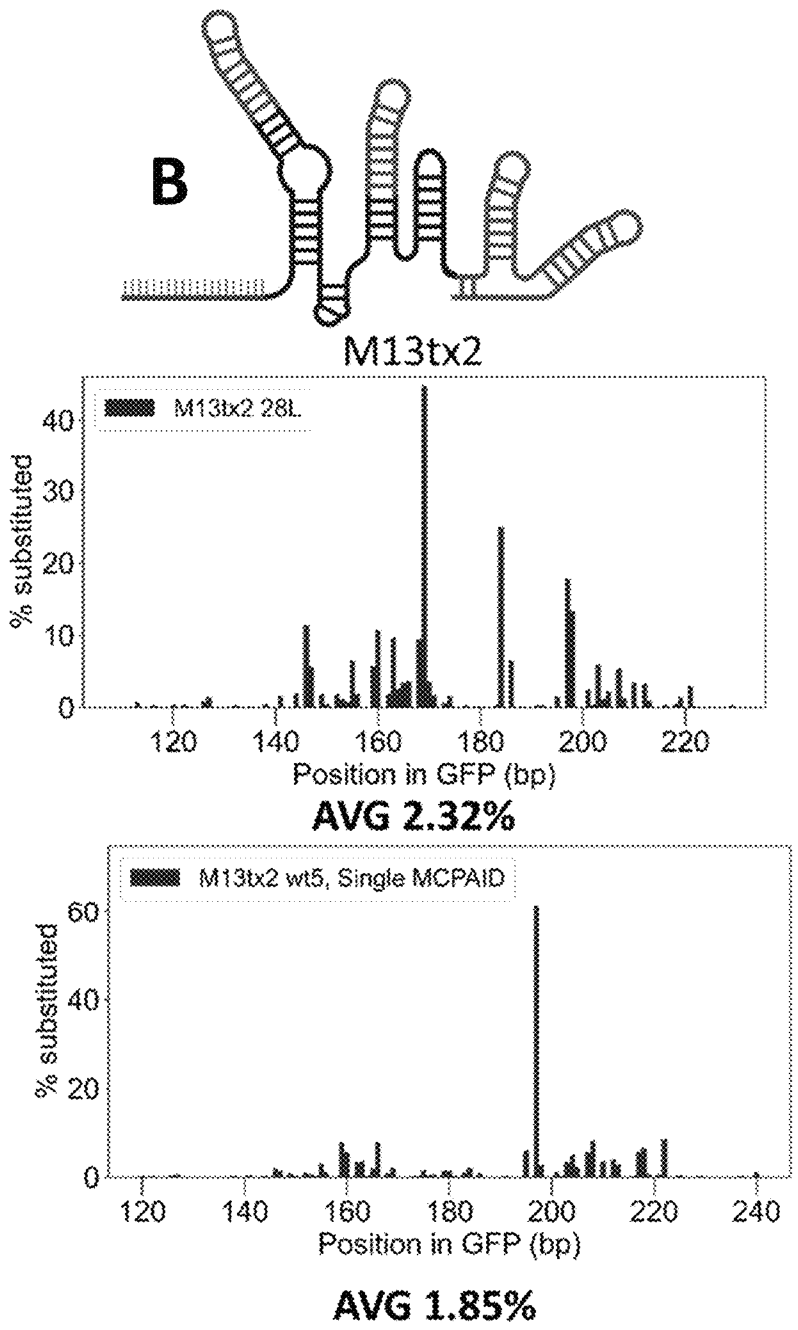
Figure 20A:
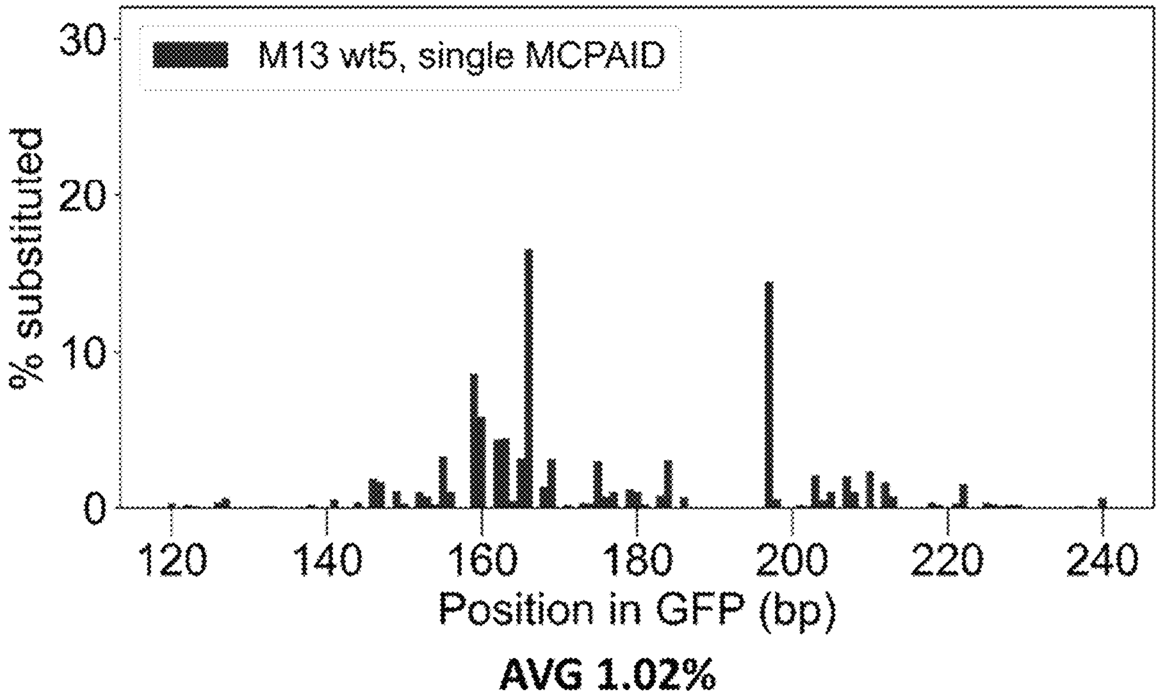
FIGS. 20A and 20B show that adding a second integrated copy of MCP-AID significantly increases the mutation rate.
Figure 20B:
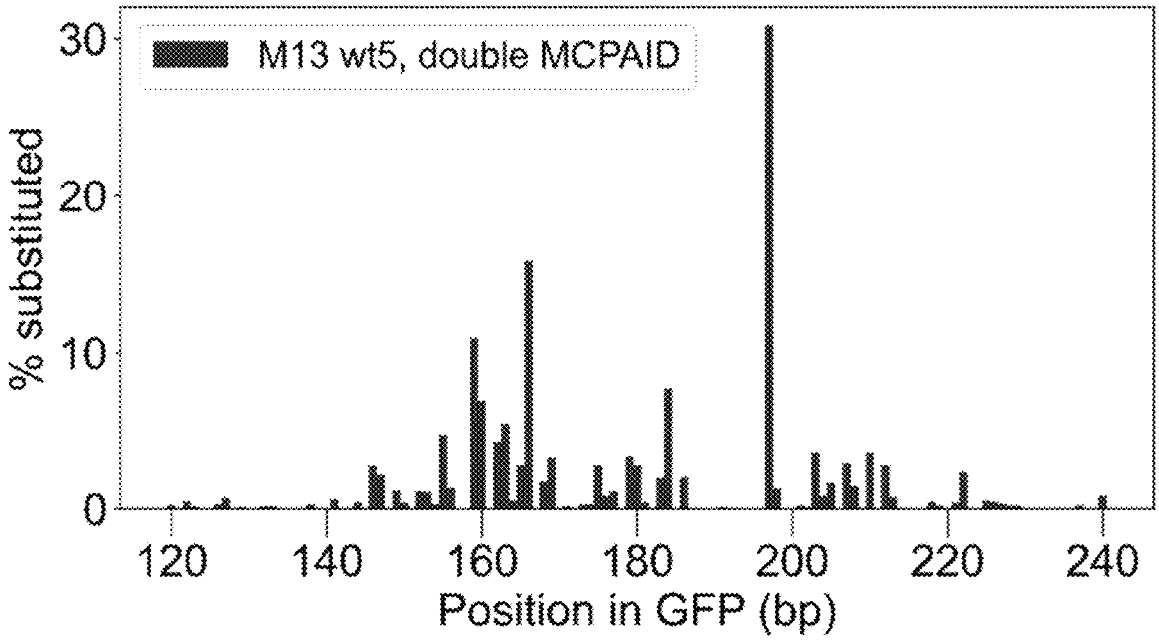

After 4 rounds of sorting, the cells were plated and the individual colonies picked to assess their affinity through yeast display. Three were found that had a substantial increase in affinity over wildtype. Genomic DNA from these yeast were purified, PCR amplified, and sequenced. A concentration of mutations were found in the CDR2 of the heavy chain. The best mutant, in terms of increased FITC signal, had a W184L mutation near its VHCDR2 (FIG. 14B). The W184L variant had a 2-fold improvement in binding over the 4420 scFV. Thus, the ability to rapidly improve an antibody sequence was demonstrated by introducing targeted mutations across a broad range of DNA using the diversifying base editor in yeast, and to select for improved protein properties using said system, i.e., to use if for in situ directed evolution.

To validate the results of the fluorescence shift assay, deep amplicon sequencing was used to characterize the mutation rate of the base editor. Critically, the S65T mutation rate correlates with the overall mutation rate. In cells with a single gRNA targeting wtGFP, the window of prominent mutation was roughly ±50 bp and centered 20 bp downstream of the PAM. Deep sequencing was also performed on the 4-4-20 scFv targeted simultaneously with 3 gRNAs. Here, the overall mutation rate within the variable heavy region was estimated to be $1\times10^{-4}$ mutations/bp/generation, a 10-fold higher mutation that has ever previously been reported for an in situ evolution system. Herein, insertions and deletions were rarely detected in the targeted DNA, making this technology well-suited for protein engineering and diversification.

Methods for high throughput sequencing: For deep sequencing, the base editor was induced for 8 days targeting the wtGFP locus with a single gRNA. Genomic DNA was collected using the Yeastar Genomic DNA Kit (Zymo Research). The wtGFP locus was amplified by PCR, and DNA concentrations were normalized using the Qubit fluorimetry system. DNA was sent to Genewiz for EZ-Amplicon sequencing (PE250 MiSeq, Illumina), generating 50,000 reads. The reads were demultiplexed using fastq-multx from ea-utils then aligned to the reference using bwa mem. Mutation rates were then calculated.

Advantages and improvements over existing methods, devices or materials. A key advantage of this technology is that it enables the highest rates of in situ DNA mutation of all such platforms to date. The CRISPR base editor with three sgRNAs, disclosed herein, has a mutation rate of $1\times10^{-4}$ mutations/bp/generation, which is 10-fold higher than previously described systems. The base editor can also make a variety of mutations (e.g., C4T, G4T). The enhanced diversifying base editor technology further facilitates rapid antibody diversification (8 days for library generation). It has been contemplated that this diversifying base editor can be extended to a wide variety of tasks.

This system is an enabling technology for studies that wish to employ direct evolution via DNA mutagenesis. The key innovation herein is simultaneously fusing an enhanced (731-variant) AID to the MCP viral protein that binds MS2 stem loops, using an optimized placement of MS2 stem loops in sgRNA scaffolds, and using interspacing of tRNAs in conjunction with multiple sgRNAs allowed a robust and targetable in situ mutation rate of $1\times10^{-4}$ mutations/bp/generation, roughly 10 fold higher than the previously reported highest rate of in situ mutations.

Because this system uses AID, it is more likely to recapitulate somatic hypermutation. Ultimately, it has been contemplated that engineered yeast can mimic the entirety of antibody production and evolution as is seen in mammalian B cells.

It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

TABLES

TABLE 1

List of 4-4-20 mutant clones collected after FACS.

| Sorted Clone | Mutations | gRNA scaffold type | Relative Fluor. in Competitive Stain | Proximal CDR | Nucleotide Changes |
|---|---|---|---|---|---|
| 1* | W108F | M13 | 6.71 | CDR3 | TGG to T**TT** |
| 2 | L45V | M13 | 2.54 | CDR2 | CTG to **G**TG |
| 3 | L45V | M13 | 2.34 | CDR2 | CTG to **G**TG |
| 4 | W47L | M13 | 2.25 | CDR2 | TGG to T**TA** |
| 5* | V23L, A24G, L45V | Mtx2 | 3.07 | CDR1 and CDR2 | GTT to **C**TT, GCC to G**G**C, and CTG to **G**TG |
| 6 | V23L, A24G, L45V | Mtx2 | 2.45 | CDR1 and CDR2 | GTT to **C**TT, GCC to G**G**C, and CTG to **G**TG |
| 7 | L45(silent), W47L | Mtx2 | 1.99 | CDR2 | CTG to CT**C**, and TGG to T**TA** |
| 8* | L45V | Mtx2 | 1.91 | CDR2 | CTG to **G**TG |

*Clones taken for further analysis. Fluorescence values are mean antigen binding (PE) of scFv-expressing cells relative to wild-type 4-4-20. Nucleotide mutations are highlighted in bold.

TABLE 2

| Description of strains constructed. | | |
|---|---|---|
| Strain | Base | Modifications to Base Strain |
| EBY101 | EBY100 | Deletion of URA3 disruption cassette via collapse of flanking AGA1 sequences |
| EBY101-wtGFP | EBY101 | YORWΔ22Δ::pTDH3-mwtGFP-tCYC1, psmTEF1-snNAT-tCYC1 |
| AC001 | EBY101-wtGFP | YPRCτ3Δ::pGAL2-MCP-AID*Δ-tVMA2, pagTEF1-klLEU2-tagTEF1, pGAL1-dCas9-tRPL3 |
| AC002 | EBY101-wtGFP | YPRCτ3Δ::pGAL2-MCP-AIDdead-tVMA2, pagTEF1-klLEU2-tagTEF1, pGAL1-dCas9-tRPL3 |
| AC003 | EBY101-wtGFP | YPRCτ3Δ::pGAL2-MCP-AID731Δ-tVMA2, pagTEF1-klLEU2-tagTEF1, pGAL1-dCas9-tRPL3 |
| AC004 | EBY101-wtGFP | YPRCτ3Δ::pGAL2-MCP-AID731Δ-tVMA2, pagTEF1-klLEU2-tagTEF1, pGAL1-dCas9RFA3-tRPL3 |
| AC005 | EBY101-wtGFP | YPRCτ3Δ::pGAL2-MCP-dCas9AID731Δ-tVMA2, pagTEF1-klLEU2-tagTEF1 |
| AC201 | EBY101-wtGFP | YPRCτ3Δ::PSNR52-18L-M13-TSUP4, psmTEF1-TRP1-tagTEF1, pGAL1-dCas9-tRPL3 |
| AC202 | EBY101-wtGFP | YPRCτ3Δ::PSNR52-t22L-M13-TSUP4, psmTEF1-TRP1-tagTEF1, pGAL1-dCas9-tRPL3 |
| AC203 | EBY101-wtGFP | YPRCτ3Δ::PSNR52-NT1-M13-TSUP4, psmTEF1-TRP1-tagTEF1, pGAL1-dCas9-tRPL3 |
| EBY100-4420 | EBY100 | YORWΔ22Δ::pGAL1-AGA2-4420-tMF(ALPHA)1, psmTEF1-snNAT-tCYC1 |
| AC301 | EBY100-4420 | YPRCτ3Δ::pGAL2-MCP-AID731Δ-tVMA2, pagTEF1-klLEU2-tagTEF1, pGAL1-dCas9-tRPL3 |
| EBY100-4m5.3 | EBY100 | YORWΔ22Δ::pGAL1-AGA2-4m5.3-tMF(ALPHA)1, psmTEF1-snNAT-tCYC1 |
| EBY100-W108F | EBY100 | YORWΔ22: pGAL1-AGA2-4420-W108F-tMF(ALPHA)1, psmTEF1-snNAT-tCYC1 |
| EBY100-L45V | EBY100 | YORWΔ22Δ::pGAL1-AGA2-4420-L45V-tMF(ALPHA)1, psmTEF1-snNAT-tCYC1 |
| EBY100-V23L, A24G, L45V | EBY100 | YORWΔ22Δ::pGAL1-AGA2-4420-V23L, A24G, L45V-tMF(ALPHA)1, psmTEF1-snNAT-tCYC1 |
| EBY101 | EBY100 | Deletion of pURA3-URA3-tURA3 via collapse of flanking AGA1 sequences |
| AC006 | EBY101 | @YORWΔ22: pTDH3-mwtGFP-tCYC1, psmTEF1-NatR-tCYC1; @YPRCτ3: pGAL2-MCP-AID*Δ-tVMA2, pagTEF1-klLEU2-tagTEF1, pGAL1-dCas9-tRPL3 |
| AC008 | EBY101 | @YORWΔ22: pTDH3-mwtGFP-tCYC1, psmTEF1-NatR-tCYC1; @YPRCτ3: pGAL2-MCP-AIDdead-tVMA2, pagTEF1-klLEU2-tagTEF1, pGAL1-dCas9-tRPL3 |
| AC011 | EBY100 | @YORWΔ22: pGAL1-AGA2-4420-tMF(ALPHA)1, psmTEF1-NatR-tCYC1; @YPRCτ3: pGAL2-MCP-AID*Δ-tVMA2, pagTEF1-klLEU2-tagTEF1, pGAL1-dCas9-tRPL3 |

Abbreviations: ag = *Ashbya gossypii*, kl = *Kluyveromyces lactis*, sm = *Saccharomyces mikatae*, sn = *Streptomyces noursei*. All other promoters/terminators are from *Saccharomyces cerevisiae*.

TABLE 3

| AID mutants | |
|---|---|
| Name | Mutations (wild type AID has 198 AA) |
| AID*Δ | K10E, T82I, E156G, 195* |
| AIDmono | (3S-K10) to PAT, L12T, H130A, R131E, 181* |
| AID*mono | (3S-K10) to PAT, L12T, T82I, H130A, R131E, E156G, 181* |
| AID731mono | (3S-K10) to PAT, L12T, R36C, L44R, T82I, Y88S, H93L, H130A, R131E, K142E, E156G, 181* |
| AID731Δ | R9S, K10E, R36C, L44R, T82I, Y88S, H93L, K142E, E156G, 195* |
| AIDdead | H56R, E58Q, 195* |

TABLE 4

| $K_d$ values based on antigen titration | | |
|---|---|---|
| scFv name | Calculated $K_d$ (nM) | 95% confidence interval (nM) |
| 4-4-20 | 13.0 | 4.79 to 48.3 |
| L45V | 0.299 | 0.0891 to 1.02 |
| V23L, A24G, L45V | 0.379 | 0.220 to 0.667 |
| W108F | 0.0364 | 0.0240 to 0.0548 |
| 4m5.3 | 0.0225 | 0.0146 to 0.0340 |

TABLE 5

Primers used in this study
NOTE: Primers are shaded in pairs used for PCR, except for the one-sided, whichnested PCRs, have primers. Repeated primers are BOLDED.

| Primer # | Sequence (5' to 3') | PCR Purpose |
|---|---|---|
| Genomic integration primers | | |
| apc001 | CGGTATTACTCGAGCCCGTAATAC (SEQ ID NO: 56) | 5' Flank for Integration at YPRCτ3 |
| apc002 | GGACACCTGGCTACTTAACCATTCGTTG TTAGTGTGTCGCATACGAGGAATAACGC CGATGGGACGTCAGCACTGTAC (SEQ ID NO: 57) | |
| apc003 | AAAGGAGGTGCACGCATTATGG (SEQ ID NO: 58) | 3' Flank for Integrating 3 Genes @YPRCτ3 |
| apc004 | CCGAACCTAGGATTAGATGTGGTCTAGC ACCATATTGCGGACATGGTCCCCCTGTT ATTCCAAGGAGGTGAAGAACGTC (SEQ ID NO: 59) | |
| apc005 | GGACACCTGGCTACTTAACCATTCGTTG TTAGTGTGTCGCATACGAGGAATAACGC CTTTGCGAAACCCTATGCTCTG (SEQ ID NO: 60) | 5' Flank for Integration @YPRCΔ15 |
| apc006 | GCCAGGCGCCTTTATATCATATAATTAA GAC (SEQ ID NO: 61) | |
| apc007 | CATTTGGATTGTAATTTCATACTGGAGT AAACATCTCCAGGTGTCTAAGTTCACAC AGGAATGGAAGGTCGGGATGAGC (SEQ ID NO: 62) | 3' Flank for Integrating 2 Genes @YPRCΔ15 |
| apc008 | ATAAAGCAGCCGCTACCAAACAG (SEQ ID NO: 63) | |
| apc009 | CGTGATAAACGATCGCCATAACTAAC (SEQ ID NO: 64) | 3' Flank for Integration @YORWΔ22 |
| apc010 | GATTGTAATTTCATACTGGAGTAAACAT CTCCAGGTGTCTAAGTTCACACAGGGGA CCAACTATCATCCGCTAATTAC (SEQ ID NO: 65) | |
| apc011 | CACCGGAGCTTGGATATGATAAAC (SEQ ID NO: 66) | 5' Flank for Integrating 2 Genes @YORWΔ22 |
| apc012 | GGCTACTTAACCATTCGTTGTTAGTGTGT CGCATACGAGGAATAACGCCTTCGCGGG CTGTTACTTATCC (SEQ ID NO: 67) | |
| apc013 | GGCGTTATTCCTCGTATGCG (SEQ ID NO: 68) | Amplify Pro-gene-Term in HR1 backbone |
| apc014 | GACAATCGCTACAGAAACGATTTTC (SEQ ID NO: 69) | |
| apc015 | AGGACCAAGCGACCTGTGTC (SEQ ID NO: 70) | Amplify Pro-gene-Term in HR2 backbone |
| apc016 | CCTGTGTGAACTTAGACACCTGGAG (SEQ ID NO: 71) | |
| apc017 | TCATTTGGATTGTAATTTCATACTGGAG (SEQ ID NO: 72) | Amplify Pro-gene-Term in HR3 backbone |
| apc018 | TAACAGGGGGACCATGTCC (SEQ ID NO: 73) | |
| apc019 | ACGAGCTTTTGAATTATGGTAATTTTG (SEQ ID NO: 74) | PCR check for integrations @YPRCΔ15 |
| apc020 | TGTTGAGTACTTCAACTTTATTTCCTTC (SEQ ID NO: 75) | |
| apc021 | CCGTGAATCAAGCTGATAAACAG (SEQ ID NO: 76) | PCR check for integrations @YPRCτ3 |

TABLE 5-continued

Primers used in this study
NOTE: Primers are shaded in pairs used for PCR, except for the one-sided, whichnested PCRs, have primers. Repeated primers are BOLDED.

| Primer # | Sequence (5' to 3') | PCR Purpose |
|---|---|---|
| apc022 | CCTGGACACTTTACTTATCTAGCG (SEQ ID NO: 77) | |
| apc023 | GGAAATATATGCGCAGTATGCTCC (SEQ ID NO: 78) | PCR check for integrations @YORWΔ22 |
| apc024 | CGAATCAAACGAATGCTTTGGAAAC (SEQ ID NO: 79) | |
| apc025 | GTTATTCCTCGTATGCGACACACTAACA ACGAATGGTTAAGTAGCCAGGTGTCCAT CCCAGTGAGTTGATTGGAAGACC (SEQ ID NO: 80) | PCR pSNR52-gRNA-tSUP4, mimicks amplification from HR1 backbone |
| apc026 | CAATCGCTACAGAAACGATTTTCAACAG TATTTACCTCGACACAGGTCGCTTGGTC CTGTGAGCTGATACCGCTCGAAG (SEQ ID NO: 81) | |
| 4-4-20 scFv and GFP | | |
| apc027 | GTTATTCCTCGTATGCGACACACTAACA ACGAATGGTTAAGTAGCCAGGTGTCCAT CACATGGCATTACCACCATATAC (SEQ ID NO: 82) | AGA2-4-4-20 for insertion |
| apc028 | CTACAGAAACGATTTTCAACAGTATTTA CCTCGACACAGGTCGCTTGGTCCTAATT CTCTTAGGATTCGATTCACATTC (SEQ ID NO: 83) | |
| apc029 | TACTTCTTATTCAAATGTAATAAAAGAT CGAATTCCCTACTTCATACATTTTCAATT AAG (SEQ ID NO: 84) | AGA2-4m5.3 Fragment 1 for pCT backbone |
| apc030 | CTAGCAGAACCACCACCACCAGAAC (SEQ ID NO: 85) | |
| apc031 | GGTGGTGGTGGTTCTGCTAGCGACGTCG TTATGAC (SEQ ID NO: 86) | AGA2-4m5.3 Fragment 2 for pCT backbone |
| apc032 | GTTACATCTACACTGTTGTTATCAGATCT CGAGCTATTACAAGTCTTCTTCAGAAAT AAGCTTTTG (SEQ ID NO: 87) | |
| apc033 | CAGAGCAGATTGTACTGGGTCTCAAATG GTGAGCAAGGGCGAGG (SEQ ID NO: 88) | wtGFP Fragment 1 for EMY backbone |
| apc034 | CGCCGTAGCTGAAGGTGGTCACGAGGGT GG (SEQ ID NO: 89) | |
| apc035 | GTGACCACCTTCAGCTACGGCGTGCAGT GCTTC (SEQ ID NO: 90) | wtGFP Fragment 2 for EMY backbone |
| apc036 | GAGCTGATACCGCTCGGTCTCTTTTACTT GTACAGCTCGTCCATG (SEQ ID NO: 91) | |
| apc037 | CATCAGAGCAGATTGTACTGGGTCTCAA ATGCAGTTACTTCGCTGTTTTTC (SEQ ID NO: 92) | AGA2-4-4-20 for EMY backbone |
| apc038 | GTGAGCTGATACCGCTCGGTCTCTTTTA CAAGTCTTCTTCAGAAATAAGCTTTTG (SEQ ID NO: 93) | |
| apc039 | AAAGGTCTCAGTGCACATGGCATTACCA CCATATACATATCC (SEQ ID NO: 94) | AGA2-4-4-20 mutants for HR backbone |
| apc040 | AAAGGTCTCAGAGGAATTCTCTTAGGAT TCGATTCACATTCATC (SEQ ID NO: 95) | |
| High-throughput sequencing | | |
| apc041 | ACACTCTTTCCCTACACGACGCTCTTCCG ATCTATCACGAATGGTGAGCAAGGGCG AGGAGC (SEQ ID NO: 96) | High-throughput sequencing of GFP |
| apc042 | GACTGGAGTTCAGACGTGTGCTCTTCCG ATCTCGATGTTCAGCTCGATGCGGTTCA CCAGG (SEQ ID NO: 97) | |
| apc 151 | ACACTCTTTCCCTACACGACGCTCTTCCG ATCTGCATCAGATGGTGACGTCAAACTG GATGAGAC (SEQ ID NO: 205) | High-throughput sequencing of 4-4-20 |
| apc 152 | GACTGGAGTTCAGACGTGTGCTCTTCCG ATCTTGAGACCATCTACACTGTTGTTATC AGATCTCGAGC (SEQ ID NO: 206) | |
| dCas9 and fusions | | |
| apc043 | CATCAGAGCAGATTGTACTGGGTCTCAA ATGGATAAAAAGTATAGTATTGGTTTAG CTATTG (SEQ ID NO: 98) | dCas9 Fragment 1 for EMY backbone |

TABLE 5-continued

Primers used in this study
NOTE: Primers are shaded in pairs used for PCR, except for the one-sided, whichnested PCRs, have primers. Repeated primers are BOLDED.

| Primer # | Sequence (5' to 3') | PCR Purpose |
|---|---|---|
| apc044 | CAAGAAAGATTGTGGAACTATGGCATCT ACATCATAATCTGAAAG (SEQ ID NO: 99) | |
| apc045 | CTTTCAGATTATGATGTAGATGCCATAG TTCCACAATCTTTCTTG (SEQ ID NO: 100) | dCas9 Fragment 2 for EMY backbone |
| apc046 | GAGCTGATACCGCTCGGTCTCTTTTAAA CCTTTCTCTTTTTCTTAGGATCCAC (SEQ ID NO: 101) | |
| apc047 | GAGCTGATACCGCTCGGTCTCTTTTAGT ATATTTCTGGGTATTTCTTACATAGTCTC (SEQ ID NO: 102) | Nested PCR to fust RFA3 to dCas9 for EMY backbone, reverse primer |
| apc048 | CTAGCGGATCCGAGACTCCTGGGACCTC AGAGTCTGCTACACCCGAAAGTTCAGGT GGATCTTCTGGTG (SEQ ID NO: 103) | forward primer 1 |
| apc049 | GGTGGATCCTAAGAAAAAGAGAAAGGT TTCCGGTGGATCTTCTGGTGGTTCTAGC GGATCCGAGACTCC (SEQ ID NO: 104) | forward primer 2 |
| apc050 | GAGCTGATACCGCTCGGTCTCTTTTATGT CCTGAATGCATCACGTAAATC (SEQ ID NO: 105) | Nested PCR to fuse AID731Δ to dCas9 for EMY backbone, reverse primer |
| apc051 | TTCAGGTGGAGGCAGTGGAGGTGGTGG ATCTATGGATTCACTATTAATGAATAGA AGTG (SEQ ID NO: 106) | forward primer 1 |
| apc052 | CGTAAGGTGGATCCTAAGAAAAAGAGA AAGGTTTCAGGTGGAGGCAGTGGAG (SEQ ID NO: 107) | forward primer 2 |
| AID variants (AID*Δ, AIDdead, AIDmono, AID*mono, AID731Δ, etc.) | | |
| apc053 | CATCAGAGCAGATTGTACTGGGTCTCAA ATGGCTAGTAATTTTACTCAATTCGTG (SEQ ID NO: 108) | MCP-AID*Δ for EMY backbone |
| apc054 | GAGCTGATACCGCTCGGTCTCTTTTATGT CCTGAATGCATCACGTAAATC (SEQ ID NO: 109) | |
| apc053 | | MCP-AIDdead Fragment 1 (MCP) for EMY backbone |
| apc055 | CTCTTTTTCTTAGGGCCTGAACC (SEQ ID NO: 110) | |
| apc056 | AGGCCCTAAGAAAAAGAGAAAAGTGG (SEQ ID NO: 111) | MCP-AIDdead Fragment 2 (AIDdead) for EMY backbone |
| apc054 | | |
| apc053 | | MCP-AIDmono Fragment 1 (MCP) for EMY backbone |
| apc057 | ATCCATGCCGGCTGCGGCCACTTTTC (SEQ ID NO: 112) | |
| apc058 | GAAAAGTGGCCGCAGCCGGCATGGATC CAGCTACCTTTACGTACCAATTTAAGAA CGTGAGATGG (SEQ ID NO: 113) | MCP-AIDmono Fragment 2 for EMY backbone |
| apc059 | CATGGTGACCAAGAGGTAAACCATGTA ACACGATAACAC (SEQ ID NO: 114) | |
| apc060 | GTGTTACATGGTTTACCTCTTGGTCACCA TGCTATG (SEQ ID NO: 115) | MCP-AIDmono Fragment 3 for EMY backbone |
| apc061 | CTGAACTCCGGCTTCGGCTAATCTTCTTA AGCCTTCAGGC (SEQ ID NO: 116) | |
| apc062 | AGGCTTAAGAAGATTAGCCGAAGCCGG AGTTCAGATTGC (SEQ ID NO: 117) | MCP-AIDmono Fragment 4 for EMY backbone |
| apc063 | GAGCTGATACCGCTCGGTCTCTTTTACT GCAATATTCTTCTTAATTGCCTAC (SEQ ID NO: 118) | |
| apc053 | | MCP-AID*mono Fragment 1 for EMY backbone |
| apc064 | GGTGACCAAGAGATAAACCATGTAACA CGATAACACC (SEQ ID NO: 119) | |
| apc065 | CGTGTTACATGGTTTATCTCTTGGTCACC ATGCTATG (SEQ ID NO: 120) | MCP-AID*mono Fragment 2 for EMY backbone |
| apc066 | AGCTTTGAAGGTTCTACCATGATTTTCG ACGAAGGTATTC (SEQ ID NO: 121) | |
| apc067 | GTCGAAAATCATGGTAGAACCTTCAAAG CTTGGG (SEQ ID NO: 122) | MCP-AID*mono Fragment 3 for EMY backbone |
| apc068 | GAGCTGATACCGCTCGGTC (SEQ ID NO: 123) | |

TABLE 5-continued

Primers used in this study
NOTE: Primers are shaded in pairs used for PCR, except for the one-sided, whichnested PCRs, have primers. Repeated primers are BOLDED.

| Primer # | Sequence (5' to 3') | PCR Purpose |
|---|---|---|
| apc053 | | AID731Δ Fragment 1 for EMY backbone |
| apc069 | GGTACAAAAATTCACTTCTATTCATTAA TAGTGAATCCATAGAG (SEQ ID NO: 124) | |
| apc070 | GGATTCACTATTAATGAATAGAAGTGAA TTTTTGTACCAATTTAAGAACGTG (SEQ ID NO: 125) | AID731Δ Fragment 2 for EMY backbone |
| apc071 | ACGAGAAAAGGAAGTTGCTGAGTCGCA TCTTTTCACTACGTAACATAGATAAG (SEQ ID NO: 126) | |
| apc072 | TGCGACTCAGCAACTTCCTTTTCTCGTGA TTTCGGTTACTTAAGAAATAAGAACG (SEQ ID NO: 127) | AID731Δ Fragment 3 for EMY backbone |
| apc073 | CAGCTACTAGTCTGGCACAATCAGAGCA TGGTGACCAAGAG (SEQ ID NO: 128) | |
| apc074 | GCTCTGATTGTGCCAGACTAGTAGCTGA TTTCTTACGTGGTAAC (SEQ ID NO: 129) | AID731Δ Fragment 4 for EMY backbone |
| apc075 | CAGCAGTAAAAGTAATCTTCGAAAGTCA TTATTGCAATCTGAAC (SEQ ID NO: 130) | |
| apc076 | GCAATAATGACTTTCGAAGATTACTTTT ACTGCTGGAATAC (SEQ ID NO: 131) | AID731Δ Fragment 5 for EMY backbone |
| apc054 | | |
| apc053 | | MCP-altcodon_AID*Δ Fragment 1 (MCP) for EMY backbone |
| apc077 | GGCTGCGGCCACTTTTCTC (SEQ ID NO: 132) | |
| apc078 | CTAAGAAAAAGAGAAAAGTGGCCGCAG CC (SEQ ID NO: 133) | MCP-altcodon_AID*Δ Fragment 2 (human or alt. yeast codon optimized AID*Δ) for EMY backbone |
| apc068 | | |
| apc079 | GAATGGTTAAGTAGCCAGGTGTCCATCG TGCCTAATCCAAGGAGGTTTAC (SEQ ID NO: 134) | MCPz-AID*Δ Fragment 1 (pGal2) for HR1 backbone |
| apc080 | GGCATCTCGAGAGACATTATGAAAGAAT TATTTTTTTTATTATGTTAATCTTGTG (SEQ ID NO: 135) | |
| apc081 | AAAATAATTCTTTCATAATGTCTCTCGA GATGCCCAAAAAG (SEQ ID NO: 136) | MCPz-AID*Δ Fragment 2 (MCPz) for HR1 backbone |
| apc082 | CACCTCCAGATCCACCTCCTCCGTAGAT GCCGGAGTTTGCTG (SEQ ID NO: 137) | |
| apc083 | GGAGGAGGTGGATCTGGAGGTGGAGGC TCTATGGATTCACTATTAATGAATAG (SEQ ID NO: 138) | MCPz-AID*Δ Fragment 3 (AID*Δ) for HR1 backbone |
| apc084 | CTTCAGCAACCGTCCTTTTATGTCCTGAA TGCATCACG (SEQ ID NO: 139) | |
| apc085 | CATTCAGGACATAAAAGGACGGTTGCTG AAGAAAAAG (SEQ ID NO: 140) | MCPz-AID*Δ Fragment 4 (Tvma2) for HR1 backbone |
| apc086 | TCGACACAGGTCGCTTGGTCCTGAGGTG TGTTCCTTGATCTTTTTC (SEQ ID NO: 141) | |
| apc079 | | MCP-AID*ΔA-RFA3 Fragment 1 (Pgal2-MCP-AID*Δ) for HR1 backbone |
| apc087 | CTGAACTTCCGCCGCTAGAACCTCCTGA AGAACCACCAGATTATGTCCTGAATGCA TCACGTAAATC (SEQ ID NO: 142) | |
| apc088 | GAGGTTCTAGCGGCGGAAGTTCAGGTGG ATCTTCTGGTGGATCCATGGCCAGCGAA ACACCAAG (SEQ ID NO: 143) | MCP-AID*Δ-RFA3 Fragment 2 (RFA3) for HR1 backbone |
| apc089 | GCAACCGTCCTTCTAGTATATTTCTGGGT ATTTCTTACATAG (SEQ ID NO: 144) | |
| apc090 | ACCCAGAAATATACTAGAAGGACGGTT GCTGAAGAAAAAG (SEQ ID NO: 145) | MCP-AID*Δ-RFA3 Fragment 3 (Tvma2) for HR1 backbone |
| apc086 | | |
| Initial gRNA scaffolds (No MS2, M13, Mtx2, M4) | | |
| apc091 | GAGCCAGTGAGTTGATTGGAAGACCTGG ATCCTCTTTGAAAAGATAATGTATGATT ATGCTT (SEQ ID NO: 146) | pSNR52 for pY120 backbone |
| apc092 | AATTCCGTCAGCCAGGGTCTCGATCATT TATCTTTCACTG (SEQ ID NO:147) | |

TABLE 5-continued

Primers used in this study
NOTE: Primers are shaded in pairs used for PCR, except for the one-sided, whichnested PCRs, have primers. Repeated primers are BOLDED.

| Primer # | Sequence (5' to 3') | PCR Purpose |
|---|---|---|
| apc093 | GATAAATGATCGAGACCCTGGCTGACGG AATTTATGCC (SEQ ID NO: 148) | Blank gap for pY120 backbone |
| apc094 | CTAGCTCTGAAACTGAGACCGAGAAAA CTCACCG (SEQ ID NO: 149) | |
| apc095 | GAGTGAGCTGATACCGCTCGAAGACGG ATCCAGACATAAAAAACAAAAAAAGCA CCG (SEQ ID NO: 150) | Nested PCR M13 for pY120 backbone |
| apc096 | GTTTCAGAGCTAGGCCAACATGAGGATC ACCCATGTCTGCAGGGCCTAGCAAG (SEQ ID NO: 151) | forward primer 1 |
| apc097 | GAGTTTTCTCGGTCTCAGTTTCAGAGCT AGGCCAACATG (SEQ ID NO: 152) | forward primer 2 |
| apc098 | GTTTTCTCGGTCTCAGTTTCAGAGCTAG AAATAGCAAGTTG (SEQ ID NO: 153) | M4 or No Ms2 for pY120 backbone |
| apc095 | | |
| apc098 | | Mtx2 Fragment 1 (gRNA scaffold) for pY120 backbone |
| apc099 | TCCCGCACCGACTCGGTGCCAC (SEQ ID NO: 154) | |
| apc 100 | AAGTGGCACCGAGTCGGTG (SEQ ID NO: 155) | Mtx2 Fragment 2 (Mtx2) for pY120 backbone |
| apc095 | | |
| Remaining gRNA scaffolds (M1, M3, M14, M34, M1tx2, M3tx2, M13tx2, Mt, M13t) | | |
| apc 101 | GAGCCAGTGAGTTGATTGGAAG (SEQ ID NO: 156) | Fragment 1 (pSNR52, blank gap, M1) for pY120 backbone |
| apc 102 | AAGTTGATAACGGACTAGCCTTATTTC (SEQ ID NO: 157) | |
| apc 103 | AGCAAGTTGAAATAAGGCTAGTCC (SEQ ID NO: 158) | Fragment 2 (No MS2 or M4) for pY120 backbone |
| apc 104 | GAGCTGATACCGCTCGAAGACCTGGATC CAG (SEQ ID NO: 159) | [Makes M1 or M14] |
| apc101 | | Fragment 1 (pSNR52, blank gap, No MS2) for pY120 backbone |
| apc102 | | |
| apc103 | | Fragment 2 (M3) for pY120 backbone |
| apc104 | | [Makes M3] |
| apc101 | | pSNR52-blank gap-[Mt or M13t] Nested PCR for pY120g backbone, forward primer |
| apc 105 | AACAAAAAAAGCACATGGGTGATCCTC ATGTGCGCGCACCGACTCGGTGCCAC (SEQ ID NO: 160) | reverse primer 1 |
| apc 106 | GCTGATACCGCTCGAAGACCTGCAGAGA CATAAAAAACAAAAAAAGCACATGGGT GATCC (SEQ ID NO: 161) | reverse primer 2 |
| apc101 | | Fragment 1 (pSNR52, blank gap, M1 or M3 or M1, 3) for pY120 backbone |
| apc 107 | TCCCGCACCGACTCGGTGCCAC (SEQ ID NO: 162) | |
| apc 108 | AAGTGGCACCGAGTCGGTG (SEQ ID NO: 163) | Fragment 2 (Mtx2) for pY120 backbone |
| apc104 | | [Makes M1tx2, M3tx2, or M13tx2] |
| apc101 | | Fragment 1 (pSNR52, blank gap, M3) for pY120 backbone |
| apc 109 | CCTCGGTGCCACTTGGCCCTGCAGACAT GGGTGATCCTCATGTTGGCCAAGTTGAT AACGGACTAGCC (SEQ ID NO: 164) | |
| apc 110 | GCAGGGCCAAGTGGCACCGAGGCCAAC (SEQ ID NO: 165) | Fragment 2 (M4) for pY120 backbone |
| apc104 | | [Makes M34] |
| gRNA spacers | | |
| apc111 | TGATCCGGCGTCGAAGCCTGTAAAG (SEQ ID NO: 166) | Anneal for NT1 |
| apc112 | AAACCTTTACAGGCTTCGACGCCGG (SEQ ID NO: 167) | |
| apc 113 | TGATCGGCGAGGGCGATGCCACCTA (SEQ ID NO: 168) | Anneal for wtGFP t74L |

TABLE 5-continued

Primers used in this study
NOTE: Primers are shaded in pairs used for PCR, except for the one-sided, whichnested PCRs, have primers. Repeated primers are BOLDED.

| Primer # | Sequence (5' to 3') | PCR Purpose |
|---|---|---|
| apc114 | AAACTAGGTGGCATCGCCCTCGCCG (SEQ ID NO: 169) | |
| apc115 | TGATCCCGGCAAGCTGCCCGTGCCC (SEQ ID NO: 170) | Anneal for wtGFP t22L |
| apc116 | AAACGGGCACGGGCAGCTTGCCGGG (SEQ ID NO: 171) | |
| apc117 | TGATCGTAGCTGAAGGTGGTCACGA (SEQ ID NO: 172) | Anneal for wtGFP 18L |
| apc118 | AAACTCGTGACCACCTTCAGCTACG (SEQ ID NO: 173) | |
| apc119 | TGATCGCACTGCACGCCGTAGCTGA (SEQ ID NO: 174) | Anneal for wtGFP 6L |
| apc 120 | AAACTCAGCTACGGCGTGCAGTGCG (SEQ ID NO: 175) | |
| apc121 | TGATCGTGGTCACGAGGGTGGGCCA (SEQ ID NO: 176) | Anneal for wtGFP 28L |
| apc 122 | AAACTGGCCCACCCTCGTGACCACG (SEQ ID NO: 177) | |
| apc 123 | TGATCGTCGTGCTGCTTCATGTGGT (SEQ ID NO: 178) | Anneal for wtGFP 29R |
| apc 124 | AAACACCACATGAAGCAGCACGACG (SEQ ID NO: 179) | |
| apc 125 | TGATCGGGCACGGGCAGCTTGCCGG (SEQ ID NO: 180) | Anneal for wtGFP 48L |
| apc 126 | AAACCCGGCAAGCTGCCCGTGCCCG (SEQ ID NO: 181) | |
| apc 127 | TGATCGACGTAGCCTTCGGGCATGG (SEQ ID NO: 182) | Anneal for wtGFP 62R |
| apc 128 | AAACCCATGCCCGAAGGCTACGTCG (SEQ ID NO: 183) | |
| apc 129 | TGATCCTTCAGGGTCAGCTTGCCGT (SEQ ID NO: 184) | Anneal for wtGFP 81L |
| apc 130 | AAACACGGCAAGCTGACCCTGAAGG (SEQ ID NO: 185) | |
| apc131 | TGATCTGAAGAAGATGGTGCGCTCC (SEQ ID NO: 186) | Anneal for wtGFP 84R |
| apc 132 | AAACGGAGCGCACCATCTTCTTCAG (SEQ ID NO: 187) | |
| apc153 | TGATCTTCAAGTCCGCCATGCCCGA (SEQ ID NO: 207) | Anneal for wtGFP c78R |
| apc 154 | AAACTCGGGCATGGCGGACTTGAAG (SEQ ID NO: 208) | |
| | **3x gRNA-tRNA cassettes** | |
| apc133 | GCGTTGGCCGATTCATTAATG (SEQ ID NO: 188) | gRNA-tRNA Fragment 1 for pUC backbone (used for Mtx2 and M13) |
| apc 134 | CTCTGAAACTGAGACCGAAGGAGAAAACTCACCGAGG (SEQ ID NO: 189) | |
| apc135 | CTCCTTCGGTCTCAGTTTCAGAGCTAGAAATAGCAAG (SEQ ID NO: 190) | Mtx2 gRNA-tRNA Fragment 2 (Mtx2) for pUC backbone |
| apc 136 | AACCACTTGCGCTTGTTTGGGAACACGAGCGACATGG (SEQ ID NO: 191) | |
| apc 137 | GTTCCCAAACAAGCGCAAGTGGTTTAGTGGTAAAATC (SEQ ID NO: 192) | Mtx2 gRNA-tRNA Fragment 3 (tRNA-Gly) for pUC backbone |
| apc 138 | GGCCTCTTCGCTATTACGCC (SEQ ID NO: 193) | |
| apc139 | CTCCTTCGGTCTCAGTTTCAGAGCTAGAAATAGCAAG (SEQ ID NO: 194) | M13 gRNA-tRNA Fragment 2 (M13) for pUC backbone |
| apc 140 | CACTTGCGCTTGTTTGCACCGACTCGGTGCCAC (SEQ ID NO: 195) | |
| apc 141 | GTCGGTGCAAACAAGCGCAAGTGGTTTAGTGG (SEQ ID NO: 196) | M13 gRNA-tRNA Fragment 3 (tRNA-Gly) for pUC backbone |
| apc 142 | GGCCTCTTCGCTATTACGCC (SEQ ID NO: 193) | |
| apc 143 | AAAGGTCTCATGATCCTCTTAAGTTGTTCATTTGCGTTTCAGAGCTAGAAATAGCAAGTTG (SEQ ID NO: 197) | mtx2 VH4420 3x cassette Fragment 1 for pY120 backbone |
| apc 144 | AAAGGTCTCAATGAAACTCTCTGCGCAAGCCCGGAATCG (SEQ ID NO: 198) | |
| apc 145 | AAAGGTCTCATCATGGGCCTCCCGTTTCAGAGCTAGAAATAGCAAGTTG (SEQ ID NO: 199) | mtx2 VH4420 3x cassette Fragment 2 for pY120 backbone |

TABLE 5-continued

| Primers used in this study<br>NOTE: Primers are shaded in pairs used for PCR, except for the one-sided, whichnested PCRs, have primers. Repeated primers are BOLDED. | | |
|---|---|---|
| Primer # | Sequence (5' to 3') | PCR Purpose |
| apc 146 | AAAGGTCTCAAAACGAGAAAGGACTGG AGTGGGTTGCGCAAGCCCGGAATCG (SEQ ID NO: 200) | |
| apc 147 | AAAGGTCTCATGATCGTCACTAAAAGTG AATCCAGGTTTCAGAGCTAGGCCAACAT G (SEQ ID NO: 201) | m13 VH4420 3x cassette Fragment 1 for pY120 backbone |
| apc 148 | AAAGGTCTCAGAAACATATTATGCGCAA GCCCGGAATCG (SEQ ID NO: 202) | |
| apc 149 | AAAGGTCTCATTTCATAATTATAGTTTC AGAGCTAGGCCAACATG (SEQ ID NO: 203) | m13 VH4420 3x cassette Fragment 2 for pY120 backbone |
| apc 150 | AAAGGTCTCAAAACGTACAGTAATAGAT ACCCATTGCGCAAGCCCGGAATCG (SEQ ID NO: 204) | |

TABLE 6

| gRNA scaffold sequences | |
|---|---|
| gRNA variant | Annotated Sequence: modifications are underlined, MS2 loops are bolded |
| No MS2 | GTTTCAGAGCTAGAAATAGCAAGTTGAAATAAGGCTAGTCCGTTATCAACTTGAAAAAGTGGCACCGAGTCGGTGC (SEQ ID NO: 1) |
| M1, 3 | GTTTCAGAGCTAGGCCA**ACATGAGGATCACCCATGT**CTGCAGGGCCTAGCAAGTTGAAATAAGGCTAGTCCGTTATCAACTTGGCCA**ACATGAGGATCACCCATGT**CTGCAGGGCCAAGTGGCACCGAGTCGGTGC (SEQ ID NO: 2) |
| Mtx2 | GTTTCAGAGCTAGAAATAGCAAGTTGAAATAAGGCTAGTCCGTTATCAACTTGAAAAAGTGGCACCGAGTCGGTGCGGGAGC**ACATGAGGATCACCCATGT**GCCACGAGCG**ACATGAGGATCACCCATGT**CGCTCGTGTTCCC (SEQ ID NO: 3) |
| Mt | GTTTCAGAGCTAGAAATAGCAAGTTGAAATAAGGCTAGTCCGTTATCAACTTGAAAAAGTGGCACCGAGTCGGTGCGCGC**ACATGAGGATCACCCATGT**GC (SEQ ID NO: 4) |
| M1 | GTTTCAGAGCTAGGCCA**ACATGAGGATCACCCATGT**CTGCAGGGCCTAGCAAGTTGAAATAAGGCTAGTCCGTTATCAACTTGAAAAAGTGGCACCGAGTCGGTGC (SEQ ID NO: 5) |
| M3 | GTTTCAGAGCTAGAAATAGCAAGTTGAAATAAGGCTAGTCCGTTATCAACTTGGCCA**ACATGAGGATCACCCATGT**CTGCAGGGCCAAGTGGCACCGAGTCGGTGC (SEQ ID NO: 6) |
| M4 | GTTTCAGAGCTAGAAATAGCAAGTTGAAATAAGGCTAGTCCGTTATCAACTTGAAAAAGTGGCACCGAGGCCA**ACATGAGGATCACCCATGT**CTGCAGGGCCTCGGTGC (SEQ ID NO: 7) |
| M14 | GTTTCAGAGCTAGGCCA**ACATGAGGATCACCCATGT**CTGCAGGGCCTAGCAAGTTGAAATAAGGCTAGTCCGTTATCAACTTGAAAAAGTGGCACCGAGGCCA**ACATGAGGATCACCCATGT**CTGCAGGGCCTCGGTGC (SEQ ID NO: 8) |
| M34 | GTTTCAGAGCTAGAAATAGCAAGTTGAAATAAGGCTAGTCCGTTATCAACTTGGCCA**ACATGAGGATCACCCATGT**CTGCAGGGCCAAGTGGCACCGAGGCCA**ACATGAGGATCACCCATGT**CTGCAGGGCCTCGGTGC (SEQ ID NO: 9) |

TABLE 6-continued

| gRNA scaffold sequences | |
|---|---|
| gRNA variant | Annotated Sequence: modifications are underlined, MS2 loops are bolded |
| M1tx2 | GTTTCAGAGCTAGGCCA**ACATGAGGATCACCCATGT**CTGCAGGGCCTAGCAAGTTGAAATAAGGCTAGTCCGTTATCAACTTGAAAAAGTGGCACCGAGTCGGTGCGGGAGC**ACATGAGGATCACCCATGT**GCCACGAGCG**ACATGAGGATCACCCATGT**CGCTCGTGTTCCC (SEQ ID NO: 10) |
| M3tx2 | GTTTCAGAGCTAGAAATAGCAAGTTGAAATAAGGCTAGTCCGTTATCAACTTGGCCA**ACATGAGGATCACCCATGT**CTGCAGGGCCAAGTGGCACCGAGTCGGTGCGGGAGC**ACATGAGGATCACCCATGT**GCCACGAGCG**ACATGAGGATCACCCATGT**CGCTCGTGTTCCC (SEQ ID NO: 11) |
| M13tx2 | GTTTCAGAGCTAGGCCA**ACATGAGGATCACCCATGT**CTGCAGGGCCTAGCAAGTTGAAATAAGGCTAGTCCGTTATCAACTTGGCCA**ACATGAGGATCACCCATGT**CTGCAGGGCCAAGTGGCACCGAGTCGGTGCGGGAGC**ACATGAGGATCACCCATGT**GCCACGAGCG**ACATGAGGATCACCCATGT**CGCTCGTGTTCCC (SEQ ID NO: 12) |
| M13t | GTTTCAGAGCTAGGCCA**ACATGAGGATCACCCATGT**CTGCAGGGCCTAGCAAGTTGAAATAAGGCTAGTCCGTTATCAACTTGGCCA**ACATGAGGATCACCCATGT**CTGCAGGGCCAAGTGGCACCGAGTCGGTGCGCGC**ACATGAGGATCACCCATGT**GC (SEQ ID NO: 13) |

TABLE 7

| gRNA spacer sequences | |
|---|---|
| gRNA Spacer Name | Sequence |
| 18L or T1 | GTAGCTGAAGGTGGTCACGA (SEQ ID NO: 26) |
| t22L or T2 | CCGGCAAGCTGCCCGTGCCC (SEQ ID NO: 27) |
| t74L or T3 | GGCGAGGGCGATGCCACCTA (SEQ ID NO: 28) |
| NT1 | CGGCGTCGAAGCCTGTAAAG (SEQ ID NO: 29) |

TABLE 7-continued

| gRNA spacer sequences | |
|---|---|
| gRNA Spacer Name | Sequence |
| 81L | CTTCAGGGTCAGCTTGCCGT (SEQ ID NO: 30) |
| 48L | GGGCACGGGCAGCTTGCCGG (SEQ ID NO: 31) |
| 28L | GTGGTCACGAGGGTGGGCCA (SEQ ID NO: 32) |
| 6L | GCACTGCACGCCGTAGCTGA (SEQ ID NO: 33) |
| 29R | GTCGTGCTGCTTCATGTGGT (SEQ ID NO: 34) |
| 62R | GACGTAGCCTTCGGGCATGG (SEQ ID NO: 35) |
| 84R | TGAAGAAGATGGTGCGCTCC (SEQ ID NO: 36) |
| t78R | TTCAAGTCCGCCATGCCCGA (SEQ ID NO: 209) |
| Mtx2, VHCDR1 | GAGAGTTTCATGGGCCTCCC (SEQ ID NO: 37) |
| Mtx2, VHCDR2 | ACCCACTCCAGTCCTTTCTC (SEQ ID NO: 38) |
| Mtx2, VHCDR3 | CTCTTAAGTTGTTCATTTGC (SEQ ID NO: 39) |
| M13, VHCDR1 | GTCACTAAAAGTGAATCCAG (SEQ ID NO: 210) |
| M13, VHCDR2 | TAATATGTTTCATAATTATA (SEQ ID NO: 211) |
| M13, VHCDR3 | ATGGGTATCTATTACTGTAC (SEQ ID NO: 212) |

TABLE 8

Substitution rates of gRNA variants

| gRNA variant | Avg substitution rate over ±50-bp window | Relative substitution rate |
|---|---|---|
| m3 | 0.62 | 1 |
| m3ext | 0.71 | 1.15 |
| m13 | 1.67 | 1 |
| m13ext | 1.75 | 1.05 |

TABLE 9

Mutations introduced after engineering promoters using yeast diversifying base editor (yDBE).

| Mutant | Mutations |
|---|---|
| L1-3 | 1 sub |
| 3x-6 | 6 subs |
| 3x-7 | 6 subs, 1 insert |
| 3x-8 | 7 subs |

TABLE 10

Alternative MS2 Loops

| Ms2 loop variant | Full gRNA scaffold sequence (loop insertion in bold, standard MS2 underlined) |
|---|---|
| Regular gRNA scaffold | GTTTCAGAGCTAGAAATAGCAAGTTGAAATAAGGCTAGTCCGTTATCAACTTGAAAAAGTGGCACCGAGTCGGTGCGCGCACATGAGGATCACCCATGTGC (SEQ ID NO: 4) |
| f63 | GTTTCAGAGCTAGAAATAGCAAGTTGAAATAAGGCTAGTCCGTTATCAACTT**GCCGTCCACAGTCACTGGGTCAGCGGC**AAGTGGCACCGAGTCGGTGC (SEQ ID NO: 14) |
| f53 | GTTTCAGAGCTAGAAATAGCAAGTTGAAATAAGGCTAGTCCGTTATCAACTT**GGCCAACCGGAGGATCACCACGGGTGCAGGGCC**AAGTGGCACCGAGTCGGTGC (SEQ ID NO: 15) |
| m3s | GTTTCAGAGCTAGAAATAGCAAGTTGAAATAAGGCTAGTCCGTTATCAACTT**GGCCACATGAGGATCACCCATGTGGCC**AAGTGGCACCGAGTCGGTGC (SEQ ID NO: 16) |
| m3ext | GTTTCAGAGCTAGAAATAGCAAGTTGAAATAAGGCTAGTCCGTTATCAACTT**GGCCACTGGACATGAGGATCACCCATGTCCAGCTGCAGGGCC**AAGTGGCACCGAGTCGGTGC (SEQ ID NO: 17) |
| m3 | GTTTCAGAGCTAGAAATAGCAAGTTGAAATAAGGCTAGTCCGTTATCAACTT**GGCCAACATGAGGATCACCCATGTCTGCAGGGCC**AAGTGGCACCGAGTCGGTGC (SEQ ID NO: 6) |
| m1, f63 | GTTTCAGAGCTA**GGCCAACATGAGGATCACCCATGTCTGCAGGGCC**TAGCAAGTTGAAATAAGGCTAGTCCGTTATCAACTT**GCCGTCCACAGTCACTGGGTCAGCGGC**AAGTGGCACCGAGTCGGTGC (SEQ ID NO: 18) |
| m1, f53 | GTTTCAGAGCTA**GGCCAACATGAGGATCACCCATGTCTGCAGGGCC**TAGCAAGTTGAAATAAGGCTAGTCCGTTATCAACTT**GGCCAACCGGAGGATCACCACGGGTGCAGGGCC**AAGTGGCACCGAGTCGGTGC (SEQ ID NO: 19) |
| m1, 3s | GTTTCAGAGCTA**GGCCAACATGAGGATCACCCATGTCTGCAGGGCC**TAGCAAGTTGAAATAAGGCTAGTCCGTTATCAACTT**GGCCACATGAGGATCACCCATGTGGCC**AAGTGGCACCGAGTCGGTGC (SEQ ID NO: 20) |
| m1, 3ext | GTTTCAGAGCTA**GGCCAACATGAGGATCACCCATGTCTGCAGGGCC**TAGCAAGTTGAAATAAGGCTAGTCCGTTATCAACTT**GGCCACTGGACATGAGGATCACCCATGTCCAGCTGCAGGGCC**AAGTGGCACCGAGTCGGTGC (SEQ ID NO: 21) |
| m1, 3 | GTTTCAGAGCTA**GGCCAACATGAGGATCACCCATGTCTGCAGGGCC**TAGCAAGTTGAAATAAGGCTAGTCCGTTATCAACTT**GGCCAACATGAGGATCACCCATGTCTGCAGGGCC**AAGTGGCACCGAGTCGGTGC (SEQ ID NO: 2) |

TABLE 11

DNA sequences of MCP-AID*Δ and dCas9

| Protein Name | DNA Sequence |
|---|---|
| MCP-AID*Δ<br>Highlighting:<br>MCP in bold<br>AID*Δ in italics<br>SV40 NLS<br>with underline | **ATGGCTAGTAATTTTACTCAATTCGTGTTAGTGGACAAC**<br>**GGTGGTACTGGTGATGTAACAGTTGCTCCATCTAATTTT**<br>**GCCAATGGCGTGGCTGAGTGGATTTCCAGTAACTCCAGA**<br>**TCACAAGCCTACAAAGTGACATGCTCCGTTCGTCAATCC**<br>**TCCGCTCAGAAGAGAAAATATACCATAAAGGTGGAAGTC**<br>**CCAAAGGTCGCCACCCAAACCGTTGGTGGAGTAGAATTA**<br>**CCTGTAGCCGCTTGGCGTTCATACTTAAACATGGAATTA**<br>**ACAATTCCCATTTTTGCCACTAACTCAGACTGTGAATTA**<br>**ATAGTAAAAGCAATGCAAGGCTTATTAAAGGATGGAAAC**<br>**CCAATCCCTTCAGCAATTGCTGCTAATTCAGGCATTTAT**<br>**TCAGCA**GGAGGTGGAGGTTCAGGCGGTGGCGGAAGTGGAG<br>GCGGTGGTTCAGGC*CCTAAGAAAAAGAGAAAAGTG*GCCGCAG<br>CCGGCTCTATGGATTCACTATTAATGAATAGAAGAGAATTT<br>TTGTACCAATTTAAGAACGTGAGATGGGCTAAAGGTAGAAG<br>GGAAACTTATCTATGTTACGTAGTGAAAAGAAGAGACTCAG<br>CAACTTCCTTTTCTTTAGATTTCGGTTACTTAAGAAATAAGA<br>ACGGCTGTCATGTTGAATTGTTGTTCTTGAGGTACATAAGTG<br>ACTGGGACCTAGATCCTGGAAGGTGTTATCGTGTTACATGG<br>TTTATCTCTTGGTCACCATGCTATGATTGTGCCAGACACGTA<br>GCTGATTTCTTACGTGGTAACCCAAATTTATCATTAAGAATT<br>TTCACCGCTAGATTGTATTTTTGCGAAGATAGGAAAGCTGA<br>GCCTGAAGGCTTAAGAAGATTACATAGAGCCGGAGTTCAGA<br>TTGCAATAATGACTTTCAAAGATTACTTTTACTGCTGGAATA<br>CCTTCGTCGAAAATCATGGTAGAACCTTCAAAGCTTGGGAA<br>GGCTTGCACGAAAACTCCGTCAGATTGAGTAGGCAATTAAG<br>AAGAATATTGCTACCCTTGTACGAAGTTGACGATTTACGTG<br>ATGCATTCAGGACATAA (SEQ ID NO: 22) |
| dCas9<br>Highlighting:<br>SV40 NLS in bold | ATGGATAAAAAGTATAGTATTGGTTTAGCTATTGGTACTAA<br>CTCTGTGGGTTGGGCAGTTATCACTGACGAATATAAAGTTC<br>CATCAAAGAAATTTAAGGTGTTAGGTAACACTGACAGACAC<br>TCAATAAAAAAGAATCTTATCGGTGCTCTTTTGTTCGACTCC<br>GGTGAAACTGCCGAGGCTACACGTTTAAAAAGAACAGCAA<br>GAAGAAGATATACCCGTAGAAAAAATAGAATATGTTATTTA<br>CAAGAAATCTTTTCTAATGAAATGGCTAAAGTTGATGATTC<br>CTTTTTCCATAGATTGGAAGAGTCATTTTTGGTTGAAGAAGA<br>CAAAAAGCATGAGAGACATCCAATCTTTGGGAATATAGTTG<br>ATGAAGTGGCTTACCATGAAAAATATCCTACCATTTATCATT<br>TAAGAAAGAAATTGGTAGATTCAACTGATAAAGCTGACCTT<br>AGATTAATCTATTTAGCACTTGCCCATATGATTAAATTTAGA<br>GGTCATTTTTTGATTGAAGGTGATTTGAACCCAGATAATTCT<br>GACGTGGATAAATTATTTATTCAATTAGTCCAAACCTACAA<br>CCAATTATTTGAGGAAAATCCAATTAATGCTAGTGGTGTCG<br>ATGCCAAAGCTATATTATCAGCCAGATTATCAAAATCTAGA<br>CGTTTGGAAAATTTGATTGCCCAATTGCCAGGAGAAAAAAA<br>GAATGGATTATTTGGAAACTTGATCGCATTATCATTGGGTTT<br>GACACCAAATTTTAAATCTAATTTTGATTTAGCTGAAGATGC<br>TAAATTACAATTATCAAAAGACACCTATGACGACGATTTGG<br>ACAATTTACTTGCTCAAATTGGTGATCAATATGCAGATTTGT<br>TCTTAGCTGCTAAAAACTTATCTGATGCTATTTTGTTGTCTG<br>ATATTTTGAGAGTGAACACAGAAATAACCAAAGCTCCATTA<br>TCAGCATCTATGATCAAACGTTATGATGAACACCATCAGGA<br>TTTGACTTTATTGAAAGCTTTGGTGAGACAACAATTGCCAG<br>AGAAGTATAAAGAAATCTTTTTCGATCAATCTAAAAACGGG<br>TATGCAGGTTATATTGATGGGGGTGCCTCCCAAGAGGAATT<br>TTACAAATTTATAAAACCTATTTTAGAAAAGATGGATGGGA<br>CTGAGGAACTTTTGGTCAAATTGAACAGAGAAGATTTGTTA<br>CGTAAACAGAGAACTTTTGATAATGGTAGTATACCTCACCA<br>AATTCATTTGGGTGAGTTGCATGCAATTTTAAGAAGACAAG<br>AAGATTTTTATCCATTTTTAAAAGATAATAGAGAAAAAATC<br>GAGAAAATTTTAACCTTTAGAATTCCATACTATGTTGGGCCT<br>TTGGCTAGAGGTAATTCAAGATTTGCCTGGATGACACGTAA<br>ATCAGAAGAAACTATTACCCCTTGGAATTTTGAAGAGGTTG<br>TTGATAAAGGAGCATCAGCACAGAGTTTTATTGAAAGAATG<br>ACCAATTTCGATAAAAACTTACCAAATGAAAAAGTTTTACC<br>AAAACATTCCTTGTTATACGAATATTTTACTGTTTACAATGA<br>ACTTACAAAGGTTAAATATGTTACTGAAGGTATGCGTAAGC<br>CAGCCTTTTTATCTGGAGAACAGAAAAAGGCAATAGTTGAT<br>TTATTGTTTAAAACAAATAGAAAAGTTACTGTTAAACAATT<br>AAAAGAAGATTACTTTAAGAAAATTGAATGTTTTGATTCAG<br>TTGAAATCAGTGGTGTTGAAGACAGATTTAATGCTAGTTTA<br>GGAACTTACCATGATTTACTTAAAATTATCAAAGATAAAGA<br>TTTCTTGGATAACGAAGAAAATGAAGACATTTTAGAAGACA<br>TTGTTTTAACCTTAACTTTATTCGAAGATAGAGAGATGATTG<br>AAGAACGTTTGAAGACTTATGCACATTTGTTTGACGATAAA<br>GTGATGAAACAGTTGAAAAGAAGACGTTATACTGGATGGG |

TABLE 11-continued

DNA sequences of MCP-AID*Δ and dCas9

| Protein Name | DNA Sequence |
|---|---|
| | GTAGATTGTCTCGTAAATTGATCAATGGAATTAGAGATAAA<br>CAAAGTGGTAAAACTATCTTGGACTTTTTGAAATCTGACGG<br>ATTTGCTAATAGAAATTTCATGCAATTGATCCACGACGATA<br>GTTTGACATTTAAAGAAGACATCCAAAAGGCCCAAGTGAGT<br>GGGCAAGGTGATTCATTACATGAACATATTGCAAATTTAGC<br>CGGATCTCCTGCTATTAAGAAAGGGATATTACAAACTGTTA<br>AAGTTGTGGATGAATTAGTGAAAGTAATGGGAAGACATAA<br>ACCTGAAAACATTGTCATTGAGATGGCAAGAGAAAATCAA<br>ACTACACAAAAAGGACAGAAAAATAGTAGAGAACGTATGA<br>AAAGAATAGAAGAGGGTATTAAAGAATTGGGTAGTCAAAT<br>ATTGAAAGAACACCCAGTGGAAAATACCCAGTTGCAAAAT<br>GAAAAATTATATCTTTACTACCTTCAAAATGGACGTGATAT<br>GTATGTTGATCAGGAATTAGATATAAATAGACTTTCAGATT<br>ATGATGTAGATGCCATAGTTCCACAATCTTTCTTGAAAGAT<br>GATTCCATAGACAATAAAGTATTAACTAGAAGTGATAAAAA<br>TAGAGGTAAAAGTGATAATGTCCCAAGTGAGGAAGTCGTCA<br>AAAAGATGAAAAATTACTGGCGTCAACTTTTGAATGCTAAA<br>TTAATTACTCAAAGAAAATTTGATAATTTGACTAAAGCAGA<br>AAGAGGTGGGCTTTCTGAATTAGATAAAGCCGGGTTCATTA<br>AAAGACAATTGGTCGAAACTAGACAAATTACTAAACATGTT<br>GCCCAAATTTTAGATTCCCGTATGAACACTAAGTATGACGA<br>AAATGATAAGTTAATACGTGAGGTTAAAGTCATTACTTTAA<br>AATCAAAACTTGTCTCTGATTTCAGAAAGGATTTCCAATTCT<br>ATAAAGTTAGAGAAATTAATAATTATCATCATGCTCATGAT<br>GCATATTTGAATGCTGTAGTTGGAACTGCTTTAATCAAGAA<br>ATACCCTAAATTAGAATCTGAATTTGTATATGGTGATTACA<br>AAGTCTATGATGTTAGAAAGATGATTGCTAAATCAGAACAA<br>GAAATTGGTAAAGCTACAGCTAAATACTTCTTTTACTCTAAC<br>ATTATGAATTTCTTTAAAACAGAAATTACTTTGGCAAACGG<br>TGAAATTAGAAAAAGACCTCTTATTGAAACAAATGGTGAGA<br>CTGGAGAGATAGTTTGGGACAAAGGGCGTGATTTCGCTACT<br>GTTAGAAAAGTTTTATCAATGCCACAAGTTAACATTGTAAA<br>GAAAACAGAGGTTCAAACTGGTGGTTTCTCAAAAGAAAGTA<br>TTTTGCCTAAAAGAAATAGTGATAAATTGATTGCCAGAAAA<br>AAGGATTGGGATCCAAAGAAATATGGTGGTTTCGACTCACC<br>AACCGTAGCCTATTCTGTTTTGGTTGTGGCAAAGGTTGAAA<br>AGGGTAAAAGTAAAAAGCTTAAATCAGTAAAAGAACTTTTG<br>GGTATTACAATAATGGAAAGAAGTTCCTTTGAAAAGAACCC<br>TATTGATTTTTTGGAAGCTAAAGGTTATAAGGAAGTAAAGA<br>AGGACTTAATAATCAAATTGCCTAAATATTCTTTATTTGAAT<br>TAGAAAATGGGAGAAAAAGAATGTTGGCTTCTGCTGGAGA<br>ATTGCAAAAGGGTAATGAATTAGCATTGCCTTCCAAATATG<br>TTAACTTCTTGTATTTAGCTTCACACTATGAAAAGTTGAAAG<br>GGTCACCAGAAGATAACGAGCAAAAACAATTATTTGTTGAA<br>CAACACAAACACTACTTAGATGAGATTATAGAACAAATTAG<br>TGAATTCAGTAAAAGAGTGATATTAGCTGATGCAAATTTAG<br>ATAAAGTTTTGTCAGCCTATAACAAACATAGAGATAAGCCA<br>ATTAGAGAACAAGCAGAAAACATTATTCACTTATTTACCCT<br>TACCAATTTAGGAGCACCTGCTGCTTTCAAGTATTTTGATAC<br>AACAATTGATCGTAAAAGATATACCTCAACAAAAGAAGTCT<br>TAGACGCCACCTTAATTCATCAATCAATCACTGGATTGTATG<br>AGACAAGAATTGATTTGTCTCAATTGGGTGGTGATGAAGGG<br>GCTGAT**CCTAAGAAGAAAAGAAAAGTTGATCCAAAGAAA**<br>**AAGCGTAAGGTGGATCCTAAGAAAAAGAGAAAGGTT**TAA<br>(SEQ ID NO: 23) |
| wtGFP | ATGGTGAGCAAGGGCGAGGAGCTGTTCACCGGGGTGGTGC<br>CCATCCTGGTCGAGCTGGACGGCGACGTAAACGGCCACAAG<br>TTCAGCGTGTCCGGCGAGGGCGAGGGCGATGCCACCTACGG<br>CAAGCTGACCCTGAAGTTCATCTGCACCACCGGCAAGCTGC<br>CCGTGCCCTGGCCCACCCTCGTGACCACCTTCAGCTACGGC<br>GTGCAGTGCTTCAGCCGCTACCCCGACCACATGAAGCAGCA<br>CGACTTCTTCAAGTCCGCCATGCCCGAAGGCTACGTCCAGG<br>AGCGCACCATCTTCTTCAAGGACGACGGCAACTACAAGACC<br>CGCGCCGAGGTGAAGTTCGAGGGCGACACCCTGGTGAACC<br>GCATCGAGCTGAAGGGCATCGACTTCAAGGAGGACGGCAA<br>CATCCTGGGGCACAAGCTGGAGTACAACTACAACAGCCACA<br>ACGTCTATATCATGGCCGACAAGCAGAAGAACGGCATCAA<br>GGTGAACTTCAAGATCCGCCACAACATCGAGGACGGCAGC<br>GTGCAGCTCGCCGACCACTACCAGCAGAACACCCCCATCGG<br>CGACGGCCCCGTGCTGCTGCCCGACAACCACTACCTGAGCA<br>CCCAGTCCGCCCTGAGCAAAGACCCCAACGAGAAGCGCGA<br>TCACATGGTCCTGCTGGAGTTCGTGACCGCCGCCGGGATCA<br>CTCTCGGCATGGACGAGCTGTACAAGTAA (SEQ ID NO: 24) |

TABLE 11-continued

| DNA sequences of MCP-AID*Δ and dCas9 | |
|---|---|
| Protein Name | DNA Sequence |
| AGA2-4420<br>Highlighting:<br>AGA2 in bold<br>4-4-20 in<br>italics<br>C-myc<br>underlined | **ATGCAGTTACTTCGCTGTTTTTCAATATTTTCTGTTATTG**<br>**CTTCAGTTTTAGCACAGGAACTGACAACTATATGCGAGC**<br>**AAATCCCCTCACCAACTTTAGAATCGACGCCGTACTCTT**<br>**TGTCAACGACTACTATTTTGGCCAACGGGAAGGCAATGC**<br>**AAGGAGTTTTTGAATATTACAAATCAGTAACGTTTGTCA**<br>**GTAATTGCGGTTCTCACCCCTCAACAACTAGCAAAGGCA**<br>**GCCCCATAAACACACAGTATGTTTTTAAGGACAATAGCT**<br>**CGACG**ATTGAAGGTAGATACCCATACGACGTTCCAGACTAC<br>GCTCTGCAGGCTAGTGGTGGTGGTGGTTCTGGTGGTGGTGG<br>TTCTGGTGGTGGTGGTTCTGCTAGC*GACGTCGTTATGACTCAA*<br>*ACACCACTATCACTTCCTGTTAGTCTAGGTGATCAAGCCTCCATC*<br>*TCTTGCAGATCTAGTCAGAGCCTTGTACACAGTAATGGAAACAC*<br>*CTATTTACGTTGGTACCTGCAGAAGCCAGGCCAGTCTCCAAAGG*<br>*TCCTGATCTACAAAGTTTCCAACCGATTTTCTGGGGTCCCAGAC*<br>*AGGTTCAGTGGCAGTGGATCAGGGACAGATTTCACACTCAAGAT*<br>*CAGCAGAGTGGAGGCTGAGGATCTGGGAGTTTATTTCTGCTCTC*<br>*AAAGTACACATGTTCCGTGGACGTTCGGTGGAGGCACCAAGCTT*<br>*GAAATTAAGTCCTCTGCTGATGATGCTAAGAAGGATGCTGCTAA*<br>*GAAGGATGATGCTAAGAAAGATGATGCTAAGAAAGATGGTGACG*<br>*TCAAACTGGATGAGACTGGAGGAGGCTTGGTGCAACCTGGGAG*<br>*GCCCATGAAACTCTCCTGTGTTGCCTCTGGATTCACTTTTAGTGA*<br>*CTACTGGATGAACTGGGTCCGCCAGTCTCCAGAGAAAGGACTG*<br>*GAGTGGGTAGCACAAATTAGAAACAAACCTTATAATTATGAAACA*<br>*TATTATTCAGATTCTGTGAAAGGCAGATTCACCATCTCAAGAGAT*<br>*GATTCCAAAAGTAGTGTCTACCTGCAAATGAACAACTTAAGAGTT*<br>*GAAGACATGGGTATCTATTACTGTACGGGTTCTTACTATGGTATG*<br>*GACTACTGGGGTCAAGGAACCTCAGTCACCGTCTCCTCA*GAAC<br>AAAAGCTTATTTCTGAAGAAGACTTGTAA (SEQ ID NO: 25) |

| SEQUENCES | | |
|---|---|---|
| SEQ ID NO | Sequence Features | Sequence |
| <SEQ ID NO: 1; DNA; > | gRNA, no MS2 loop | TAGTCCGTTATCAACTTGAAAAAGTGGCACCGAGT<br>GTTTCAGAGCTAGAAATAGCAAGTTGAAATAAGGC<br>CGGTGC |
| <SEQ ID NO: 2; DNA;; > | gRNA, m1, 3 (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGGCCAACATGAGGATCACCCATGT<br>CTGCAGGGCCAAGTGGCACCGAGTCGGTGC |
| <SEQ ID NO: 3; DNA; > | gRNA, mtx2 (MS2 loop underlined) | GTTTCAGAGCTAGAAATAGCAAGTTGAAATAAGGC<br>TAGTCCGTTATCAACTTGAAAAAGTGGCACCGAGT<br>CGGTGCGGGAGCACATGAGGATCACCCATGTGCCA<br>CGAGCGACATGAGGATCACCCATGTCGCTCGTGTT<br>ccc |
| <SEQ ID NO: 4; DNA; > | gRNA, mtx1 (MS2 loop underlined) | GTTTCAGAGCTAGAAATAGCAAGTTGAAATAAGGC<br>TAGTCCGTTATCAACTTGAAAAAGTGGCACCGAGT<br>CGGTGCGCGCACATGAGGATCACCCATGTGC |
| <SEQ ID NO: 5; DNA; > | gRNA, m1 (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGAAAAAGTGGCACCGAGTCGGTG<br>C |
| <SEQ ID NO: 6; DNA; > | gRNA, m3 (MS2 loop underlined) | GTTTCAGAGCTAGAAATAGCAAGTTGAAATAAGGC<br>TAGTCCGTTATCAACTTGGCCAACATGAGGATCACC<br>CATGTCTGCAGGGCCAAGTGGCACCGAGTCGGTGC |
| <SEQ ID NO: 7; DNA; > | gRNA, m4 (MS2<br><br>loop underlined) | GTTTCAGAGCTAGAAATAGCAAGTTGAAATAAGGC<br>TAGTCCGTTATCAACTTGAAAAAGTGGCACCGAGG<br>CCAACATGAGGATCACCCATGTCTGCAGGGCCTCG<br>GTGC |
| <SEQ ID NO: 8; DNA; > | gRNA, m1, 4 (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGAAAAAGTGGCACCGAGGCCAAC<br>ATGAGGATCACCCATGTCTGCAGGGCCTCGGTGC |

-continued

SEQUENCES

| SEQ ID NO | Sequence Features | Sequence |
|---|---|---|
| <SEQ ID NO: 9; DNA; > | gRNA, m3, 4 (MS2 loop underlined) | GTTTCAGAGCTAGAAATAGCAAGTTGAAATAAGGC<br>TAGTCCGTTATCAACTTGGCCAACATGAGGATCACC<br>CATGTCTGCAGGGCCAAGTGGCACCGAGGCCAACA<br>TGAGGATCACCCATGTCTGCAGGGCCTCGGTGC |
| <SEQ ID NO: 10; DNA; > | gRNA, m1, tx2 (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGAAAAAGTGGCACCGAGTCGGTG<br>CGGGAGCACATGAGGATCACCCATGTGCCACGAGC<br>GACATGAGGATCACCCATGTCGCTCGTGTTCCC |
| <SEQ ID NO: 11; DNA; > | gRNA, m3, tx2 (MS2 loop underlined) | GTTTCAGAGCTAGAAATAGCAAGTTGAAATAAGGC<br>TAGTCCGTTATCAACTTGGCCAACATGAGGATCACC<br>CATGTCTGCAGGGCCAAGTGGCACCGAGTCGGTGC<br>GGGAGCACATGAGGATCACCCATGTGCCACGAGCG<br>ACATGAGGATCACCCATGTCGCTCGTGTTCCC |
| <SEQ ID NO: 12; DNA; > | gRNA, m1, 3, tx2 (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGGCCAACATGAGGATCACCCATGT<br>CTGCAGGGCCAAGTGGCACCGAGTCGGTGCGGGAG<br>CACATGAGGATCACCCATGTGCCACGAGCGACATG<br>AGGATCACCCATGTCGCTCGTGTTCCC |
| <SEQ ID NO: 13; DNA; > | gRNA, m1, 3, tx1 (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGGCCAACATGAGGATCACCCATGT<br>CTGCAGGGCCAAGTGGCACCGAGTCGGTGCGCGCA<br>CATGAGGATCACCCATGTGC |
| <SEQ ID NO: 14; DNA; > | gRNA, f63 (MS2 loop underlined) | GTTTCAGAGCTAGAAATAGCAAGTTGAAATAAGGC<br>TAGTCCGTTATCAACTTGCCGTCCACAGTCACTGGG<br>TCAGCGGCAAGTGGCACCGAGTCGGTGC |
| <SEQ ID NO: 15; DNA; | gRNA, f53 (MS2 loop underlined) | GTTTCAGAGCTAGAAATAGCAAGTTGAAATAAGGC<br>TAGTCCGTTATCAACTTGGCCAACCGGAGGATCAC<br>CACGGGTGCAGGGCCAAGTGGCACCGAGTCGGTGC |
| <SEQ ID NO: 16; DNA; | gRNA, m3s (MS2 loop underlined) | GTTTCAGAGCTAGAAATAGCAAGTTGAAATAAGGC<br>TAGTCCGTTATCAACTTGGCCACATGAGGATCACCC<br>ATGTGGCCAAGTGGCACCGAGTCGGTGC |
| <SEQ ID NO: 17; DNA; > | gRNA, m3ext (MS2 loop underlined) | GTTTCAGAGCTAGAAATAGCAAGTTGAAATAAGGC<br>TAGTCCGTTATCAACTTGGCCACTGGACATGAGGAT<br>CACCCATGTCCAGCTGCAGGGCCAAGTGGCACCGA<br>GTCGGTGC |
| <SEQ ID NO: 18; DNA; > | gRNA, m1, f63 (MS2) loop underlined) | GTTTCAGAGCTAGGCCAACATGAGGATCACCCATG<br>TCTGCAGGGCCTAGCAAGTTGAAATAAGGCTAGTC<br>CGTTATCAACTTGCCGTCCACAGTCACTGGGTCAGC<br>GGCAAGTGGCACCGAGTCGGTGC |
| <SEQ ID NO: 19; DNA; > | gRNA, m1, f53 (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGGCCAACCGGAGGATCACCACGG<br>GTGCAGGGCCAAGTGGCACCGAGTCGGTGC |
| <SEQ ID NO: 20; DNA; > | gRNA, m1, 3s (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGGCCACATGAGGATCACCCATGTG<br>GCCAAGTGGCACCGAGTCGGTGC |
| <SEQ ID NO: 21; DNA; > | gRNA, m1, 3ext (MS2 loop underlined) | GTTTCAGAGCTAGGCCAACATGAGGATCACCCATG<br>TCTGCAGGGCCTAGCAAGTTGAAATAAGGCTAGTC<br>CGTTATCAACTTGGCCACTGGACATGAGGATCACC<br>CATGTCCAGCTGCAGGGCCAAGTGGCACCGAGTCG<br>GTGC |
| <SEQ ID NO: 22; DNA; > | MCP-AID*Δ | ATGGCTAGTAATTTTACTCAATTCGTGTTAGTGGAC<br>AACGGTGGTACTGGTGATGTAACAGTTGCTCCATCT<br>AATTTTGCCAATGGCGTGGCTGAGTGGATTTCCAGT<br>AACTCCAGATCACAAGCCTACAAAGTGACATGCTC<br>CGTTCGTCAATCCTCCGCTCAGAAGAGAAAATATA<br>CCATAAAGGTGGAAGTCCCAAAGGTCGCCACCCAA<br>ACCGTTGGTGGAGTAGAATTACCTGTAGCCGCTTGG |

-continued

| SEQUENCES | | |
|---|---|---|
| SEQ ID NO | Sequence Features | Sequence |
| | | CGTTCATACTTAAACATGGAATTAACAATTCCCATT TTTGCCACTAACTCAGACTGTGAATTAATAGTAAAA GCAATGCAAGGCTTATTAAAGGATGGAAACCCAAT CCCTTCAGCAATTGCTGCTAATTCAGGCATTTATTC AGCAGGAGGTGGAGGTTCAGGCGGTGGCGGAAGTG GAGGCGGTGGTTCAGGCCCTAAGAAAAAGAGAAA AGTGGCCGCAGCCGGCTCTATGGATTCACTATTAAT GAATAGAAGAGAATTTTTGTACCAATTTAAGAACG TGAGATGGGCTAAAGGTAGAAGGGAAACTTATCTA TGTTACGTAGTGAAAAGAAGAGACTCAGCAACTTC CTTTTCTTTAGATTTCGGTTACTTAAGAAATAAGAA CGGCTGTCATGTTGAATTGTTGTTCTTGAGGTACAT AAGTGACTGGGACCTAGATCCTGGAAGGTGTTATC GTGTTACATGGTTTATCTCTTGGTCACCATGCTATG ATTGTGCCAGACACGTAGCTGATTTCTTACGTGGTA ACCCAAATTTATCATTAAGAATTTTCACCGCTAGAT TGTATTTTTGCGAAGATAGGAAAGCTGAGCCTGAA GGCTTAAGAAGATTACATAGAGCCGGAGTTCAGAT TGCAATAATGACTTTCAAAGATTACTTTTACTGCTG GAATACCTTCGTCGAAAATCATGGTAGAACCTTCA AAGCTTGGGAAGGCTTGCACGAAAACTCCGTCAGA TTGAGTAGGCAATTAAGAAGAATATTGCTACCCTTG TACGAAGTTGACGATTTACGTGATGCATTCAGGAC ATAA |
| <SEQ ID NO: 23; DNA; | >dCas9 | ATGGATAAAAAGTATAGTATTGGTTTAGCTATTGGT ACTAACTCTGTGGGTTGGGCAGTTATCACTGACGAA TATAAAGTTCCATCAAAGAAATTTAAGGTGTTAGGT AACACTGACAGACACTCAATAAAAAAGAATCTTAT CGGTGCTCTTTTGTTCGACTCCGGTGAAACTGCCGA GGCTACACGTTTAAAAAGAACAGCAAGAAGAAGAT ATACCCGTAGAAAAAATAGAATATGTTATTTACAA GAAATCTTTTCTAATGAAATGGCTAAAGTTGATGAT TCCTTTTTCCATAGATTGGAAGAGTCATTTTTGGTT GAAGAAGACAAAAAGCATGAGAGACATCCAATCTT TGGGAATATAGTTGATGAAGTGGCTTACCATGAAA AATATCCTACCATTTATCATTTAAGAAAGAAATTGG TAGATTCAACTGATAAAGCTGACCTTAGATTAATCT ATTTAGCACTTGCCCATATGATTAAATTTAGAGGTC ATTTTTTGATTGAAGGTGATTTGAACCCAGATAATT CTGACGTGGATAAATTATTTATTCAATTAGTCCAAA CCTACAACCAATTATTTGAGGAAAATCCAATTAATG CTAGTGGTGTCGATGCCAAAGCTATATTATCAGCCA GATTATCAAAATCTAGACGTTTGGAAAATTTGATTG CCCAATTGCCAGGAGAAAAAAAGAATGGATTATTT GGAAACTTGATCGCATTATCATTGGGTTTGACACCA AATTTTAAATCTAATTTTGATTTAGCTGAAGATGCT AAATTACAATTATCAAAAGACACCTATGACGACGA TTTGGACAATTTACTTGCTCAAATTGGTGATCAATA TGCAGATTTGTTCTTAGCTGCTAAAAACTTATCTGA TGCTATTTTGTTGTCTGATATTTTGAGAGTGAACAC AGAAATAACCAAAGCTCCATTATCAGCATCTATGA TCAAACGTTATGATGAACACCATCAGGATTTGACTT TATTGAAAGCTTTGGTGAGACAACAATTGCCAGAG AAGTATAAAGAAATCTTTTTCGATCAATCTAAAAAC GGGTATGCAGGTTATATTGATGGGGGTGCCTCCCA AGAGGAATTTTACAAATTTATAAAACCTATTTTAGA AAAGATGGATGGGACTGAGGAACTTTTGGTCAAAT TGAACAGAGAAGATTTGTTACGTAAACAGAGAACT TTTGATAATGGTAGTATACCTCACCAAATTCATTTG GGTGAGTTGCATGCAATTTTAAGAAGACAAGAAGA TTTTTATCCATTTTTAAAAGATAATAGAGAAAAAAT CGAGAAAATTTTAACCTTTAGAATTCCATACTATGT TGGGCCTTTGGCTAGAGGTAATTCAAGATTTGCCTG GATGACACGTAAATCAGAAGAAACTATTACCCCTT GGAATTTTGAAGAGGTTGTTGATAAAGGAGCATCA GCACAGAGTTTTATTGAAAGAATGACCAATTTCGAT AAAAACTTACCAAATGAAAAAGTTTTACCAAAACA TTCCTTGTTATACGAATATTTTACTGTTTACAATGA ACTTACAAAGGTTAAATATGTTACTGAAGGTATGC GTAAGCCAGCCTTTTTATCTGGAGAACAGAAAAAG GCAATAGTTGATTTATTGTTTAAAACAAATAGAAA AGTTACTGTTAAACAATTAAAAGAAGATTACTTTAA GAAAATTGAATGTTTTGATTCAGTTGAAATCAGTGG TGTTGAAGACAGATTTAATGCTAGTTTAGGAACTTA |

-continued

SEQUENCES

| SEQ ID NO | Sequence Features | Sequence |
|---|---|---|
| | | CCATGATTTACTTAAAATTATCAAAGATAAAGATTT<br>CTTGGATAACGAAGAAAATGAAGACATTTTAGAAG<br>ACATTGTTTTAACCTTAACTTTATTCGAAGATAGAG<br>AGATGATTGAAGAACGTTTGAAGACTTATGCACAT<br>TTGTTTGACGATAAAGTGATGAAACAGTTGAAAAG<br>AAGACGTTATACTGGATGGGGTAGATTGTCTCGTA<br>AATTGATCAATGGAATTAGAGATAAACAAAGTGGT<br>AAAACTATCTTGGACTTTTTGAAATCTGACGGATTT<br>GCTAATAGAAATTTCATGCAATTGATCCACGACGAT<br>AGTTTGACATTTAAAGAAGACATCCAAAAGGCCCA<br>AGTGAGTGGGCAAGGTGATTCATTACATGAACATA<br>TTGCAAATTTAGCCGGATCTCCTGCTATTAAGAAAG<br>GGATATTACAAACTGTTAAAGTTGTGGATGAATTA<br>GTGAAAGTAATGGGAAGACATAAACCTGAAAACAT<br>TGTCATTGAGATGGCAAGAGAAAATCAAACTACAC<br>AAAAAGGACAGAAAAATAGTAGAGAACGTATGAA<br>AAGAATAGAAGAGGGTATTAAAGAATTGGGTAGTC<br>AAATATTGAAAGAACACCCAGTGGAAAATACCCAG<br>TTGCAAAATGAAAAATTATATCTTTACTACCTTCAA<br>AATGGACGTGATATGTATGTTGATCAGGAATTAGA<br>TATAAATAGACTTTCAGATTATGATGTAGATGCCAT<br>AGTTCCACAATCTTTCTTGAAAGATGATTCCATAGA<br>CAATAAAGTATTAACTAGAAGTGATAAAAATAGAG<br>GTAAAAGTGATAATGTCCCAAGTGAGGAAGTCGTC<br>AAAAAGATGAAAAATTACTGGCGTCAACTTTTGAA<br>TGCTAAATTAATTACTCAAAGAAAATTTGATAATTT<br>GACTAAAGCAGAAAGAGGTGGGCTTTCTGAATTAG<br>ATAAAGCCGGGTTCATTAAAAGACAATTGGTCGAA<br>ACTAGACAAATTACTAAACATGTTGCCCAAATTTTA<br>GATTCCCGTATGAACACTAAGTATGACGAAAATGA<br>TAAGTTAATACGTGAGGTTAAAGTCATTACTTTAAA<br>ATCAAAACTTGTCTCTGATTTCAGAAAGGATTTCCA<br>ATTCTATAAAGTTAGAGAAATTAATAATTATCATCA<br>TGCTCATGATGCATATTTGAATGCTGTAGTTGGAAC<br>TGCTTTAATCAAGAAATACCCTAAATTAGAATCTGA<br>ATTTGTATATGGTGATTACAAAGTCTATGATGTTAG<br>AAAGATGATTGCTAAATCAGAACAAGAAATTGGTA<br>AAGCTACAGCTAAATACTTCTTTTACTCTAACATTA<br>TGAATTTCTTTAAAACAGAAATTACTTTGGCAAACG<br>GTGAAATTAGAAAAAGACCTCTTATTGAAACAAAT<br>GGTGAGACTGGAGAGATAGTTTGGGACAAAGGGCG<br>TGATTTCGCTACTGTTAGAAAAGTTTTATCAATGCC<br>ACAAGTTAACATTGTAAAGAAAACAGAGGTTCAAA<br>CTGGTGGTTTCTCAAAAGAAAGTATTTTGCCTAAAA<br>GAAATAGTGATAAATTGATTGCCAGAAAAAAGGAT<br>TGGGATCCAAAGAAATATGGTGGTTTCGACTCACC<br>AACCGTAGCCTATTCTGTTTTGGTTGTGGCAAAGGT<br>TGAAAAGGGTAAAAGTAAAAAGCTTAAATCAGTAA<br>AAGAACTTTTGGGTATTACAATAATGGAAAGAAGT<br>TCCTTTGAAAAGAACCCTATTGATTTTTTGGAAGCT<br>AAAGGTTATAAGGAAGTAAAGAAGGACTTAATAAT<br>CAAATTGCCTAAATATTCTTTATTTGAATTAGAAAA<br>TGGGAGAAAAAGAATGTTGGCTTCTGCTGGAGAAT<br>TGCAAAAGGGTAATGAATTAGCATTGCCTTCCAAA<br>TATGTTAACTTCTTGTATTTAGCTTCACACTATGAA<br>AAGTTGAAAGGGTCACCAGAAGATAACGAGCAAA<br>AACAATTATTTGTTGAACAACACAAACACTACTTAG<br>ATGAGATTATAGAACAAATTAGTGAATTCAGTAAA<br>AGAGTGATATTAGCTGATGCAAATTTAGATAAAGT<br>TTTGTCAGCCTATAACAAACATAGAGATAAGCCAA<br>TTAGAGAACAAGCAGAAAACATTATTCACTTATTTA<br>CCCTTACCAATTTAGGAGCACCTGCTGCTTTCAAGT<br>ATTTTGATACAACAATTGATCGTAAAAGATATACCT<br>CAACAAAAGAAGTCTTAGACGCCACCTTAATTCAT<br>CAATCAATCACTGGATTGTATGAGACAAGAATTGA<br>TTTGTCTCAATTGGGTGGTGATGAAGGGGCTGATCC<br>TAAGAAGAAAAGAAAAGTTGATCCAAAGAAAAAG<br>CGTAAGGTGGATCCTAAGAAAAAGAGAAAGGTTTAA |
| <SEQ ID NO: 24; DNA; > | wtGFP | ATGGTGAGCAAGGGCGAGGAGCTGTTCACCGGGGT<br>GGTGCCCATCCTGGTCGAGCTGGACGGCGACGTAA<br>ACGGCCACAAGTTCAGCGTGTCCGGCGAGGGCGAG<br>GGCGATGCCACCTACGGCAAGCTGACCCTGAAGTT<br>CATCTGCACCACCGGCAAGCTGCCCGTGCCCTGGC<br>CCACCCTCGTGACCACCTTCAGCTACGGCGTGCAGT |

-continued

| SEQUENCES | | |
|---|---|---|
| SEQ ID NO | Sequence Features | Sequence |
| | | GCTTCAGCCGCTACCCCGACCACATGAAGCAGCAC<br>GACTTCTTCAAGTCCGCCATGCCCGAAGGCTACGTC<br>CAGGAGCGCACCATCTTCTTCAAGGACGACGGCAA<br>CTACAAGACCCGCGCCGAGGTGAAGTTCGAGGGCG<br>ACACCCTGGTGAACCGCATCGAGCTGAAGGGCATC<br>GACTTCAAGGAGGACGGCAACATCCTGGGGCACAA<br>GCTGGAGTACAACTACAACAGCCACAACGTCTATA<br>TCATGGCCGACAAGCAGAAGAACGGCATCAAGGTG<br>AACTTCAAGATCCGCCACAACATCGAGGACGGCAG<br>CGTGCAGCTCGCCGACCACTACCAGCAGAACACCC<br>CCATCGGCGACGGCCCCGTGCTGCTGCCCGACAAC<br>CACTACCTGAGCACCCAGTCCGCCCTGAGCAAAGA<br>CCCCAACGAGAAGCGCGATCACATGGTCCTGCTGG<br>AGTTCGTGACCGCCGCCGGGATCACTCTCGGCATG<br>GACGAGCTGTACAAGTAA |
| <SEQ ID NO: 25; DNA; > | AGA2-4420 | ATGCAGTTACTTCGCTGTTTTTCAATATTTTCTGTTA<br>TTGCTTCAGTTTTAGCACAGGAACTGACAACTATAT<br>GCGAGCAAATCCCCTCACCAACTTTAGAATCGACG<br>CCGTACTCTTTGTCAACGACTACTATTTTGGCCAAC<br>GGGAAGGCAATGCAAGGAGTTTTTGAATATTACAA<br>ATCAGTAACGTTTGTCAGTAATTGCGGTTCTCACCC<br>CTCAACAACTAGCAAAGGCAGCCCCATAAACACAC<br>AGTATGTTTTTAAGGACAATAGCTCGACGATTGAA<br>GGTAGATACCCATACGACGTTCCAGACTACGCTCT<br>GCAGGCTAGTGGTGGTGGTGGTTCTGGTGGTGGTG<br>GTTCTGGTGGTGGTGGTTCTGCTAGCGACGTCGTTA<br>TGACTCAAACACCACTATCACTTCCTGTTAGTCTAG<br>GTGATCAAGCCTCCATCTCTTGCAGATCTAGTCAGA<br>GCCTTGTACACAGTAATGGAAACACCTATTTACGTT<br>GGTACCTGCAGAAGCCAGGCCAGTCTCCAAAGGTC<br>CTGATCTACAAAGTTTCCAACCGATTTTCTGGGGTC<br>CCAGACAGGTTCAGTGGCAGTGGATCAGGGACAGA<br>TTTCACACTCAAGATCAGCAGAGTGGAGGCTGAGG<br>ATCTGGGAGTTTATTTCTGCTCTCAAAGTACACATG<br>TTCCGTGGACGTTCGGTGGAGGCACCAAGCTTGAA<br>ATTAAGTCCTCTGCTGATGATGCTAAGAAGGATGCT<br>GCTAAGAAGGATGATGCTAAGAAAGATGATGCTAA<br>GAAAGATGGTGACGTCAAACTGGATGAGACTGGAG<br>GAGGCTTGGTGCAACCTGGGAGGCCCATGAAACTC<br>TCCTGTGTTGCCTCTGGATTCACTTTTAGTGACTACT<br>GGATGAACTGGGTCCGCCAGTCTCCAGAGAAAGGA<br>CTGGAGTGGGTAGCACAAATTAGAAACAAACCTTA<br>TAATTATGAAACATATTATTCAGATTCTGTGAAAGG<br>CAGATTCACCATCTCAAGAGATGATTCCAAAAGTA<br>GTGTCTACCTGCAAATGAACAACTTAAGAGTTGAA<br>GACATGGGTATCTATTACTGTACGGGTTCTTACTAT<br>GGTATGGACTACTGGGGTCAAGGAACCTCAGTCAC<br>CGTCTCCTCAGAACAAAAGCTTATTTCTGAAGAAG<br>ACTTGTAA |
| <SEQ ID NO: 26; DNA; > | T1 gRNA spacer | GTAGCTGAAGGTGGTCACGA |
| <SEQ ID NO: 27; DNA; > | T2 gRNA spacer | CCGGCAAGCTGCCCGTGCCC |
| <SEQ ID NO: 28; DNA; > | T3 gRNA spacer | GGCGAGGGCGATGCCACCTA |
| <SEQ ID NO: 29; DNA; > | NT1 gRNA spacer | CGGCGTCGAAGCCTGTAAAG |
| <SEQ ID NO: 30; DNA; > | 81L gRNA spacer | CTTCAGGGTCAGCTTGCCGT |
| <SEQ ID NO: 31; DNA; > | 48L gRNA spacer | GGGCACGGGCAGCTTGCCGG |
| <SEQ ID NO: 32; DNA; > | 28L gRNA spacer | GTGGTCACGAGGGTGGGCCA |
| <SEQ ID NO: 33; DNA; > | 6L gRNA spacer | GCACTGCACGCCGTAGCTGA |
| <SEQ ID NO: 34; DNA; > | 29R gRNA spacer | GTCGTGCTGCTTCATGTGGT |
| <SEQ ID NO: 35; DNA; > | 62R gRNA spacer | GACGTAGCCTTCGGGCATGG |
| <SEQ ID NO: 36; DNA; > | 84R gRNA spacer | TGAAGAAGATGGTGCGCTCC |
| <SEQ ID NO: 37; DNA; > | HCDR1 | GAGAGTTTCATGGGCCTCCC |

-continued

SEQUENCES

| SEQ ID NO | Sequence Features | Sequence |
|---|---|---|
| <SEQ ID NO: 38; DNA; > | HCDR2 | ACCCACTCCAGTCCTTTCTC |
| <SEQ ID NO: 39; DNA; > | HCDR3 | CTCTTAAGTTGTTCATTTGC |
| <SEQ ID NO: 40; DNA; > | MCP-GGGGS(3x)-SV40NLS (linker sequences are bolded, nuclear localization sequences (NLS) is underlined) | ATGGCTAGTAATTTTACTCAATTCGTGTTAGTGGAC<br>AACGGTGGTACTGGTGATGTAACAGTTGCTCCATCT<br>AATTTTGCCAATGGCGTGGCTGAGTGGATTTCCAGT<br>AACTCCAGATCACAAGCCTACAAAGTGACATGCTC<br>CGTTCGTCAATCCTCCGCTCAGAAGAGAAAATATA<br>CCATAAAGGTGGAAGTCCCAAAGGTCGCCACCCAA<br>ACCGTTGGTGGAGTAGAATTACCTGTAGCCGCTTGG<br>CGTTCATACTTAAACATGGAATTAACAATTCCCATT<br>TTTGCCACTAACTCAGACTGTGAATTAATAGTAAAA<br>GCAATGCAAGGCTTATTAAAGGATGGAAACCCAAT<br>CCCTTCAGCAATTGCTGCTAATTCAGGCATTTATTC<br>AGCA**GGAGGTGGAGGTTCAGGCGGTGGCGGAA**<br>**GTGGAGGCGGTGGTTCAGGC**CCTAAGAAAAAGA<br>GAAAAGTG**GCCGCAGCCGGCTCT** |
| <SEQ ID NO: 41; AA; > | MCP-GGGGS(3x)-SV40NLS (linker sequences are bolded, nuclear localization sequences (NLS) is underlined) | MASNFTQFVLVDNGGTGDVTVAPSNFANGVAEWISS<br>NSRSQAYKVTCSVRQSSAQKRKYTIKVEVPKVATQT<br>VGGVELPVAAWRSYLNMELTIPIFATNSDCELIVKAM<br>QGLLKDGNPIPSAIAANSGIYSA**GGGGSGGGGSGGG**<br>**GSG**PKKKRKV**AAAGS** |
| <SEQ ID NO: 42; DNA; > | AID*Δ | ATGGATTCACTATTAATGAATAGAAGAGAATTTTTG<br>TACCAATTTAAGAACGTGAGATGGGCTAAAGGTAG<br>AAGGGAAACTTATCTATGTTACGTAGTGAAAAGAA<br>GAGACTCAGCAACTTCCTTTTCTTTAGATTTCGGTT<br>ACTTAAGAAATAAGAACGGCTGTCATGTTGAATTG<br>TTGTTCTTGAGGTACATAAGTGACTGGGACCTAGAT<br>CCTGGAAGGTGTTATCGTGTTACATGGTTTATCTCT<br>TGGTCACCATGCTATGATTGTGCCAGACACGTAGCT<br>GATTTCTTACGTGGTAACCCAAATTTATCATTAAGA<br>ATTTTCACCGCTAGATTGTATTTTTGCGAAGATAGG<br>AAAGCTGAGCCTGAAGGCTTAAGAAGATTACATAG<br>AGCCGGAGTTCAGATTGCAATAATGACTTTCAAAG<br>ATTACTTTTACTGCTGGAATACCTTCGTCGAAAATC<br>ATGGTAGAACCTTCAAAGCTTGGGAAGGCTTGCAC<br>GAAAACTCCGTCAGATTGAGTAGGCAATTAAGAAG<br>AATATTGCTACCCTTGTACGAAGTTGACGATTTACG<br>TGATGCATTCAGGACATAA |
| <SEQ ID NO: 43; AA; > | AID*Δ | MDSLLMNRREFLYQFKNVRWAKGRRETYLCYVVKR<br>RDSATSFSLDFGYLRNKNGCHVELLFLRYISDWDLDP<br>GRCYRVTWFISWSPCYDCARHVADFLRGNPNLSLRIF<br>TARLYFCEDRKAEPEGLRRLHRAGVQIAIMTFKDYFY<br>CWNTFVENHGRTFKAWEGLHENSVRLSRQLRRILLPL<br>YEVDDLRDAFRT* |
| <SEQ ID NO: 44; DNA; > | AID731Δ | ATGGATTCACTATTAATGAATAGAAGTGAATTTTTG<br>TACCAATTTAAGAACGTGAGATGGGCTAAAGGTAG<br>AAGGGAAACTTATCTATGTTACGTAGTGAAAAGAT<br>GCGACTCAGCAACTTCCTTTTCTCGTGATTTCGGTT<br>ACTTAAGAAATAAGAACGGCTGTCATGTTGAATTG<br>TTGTTCTTGAGGTACATAAGTGACTGGGACCTAGAT<br>CCTGGAAGGTGTTATCGTGTTACATGGTTTATCTCT<br>TGGTCACCATGCTCTGATTGTGCCAGACTAGTAGCT<br>GATTTCTTACGTGGTAACCCAAATTTATCATTAAGA<br>ATTTTCACCGCTAGATTGTATTTTTGCGAAGATAGG<br>AAAGCTGAGCCTGAAGGCTTAAGAAGATTACATAG<br>AGCCGGAGTTCAGATTGCAATAATGACTTTCGAAG<br>ATTACTTTTACTGCTGGAATACCTTCGTCGAAAATC<br>ATGGTAGAACCTTCAAAGCTTGGGAAGGCTTGCAC<br>GAAAACTCCGTCAGATTGAGTAGGCAATTAAGAAG<br>AATATTGCTACCCTTGTACGAAGTTGACGATTTACG<br>TGATGCATTCAGGACATAA |

-continued

SEQUENCES

| SEQ ID NO | Sequence Features | Sequence |
|---|---|---|
| <SEQ ID NO: 45; AA; > | AID731Δ | MDSLLMNRSEFLYQFKNVRWAKGRRETYLCYVVKR<br>CDSATSFSRDFGYLRNKNGCHVELLFLRYISDWDLDP<br>GRCYRVTWFISWSPCSDCARLVADFLRGNPNLSLRIF<br>TARLYFCEDRKAEPEGLRRLHRAGVQIAIMTFEDYFY<br>CWNTFVENHGRTFKAWEGLHENSVRLSRQLRRILLPL<br>YEVDDLRDAFRT* |
| <SEQ ID NO: 46; DNA; > | AID731mono | ATGGATCCAGCTACCTTTACGTACCAATTTAAGAAC<br>GTGAGATGGGCTAAAGGTAGAAGGGAAACTTATCT<br>ATGTTACGTAGTGAAAAGATGCGACTCAGCAACTT<br>CCTTTTCTCGTGATTTCGGTTACTTAAGAAATAAGA<br>ACGGCTGTCATGTTGAATTGTTGTTCTTGAGGTACA<br>TAAGTGACTGGGACCTAGATCCTGGAAGGTGTTAT<br>CGTGTTACATGGTTTATCTCTTGGTCACCATGCTCT<br>GATTGTGCCAGACTAGTAGCTGATTTCTTACGTGGT<br>AACCCAAATTTATCATTAAGAATTTTCACCGCTAGA<br>TTGTATTTTTGCGAAGATAGGAAAGCTGAGCCTGA<br>AGGCTTAAGAAGATTAGCCGAAGCCGGAGTTCAGA<br>TTGCAATAATGACTTTCGAAGATTACTTTTACTGCT<br>GGAATACCTTCGTCGAAAATCATGGTAGAACCTTC<br>AAAGCTTGGGAAGGCTTGCACGAAAACTCCGTCAG<br>ATTGAGTAGGCAATTAAGAAGAATATTGCAGTAA |
| <SEQ ID NO: 47; AA; > | AID731mono | MDPATFTYQFKNVRWAKGRRETYLCYVVKRCDSAT<br>SFSRDFGYLRNKNGCHVELLFLRYISDWDLDPGRCYR<br>VTWFISWSPCSDCARLVADFLRGNPNLSLRIFTARLYF<br>CEDRKAEPEGLRRLAEAGVQIAIMTFEDYFYCWNTFV<br>ENHGRTFKAWEGLHENSVRLSRQLRRILQ* |
| <SEQ ID NO: 48; DNA; > | AID*mono | ATGGATCCAGCTACCTTTACGTACCAATTTAAGAAC<br>GTGAGATGGGCTAAAGGTAGAAGGGAAACTTATCT<br>ATGTTACGTAGTGAAAAGAAGAGACTCAGCAACTT<br>CCTTTTCTTTAGATTTCGGTTACTTAAGAAATAAGA<br>ACGGCTGTCATGTTGAATTGTTGTTCTTGAGGTACA<br>TAAGTGACTGGGACCTAGATCCTGGAAGGTGTTAT<br>CGTGTTACATGGTTTATCTCTTGGTCACCATGCTAT<br>GATTGTGCCAGACACGTAGCTGATTTCTTACGTGGT<br>AACCCAAATTTATCATTAAGAATTTTCACCGCTAGA<br>TTGTATTTTTGCGAAGATAGGAAAGCTGAGCCTGA<br>AGGCTTAAGAAGATTAGCCGAAGCCGGAGTTCAGA<br>TTGCAATAATGACTTTCAAAGATTACTTTTACTGCT<br>GGAATACCTTCGTCGAAAATCATGGTAGAACCTTC<br>AAAGCTTGGGAAGGCTTGCACGAAAACTCCGTCAG<br>ATTGAGTAGGCAATTAAGAAGAATATTGCAGTAA |
| <SEQ ID NO: 49; AA; > | AID*mono | MDPATFTYQFKNVRWAKGRRETYLCYVVKRRDSAT<br>SFSLDFGYLRNKNGCHVELLFLRYISDWDLDPGRCYR<br>VTWFISWSPCYDCARHVADFLRGNPNLSLRIFTARLY<br>FCEDRKAEPEGLRRLAEAGVQIAIMTFKDYFYCWNTF<br>VENHGRTFKAWEGLHENSVRLSRQLRRILQ* |
| <SEQ ID NO: 50; DNA; > | AIDmono | ATGGATCCAGCTACCTTTACGTACCAATTTAAGAAC<br>GTGAGATGGGCTAAAGGTAGAAGGGAAACTTATCT<br>ATGTTACGTAGTGAAAAGAAGAGACTCAGCAACTT<br>CCTTTTCTTTAGATTTCGGTTACTTAAGAAATAAGA<br>ACGGCTGTCATGTTGAATTGTTGTTCTTGAGGTACA<br>TAAGTGACTGGGACCTAGATCCTGGAAGGTGTTAT<br>CGTGTTACATGGTTTACCTCTTGGTCACCATGCTAT<br>GATTGTGCCAGACACGTAGCTGATTTCTTACGTGGT<br>AACCCAAATTTATCATTAAGAATTTTCACCGCTAGA<br>TTGTATTTTTGCGAAGATAGGAAAGCTGAGCCTGA<br>AGGCTTAAGAAGATTAGCCGAAGCCGGAGTTCAGA<br>TTGCAATAATGACTTTCAAAGATTACTTTTACTGCT<br>GGAATACCTTCGTCGAAAATCATGAAAGAACCTTC<br>AAAGCTTGGGAAGGCTTGCACGAAAACTCCGTCAG<br>ATTGAGTAGGCAATTAAGAAGAATATTGCAGTAA |
| <SEQ ID NO: 51; AA; > | AIDmono | MDPATFTYQFKNVRWAKGRRETYLCYVVKRRDSAT<br>SFSLDFGYLRNKNGCHVELLFLRYISDWDLDPGRCYR<br>VTWFTSWSPCYDCARHVADFLRGNPNLSLRIFTARLY<br>FCEDRKAEPEGLRRLAEAGVQIAIMTFKDYFYCWNTF<br>VENHERTFKAWEGLHENSVRLSRQLRRILQ* |
| <SEQ ID NO: 52; DNA; > | Pk1leu2 wild-type promoter | GCTGTGAAGATCCCAGCAAAGGCTTACAAAGTGTT<br>ATCTCTTTTGAGACTTGTTGAGTTGAACACTGGTGT |

-continued

| SEQUENCES | | |
|---|---|---|
| SEQ ID NO | Sequence Features | Sequence |
| | | TTTCATCAAACTTACCAAGGACGTGTACCCATTGTT GAAACTTGTATCACCATATATTGTTATCGGACAACC TTCACTTGCATCTATCCGTTCTTTAATCCAAAAGAG ATCTAGAATAATGTGGCAAAGGCCAGAAGATAAAG AACCAAAAGAGATAATCTTGAATGACAACAATATC GTTGAAGAGAAATTAGGTGATGAAGGTGTCATTTG TATCGAGGATATCATCCATGAGATTTCGACGTTGGG CGAAAATTTCTCGAAATGTACTTTCTTCCTATTACC ATTCAAATTGAACAGAGAAGTCAGTGGATTCGGTG CCATCTCCCGTTTGAATAAACTGAAAATGCGCGAA CAAAACAACAAGACACGTCAAATTTCAAACGCTGC CACGGCTCCAGTTATCCAAGTAGATATCGACACAA TGATTTCCAAGTTGAATTGATTAACTATAAAAGGAA AATATCTGTACAATAGACATCGGGCTCCCATTGGCC CTACCCACATATGTAGAAATACATTACTCTATTCAC TACTGCATTTAGTTATGTTTAACATTTGATATAGCA GACTACCGCCAGGCACAATATATTCCCCTTCCCTCT TGCCATTCGCTGTACTTGTGGTGGATTCCAATTCAG CGCAGTCACGTGCTAGTAATCACCGCATTTTTTTCT TTTCCTTTCAGGCTAAAACCGGTTCCGGGCCTGATC CCTGCACTCATTTTCTAACGGAAAACCTTCAGAAGC ATAACTACCCATTCCAGTTTAGAGACATGACAGGTT CAACATCAGATGCTTCATATACTTTTATATATTGAA TTATATAAATATATCTATGTACTCTAAGTAAGTACA TCTGCTTTAACGCATTCCTACATTTGCTTCGATTTAT TTTTATTGTTGATACCTATTTGAAGAAGTAAAAAGT ATCCCACACTACACAGATTATA |
| <SEQ ID NO: 53; DNA; > | Pkl1eu2 “3x-6” promoter | GCTGTGAAGATCCCAGCAAAGGCTTACAAAGTGTT ATCTCTTTTGAGACTTGTTGAGTTGAACACTGGTGT TTTCATCAAACTTACCAAGGACGTGTACCCATTGTT GAAACTTGTATCACCATATATTGTTATCGGACAACC TTCACTTGCATCTATCCGTTCTTTAATCCAAAAGAG ATCTAGAATAATGTGGCAAAGGCCAGAAGATAAAG AACCAAAAGAGATAATCTTGAATGACAACAATATC GTTGAAGAGAAATTAGGTGATGAAGGTGTCATTTG TATCGAGGATATCATCCATGAGATTTCGACGTTGGG CGAAAATTTCTCGAAATGTACTTTCTTCCTATTACC ATTCAAATTGAACAGAGAAGTCAGTGGATTTGGTG CCATCTCCCGTTTGAATAAACTGAAAATGCGCGAA CAAAACAACAAGACACGTCAAATTTCAAACGCTGC CACGGCTCCAGTTATCCAAGTAGATATCGACACAA TGATTTCCAAGTTGAATTGATTAACTATAAAAGGAA AATATCTGTACAATAGACATCGGGCTCCCATTGGCC CTACCCACATATGTAGAAATACATTACTCTATTCAC TACTGCATTTAGTTATGTTTAACATTTGATATAGCA GACTACCGCCAGGCACAATATATTCCCCTTCCCTCT TGCCATTCGCTATACTTGTGGTGGATTCCAATTCAG CGCAGTCACGTGCTAGTAATCACCGCATTTTTTTCT TTTCCTTTCAGGCTAAAACCGGTTCCGGGCCTGATC CCTGCACTCATTTTCTAACGGAAAACCTTCAGAAGC ATAACCAGCCATTCCAGTTTAGAGACATGACAGAT TCAACATCAGATGCTTCATATACTTTTATATATTCA ATTATATAAATATATCTATGTACTCTAAGTAAGTAC ATCTGCTTTAACGCATTCCTACATTTGCTTCGATTTA TTTTTATTGTTGATACCTATTTGAAGAAGTAAAAAG TATCCCACACTACACAGATTATA |
| <SEQ ID NO: 54; DNA; > | Pkl1eu2 “3x-7” promoter | GCTGTGAAGATCCCAGCAAAGGCTTACAAAGTGTT ATCTCTTTTGAGACTTGTTGAGTTGAACACTGGTGT TTTCATCAAACTTACCAAGGACGTGTACCCATTGTT GAAACTTGTATCACCATATATTGTTATCGGACAACC TTCACTTGCATCTATCCGTTCTTTAATCCAAAAGAG ATCTAGAATAATGTGGCAAAGGCCAGAAGATAAAG AACCAAAAGAGATAATCTTGAATGACAACAATATC GTTGAAGAGAAATTAGGTGATGAAGGTGTCATTTG TATCGAGGATATCATCCATGAGATTTCGACGTTGGG CGAAAATTTCTCGAAATGTACTTTCTTCCTATTACC ATTCAAATTGAACAGAGAAGTCAGTGGATTTGGTG CCATCTCCCGTTTGAATAAACTGAAAATGCGCGAA CAAAACAACAAGACACGTCAAATTTCAAACGCTGC CACGGCTTCAGTTATCCAAGTAGATATCGACACAAT GATTTCCAAGTTGAATTGATTAACTATAAAAGGAA AATATCTGTACAATAGACATCGGGCTCCCATTGGCC CTACCCACATATGTAGAAATACATTACTCTATTCAC |

-continued

| SEQUENCES | | |
|---|---|---|
| SEQ ID NO | Sequence Features | Sequence |
| | | TACTGCATTTAGTTATGTTTAACATTTGATATAGCA GACTACCGCCAGGCACAATATATTCCCCTTCCCTCT TGCCATTCGCTGTACTTGTGGTGGATTCCAATTCAG CGCAGTCACGTGCTAGTAATCACCGCATTTTTTTCT TTTCCTTTCAGGCTAAAACCGGTTCCGGGCCTGATC CCTGCACTCATTTTCTAACGGAAAAATCTTAAGAAG TATAAATACCCATTCCAGTTTAGAGACATGACAGCT TCAACATCAGATGCTTCATATACTTTTATATATTGA ATTATATAAATATATCTATGTACTCTAAGTAAGTAC ATCTGCTTTAACGCATTCCTACATTTGCTTCGATTTA TTTTTATTGTTGATACCTATTTGAAGAAGTAAAAAG TATCCCACACTACACAGATTATA |
| <SEQ ID NO: 55; DNA; > | Pklleu2 "3x-8" promoter | GCTGTGAAGATCCCAGCAAAGGCTTACAAAGTGTT ATCTCTTTTGAGACTTGTTGAGTTGAACACTGGTGT TTTCATCAAACTTACCAAGGACGTGTACCCATTGTT GAAACTTGTATCACCATATATTGTTATCGGACAACC TTCACTTGCATCTATCCGTTCTTTAATCCAAAAGAG ATCTAGAATAATGTGGCAAAGGCCAGAAGATAAAG AACCAAAAGAGATAATCTTGAATGACAACAATATC GTTGAAGAGAAATTAGGTGATGAAGGTGTCATTTG TATCGAGGATATCATCCATGAGATTTCGACGTTGGG CGAAAATTTCTCGAAATGTACTTTCTTCCTATTACC ATTCAAATTGAACAGAGAAGTCAGTGGATTTGGTG CCATCTCCCGTTTGAATAAACTGAAAATGCGCGAA CAAAACAACAAGACACGTCAAATTTCAAACGCTGC CACGGCTCCAGTTATCCAAGTAGATATCGACACAA TGATTTCCAAGTTGAATTGATTAACTATAAAAGGAA AATATCTGTACAATAGACATCGGGCTCCCATTGGCC CTACCCACATATGTAGAAATACATTACTCTATTCAC TACTGCATTTAGTTATGTTTAACATTTGATATAGCA GACTACCGCCAGGCACAATATATTCCCCTTCCCTCT TGCCATTCGCTATACTTGTGGTGGATTCCAATTCAG CGCAGTCACGTGCTAGTAATCACCGCATTTTTTTCT TTTCCTTTCAGGCTAAAACCGGTTCCGGGCCTGATC CCTGCACTCATTTTCTAACGGAAAACCTTCAGAAGC ATAACCAGCCATTCGAGTTTAGAGACATGACAGAT TCAACATCAGATGCTTCATATACTTTTATATATTCA ATTATATAAATATATCTATGTACTCTAAGTAAGTAC ATCTGCTTTAACGCATTCCTACATTTGCTTCGATTTA TTTTTATTGTTGATACCTATTTGAAGAAGTAAAAAG TATCCCACACTACACAGATTAT |
| <SEQ ID NO: 56; DNA; > | Primer # apc001; 5' Flank for Integration at YPRCτ3 | CGGTATTACTCGAGCCCGTAATAC |
| <SEQ ID NO: 57; DNA; > | Primer # apc002; 5' Flank for Integration at YPRCτ3 | GGACACCTGGCTACTTAACCATTCGTTGTTAGTGTG TCGCATACGAGGAATAACGCCGATGGGACGTCAGC ACTGTAC |
| <SEQ ID NO: 58; DNA; > | Primer # apc003; 3' Flank for Integrating 3 Genes @YPRCτ3 | AAAGGAGGTGCACGCATTATGG |
| <SEQ ID NO: 59; DNA; > | Primer # apc004; 3' Flank for Integrating 3 Genes @YPRCτ3 | CCGAACCTAGGATTAGATGTGGTCTAGCACCATATT GCGGACATGGTCCCCCTGTTATTCCAAGGAGGTGA AGAACGTC |
| <SEQ ID NO: 60; DNA; > | Primer # apc005; 5' Flank for Integration @YPRCΔ15 | GGACACCTGGCTACTTAACCATTCGTTGTTAGTGTG TCGCATACGAGGAATAACGCCTTTGCGAAACCCTA TGCTCTG |
| <SEQ ID NO: 61; DNA; > | Primer # apc006; 5' Flank for Integration @YPRCΔ15 | GCCAGGCGCCTTTATATCATATAATTAAGAC |
| <SEQ ID NO: 62; DNA; > | Primer # apc007; 3' Flank for Integrating 2 Genes @YPRCΔ15 | CATTTGGATTGTAATTTCATACTGGAGTAAACATCT CCAGGTGTCTAAGTTCACACAGGAATGGAAGGTCG GGATGAGC |

-continued

| SEQUENCES | | |
|---|---|---|
| SEQ ID NO | Sequence Features | Sequence |
| <SEQ ID NO: 63; DNA; > | Primer # apc008; 3' Flank for Integrating 2 Genes @YPRCΔ15 | ATAAAGCAGCCGCTACCAAACAG |
| <SEQ ID NO: 64; DNA; > | Primer # apc009; 3' Flank for Integration @YORWΔ22 | CGTGATAAACGATCGCCATAACTAAC |
| <SEQ ID NO: 65; DNA; > | Primer # apc010; 3' Flank for Integration @YORWΔ22 | GATTGTAATTTCATACTGGAGTAAACATCTCCAGGT GTCTAAGTTCACACAGGGGACCAACTATCATCCGC TAATTAC |
| <SEQ ID NO: 66; DNA; > | Primer # apc011; 5' Flank for Integrating 2 Genes @YORWΔ22 | CACCGGAGCTTGGATATGATAAAC |
| <SEQ ID NO: 67; DNA; > | Primer # apc012; 5' Flank for Integrating 2 Genes @YORWΔ22 | GGCTACTTAACCATTCGTTGTTAGTGTGTCGCATAC GAGGAATAACGCCTTCGCGGGCTGTTACTTATCC |
| <SEQ ID NO: 68; DNA; > | Primer # apc013; Amplify Pro-gene-Term in HR1 backbone | GGCGTTATTCCTCGTATGCG |
| <SEQ ID NO: 69; DNA; > | Primer # apc014; Amplify Pro-gene-Term in HR1 backbone | GACAATCGCTACAGAAACGATTTTC |
| <SEQ ID NO: 70; DNA; > | Primer # apc015; Amplify Pro-gene-Term in HR2 backbone | AGGACCAAGCGACCTGTGTC |
| <SEQ ID NO: 71; DNA; > | Primer # apc016; Amplify Pro-gene-Term in HR2 backbone | CCTGTGTGAACTTAGACACCTGGAG |
| <SEQ ID NO: 72; DNA; > | Primer # apc017; Amplify Pro-gene-Term in HR3 backbone | TCATTTGGATTGTAATTTCATACTGGAG |
| <SEQ ID NO: 73; DNA; > | Primer # apc018; Amplify Pro-gene-Term in HR3 backbone | TAACAGGGGGACCATGTCC |
| <SEQ ID NO: 74; DNA; > | Primer # apc019; PCR check for integrations @YPRCΔ15 | ACGAGCTTTTGAATTATGGTAATTTTG |
| <SEQ ID NO: 75; DNA; > | Primer # apc020; PCR check for integrations @YPRCΔ15 | TGTTGAGTACTTCAACTTTATTTCCTTC |
| <SEQ ID NO: 76; DNA; > | Primer # apc021; PCR check for integrations @YPRCτ3 | CCGTGAATCAAGCTGATAAACAG |
| <SEQ ID NO: 77; DNA; > | Primer # apc022; PCR check for integrations @YPRCτ3 | CCTGGACACTTTACTTATCTAGCG |

-continued

SEQUENCES

| SEQ ID NO | Sequence Features | Sequence |
|---|---|---|
| <SEQ ID NO: 78; DNA; > | Primer # apc023; PCR check for integrations @YORWΔ22 | GGAAATATATGCGCAGTATGCTCC |
| <SEQ ID NO: 79; DNA; > | Primer # apc024; PCR check for integrations @YORWΔ22 | CGAATCAAACGAATGCTTTGGAAAC |
| <SEQ ID NO: 80; DNA; > | Primer # apc025; PCR pSNR52-gRNA-tSUP4, mimicks amplification from HR1 backbone | GTTATTCCTCGTATGCGACACACTAACAACGAATGG<br>TTAAGTAGCCAGGTGTCCATCCCAGTGAGTTGATTG<br>GAAGACC |
| <SEQ ID NO: 81; DNA; > | Primer # apc026; PCR pSNR52-gRNA-tSUP4, mimicks amplification from HR1 backbone | CAATCGCTACAGAAACGATTTTCAACAGTATTTACC<br>TCGACACAGGTCGCTTGGTCCTGTGAGCTGATACCG<br>CTCGAAG |
| <SEQ ID NO: 82; DNA; > | Primer # apc027 AGA2-4-4-20 for insertion | GTTATTCCTCGTATGCGACACACTAACAACGAATGG<br>TTAAGTAGCCAGGTGTCCATCACATGGCATTACCAC<br>CATATAC |
| <SEQ ID NO: 83; DNA; > | Primer # apc028 AGA2-4-4-20 for insertion | CTACAGAAACGATTTTCAACAGTATTTACCTCGACA<br>CAGGTCGCTTGGTCCTAATTCTCTTAGGATTCGATT<br>CACATTC |
| <SEQ ID NO: 84; DNA; > | Primer # apc029; AGA2-4m5.3 Fragment 1 for pCT backbone | TACTTCTTATTCAAATGTAATAAAAGATCGAATTCC<br>CTACTTCATACATTTTCAATTAAG |
| <SEQ ID NO: 85; DNA; > | Primer # apc030; AGA2-4m5.3 Fragment 1 for pCT backbone | CTAGCAGAACCACCACCACCAGAAC |
| <SEQ ID NO: 86; DNA; > | Primer # apc031; AGA2-4m5.3 Fragment 2 for pCT backbone | GGTGGTGGTGGTTCTGCTAGCGACGTCGTTATGAC |
| <SEQ ID NO: 87; DNA; > | Primer # apc032; AGA2-4m5.3 Fragment 2 for pCT backbone | GTTACATCTACACTGTTGTTATCAGATCTCGAGCTA<br>TTACAAGTCTTCTTCAGAAATAAGCTTTTG |
| <SEQ ID NO: 88; DNA; > | Primer # apc033; wtGFP Fragment 1 for EMY backbone | CAGAGCAGATTGTACTGGGTCTCAAATGGTGAGCA<br>AGGGCGAGG |
| <SEQ ID NO: 89; DNA; > | Primer # apc034; wtGFP Fragment 1 for EMY backbone | CGCCGTAGCTGAAGGTGGTCACGAGGGTGG |
| <SEQ ID NO: 90; DNA; > | Primer # apc035; wtGFP Fragment 2 for EMY backbone | GTGACCACCTTCAGCTACGGCGTGCAGTGCTTC |
| <SEQ ID NO: 91; DNA; > | Primer # apc036; wGFP Fragment 2 for EMY backbone | GAGCTGATACCGCTCGGTCTCTTTTACTTGTACAGC<br>TCGTCCATG |
| <SEQ ID NO: 92; DNA;; > | Primer # apc037; AGA2-4-4-20 for EMY backbone | CATCAGAGCAGATTGTACTGGGTCTCAAATGCAGTT<br>ACTTCGCTGTTTTTC |
| <SEQ ID NO: 93; DNA; > | Primer # apc038; AGA2-4-4-20 for EMY backbone | GTGAGCTGATACCGCTCGGTCTCTTTTACAAGTCTT<br>CTTCAGAAATAAGCTTTTG |

-continued

| SEQUENCES | | |
|---|---|---|
| SEQ ID NO | Sequence Features | Sequence |
| <SEQ ID NO: 94; DNA; > | Primer # apc039; AGA2-4-4-20 mutants for HR backbone | AAAGGTCTCAGTGCACATGGCATTACCACCATATA CATATCC |
| <SEQ ID NO: 95; DNA; > | Primer # apc040; AGA2-4-4-20 mutants for HR backbone | AAAGGTCTCAGAGGAATTCTCTTAGGATTCGATTCA CATTCATC |
| <SEQ ID NO: 96; DNA; > | Primer # apc041; High-throughput sequencing of GFP | ACACTCTTTCCCTACACGACGCTCTTCCGATCTATC ACGAATGGTGAGCAAGGGCGAGGAGC |
| <SEQ ID NO: 97; DNA; > | Primer # apc042; High-throughput sequencing of GFP | GACTGGAGTTCAGACGTGTGCTCTTCCGATCTCGAT GTTCAGCTCGATGCGGTTCACCAGG |
| <SEQ ID NO: 98; DNA; > | Primer # apc043; dCas9 Fragment 1 for EMY backbone | CATCAGAGCAGATTGTACTGGGTCTCAAATGGATA AAAAGTATAGTATTGGTTTAGCTATTG |
| <SEQ ID NO: 99; DNA; > | Primer # apc044; dCas9 Fragment 1 for EMY backbone | CAAGAAAGATTGTGGAACTATGGCATCTACATCAT AATCTGAAAG |
| <SEQ ID NO: 100; DNA; > | Primer # apc045; dCas9 Fragment 2 for EMY backbone | CTTTCAGATTATGATGTAGATGCCATAGTTCCACAA TCTTTCTTG |
| <SEQ ID NO: 101; DNA; > | Primer # apc046; dCas9 Fragment 2 for EMY backbone | GAGCTGATACCGCTCGGTCTCTTTTAAACCTTTCTC TTTTTCTTAGGATCCAC |
| <SEQ ID NO: 102; DNA;; > | Primer # apc047; Nested PCR to fust RFA3 to dCas9 for EMY backbone, reverse primer | GAGCTGATACCGCTCGGTCTCTTTTAGTATATTTCT GGGTATTTCTTACATAGTCTC |
| <SEQ ID NO: 103; DNA; > | Primer # apc048; forward primer 1 | CTAGCGGATCCGAGACTCCTGGGACCTCAGAGTCT GCTACACCCGAAAGTTCAGGTGGATCTTCTGGTG |
| <SEQ ID NO: 104; DNA; > | Primer # apc049; forward primer 2 | GGTGGATCCTAAGAAAAAGAGAAAGGTTTCCGGTG GATCTTCTGGTGGTTCTAGCGGATCCGAGACTCC |
| <SEQ ID NO: 105; DNA; > | Primer # apc050; Nested PCR to fuse AID731Δ to dCas9 for EMY backbone, reverse primer | GAGCTGATACCGCTCGGTCTCTTTTATGTCCTGAAT GCATCACGTAAATC |
| <SEQ ID NO: 106; DNA; > | Primer # apc051; forward primer 1 | TTCAGGTGGAGGCAGTGGAGGTGGTGGATCTATGG ATTCACTATTAATGAATAGAAGTG |
| <SEQ ID NO: 107; DNA; > | Primer # apc052; forward primer 2 | CGTAAGGTGGATCCTAAGAAAAAGAGAAAGGTTTC AGGTGGAGGCAGTGGAG |
| <SEQ ID NO: 108; DNA; > | Primer # apc053; MCP-AID*Δ for EMY backbone | CATCAGAGCAGATTGTACTGGGTCTCAAATGGCTA GTAATTTTACTCAATTCGTG |
| <SEQ ID NO: 109; DNA; > | Primer # apc054; MCP-AID*Δ for EMY backbone | GAGCTGATACCGCTCGGTCTCTTTTATGTCCTGAAT GCATCACGTAAATC |
| <SEQ ID NO: 110; DNA; > | Primer # apc055; MCP-AIDdead Fragment 1 (MCP) for EMY backbone | CTCTTTTTCTTAGGGCCTGAACC |

-continued

| SEQUENCES | | |
|---|---|---|
| SEQ ID NO | Sequence Features | Sequence |
| <SEQ ID NO: 111; DNA; > | Primer # apc056; MCP-AIDdead Fragment 2 (AIDdead) for EMY backbone | AGGCCCTAAGAAAAAGAGAAAAGTGG |
| <SEQ ID NO: 112; DNA;; > | Primer # apc057; MCP-AIDmono Fragment 1 (MCP) for EMY backbone | ATCCATGCCGGCTGCGGCCACTTTTC |
| <SEQ ID NO: 113; DNA; > | Primer # apc058; MCP-AIDmono Fragment 2 for backbone | EMYTTTACGTACCAATTTAAGAACGTGAGATGG GAAAAGTGGCCGCAGCCGGCATGGATCCAGCTACC |
| <SEQ ID NO: 114; DNA; > | Primer # apc059; MCP-AIDmono Fragment 2 for EMY backbone | ACAC CATGGTGACCAAGAGGTAAACCATGTAACACGATA |
| <SEQ ID NO: 115; DNA; > | Primer # apc060 MCP-AIDmono Fragment 3 for EMY backbone | GTGTTACATGGTTTACCTCTTGGTCACCATGCTATG |
| <SEQ ID NO: 116; DNA; > | Primer # apc061; MCP-AIDmono Fragment 3 for EMY backbone | CTGAACTCCGGCTTCGGCTAATCTTCTTAAGCCTTC AGGC |
| <SEQ ID NO: 117; DNA; > | Primer # apc062; MCP-AIDmono Fragment 4 for EMY backbone | AGGCTTAAGAAGATTAGCCGAAGCCGGAGTTCAGA TTGC |
| <SEQ ID NO: 118; DNA; > | Primer # apc063; MCP-AIDmono Fragment 4 for EMY backbone | CTTCTTAATTGCCTAC GAGCTGATACCGCTCGGTCTCTTTTACTGCAATATT |
| <SEQ ID NO: 119; DNA; > | Primer # apc064; MCP-AID*mono Fragment 1 for EMY backbone | CC GGTGACCAAGAGATAAACCATGTAACACGATAACA |
| <SEQ ID NO: 120; DNA; > | Primer # apc065; MCP-AID*mono Fragment 2 for EMY backbone | CGTGTTACATGGTTTATCTCTTGGTCACCATGCTAT G |
| <SEQ ID NO: 121; DNA; > | Primer # apc066; MCP-AID*mono Fragment 2 for EMY backbone | AGCTTTGAAGGTTCTACCATGATTTTCGACGAAGGT ATTC |
| <SEQ ID NO:122; DNA;; > | Primer # apc067; MCP-AID*mono Fragment 3 for EMY backbone | GTCGAAAATCATGGTAGAACCTTCAAAGCTTGGG |
| <SEQ ID NO: 123; DNA; > | Primer # apc068; MCP-AID*mono Fragment 3 for EMY backbone | GAGCTGATACCGCTCGGTC |
| <SEQ ID NO: 124; DNA; > | Primer # apc069; AID731Δ Fragment 1 for EMY backbone | GGTACAAAAATTCACTTCTATTCATTAATAGTGAAT CCATAGAG |

-continued

| SEQUENCES | | |
|---|---|---|
| SEQ ID NO | Sequence Features | Sequence |
| <SEQ ID NO: 125; DNA; > | Primer # apc070; AID731Δ Fragment 2 for EMY backbone | GGATTCACTATTAATGAATAGAAGTGAATTTTTGTA CCAATTTAAGAACGTG |
| <SEQ ID NO: 126; DNA; > | Primer # apc071; AID731Δ Fragment 2 for EMY backbone | ACGAGAAAAGGAAGTTGCTGAGTCGCATCTTTTCA CTACGTAACATAGATAAG |
| <SEQ ID NO: 127; DNA; > | Primer # apc072; AID731Δ Fragment 3 for EMY backbone | ACTTAAGAAATAAGAACG TGCGACTCAGCAACTTCCTTTTCTCGTGATTTCGGTT |
| <SEQ ID NO: 128; DNA; > | Primer # apc073; AID731Δ Fragment 3 for EMY backbone | CAAGAG CAGCTACTAGTCTGGCACAATCAGAGCATGGTGAC |
| <SEQ ID NO: 129; DNA; > | Primer # apc074; AID731Δ Fragment 4 for EMY backbone | GCTCTGATTGTGCCAGACTAGTAGCTGATTTCTTAC GTGGTAAC |
| <SEQ ID NO: 130; DNA; > | Primer # apc075; AID731Δ Fragment 4 for EMY backbone | CAGCAGTAAAAGTAATCTTCGAAAGTCATTATTGC AATCTGAAC |
| <SEQ ID NO: 131; DNA; > | Primer # apc076; AID731Δ Fragment 5 for EMY backbone | AATAC GCAATAATGACTTTCGAAGATTACTTTTACTGCTGG |
| <SEQ ID NO: 132; DNA;; > | Primer # apc077; MCP-altcodon_AID*Δ Fragment 1 (MCP) for EMY backbone | GGCTGCGGCCACTTTTCTC |
| <SEQ ID NO: 133; DNA; > | Primer # apc078; MCP-altcodon_AID*Δ Fragment 2 (human or alt. yeast codon optimized AID*Δ) for EMY backbone | CTAAGAAAAAGAGAAAAGTGGCCGCAGCC |
| <SEQ ID NO: 134; DNA; > | Primer # apc079; MCPz-AID*Δ Fragment 1 (pGal2) for HR1 backbone | GAATGGTTAAGTAGCCAGGTGTCCATCGTGCCTAAT CCAAGGAGGTTTAC |
| <SEQ ID NO: 135; DNA; > | Primer # apc080; MCPz-AID*Δ Fragment 1 (pGal2) for HR1 backbone | GGCATCTCGAGAGACATTATGAAAGAATTATTTTTT TTATTATGTTAATCTTGTG |
| <SEQ ID NO: 136; DNA; > | Primer # apc081; MCPz-AID*Δ Fragment 2 (MCPz) for HR1 backbone | AAAATAATTCTTTCATAATGTCTCTCGAGATGCCCA AAAAG |
| <SEQ ID NO: 137; DNA; > | Primer # apc082; MCPz-AID*Δ Fragment 2 (MCPz) for HR1 backbone | CACCTCCAGATCCACCTCCTCCGTAGATGCCGGAGT TTGCTG |
| <SEQ ID NO: 138; DNA; > | Primer # apc083; MCPz-AID*Δ Fragment 3 (AID*Δ) for HR1 backbone | TTCACTATTAATGAATAG GGAGGAGGTGGATCTGGAGGTGGAGGCTCTATGGA |
| <SEQ ID NO: 139; DNA; > | Primer # apc084; MCPz-AID*Δ Fragment 3 (AID*Δ) for HR1 backbone | CTTCAGCAACCGTCCTTTTATGTCCTGAATGCATCA CG |

-continued

SEQUENCES

| SEQ ID NO | Sequence Features | Sequence |
|---|---|---|
| <SEQ ID NO: 140; DNA; > | Primer # apc085; MCPz-AID*Δ Fragment 4 (Tvma2) for HR1 backbone | CATTCAGGACATAAAAGGACGGTTGCTGAAGAAAA AG |
| <SEQ ID NO: 141; DNA; > | Primer # apc086; MCPz-AID*Δ Fragment 4 (Tvma2) for HR1 backbone | GATCTTTTTC TCGACACAGGTCGCTTGGTCCTGAGGTGTGTTCCTT |
| <SEQ ID NO: 142; DNA;; > | Primer # apc087; MCP-AID*Δ-RFA3 Fragment 1 (Pgal2-MCP-AID*Δ) for HR1 backbone | CTGAACTTCCGCCGCTAGAACCTCCTGAAGAACCA CCAGATTATGTCCTGAATGCATCACGTAAATC |
| <SEQ ID NO: 143; DNA; > | Primer # apc088; MCP-AID*Δ-RFA3 Fragment 2 (RFA3) for HR1 backbone | GAGGTTCTAGCGGCGGAAGTTCAGGTGGATCTTCT GGTGGATCCATGGCCAGCGAAACACCAAG |
| <SEQ ID NO: 144; DNA; > | Primer # apc089; MCP-AID*Δ-RFA3 Fragment 2 (RFA3) for HR1 backbone | GCAACCGTCCTTCTAGTATATTTCTGGGTATTTCTTA CATAG |
| <SEQ ID NO: 145; DNA; > | Primer # apc090; MCP-AID*Δ-RFA3 Fragment 3 (Tvma2) for HR1 backbone | ACCCAGAAATATACTAGAAGGACGGTTGCTGAAGA AAAAG |
| <SEQ ID NO: 146; DNA; > | Primer # apc091; pSNR52 for pY120 backbone | GAGCCAGTGAGTTGATTGGAAGACCTGGATCCTCTT TGAAAAGATAATGTATGATTATGCTT |
| <SEQ ID NO: 147; DNA; > | Primer # apc092; pSNR52 for pY120 backbone | AATTCCGTCAGCCAGGGTCTCGATCATTTATCTTTC ACTG |
| <SEQ ID NO: 148; DNA; > | Primer # apc093; Blank gap for pY120 backbone | GATAAATGATCGAGACCCTGGCTGACGGAATTTAT GCC |
| <SEQ ID NO: 149; DNA; > | Primer # apc094; Blank gap for pY120 backbone | CTAGCTCTGAAACTGAGACCGAGAAAACTCACCG |
| <SEQ ID NO: 150; DNA; > | Primer # apc095; Nested PCR M13 for pY120 backbone | GAGTGAGCTGATACCGCTCGAAGACGGATCCAGAC ATAAAAAACAAAAAAAGCACCG |
| <SEQ ID NO: 151; DNA; > | Primer # apc096; forward primer 1 | GTTTCAGAGCTAGGCCAACATGAGGATCACCCATG TCTGCAGGGCCTAGCAAG |
| <SEQ ID NO: 152; DNA;; > | Primer # apc097; forward primer 2 | GAGTTTTCTCGGTCTCAGTTTCAGAGCTAGGCCAAC ATG |
| <SEQ ID NO: 153; DNA; > | Primer # apc098; M4 or No Ms2 for pY120 backbone | GTTTTCTCGGTCTCAGTTTCAGAGCTAGAAATAGCA AGTTG |
| <SEQ ID NO: 154; DNA; > | Primer # apc099; Mtx2 Fragment 1 (gRNA scaffold) for pY120 backbone | TCCCGCACCGACTCGGTGCCAC |
| <SEQ ID NO: 155; DNA; > | Primer # apc100; Mtx2 Fragment 2 (Mtx2) for pY120 backbone | AAGTGGCACCGAGTCGGTG |

-continued

| SEQUENCES | | |
|---|---|---|
| SEQ ID NO | Sequence Features | Sequence |
| <SEQ ID NO: 156; DNA; > | Primer # apc101; Fragment 1 (pSNR52, blank gap, M1) for pY120 backbone | GAGCCAGTGAGTTGATTGGAAG |
| <SEQ ID NO: 157; DNA; > | Primer # apc102; Fragment 1 (pSNR52, blank gap, M1) for pY120 backbone | AAGTTGATAACGGACTAGCCTTATTTC |
| <SEQ ID NO: 158; DNA; > | Primer # apc103; Fragment 2 (No MS2 or M4) for pY120 backbone | AGCAAGTTGAAATAAGGCTAGTCC |
| <SEQ ID NO: 159; DNA; > | Primer # apc104; [Makes M1 or M14] | GAGCTGATACCGCTCGAAGACCTGGATCCAG |
| <SEQ ID NO: 160; DNA; > | Primer # apc105; pSNR52-blank gap-[Mt or M13t] Nested PCR for pY120g backbone, reverse primer 1 | AACAAAAAAAGCACATGGGTGATCCTCATGTGCGC GCACCGACTCGGTGCCAC |
| <SEQ ID NO: 161; DNA; > | Primer # apc106; pSNR52-blank gap-[Mt or M13t] Nested PCR for pY120g backbone, reverse primer 2 | GCTGATACCGCTCGAAGACCTGCAGAGACATAAAA AACAAAAAAAGCACATGGGTGATCC |
| <SEQ ID NO: 162; DNA; > | Primer # apc107; Fragment 1 (pSNR52, blank gap, M1 or M3 or M1, 3) for pY120 backbone | TCCCGCACCGACTCGGTGCCAC |
| <SEQ ID NO: 163; DNA; > | Primer # apc108; Fragment 2 (Mtx2) for pY120 backbone | AAGTGGCACCGAGTCGGTG |
| <SEQ ID NO: 164; DNA; > | Primer # apc109; Fragment 1 (pSNR52, blank gap, M3) for pY120 backbone | CCTCGGTGCCACTTGGCCCTGCAGACATGGGTGATC CTCATGTTGGCCAAGTTGATAACGGACTAGCC |
| <SEQ ID NO: 165; DNA; > | Primer # apc110; Fragment 2 (M4) for pY120 backbone | GCAGGGCCAAGTGGCACCGAGGCCAAC |
| <SEQ ID NO: 166; DNA; > | Primer # apc111; Anneal for NT1 | TGATCCGGCGTCGAAGCCTGTAAAG |
| <SEQ ID NO: 167; DNA; > | Primer # apc112; Anneal for NT1 | AAACCTTTACAGGCTTCGACGCCGG |
| <SEQ ID NO: 168; DNA; > | Primer # apc113; Anneal for wtGFP t74L | TGATCGGCGAGGGCGATGCCACCTA |
| <SEQ ID NO: 169; DNA; > | Primer # apc114; Anneal for wtGFP t74L | AAACTAGGTGGCATCGCCCTCGCCG |
| <SEQ ID NO: 170; DNA; > | Primer # apc115; Anneal for wtGFP t22L | TGATCCCGGCAAGCTGCCCGTGCCC |
| <SEQ ID NO: 171; DNA; > | Primer # apc116; Anneal for wtGFP t22L | AAACGGGCACGGGCAGCTTGCCGGG |

-continued

| SEQUENCES | | |
|---|---|---|
| SEQ ID NO | Sequence Features | Sequence |
| <SEQ ID NO: 172; DNA; > | Primer # apc117; Anneal for wtGFP 18L | TGATCGTAGCTGAAGGTGGTCACGA |
| <SEQ ID NO: 173; DNA; > | Primer # apc118; Anneal for wtGFP 18L | AAACTCGTGACCACCTTCAGCTACG |
| <SEQ ID NO: 174; DNA; > | Primer # apc119; Anneal for wtGFP 16L | TGATCGCACTGCACGCCGTAGCTGA |
| <SEQ ID NO: 175; DNA; > | Primer # apc120; Anneal for wtGFP 6L | AAACTCAGCTACGGCGTGCAGTGCG |
| <SEQ ID NO: 176; DNA; > | Primer # apc121; Anneal for wtGFP 28L | TGATCGTGGTCACGAGGGTGGGCCA |
| <SEQ ID NO: 177; DNA; > | Primer # apc122; Anneal for wtGFP 28L | AAACTGGCCCACCCTCGTGACCACG |
| <SEQ ID NO: 178; DNA; > | Primer # apc123; Anneal for wtGFP 29R | TGATCGTCGTGCTGCTTCATGTGGT |
| <SEQ ID NO: 179; DNA; > | Primer # apc124; Anneal for wtGFP 29R | AAACACCACATGAAGCAGCACGACG |
| <SEQ ID NO: 180; DNA; > | Primer # apc125; Anneal for wtGFP 48L | TGATCGGGCACGGGCAGCTTGCCGG |
| <SEQ ID NO: 181; DNA; > | Primer # apc126; Anneal for wtGFP 48L | AAACCCGGCAAGCTGCCCGTGCCCG |
| <SEQ ID NO: 182; DNA; > | Primer # apc127; Anneal for wtGFP 62R | TGATCGACGTAGCCTTCGGGCATGG |
| <SEQ ID NO: 183; DNA; > | Primer # apc128; Anneal for wtGFP 62R | AAACCCATGCCCGAAGGCTACGTCG |
| <SEQ ID NO: 184; DNA; > | Primer # apc129; Anneal for wtGFP 81L | TGATCCTTCAGGGTCAGCTTGCCGT |
| <SEQ ID NO: 185; DNA; > | Primer # apc130; Anneal for wtGFP 81L | AAACACGGCAAGCTGACCCTGAAGG |
| <SEQ ID NO: 186; DNA; > | Primer # apc131; Anneal for wtGFP 84R | TGATCTGAAGAAGATGGTGCGCTCC |
| <SEQ ID NO: 187; DNA; > | Primer # apc132; Anneal for wtGFP 84R | AAACGGAGCGCACCATCTTCTTCAG |
| <SEQ ID NO: 188; DNA; > | Primer # apc133; gRNA-tRNA Fragment 1 for pUC backbone (used for Mtx2 and M13) | GCGTTGGCCGATTCATTAATG |

-continued

| SEQUENCES | | |
|---|---|---|
| SEQ ID NO | Sequence Features | Sequence |
| <SEQ ID NO: 189; DNA; > | Primer # apc134; gRNA-tRNA Fragment 1 for pUC backbone (used for Mtx2 and M13) | CTCTGAAACTGAGACCGAAGGAGAAAACTCACCGAGG |
| <SEQ ID NO: 190; DNA; > | Primer # apc135; Mtx2 gRNA-tRNA Fragment 2 (Mtx2) for pUC backbone | CTCCTTCGGTCTCAGTTTCAGAGCTAGAAATAGCAAG |
| <SEQ ID NO: 191; DNA; > | Primer # apc136; Mtx2 gRNA-tRNA Fragment 2 (Mtx2) for pUC backbone | AACCACTTGCGCTTGTTTGGGAACACGAGCGACATGG |
| <SEQ ID NO: 192; DNA; > | Primer # apc137; Mtx2 gRNA-tRNA Fragment 3 (tRNA-Gly) for pUC backbone | GTTCCCAAACAAGCGCAAGTGGTTTAGTGGTAAAATC |
| <SEQ ID NO: 193; DNA; > | Primer # apc138; Mtx2 gRNA-tRNA Fragment 3 (tRNA-Gly) for pUC backbone and Primer # apc142; M13 gRNA-tRNA Fragment 3 (tRNA-Gly) for pUC backbone | GGCCTCTTCGCTATTACGCC |
| <SEQ ID NO: 194; DNA; > | Primer # apc139; M13 gRNA-tRNA Fragment 2 (M13) for pUC backbone | CTCCTTCGGTCTCAGTTTCAGAGCTAGAAATAGCAAG |
| <SEQ ID NO: 195; DNA; > | Primer # apc140; M13 gRNA-tRNA Fragment 2 (M13) for pUC backbone | CACTTGCGCTTGTTTGCACCGACTCGGTGCCAC |
| <SEQ ID NO: 196; DNA; > | Primer # apc141; M13 gRNA-tRNA Fragment 3 (tRNA-Gly) for pUC backbone | GTCGGTGCAAACAAGCGCAAGTGGTTTAGTGG |
| <SEQ ID NO: 197; DNA; > | Primer # apc143; mtx2 VH4420 3x cassette Fragment 1 for pY120 backbone | AAAGGTCTCATGATCCTCTTAAGTTGTTCATTTGCGTTTCAGAGCTAGAAATAGCAAGTTG |
| <SEQ ID NO: 198; DNA; > | Primer # apc144; mtx2 VH4420 3x cassette Fragment 1 for pY120 backbone | AAAGGTCTCAATGAAACTCTCTGCGCAAGCCCGGAATCG |
| <SEQ ID NO: 199; DNA; > | Primer # apc145; mtx2 VH4420 3x cassette Fragment 2 for pY120 backbone | AAAGGTCTCATCATGGGCCTCCCGTTTCAGAGCTAGAAATAGCAAGTTG |
| <SEQ ID NO: 200; DNA; > | Primer # apc146; mtx2 VH4420 3x cassette Fragment 2 for pY120 backbone | AAAGGTCTCAAAACGAGAAAGGACTGGAGTGGGTTGCGCAAGCCCGGAATCG |
| <SEQ ID NO: 201; DNA; > | Primer # apc147; m13 VH4420 3x cassette Fragment 1 for pY120 backbone | AAAGGTCTCATGATCGTCACTAAAAGTGAATCCAGGTTTCAGAGCTAGGCCAACATG |

-continued

| SEQUENCES | | |
|---|---|---|
| SEQ ID NO | Sequence Features | Sequence |
| <SEQ ID NO: 202; DNA; > | Primer # apc148; m13 VH4420 3x cassette Fragment 1 for pY120 backbone | AAAGGTCTCAGAAACATATTATGCGCAAGCCCGGA ATCG |
| <SEQ ID NO: 203; DNA; > | Primer # apc 149; m13 VH4420 3x cassette Fragment 2 for pY120 backbone | AAAGGTCTCATTTCATAATTATAGTTTCAGAGCTAG GCCAACATG |
| <SEQ ID NO: 204; DNA; > | Primer # apc150; m13 VH4420 3x cassette Fragment 2 for pY120 backbone | AAAGGTCTCAAAACGTACAGTAATAGATACCCATT GCGCAAGCCCGGAATCG |
| <SEQ ID NO: 205; DNA; > | Primer # apc151; High-throughput sequencing of 4-4-20 | ACACTCTTTCCCTACACGACGCTCTTCCGATCTGCA TCAGATGGTGACGTCAAACTGGATGAGAC |
| <SEQ ID NO: 206; DNA; > | Primer # apc152; High-throughput sequencing of 4-4-20 | GACTGGAGTTCAGACGTGTGCTCTTCCGATCTTGAG ACCATCTACACTGTTGTTATCAGATCTCGAGC |
| <SEQ ID NO: 207; DNA; > | Primer # apc153; Anneal for wtGFP c78R | TGATCTTCAAGTCCGCCATGCCCGA |
| <SEQ ID NO: 208; DNA; > | Primer # apc154; Anneal for wtGFP c78R | AAACTCGGGCATGGCGGACTTGAAG |
| <SEQ ID NO: 209; DNA; > | t78R gRNA spacer | TTCAAGTCCGCCATGCCCGA |
| <SEQ ID NO: 210; DNA; > | m13, VHCDR1 gRNA spacer | GTCACTAAAAGTGAATCCAG |
| <SEQ ID NO: 211; DNA; > | m13, VHCDR2 gRNA spacer | TAATATGTTTCATAATTATA |
| <SEQ ID NO: 212; DNA; > | m13, VHCDR3 gRNA spacer | ATGGGTATCTATTACTGTAC |

What is claimed is:

1. A gene editing system comprising a CRISPR base editor comprising a catalytically inactive nuclease, at least one guide RNA (gRNA), and a MS2 phage coat protein (MCP), wherein the MCP is operably linked to an activation-induced deaminase (AID), the at least one gRNA comprises at least one bacteriophage aptamer and at least one protospacer adjacent motif (PAM) sequence, and the gene editing system is coupled with a yeast display system to introduce a mutation into a target protein within a yeast cell, wherein (a) the MCP comprises at least 90% sequence identity to SEQ ID NO: 41; (b) the AID comprises SEQ ID NO: 43, SEQ ID NO: 45, SEQ ID NO: 47, SEQ ID NO: 49 or SEQ ID NO: 51, (c) the one or more nucleic acid sequences encoding the catalytically inactive nuclease comprises at least 90% sequence identity to SEQ ID NO: 23; or (d) the at least one gRNA comprises SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 or SEQ ID NO: 21.

2. The gene editing system of claim 1, wherein the gRNA binds a target nucleic acid encoding a target protein, or a fragment thereof.

3. The gene editing system of claim 1, wherein the MCP binds the at least one bacteriophage aptamer of the gRNA.

4. The gene editing system of claim 1, wherein the MCP comprises a nuclear localization signal (NLS).

5. The gene editing system of claim 1, wherein the AID mutates the target nucleic acid encoding the target protein, or a fragment thereof.

6. The gene editing system of claim 1, wherein the yeast cell expresses a mutant of the target protein.

7. The gene editing system of claim 1, wherein the catalytically inactive nuclease comprises a dead Cas 9 (dCas9) or a dead Cas12 (dCas12).

8. The gene editing system of claim 1, wherein the at least one bacteriophage aptamer comprises at least one MS2 aptamer.

9. The gene editing system of claim 1, wherein the AID comprises a cytidine activation-induced deaminase or an adenine activation-induced deaminase.

10. The gene editing system of claim 1, wherein the yeast display system or yeast cell comprises *Saccharomyces cerevisiae* (*S. cerevisiae*).

11. An expression vector comprising one or more nucleic acid sequences encoding a CRISPR base editor, wherein the CRISPR base editor comprises a catalytically inactive nuclease, a MS2 phage coat protein (MCP), a nucleic acid sequence encoding at least one guide RNA (gRNA) comprising at least one bacteriophage aptamer and at least one protospacer adjacent motif (PAM) sequence, and an activation-induced deaminase (AID), wherein expression of the CRISPR base editor is under control of a yeast-derived promoter sequence and a yeast-derived terminator sequence, wherein (a) the MCP comprises at least 90% sequence identity to SEQ ID NO: 41; (b) the AID comprises SEQ ID NO: 43, SEQ ID NO: 45, SEQ ID NO: 47, SEQ ID NO: 49 or SEQ ID NO: 51 (c) the one or more nucleic acid sequences encoding the catalytically inactive nuclease comprises at least 90% sequence identity to SEQ ID NO: 23; or (d) the at least one gRNA comprises SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 or SEQ ID NO: 21.

12. The vector of claim 11, wherein the catalytically inactive nuclease comprises a dead Cas 9 (dCas9) or a dead Cas12 (dCas12).

13. The vector of claim 11, wherein the at least one PAM sequence comprises SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or a variant thereof.

14. A method of mutating a target protein with a CRISPR base editor system expressed in a yeast cell, the method comprising:

identifying a target nucleic acid sequence encoding the target protein;

incorporating into a yeast genome at least one expression vector comprising one or more nucleic acid sequences encoding the target nucleic acid sequence and a CRISPR base editor, wherein the CRISPR base editor comprises a catalytically inactive nuclease, at least one guide RNA (gRNA) comprising at least one bacteriophage aptamer and at least one protospacer adjacent motif (PAM) sequence, a MS2 phage coat protein (MCP), and an activation-induced deaminase (AID), and wherein expression of the CRISPR base editor is under control of a yeast-derived promoter sequence and a yeast-derived terminator sequence;

inducing a mutation into the target protein, wherein the AID incorporates a mutation into the target nucleic acid sequence and the target nucleic acid is translated into the target protein, and wherein the mutation increases a function of the target protein relative to a wild-type control protein;

expressing the target protein comprising the mutation in the yeast; and isolating the target protein comprising the mutation, wherein (a) the MCP comprises at least 90% sequence identity to SEQ ID NO: 41; (b) the AID comprises SEQ ID NO: 43, SEQ ID NO: 45, SEQ ID NO: 47, SEQ ID NO: 49 or SEQ ID NO: 51, (c) the one or more nucleic acid sequences encoding the catalytically inactive nuclease comprises at least 90% sequence identity to SEQ ID NO: 23; or (d) the at least one gRNA comprises SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 or SEQ ID NO: 21.

* * * * *

SEQUENCE LISTING

```
Sequence total quantity: 212
SEQ ID NO: 1            moltype = RNA  length = 76
FEATURE                 Location/Qualifiers
misc_feature            1..76
                        note = Description of sequence: gRNA
source                  1..76
                        mol_type = other RNA
                        organism = synthetic construct
SEQUENCE: 1
gtttcagagc tagaaatagc aagttgaaat aaggctagtc cgttatcaac ttgaaaaagt  60
ggcaccgagt cggtgc                                                  76

SEQ ID NO: 2            moltype = RNA  length = 136
FEATURE                 Location/Qualifiers
misc_feature            1..136
                        note = Description of sequence: gRNA, m1,3
source                  1..136
                        mol_type = other RNA
                        organism = synthetic construct
stem_loop               18..36
                        note = MS2 Loop
stem_loop               88..106
                        note = MS2 Loop
SEQUENCE: 2
gtttcagagc taggccaaca tgaggatcac ccatgtctgc agggcctagc aagttgaaat  60
aaggctagtc cgttatcaac ttggccaaca tgaggatcac ccatgtctgc agggccaagt  120
```

```
ggcaccgagt cggtgc                                                 136

SEQ ID NO: 3            moltype = RNA  length = 143
FEATURE                 Location/Qualifiers
misc_feature            1..143
                        note = Description of sequence: gRNA, mtx2
source                  1..143
                        mol_type = other RNA
                        organism = synthetic construct
stem_loop               83..101
                        note = MS2 Loop
stem_loop               112..130
                        note = MS2 Loop
SEQUENCE: 3
gtttcagagc tagaaatagc aagttgaaat aaggctagtc cgttatcaac ttgaaaaagt  60
ggcaccgagt cggtgcggga gcacatgagg atcacccatg tgccacgagc gacatgagga  120
tcacccatgt cgctcgtgtt ccc                                          143

SEQ ID NO: 4            moltype = RNA  length = 101
FEATURE                 Location/Qualifiers
misc_feature            1..101
                        note = Description of sequence: gRNA, mtx1
source                  1..101
                        mol_type = other RNA
                        organism = synthetic construct
stem_loop               81..91
                        note = MS2 Loop
SEQUENCE: 4
gtttcagagc tagaaatagc aagttgaaat aaggctagtc cgttatcaac ttgaaaaagt  60
ggcaccgagt cggtgcgcgc acatgaggat cacccatgtg c                      101

SEQ ID NO: 5            moltype = RNA  length = 106
FEATURE                 Location/Qualifiers
misc_feature            1..106
                        note = Description of sequence: gRNA, m1
source                  1..106
                        mol_type = other RNA
                        organism = synthetic construct
stem_loop               18..36
                        note = MS2 Loop
SEQUENCE: 5
gtttcagagc taggccaaca tgaggatcac ccatgtctgc agggcctagc aagttgaaat  60
aaggctagtc cgttatcaac ttgaaaaagt ggcaccgagt cggtgc                 106

SEQ ID NO: 6            moltype = RNA  length = 106
FEATURE                 Location/Qualifiers
misc_feature            1..106
                        note = Description of sequence: gRNA, m3
source                  1..106
                        mol_type = other RNA
                        organism = synthetic construct
stem_loop               58..76
                        note = MS2 Loop
SEQUENCE: 6
gtttcagagc tagaaatagc aagttgaaat aaggctagtc cgttatcaac ttggccaaca  60
tgaggatcac ccatgtctgc agggccaagt ggcaccgagt cggtgc                 106

SEQ ID NO: 7            moltype = RNA  length = 109
FEATURE                 Location/Qualifiers
misc_feature            1..109
                        note = Description of sequence: gRNA, m4
source                  1..109
                        mol_type = other RNA
                        organism = synthetic construct
stem_loop               74..92
                        note = MS2 Loop
SEQUENCE: 7
gtttcagagc tagaaatagc aagttgaaat aaggctagtc cgttatcaac ttgaaaaagt  60
ggcaccgagg ccaacatgag gatcacccat gtctgcaggg cctcggtgc              109

SEQ ID NO: 8            moltype = RNA  length = 139
FEATURE                 Location/Qualifiers
misc_feature            1..139
                        note = Description of sequence: gRNA, m1,4
source                  1..139
                        mol_type = other RNA
                        organism = synthetic construct
stem_loop               18..36
                        note = MS2 Loop
```

```
stem_loop               104..122
                        note = MS2 Loop
SEQUENCE: 8
gtttcagagc taggccaaca tgaggatcac ccatgtctgc agggcctagc aagttgaaat  60
aaggctagtc cgttatcaac ttgaaaaagt ggcaccgagg ccaacatgag gatcacccat  120
gtctgcaggg cctcggtgc                                               139

SEQ ID NO: 9            moltype = RNA  length = 139
FEATURE                 Location/Qualifiers
misc_feature            1..139
                        note = Description of sequence: gRNA, m3,4
source                  1..139
                        mol_type = other RNA
                        organism = synthetic construct
stem_loop               58..76
                        note = MS2 Loop
stem_loop               104..122
                        note = MS2 Loop
SEQUENCE: 9
gtttcagagc tagaaatagc aagttgaaat aaggctagtc cgttatcaac ttggccaaca  60
tgaggatcac ccatgtctgc agggccaagt ggcaccgagg ccaacatgag gatcacccat  120
gtctgcaggg cctcggtgc                                               139

SEQ ID NO: 10           moltype = RNA  length = 173
FEATURE                 Location/Qualifiers
misc_feature            1..173
                        note = Description of sequence: gRNA, m1,tx2
source                  1..173
                        mol_type = other RNA
                        organism = synthetic construct
stem_loop               18..36
                        note = MS2 Loop
stem_loop               113..131
                        note = MS2 Loop
stem_loop               142..160
                        note = MS2 Loop
SEQUENCE: 10
gtttcagagc taggccaaca tgaggatcac ccatgtctgc agggcctagc aagttgaaat  60
aaggctagtc cgttatcaac ttgaaaaagt ggcaccgagt cggtgcggga gcacatgagg  120
atcacccatg tgccacgagc gacatgagga tcacccatgt cgctcgtgtt ccc         173

SEQ ID NO: 11           moltype = RNA  length = 173
FEATURE                 Location/Qualifiers
misc_feature            1..173
                        note = Description of sequence: gRNA, m3,tx2
source                  1..173
                        mol_type = other RNA
                        organism = synthetic construct
stem_loop               58..76
                        note = MS2 Loop
stem_loop               113..131
                        note = MS2 Loop
stem_loop               143..161
                        note = MS2 Loop
SEQUENCE: 11
gtttcagagc tagaaatagc aagttgaaat aaggctagtc cgttatcaac ttggccaaca  60
tgaggatcac ccatgtctgc agggccaagt ggcaccgagt cggtgcggga gcacatgagg  120
atcacccatg tgccacgagc gacatgagga tcacccatgt cgctcgtgtt ccc         173

SEQ ID NO: 12           moltype = RNA  length = 203
FEATURE                 Location/Qualifiers
misc_feature            1..203
                        note = Description of sequence: gRNA, m1,3,tx2
source                  1..203
                        mol_type = other RNA
                        organism = synthetic construct
stem_loop               18..36
                        note = MS2 Loop
stem_loop               88..106
                        note = MS2 Loop
stem_loop               143..161
                        note = MS2 Loop
stem_loop               172..190
                        note = MS2 Loop
SEQUENCE: 12
gtttcagagc taggccaaca tgaggatcac ccatgtctgc agggcctagc aagttgaaat  60
aaggctagtc cgttatcaac ttggccaaca tgaggatcac ccatgtctgc agggccaagt  120
ggcaccgagt cggtgcggga gcacatgagg atcacccatg tgccacgagc gacatgagga  180
tcacccatgt cgctcgtgtt ccc                                          203
```

```
SEQ ID NO: 13          moltype = RNA  length = 161
FEATURE                Location/Qualifiers
misc_feature           1..161
                       note = Description of sequence: gRNA, m1,3,tx1
source                 1..161
                       mol_type = other RNA
                       organism = synthetic construct
stem_loop              18..36
                       note = MS2 Loop
stem_loop              88..106
                       note = MS2 Loop
stem_loop              141..159
                       note = MS2 Loop
SEQUENCE: 13
gtttcagagc taggccaaca tgaggatcac ccatgtctgc agggcctagc aagttgaaat  60
aaggctagtc cgttatcaac ttggccaaca tgaggatcac ccatgtctgc agggccaagt  120
ggcaccgagt cggtgcgcgc acatgaggat cacccatgtg c                      161

SEQ ID NO: 14          moltype = RNA  length = 99
FEATURE                Location/Qualifiers
misc_feature           1..99
                       note = Description of sequence: gRNA, f63
source                 1..99
                       mol_type = other RNA
                       organism = synthetic construct
stem_loop              53..79
                       note = MS2 Loop
SEQUENCE: 14
gtttcagagc tagaaatagc aagttgaaat aaggctagtc cgttatcaac ttgccgtcca  60
cagtcactgg gtcagcggca agtggcaccg agtcggtgc                         99

SEQ ID NO: 15          moltype = RNA  length = 105
FEATURE                Location/Qualifiers
misc_feature           1..105
                       note = Description of sequence: gRNA, f53
source                 1..105
                       mol_type = other RNA
                       organism = synthetic construct
stem_loop              53..85
                       note = MS2 Loop
SEQUENCE: 15
gtttcagagc tagaaatagc aagttgaaat aaggctagtc cgttatcaac ttggccaacc  60
ggaggatcac cacgggtgca gggccaagtg gcaccgagtc ggtgc                  105

SEQ ID NO: 16          moltype = RNA  length = 99
FEATURE                Location/Qualifiers
misc_feature           1..99
                       note = Description of sequence: gRNA, m3s
source                 1..99
                       mol_type = other RNA
                       organism = synthetic construct
stem_loop              53..79
                       note = MS2 Loop
SEQUENCE: 16
gtttcagagc tagaaatagc aagttgaaat aaggctagtc cgttatcaac ttggccacat  60
gaggatcacc catgtggcca agtggcaccg agtcggtgc                         99

SEQ ID NO: 17          moltype = RNA  length = 114
FEATURE                Location/Qualifiers
misc_feature           1..114
                       note = Description of sequence: gRNA, m3ext
source                 1..114
                       mol_type = other RNA
                       organism = synthetic construct
stem_loop              53..94
                       note = MS2 Loop
SEQUENCE: 17
gtttcagagc tagaaatagc aagttgaaat aaggctagtc cgttatcaac ttggccactg  60
gacatgagga tcacccatgt ccagctgcag ggccaagtgg caccgagtcg gtgc        114

SEQ ID NO: 18          moltype = RNA  length = 129
FEATURE                Location/Qualifiers
misc_feature           1..129
                       note = Description of sequence: gRNA, m1,f63
source                 1..129
                       mol_type = other RNA
                       organism = synthetic construct
stem_loop              13..46
```

```
                        note = MS2 Loop
stem_loop               83..109
                        note = MS2 Loop
SEQUENCE: 18
gtttcagagc taggccaaca tgaggatcac ccatgtctgc agggcctagc aagttgaaat  60
aaggctagtc cgttatcaac ttgccgtcca cagtcactgg gtcagcggca agtggcaccg  120
agtcggtgc                                                          129

SEQ ID NO: 19           moltype = RNA  length = 135
FEATURE                 Location/Qualifiers
misc_feature            1..135
                        note = Description of sequence: gRNA, m1,f53
source                  1..135
                        mol_type = other RNA
                        organism = synthetic construct
stem_loop               13..46
                        note = MS2 Loop
stem_loop               83..115
                        note = MS2 Loop
SEQUENCE: 19
gtttcagagc taggccaaca tgaggatcac ccatgtctgc agggcctagc aagttgaaat  60
aaggctagtc cgttatcaac ttggccaacc ggaggatcac cacgggtgca gggccaagtg  120
gcaccgagtc ggtgc                                                   135

SEQ ID NO: 20           moltype = RNA  length = 129
FEATURE                 Location/Qualifiers
misc_feature            1..129
                        note = Description of sequence: gRNA, m1,3s
source                  1..129
                        mol_type = other RNA
                        organism = synthetic construct
stem_loop               13..46
                        note = MS2 Loop
stem_loop               83..108
                        note = MS2 Loop
SEQUENCE: 20
gtttcagagc taggccaaca tgaggatcac ccatgtctgc agggcctagc aagttgaaat  60
aaggctagtc cgttatcaac ttggccacat gaggatcacc catgtggcca agtggcaccg  120
agtcggtgc                                                          129

SEQ ID NO: 21           moltype = RNA  length = 144
FEATURE                 Location/Qualifiers
misc_feature            1..144
                        note = Description of sequence: gRNA, m1,3ext
source                  1..144
                        mol_type = other RNA
                        organism = synthetic construct
stem_loop               13..46
                        note = MS2 Loop
stem_loop               83..124
                        note = MS2 Loop
SEQUENCE: 21
gtttcagagc taggccaaca tgaggatcac ccatgtctgc agggcctagc aagttgaaat  60
aaggctagtc cgttatcaac ttggccactg gacatgagga tcacccatgt ccagctgcag  120
ggccaagtgg caccgagtcg gtgc                                         144

SEQ ID NO: 22           moltype = DNA  length = 1068
FEATURE                 Location/Qualifiers
misc_feature            1..1068
                        note = Description of sequence: MCP-AID*Delta
source                  1..1068
                        mol_type = other DNA
                        organism = synthetic construct
SEQUENCE: 22
atggctagta attttactca attcgtgtta gtggacaacg gtggtactgg tgatgtaaca  60
gttgctccat ctaattttgc caatggcgtg gctgagtgga tttccagtaa ctccagatca  120
caagcctaca aagtgacatg ctccgttcgt caatcctccg ctcagaagag aaaatatacc  180
ataaaggtgg aagtcccaaa ggtcgccacc caaaccgttg gtggagtaga attacctgta  240
gccgcttggc gttcatactt aaacatggaa ttaacaattc ccattttttgc cactaactca  300
gactgtgaat taatagtaaa agcaatgcaa ggcttattaa aggatggaaa cccaatccct  360
tcagcaattg ctgctaattc aggcatttat tcagcaggag gtggaggttc aggcggtggc  420
ggaagtggag gcggtggttc aggccctaag aaaaagagaa aagtggccgc agccggctct  480
atggattcac tattaatgaa tagaagagaa tttttgtacc aatttaagaa cgtgagatgg  540
gctaaaggta gaagggaaac ttatctatgt tacgtagtga aaagaagaga ctcagcaact  600
tccttttctt tagatttcgg ttacttaaga aataagaacg gctgtcatgt tgaattgttg  660
ttcttgaggt acataagtga ctgggaccta gatcctggaa ggtgttatcg tgttacatgg  720
tttatctctt ggtcaccatg ctatgattgt gccagacacg tagctgattt cttacgtggt  780
aacccaaatt tatcattaag aattttcacc gctagattgt atttttgcga agataggaaa  840
gctgagcctg aaggcttaag aagattacat agagccggag ttcagattgc aataatgact  900
```

```
ttcaaagatt acttttactg ctggaatacc ttcgtcgaaa atcatggtag aaccttcaaa  960
gcttgggaag gcttgcacga aaactccgtc agattgagta ggcaattaag aagaatattg  1020
ctacccttgt acgaagttga cgatttacgt gatgcattca ggacataa               1068

SEQ ID NO: 23           moltype = DNA  length = 4188
FEATURE                 Location/Qualifiers
misc_feature            1..4188
                        note = Description of sequence: dCas9
source                  1..4188
                        mol_type = other DNA
                        organism = synthetic construct
SEQUENCE: 23
atggataaaa agtatagtat tggtttagct attggtacta actctgtggg ttgggcagtt  60
atcactgacg aatataaagt tccatcaaag aaatttaagg tgttaggtaa cactgacaga  120
cactcaataa aaaagaatct tatcggtgct cttttgttcg actccggtga aactgccgag  180
gctacacgtt taaaaagaac agcaagaaga agatataccc gtagaaaaaa tagaatatgt  240
tatttacaag aaatcttttc taatgaaatg gctaaagttg atgattcctt tttccataga  300
ttggaagagt catttttggt tgaagaagac aaaaagcatg agagacatcc aatctttggg  360
aatatagttg atgaagtggc ttaccatgaa aaatatccta ccatttatca tttaagaaag  420
aaattggtag attcaactga taaagctgac cttagattaa tctatttagc acttgcccat  480
atgattaaat ttagaggtca ttttttgatt gaaggtgatt tgaacccaga taattctgac  540
gtggataaat tatttattca attagtccaa acctacaacc aattatttga ggaaaatcca  600
attaatgcta gtggtgtcga tgccaaagct atattatcag ccagattatc aaaatctaga  660
cgtttggaaa atttgattgc ccaattgcca ggagaaaaaa agaatggatt atttggaaac  720
ttgatcgcat tatcattggg tttgacacca aattttaaat ctaattttga tttagctgaa  780
gatgctaaat tacaattatc aaaagacacc tatgacgacg atttggacaa tttacttgct  840
caaattggtg atcaatatgc agatttgttc ttagctgcta aaaacttatc tgatgctatt  900
ttgttgtctg atattttgag agtgaacaca gaaataacca aagctccatt atcagcatct  960
atgatcaaac gttatgatga acaccatcag gatttgactt tattgaaagc tttggtgaga  1020
caacaattgc cagagaagta taaagaaatc tttttcgatc aatctaaaaa cgggtatgca  1080
ggttatattg atgggggtgc ctcccaagag gaattttaca aatttataaa acctatttta  1140
gaaaagatgg atgggactga ggaacttttg gtcaaattga acagagaaga tttgttacgt  1200
aaacagagaa cttttgataa tggtagtata cctcaccaaa ttcatttggg tgagttgcat  1260
gcaattttaa gaagacaaga agatttttat ccatttttaa aagataatag agaaaaaatc  1320
gagaaaattt taacctttag aattccatac tatgttgggc ctttggctag aggtaattca  1380
agatttgcct ggatgacacg taaatcagaa gaaactatta ccccttggaa ttttgaagag  1440
gttgttgata aaggagcatc agcacagagt tttattgaaa gaatgaccaa tttcgataaa  1500
aacttaccaa atgaaaaagt tttaccaaaa cattccttgt tatacgaata ttttactgtt  1560
tacaatgaac ttacaaaggt taaatatgtt actgaaggta tgcgtaagcc agccttttta  1620
tctggagaac agaaaaaggc aatagttgat ttattgttta aaacaaatag aaaagttact  1680
gttaaacaat taaaagaaga ttactttaag aaaattgaat gttttgattc agttgaaatc  1740
agtggtgttg aagacagatt taatgctagt ttaggaactt accatgattt acttaaaatt  1800
atcaaagata aagatttctt ggataacgaa gaaaatgaag acattttaga agacattgtt  1860
ttaaccttaa ctttattcga agatagagag atgattgaag aacgtttgaa gacttatgca  1920
catttgtttg acgataaagt gatgaaacag ttgaaaagaa gacgttatac tggatggggt  1980
agattgtctc gtaaattgat caatggaatt agagataaac aaagtggtaa aactatcttg  2040
gactttttga aatctgacgg atttgctaat agaaatttca tgcaattgat ccacgacgat  2100
agtttgacat ttaaagaaga catccaaaag gcccaagtga gtgggcaagg tgattcatta  2160
catgaacata ttgcaaattt agccggatct cctgctatta agaaagggat attacaaact  2220
gttaaagttg tggatgaatt agtgaaagta atgggaagac ataaacctga aaacattgtc  2280
attgagatgg caagagaaaa tcaaactaca caaaaaggac agaaaaatag tagagaacgt  2340
atgaaaagaa tagaagaggg tattaaagaa ttgggtagtc aaatattgaa agaacaccca  2400
gtggaaaata cccagttgca aaatgaaaaa ttatatcttt actaccttca aaatggacgt  2460
gatatgtatg ttgatcagga attagatata aatagacttt cagattatga tgtagatgcc  2520
atagttccac aatctttctt gaaagatgat tccatagaca ataaagtatt aactagaagt  2580
gataaaaata gaggtaaaag tgataatgtc ccaagtgagg aagtcgtcaa aaagatgaaa  2640
aattactggc gtcaactttt gaatgctaaa ttaattactc aaagaaaatt tgataatttg  2700
actaaagcag aaagaggtgg gctttctgaa ttagataaag ccgggttcat taaaagacaa  2760
ttggtcgaaa ctagacaaat tactaaacat gttgcccaaa ttttagattc ccgtatgaac  2820
actaagtatg acgaaaatga taagttaata cgtgaggtta aagtcattac tttaaaatca  2880
aaacttgtct ctgatttcag aaaggatttc caattctata aagttagaga aattaataat  2940
tatcatcatg ctcatgatgc atatttgaat gctgtagttg gaactgcttt aatcaagaaa  3000
taccctaaat tagaatctga atttgtatat ggtgattaca aagtctatga tgttagaaag  3060
atgattgcta aatcagaaca agaaattggt aaagctacag ctaaatactt cttttactct  3120
aacattatga atttctttaa aacagaaatt actttggcaa acggtgaaat tagaaaaaga  3180
cctcttattg aaacaaatgg tgagactgga gagatagttt gggacaaagg gcgtgatttc  3240
gctactgtta gaaaagtttt atcaatgcca caagttaaca ttgtaaagaa aacagaggtt  3300
caaactggtg gtttctcaaa agaaagtatt ttgcctaaaa gaaatagtga taaattgatt  3360
gccagaaaaa aggattggga tccaaagaaa tatggtggtt tcgactcacc aaccgtagcc  3420
tattctgttt tggttgtggc aaaggttgaa aagggtaaaa gtaaaaagct taaatcagta  3480
aaagaacttt tgggtattac aataatggaa agaagttcct ttgaaaagaa ccctattgat  3540
tttttggaag ctaaaggtta taaggaagta aagaaggact taataatcaa attgcctaaa  3600
tattctttat ttgaattaga aaatgggaga aaaagaatgt tggcttctgc tggagaattg  3660
caaaagggta atgaattagc attgccttcc aaatatgtta acttcttgta tttagcttca  3720
cactatgaaa agttgaaagg gtcaccagaa gataacgagc aaaaacaatt atttgttgaa  3780
caacacaaac actacttaga tgagattata gaacaaatta gtgaattcag taaaagagtg  3840
atattagctg atgcaaattt agataaagtt ttgtcagcct ataacaaaca tagagataag  3900
ccaattagag aacaagcaga aaacattatt cacttattta cccttaccaa tttaggagca  3960
cctgctgctt tcaagtattt tgatacaaca attgatcgta aaagatatac ctcaacaaaa  4020
```

```
gaagtcttag acgccacctt aattcatcaa tcaatcactg gattgtatga gacaagaatt  4080
gatttgtctc aattgggtgg tgatgaaggg gctgatccta agaagaaaag aaaagttgat  4140
ccaaagaaaa agcgtaaggt ggatcctaag aaaaagagaa aggtttaa              4188

SEQ ID NO: 24          moltype = DNA  length = 720
FEATURE                Location/Qualifiers
misc_feature           1..720
                       note = Description of sequence: wtGFP
source                 1..720
                       mol_type = other DNA
                       organism = synthetic construct
SEQUENCE: 24
atggtgagca agggcgagga gctgttcacc ggggtggtgc ccatcctggt cgagctggac  60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccttcagcta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtaa  720

SEQ ID NO: 25          moltype = DNA  length = 1179
FEATURE                Location/Qualifiers
misc_feature           1..1179
                       note = Description of sequence: AGA2-4420
source                 1..1179
                       mol_type = other DNA
                       organism = synthetic construct
SEQUENCE: 25
atgcagttac ttcgctgttt ttcaatattt tctgttattg cttcagtttt agcacaggaa  60
ctgacaacta tatgcgagca aatcccctca ccaactttag aatcgacgcc gtactctttg  120
tcaacgacta ctattttggc caacgggaag gcaatgcaag gagtttttga atattacaaa  180
tcagtaacgt ttgtcagtaa ttgcggttct cacccctcaa caactagcaa aggcagcccc  240
ataaacacac agtatgtttt taaggacaat agctcgacga ttgaaggtag atacccatac  300
gacgttccag actacgctct gcaggctagt ggtggtggtg gttctggtgg tggtggttct  360
ggtggtggtg gttctgctag cgacgtcgtt atgactcaaa caccactatc acttcctgtt  420
agtctaggtg atcaagcctc catctcttgc agatctagtc agagccttgt acacagtaat  480
ggaaacacct atttacgttg gtacctgcag aagccaggcc agtctccaaa ggtcctgatc  540
tacaaagttt ccaaccgatt ttctggggtc ccagacaggt tcagtggcag tggatcaggg  600
acagatttca cactcaagat cagcagagtg gaggctgagg atctgggagt ttatttctgc  660
tctcaaagta cacatgttcc gtggacgttc ggtggaggca ccaagcttga aattaagtcc  720
tctgctgatg atgctaagaa ggatgctgct aagaaggatg atgctaagaa agatgatgct  780
aagaaagatg gtgacgtcaa actggatgag actggaggag gcttggtgca acctgggagg  840
cccatgaaac tctcctgtgt tgcctctgga ttcactttta gtgactactg gatgaactgg  900
gtccgccagt ctccagagaa aggactggag tgggtagcac aaattagaaa caaaccttat  960
aattatgaaa catattattc agattctgtg aaaggcagat tcaccatctc aagagatgat  1020
tccaaaagta gtgtctacct gcaaatgaac aacttaagag ttgaagacat gggtatctat  1080
tactgtacgg gttcttacta tggtatggac tactggggtc aaggaacctc agtcaccgtc  1140
tcctcagaac aaaagcttat ttctgaagaa gacttgtaa                        1179

SEQ ID NO: 26          moltype = RNA  length = 20
FEATURE                Location/Qualifiers
misc_feature           1..20
                       note = Description of sequence: T1 gRNA spacer
source                 1..20
                       mol_type = other RNA
                       organism = synthetic construct
SEQUENCE: 26
gtagctgaag gtggtcacga                                             20

SEQ ID NO: 27          moltype = RNA  length = 20
FEATURE                Location/Qualifiers
misc_feature           1..20
                       note = Description of sequence: T2 gRNA spacer
source                 1..20
                       mol_type = other RNA
                       organism = synthetic construct
SEQUENCE: 27
ccggcaagct gcccgtgccc                                             20

SEQ ID NO: 28          moltype = RNA  length = 20
FEATURE                Location/Qualifiers
misc_feature           1..20
                       note = Description of sequence: T3 gRNA spacer
source                 1..20
```

```
                         mol_type = other RNA
                         organism = synthetic construct
SEQUENCE: 28
ggcgagggcg atgccaccta                                                20

SEQ ID NO: 29            moltype = RNA  length = 20
FEATURE                  Location/Qualifiers
misc_feature             1..20
                         note = Description of sequence: NT1 gRNA spacer
source                   1..20
                         mol_type = other RNA
                         organism = synthetic construct
SEQUENCE: 29
cggcgtcgaa gcctgtaaag                                                20

SEQ ID NO: 30            moltype = RNA  length = 20
FEATURE                  Location/Qualifiers
misc_feature             1..20
                         note = Description of sequence: 81L gRNA spacer
source                   1..20
                         mol_type = other RNA
                         organism = synthetic construct
SEQUENCE: 30
cttcagggtc agcttgccgt                                                20

SEQ ID NO: 31            moltype = RNA  length = 20
FEATURE                  Location/Qualifiers
misc_feature             1..20
                         note = Description of sequence: 48L gRNA spacer
source                   1..20
                         mol_type = other RNA
                         organism = synthetic construct
SEQUENCE: 31
gggcacgggc agcttgccgg                                                20

SEQ ID NO: 32            moltype = RNA  length = 20
FEATURE                  Location/Qualifiers
misc_feature             1..20
                         note = Description of sequence: 28L gRNA spacer
source                   1..20
                         mol_type = other RNA
                         organism = synthetic construct
SEQUENCE: 32
gtggtcacga gggtgggcca                                                20

SEQ ID NO: 33            moltype = RNA  length = 20
FEATURE                  Location/Qualifiers
misc_feature             1..20
                         note = Description of sequence: 6L gRNA spacer
source                   1..20
                         mol_type = other RNA
                         organism = synthetic construct
SEQUENCE: 33
gcactgcacg ccgtagctga                                                20

SEQ ID NO: 34            moltype = RNA  length = 20
FEATURE                  Location/Qualifiers
misc_feature             1..20
                         note = Description of sequence: 29R gRNA spacer
source                   1..20
                         mol_type = other RNA
                         organism = synthetic construct
SEQUENCE: 34
gtcgtgctgc ttcatgtggt                                                20

SEQ ID NO: 35            moltype = RNA  length = 20
FEATURE                  Location/Qualifiers
misc_feature             1..20
                         note = Description of sequence: 62R gRNA spacer
source                   1..20
                         mol_type = other RNA
                         organism = synthetic construct
SEQUENCE: 35
gacgtagcct tcgggcatgg                                                20

SEQ ID NO: 36            moltype = RNA  length = 20
FEATURE                  Location/Qualifiers
misc_feature             1..20
                         note = Description of sequence: 84R gRNA spacer
```

```
source                  1..20
                        mol_type = other RNA
                        organism = synthetic construct
SEQUENCE: 36
tgaagaagat ggtgcgctcc                                           20

SEQ ID NO: 37           moltype = RNA  length = 20
FEATURE                 Location/Qualifiers
misc_feature            1..20
                        note = Description of sequence: HCDR1
source                  1..20
                        mol_type = other RNA
                        organism = synthetic construct
SEQUENCE: 37
gagagtttca tgggcctccc                                           20

SEQ ID NO: 38           moltype = RNA  length = 20
FEATURE                 Location/Qualifiers
misc_feature            1..20
                        note = Description of sequence: HCDR2
source                  1..20
                        mol_type = other RNA
                        organism = synthetic construct
SEQUENCE: 38
acccactcca gtcctttctc                                           20

SEQ ID NO: 39           moltype = RNA  length = 20
FEATURE                 Location/Qualifiers
misc_feature            1..20
                        note = Description of sequence: HCDR3
source                  1..20
                        mol_type = other RNA
                        organism = synthetic construct
SEQUENCE: 39
ctcttaagtt gttcatttgc                                           20

SEQ ID NO: 40           moltype = DNA  length = 480
FEATURE                 Location/Qualifiers
misc_feature            1..480
                        note = Description of sequence: MCP-GGGGS(3x)-SV40NLS
source                  1..480
                        mol_type = other DNA
                        organism = synthetic construct
SEQUENCE: 40
atggctagta attttactca attcgtgtta gtggacaacg gtggtactgg tgatgtaaca  60
gttgctccat ctaattttgc caatggcgtg gctgagtgga tttccagtaa ctccagatca  120
caagcctaca aagtgacatg ctccgttcgt caatcctccg ctcagaagag aaaatatacc  180
ataaaggtgg aagtcccaaa ggtcgccacc caaaccgttg gtggagtaga attacctgta  240
gccgcttggc gttcatactt aaacatggaa ttaacaattc ccatttttgc cactaactca  300
gactgtgaat taatagtaaa agcaatgcaa ggcttattaa aggatggaaa cccaatccct  360
tcagcaattg ctgctaattc aggcatttat tcagcaggag gtggaggttc aggcggtggc  420
ggaagtggag gcggtggttc aggccctaag aaaaagagaa aagtggccgc agccggctct  480

SEQ ID NO: 41           moltype = AA  length = 160
FEATURE                 Location/Qualifiers
REGION                  1..160
                        note = Description of sequence: MCP-GGGGS(3x)-SV40NLS
source                  1..160
                        mol_type = protein
                        organism = synthetic construct
SEQUENCE: 41
MASNFTQFVL VDNGGTGDVT VAPSNFANGV AEWISSNSRS QAYKVTCSVR QSSAQKRKYT  60
IKVEVPKVAT QTVGGVELPV AAWRSYLNME LTIPIFATNS DCELIVKAMQ GLLKDGNPIP  120
SAIAANSGIY SAGGGGSGGG GSGGGGSGPK KKRKVAAAGS                        160

SEQ ID NO: 42           moltype = DNA  length = 588
FEATURE                 Location/Qualifiers
misc_feature            1..588
                        note = Description of sequence: AID*Delta
source                  1..588
                        mol_type = other DNA
                        organism = synthetic construct
SEQUENCE: 42
atggattcac tattaatgaa tagaagagaa tttttgtacc aatttaagaa cgtgagatgg  60
gctaaaggta gaagggaaac ttatctatgt tacgtagtga aaagaagaga ctcagcaact  120
tccttttctt tagatttcgg ttacttaaga aataagaacg gctgtcatgt tgaattgttg  180
ttcttgaggt acataagtga ctgggaccta gatcctggaa ggtgttatcg tgttacatgg  240
tttatctctt ggtcaccatg ctatgattgt gccagacacg tagctgattt cttacgtggt  300
aacccaaatt tatcattaag aattttcacc gctagattgt atttttgcga agataggaaa  360
```

```
gctgagcctg aaggcttaag aagattacat agagccggag ttcagattgc aataatgact  420
ttcaaagatt acttttactg ctggaatacc ttcgtcgaaa atcatggtag aaccttcaaa  480
gcttgggaag gcttgcacga aaactccgtc agattgagta ggcaattaag aagaatattg  540
ctacccttgt acgaagttga cgatttacgt gatgcattca ggacataa             588

SEQ ID NO: 43          moltype = AA  length = 195
FEATURE                Location/Qualifiers
REGION                 1..195
                       note = Description of sequence: AID*Delta
source                 1..195
                       mol_type = protein
                       organism = synthetic construct
SEQUENCE: 43
MDSLLMNRRE FLYQFKNVRW AKGRRETYLC YVVKRRDSAT SFSLDFGYLR NKNGCHVELL  60
FLRYISDWDL DPGRCYRVTW FISWSPCYDC ARHVADFLRG NPNLSLRIFT ARLYFCEDRK  120
AEPEGLRRLH RAGVQIAIMT FKDYFYCWNT FVENHGRTFK AWEGLHENSV RLSRQLRRIL  180
LPLYEVDDLR DAFRT                                                  195

SEQ ID NO: 44          moltype = DNA  length = 588
FEATURE                Location/Qualifiers
misc_feature           1..588
                       note = Description of sequence: AID731-Delta
source                 1..588
                       mol_type = other DNA
                       organism = synthetic construct
SEQUENCE: 44
atggattcac tattaatgaa tagaagtgaa tttttgtacc aatttaagaa cgtgagatgg  60
gctaaaggta gaagggaaac ttatctatgt tacgtagtga aaagatgcga ctcagcaact  120
tccttttctc gtgatttcgg ttacttaaga aataagaacg gctgtcatgt tgaattgttg  180
ttcttgaggt acataagtga ctgggaccta gatcctggaa ggtgttatcg tgttacatgg  240
tttatctctt ggtcaccatg ctctgattgt gccagactag tagctgattt cttacgtggt  300
aacccaaatt tatcattaag aattttcacc gctagattgt atttttgcga agataggaaa  360
gctgagcctg aaggcttaag aagattacat agagccggag ttcagattgc aataatgact  420
ttcgaagatt acttttactg ctggaatacc ttcgtcgaaa atcatggtag aaccttcaaa  480
gcttgggaag gcttgcacga aaactccgtc agattgagta ggcaattaag aagaatattg  540
ctacccttgt acgaagttga cgatttacgt gatgcattca ggacataa             588

SEQ ID NO: 45          moltype = AA  length = 195
FEATURE                Location/Qualifiers
REGION                 1..195
                       note = Description of sequence: AID731-Delta
source                 1..195
                       mol_type = protein
                       organism = synthetic construct
SEQUENCE: 45
MDSLLMNRSE FLYQFKNVRW AKGRRETYLC YVVKRCDSAT SFSRDFGYLR NKNGCHVELL  60
FLRYISDWDL DPGRCYRVTW FISWSPCSDC ARLVADFLRG NPNLSLRIFT ARLYFCEDRK  120
AEPEGLRRLH RAGVQIAIMT FEDYFYCWNT FVENHGRTFK AWEGLHENSV RLSRQLRRIL  180
LPLYEVDDLR DAFRT                                                  195

SEQ ID NO: 46          moltype = DNA  length = 531
FEATURE                Location/Qualifiers
misc_feature           1..531
                       note = Description of sequence: AID731mono
source                 1..531
                       mol_type = other DNA
                       organism = synthetic construct
SEQUENCE: 46
atggatccag ctacctttac gtaccaattt aagaacgtga gatgggctaa aggtagaagg  60
gaaacttatc tatgttacgt agtgaaaaga tgcgactcag caacttcctt ttctcgtgat  120
ttcggttact taagaaataa gaacggctgt catgttgaat tgttgttctt gaggtacata  180
agtgactggg acctagatcc tggaaggtgt tatcgtgtta catggtttat ctcttggtca  240
ccatgctctg attgtgccag actagtagct gatttcttac gtggtaaccc aaatttatca  300
ttaagaattt tcaccgctag attgtatttt tgcgaagata ggaaagctga gcctgaaggc  360
ttaagaagat tagccgaagc cggagttcag attgcaataa tgactttcga agattacttt  420
tactgctgga ataccttcgt cgaaaatcat ggtagaacct tcaaagcttg ggaaggcttg  480
cacgaaaact ccgtcagatt gagtaggcaa ttaagaagaa tattgcagta a          531

SEQ ID NO: 47          moltype = AA  length = 176
FEATURE                Location/Qualifiers
REGION                 1..176
                       note = Description of sequence: AID731mono
source                 1..176
                       mol_type = protein
                       organism = synthetic construct
SEQUENCE: 47
MDPATFTYQF KNVRWAKGRR ETYLCYVVKR CDSATSFSRD FGYLRNKNGC HVELLFLRYI  60
SDWDLDPGRC YRVTWFISWS PCSDCARLVA DFLRGNPNLS LRIFTARLYF CEDRKAEPEG  120
LRRLAEAGVQ IAIMTFEDYF YCWNTFVENH GRTFKAWEGL HENSVRLSRQ LRRILQ      176
```

```
SEQ ID NO: 48          moltype = DNA  length = 531
FEATURE                Location/Qualifiers
misc_feature           1..531
                       note = Description of sequence: AID*mono
source                 1..531
                       mol_type = other DNA
                       organism = synthetic construct
SEQUENCE: 48
atggatccag ctacctttac gtaccaattt aagaacgtga gatgggctaa aggtagaagg  60
gaaacttatc tatgttacgt agtgaaaaga agagactcag caacttcctt ttctttagat  120
ttcggttact taagaaataa gaacggctgt catgttgaat tgttgttctt gaggtacata  180
agtgactggg acctagatcc tggaaggtgt tatcgtgtta catggtttat ctcttggtca  240
ccatgctatg attgtgccag acacgtagct gatttcttac gtggtaaccc aaatttatca  300
ttaagaattt tcaccgctag attgtatttt tgcgaagata ggaaagctga gcctgaaggc  360
ttaagaagat tagccgaagc cggagttcag attgcaataa tgactttcaa agattacttt  420
tactgctgga ataccttcgt cgaaaatcat ggtagaacct tcaaagcttg ggaaggcttg  480
cacgaaaact ccgtcagatt gagtaggcaa ttaagaagaa tattgcagta a           531

SEQ ID NO: 49          moltype = AA  length = 176
FEATURE                Location/Qualifiers
REGION                 1..176
                       note = Description of sequence: AID*mono
source                 1..176
                       mol_type = protein
                       organism = synthetic construct
SEQUENCE: 49
MDPATFTYQF KNVRWAKGRR ETYLCYVVKR RDSATSFSLD FGYLRNKNGC HVELLFLRYI  60
SDWDLDPGRC YRVTWFISWS PCYDCARHVA DFLRGNPNLS LRIFTARLYF CEDRKAEPEG  120
LRRLAEAGVQ IAIMTFKDYF YCWNTFVENH GRTFKAWEGL HENSVRLSRQ LRRILQ      176

SEQ ID NO: 50          moltype = DNA  length = 531
FEATURE                Location/Qualifiers
misc_feature           1..531
                       note = Description of sequence: AIDmono
source                 1..531
                       mol_type = other DNA
                       organism = synthetic construct
SEQUENCE: 50
atggatccag ctacctttac gtaccaattt aagaacgtga gatgggctaa aggtagaagg  60
gaaacttatc tatgttacgt agtgaaaaga agagactcag caacttcctt ttctttagat  120
ttcggttact taagaaataa gaacggctgt catgttgaat tgttgttctt gaggtacata  180
agtgactggg acctagatcc tggaaggtgt tatcgtgtta catggtttac ctcttggtca  240
ccatgctatg attgtgccag acacgtagct gatttcttac gtggtaaccc aaatttatca  300
ttaagaattt tcaccgctag attgtatttt tgcgaagata ggaaagctga gcctgaaggc  360
ttaagaagat tagccgaagc cggagttcag attgcaataa tgactttcaa agattacttt  420
tactgctgga ataccttcgt cgaaaatcat gaaagaacct tcaaagcttg ggaaggcttg  480
cacgaaaact ccgtcagatt gagtaggcaa ttaagaagaa tattgcagta a           531

SEQ ID NO: 51          moltype = AA  length = 176
FEATURE                Location/Qualifiers
REGION                 1..176
                       note = Description of sequence: AIDmono
source                 1..176
                       mol_type = protein
                       organism = synthetic construct
SEQUENCE: 51
MDPATFTYQF KNVRWAKGRR ETYLCYVVKR RDSATSFSLD FGYLRNKNGC HVELLFLRYI  60
SDWDLDPGRC YRVTWFTSWS PCYDCARHVA DFLRGNPNLS LRIFTARLYF CEDRKAEPEG  120
LRRLAEAGVQ IAIMTFKDYF YCWNTFVENH ERTFKAWEGL HENSVRLSRQ LRRILQ      176

SEQ ID NO: 52          moltype = DNA  length = 1023
FEATURE                Location/Qualifiers
misc_feature           1..1023
                       note = Description of sequence: Pkl1eu2 wild-type promoter
source                 1..1023
                       mol_type = genomic DNA
                       organism = Kluyveromyces lactis
SEQUENCE: 52
gctgtgaaga tcccagcaaa ggcttacaaa gtgttatctc ttttgagact tgttgagttg  60
aacactggtg ttttcatcaa acttaccaag gacgtgtacc cattgttgaa acttgtatca  120
ccatatattg ttatcggaca accttcactt gcatctatcc gttctttaat ccaaaagaga  180
tctagaataa tgtggcaaag gccagaagat aaagaaccaa aagagataat cttgaatgac  240
aacaatatcg ttgaagagaa attaggtgat gaaggtgtca tttgtatcga ggatatcatc  300
catgagattt cgacgttggg cgaaaatttc tcgaaatgta ctttcttcct attaccattc  360
aaattgaaca gagaagtcag tggattcggt gccatctccc gtttgaataa actgaaaatg  420
cgcgaacaaa acaacaagac acgtcaaatt tcaaacgctg ccacggctcc agttatccaa  480
gtagatatcg acacaatgat ttccaagttg aattgattaa ctataaaagg aaaatatctg  540
tacaatagac atcgggctcc cattggccct acccacatat gtagaaatac attactctat  600
```

```
tcactactgc atttagttat gtttaacatt tgatatagca gactaccgcc aggcacaata  660
tattcccctt ccctcttgcc attcgctgta cttgtggtgg attccaattc agcgcagtca  720
cgtgctagta atcaccgcat ttttttcttt tcctttcagg ctaaaaccgg ttccgggcct  780
gatccctgca ctcattttct aacggaaaac cttcagaagc ataactaccc attccagttt  840
agagacatga caggttcaac atcagatgct tcatatactt ttatatattg aattatataa  900
atatatctat gtactctaag taagtacatc tgctttaacg cattcctaca tttgcttcga  960
tttatttta ttgttgatac ctatttgaag aagtaaaaag tatcccacac tacacagatt  1020
ata                                                                1023

SEQ ID NO: 53          moltype = DNA  length = 1023
FEATURE                Location/Qualifiers
misc_feature           1..1023
                       note = Description of sequence: Pklleu2 "3x-6" promoter
source                 1..1023
                       mol_type = genomic DNA
                       organism = Kluyveromyces lactis
SEQUENCE: 53
gctgtgaaga tcccagcaaa ggcttacaaa gtgttatctc ttttgagact tgttgagttg  60
aacactggtg ttttcatcaa acttaccaag gacgtgtacc cattgttgaa acttgtatca  120
ccatatattg ttatcggaca accttcactt gcatctatcc gttctttaat ccaaaagaga  180
tctagaataa tgtggcaaag gccagaagat aaagaaccaa aagagataat cttgaatgac  240
aacaatatcg ttgaagagaa attaggtgat gaaggtgtca tttgtatcga ggatatcatc  300
catgagattt cgacgttggg cgaaaatttc tcgaaatgta ctttcttcct attaccattc  360
aaattgaaca gagaagtcag tggatttggt gccatctccc gtttgaataa actgaaaatg  420
cgcgaacaaa acaacaagac acgtcaaatt tcaaacgctg ccacggctcc agttatccaa  480
gtagatatcg acacaatgat ttccaagttg aattgattaa ctataaaagg aaaatatctg  540
tacaatagac atcgggctcc cattggccct acccacatat gtagaaatac attactctat  600
tcactactgc atttagttat gtttaacatt tgatatagca gactaccgcc aggcacaata  660
tattcccctt ccctcttgcc attcgctata cttgtggtgg attccaattc agcgcagtca  720
cgtgctagta atcaccgcat ttttttcttt tcctttcagg ctaaaaccgg ttccgggcct  780
gatccctgca ctcattttct aacggaaaac cttcagaagc ataaccagcc attccagttt  840
agagacatga cagattcaac atcagatgct tcatatactt ttatatattc aattatataa  900
atatatctat gtactctaag taagtacatc tgctttaacg cattcctaca tttgcttcga  960
tttatttta ttgttgatac ctatttgaag aagtaaaaag tatcccacac tacacagatt  1020
ata                                                                1023

SEQ ID NO: 54          moltype = DNA  length = 1024
FEATURE                Location/Qualifiers
misc_feature           1..1024
                       note = Description of sequence: Pklleu2 "3x-7" promoter
source                 1..1024
                       mol_type = genomic DNA
                       organism = Kluyveromyces lactis
SEQUENCE: 54
gctgtgaaga tcccagcaaa ggcttacaaa gtgttatctc ttttgagact tgttgagttg  60
aacactggtg ttttcatcaa acttaccaag gacgtgtacc cattgttgaa acttgtatca  120
ccatatattg ttatcggaca accttcactt gcatctatcc gttctttaat ccaaaagaga  180
tctagaataa tgtggcaaag gccagaagat aaagaaccaa aagagataat cttgaatgac  240
aacaatatcg ttgaagagaa attaggtgat gaaggtgtca tttgtatcga ggatatcatc  300
catgagattt cgacgttggg cgaaaatttc tcgaaatgta ctttcttcct attaccattc  360
aaattgaaca gagaagtcag tggatttggt gccatctccc gtttgaataa actgaaaatg  420
cgcgaacaaa acaacaagac acgtcaaatt tcaaacgctg ccacggcttc agttatccaa  480
gtagatatcg acacaatgat ttccaagttg aattgattaa ctataaaagg aaaatatctg  540
tacaatagac atcgggctcc cattggccct acccacatat gtagaaatac attactctat  600
tcactactgc atttagttat gtttaacatt tgatatagca gactaccgcc aggcacaata  660
tattcccctt ccctcttgcc attcgctgta cttgtggtgg attccaattc agcgcagtca  720
cgtgctagta atcaccgcat ttttttcttt tcctttcagg ctaaaaccgg ttccgggcct  780
gatccctgca ctcattttct aacggaaaaa tcttaagaag tataaatacc cattccagtt  840
tagagacatg acagcttcaa catcagatgc ttcatatact tttatatatt gaattatata  900
aatatatcta tgtactctaa gtaagtacat ctgctttaac gcattcctac atttgcttcg  960
atttattttt attgttgata cctatttgaa gaagtaaaaa gtatcccaca ctacacagat  1020
tata                                                               1024

SEQ ID NO: 55          moltype = DNA  length = 1022
FEATURE                Location/Qualifiers
misc_feature           1..1022
                       note = Description of sequence: Pklleu2 "3x-8" promoter
source                 1..1022
                       mol_type = genomic DNA
                       organism = Kluyveromyces lactis
SEQUENCE: 55
gctgtgaaga tcccagcaaa ggcttacaaa gtgttatctc ttttgagact tgttgagttg  60
aacactggtg ttttcatcaa acttaccaag gacgtgtacc cattgttgaa acttgtatca  120
ccatatattg ttatcggaca accttcactt gcatctatcc gttctttaat ccaaaagaga  180
tctagaataa tgtggcaaag gccagaagat aaagaaccaa aagagataat cttgaatgac  240
aacaatatcg ttgaagagaa attaggtgat gaaggtgtca tttgtatcga ggatatcatc  300
catgagattt cgacgttggg cgaaaatttc tcgaaatgta ctttcttcct attaccattc  360
aaattgaaca gagaagtcag tggatttggt gccatctccc gtttgaataa actgaaaatg  420
cgcgaacaaa acaacaagac acgtcaaatt tcaaacgctg ccacggctcc agttatccaa  480
```

```
gtagatatcg acacaatgat ttccaagttg aattgattaa ctataaaagg aaaatatctg  540
tacaatagac atcgggctcc cattggccct acccacatat gtagaaatac attactctat  600
tcactactgc atttagttat gtttaacatt tgatatagca gactaccgcc aggcacaata  660
tattcccctt ccctcttgcc attcgctata cttgtggtgg attccaattc agcgcagtca  720
cgtgctagta atcaccgcat ttttttcttt tcctttcagg ctaaaaccgg ttccgggcct  780
gatccctgca ctcattttct aacggaaaac cttcagaagc ataaccagcc attcgagttt  840
agagacatga cagattcaac atcagatgct tcatatactt ttatatattc aattatataa  900
atatatctat gtactctaag taagtacatc tgctttaacg cattcctaca tttgcttcga  960
tttattttta ttgttgatac ctatttgaag aagtaaaaag tatcccacac tacacagatt  1020
at                                                                1022

SEQ ID NO: 56          moltype = DNA  length = 24
FEATURE                Location/Qualifiers
misc_feature           1..24
                       note = Description of sequence: Primer # apc001; 5' Flank
                        for Integration at YPRC?3
source                 1..24
                       mol_type = other DNA
                       organism = synthetic construct
SEQUENCE: 56
cggtattact cgagcccgta atac                                        24

SEQ ID NO: 57          moltype = DNA  length = 78
FEATURE                Location/Qualifiers
misc_feature           1..78
                       note = Description of sequence: Primer # apc002; 5' Flank
                        for Integration at YPRC?3
source                 1..78
                       mol_type = other DNA
                       organism = synthetic construct
SEQUENCE: 57
ggacacctgg ctacttaacc attcgttgtt agtgtgtcgc atacgaggaa taacgccgat  60
gggacgtcag cactgtac                                               78

SEQ ID NO: 58          moltype = DNA  length = 22
FEATURE                Location/Qualifiers
misc_feature           1..22
                       note = Description of sequence: Primer # apc003; 3' Flank
                        for Integrating 3 Genes YPRC?3
source                 1..22
                       mol_type = other DNA
                       organism = synthetic construct
SEQUENCE: 58
aaaggaggtg cacgcattat gg                                          22

SEQ ID NO: 59          moltype = DNA  length = 79
FEATURE                Location/Qualifiers
misc_feature           1..79
                       note = Description of sequence: Primer # apc004; 3' Flank
                        for Integrating 3 Genes YPRC?3
source                 1..79
                       mol_type = other DNA
                       organism = synthetic construct
SEQUENCE: 59
ccgaacctag gattagatgt ggtctagcac catattgcgg acatggtccc cctgttattc  60
caaggaggtg aagaacgtc                                              79

SEQ ID NO: 60          moltype = DNA  length = 78
FEATURE                Location/Qualifiers
misc_feature           1..78
                       note = Description of sequence: Primer # apc005; 5' Flank
                        for Integration YPRC-delta-15
source                 1..78
                       mol_type = other DNA
                       organism = synthetic construct
SEQUENCE: 60
ggacacctgg ctacttaacc attcgttgtt agtgtgtcgc atacgaggaa taacgccttt  60
gcgaaaccct atgctctg                                               78

SEQ ID NO: 61          moltype = DNA  length = 31
FEATURE                Location/Qualifiers
misc_feature           1..31
                       note = Description of sequence: Primer # apc006; 5' Flank
                        for Integration YPRC-delta-15
source                 1..31
                       mol_type = other DNA
                       organism = synthetic construct
SEQUENCE: 61
gccaggcgcc tttatatcat ataattaaga c                                31
```

```
SEQ ID NO: 62          moltype = DNA  length = 79
FEATURE                Location/Qualifiers
misc_feature           1..79
                       note = Description of sequence: Primer # apc007; 3' Flank
                        for Integrating 2 Genes YPRC-delta-15
source                 1..79
                       mol_type = other DNA
                       organism = synthetic construct
SEQUENCE: 62
catttggatt gtaatttcat actggagtaa acatctccag gtgtctaagt tcacacagga  60
atggaaggtc gggatgagc                                                79

SEQ ID NO: 63          moltype = DNA  length = 23
FEATURE                Location/Qualifiers
misc_feature           1..23
                       note = Description of sequence: Primer # apc008; 3' Flank
                        for Integrating 2 Genes YPRC-delta-15
source                 1..23
                       mol_type = other DNA
                       organism = synthetic construct
SEQUENCE: 63
ataaagcagc cgctaccaaa cag                                           23

SEQ ID NO: 64          moltype = DNA  length = 26
FEATURE                Location/Qualifiers
misc_feature           1..26
                       note = Description of sequence: Primer # apc009; 3' Flank
                        for Integration YORW-delta-22
source                 1..26
                       mol_type = other DNA
                       organism = synthetic construct
SEQUENCE: 64
cgtgataaac gatcgccata actaac                                        26

SEQ ID NO: 65          moltype = DNA  length = 78
FEATURE                Location/Qualifiers
misc_feature           1..78
                       note = Description of sequence: Primer # apc010; 3' Flank
                        for Integration YORW-delta-22
source                 1..78
                       mol_type = other DNA
                       organism = synthetic construct
SEQUENCE: 65
gattgtaatt tcatactgga gtaaacatct ccaggtgtct aagttcacac aggggaccaa  60
ctatcatccg ctaattac                                                 78

SEQ ID NO: 66          moltype = DNA  length = 24
FEATURE                Location/Qualifiers
misc_feature           1..24
                       note = Description of sequence: Primer # apc011; 5' Flank
                        for Integrating 2 Genes YORW-delta-22
source                 1..24
                       mol_type = other DNA
                       organism = synthetic construct
SEQUENCE: 66
caccggagct tggatatgat aaac                                          24

SEQ ID NO: 67          moltype = DNA  length = 70
FEATURE                Location/Qualifiers
misc_feature           1..70
                       note = Description of sequence: Primer # apc012; 5' Flank
                        for Integrating 2 Genes YORW-delta-22
source                 1..70
                       mol_type = other DNA
                       organism = synthetic construct
SEQUENCE: 67
ggctacttaa ccattcgttg ttagtgtgtc gcatacgagg aataacgcct tcgcgggctg  60
ttacttatcc                                                          70

SEQ ID NO: 68          moltype = DNA  length = 20
FEATURE                Location/Qualifiers
misc_feature           1..20
                       note = Description of sequence: Primer # apc013; Amplify
                        Pro-gene-Term in HR1 backbone
source                 1..20
                       mol_type = other DNA
                       organism = synthetic construct
SEQUENCE: 68
```

```
ggcgttattc ctcgtatgcg                                              20

SEQ ID NO: 69          moltype = DNA  length = 25
FEATURE                Location/Qualifiers
misc_feature           1..25
                       note = Description of sequence: Primer # apc014; Amplify
                        Pro-gene-Term in HR1 backbone
source                 1..25
                       mol_type = other DNA
                       organism = synthetic construct
SEQUENCE: 69
gacaatcgct acagaaacga ttttc                                        25

SEQ ID NO: 70          moltype = DNA  length = 20
FEATURE                Location/Qualifiers
misc_feature           1..20
                       note = Description of sequence: Primer # apc015; Amplify
                        Pro-gene-Term in HR2 backbone
source                 1..20
                       mol_type = other DNA
                       organism = synthetic construct
SEQUENCE: 70
aggaccaagc gacctgtgtc                                              20

SEQ ID NO: 71          moltype = DNA  length = 25
FEATURE                Location/Qualifiers
misc_feature           1..25
                       note = Description of sequence: Primer # apc016; Amplify
                        Pro-gene-Term in HR2 backbone
source                 1..25
                       mol_type = other DNA
                       organism = synthetic construct
SEQUENCE: 71
cctgtgtgaa cttagacacc tggag                                        25

SEQ ID NO: 72          moltype = DNA  length = 28
FEATURE                Location/Qualifiers
misc_feature           1..28
                       note = Description of sequence: Primer # apc017; Amplify
                        Pro-gene-Term in HR3 backbone
source                 1..28
                       mol_type = other DNA
                       organism = synthetic construct
SEQUENCE: 72
tcatttggat tgtaatttca tactggag                                     28

SEQ ID NO: 73          moltype = DNA  length = 19
FEATURE                Location/Qualifiers
misc_feature           1..19
                       note = Description of sequence: Primer # apc018; Amplify
                        Pro-gene-Term in HR3 backbone
source                 1..19
                       mol_type = other DNA
                       organism = synthetic construct
SEQUENCE: 73
taacaggggg accatgtcc                                               19

SEQ ID NO: 74          moltype = DNA  length = 27
FEATURE                Location/Qualifiers
misc_feature           1..27
                       note = Description of sequence: Primer # apc019; PCR check
                        for integrations YPRC-delta-15
source                 1..27
                       mol_type = other DNA
                       organism = synthetic construct
SEQUENCE: 74
acgagctttt gaattatggt aattttg                                      27

SEQ ID NO: 75          moltype = DNA  length = 28
FEATURE                Location/Qualifiers
misc_feature           1..28
                       note = Description of sequence: Primer # apc020; PCR check
                        for integrations YPRC-delta-15
source                 1..28
                       mol_type = other DNA
                       organism = synthetic construct
SEQUENCE: 75
tgttgagtac ttcaacttta tttccttc                                     28
```

```
SEQ ID NO: 76          moltype = DNA  length = 23
FEATURE                Location/Qualifiers
misc_feature           1..23
                       note = Description of sequence: Primer # apc021; PCR check
                        for integrations YPRC?3
source                 1..23
                       mol_type = other DNA
                       organism = synthetic construct
SEQUENCE: 76
ccgtgaatca agctgataaa cag                                         23

SEQ ID NO: 77          moltype = DNA  length = 24
FEATURE                Location/Qualifiers
misc_feature           1..24
                       note = Description of sequence: Primer # apc022; PCR check
                        for integrations YPRC?3
source                 1..24
                       mol_type = other DNA
                       organism = synthetic construct
SEQUENCE: 77
cctggacact ttacttatct agcg                                        24

SEQ ID NO: 78          moltype = DNA  length = 24
FEATURE                Location/Qualifiers
misc_feature           1..24
                       note = Description of sequence: Primer # apc023; PCR check
                        for integrations YORW-delta-22
source                 1..24
                       mol_type = other DNA
                       organism = synthetic construct
SEQUENCE: 78
ggaaatatat gcgcagtatg ctcc                                        24

SEQ ID NO: 79          moltype = DNA  length = 25
FEATURE                Location/Qualifiers
misc_feature           1..25
                       note = Description of sequence: Primer # apc024; PCR check
                        for integrations YORW-delta-22
source                 1..25
                       mol_type = other DNA
                       organism = synthetic construct
SEQUENCE: 79
cgaatcaaac gaatgctttg gaaac                                       25

SEQ ID NO: 80          moltype = DNA  length = 79
FEATURE                Location/Qualifiers
misc_feature           1..79
                       note = Description of sequence: Primer # apc025; PCR
                        pSNR52-gRNA-tSUP4, mimicks amplification from HR1 backbone
source                 1..79
                       mol_type = other DNA
                       organism = synthetic construct
SEQUENCE: 80
gttattcctc gtatgcgaca cactaacaac gaatggttaa gtagccaggt gtccatccca  60
gtgagttgat tggaagacc                                              79

SEQ ID NO: 81          moltype = DNA  length = 79
FEATURE                Location/Qualifiers
misc_feature           1..79
                       note = Description of sequence: Primer # apc026; PCR
                        pSNR52-gRNA-tSUP4, mimicks amplification from HR1 backbone
source                 1..79
                       mol_type = other DNA
                       organism = synthetic construct
SEQUENCE: 81
caatcgctac agaaacgatt ttcaacagta tttacctcga cacaggtcgc ttggtcctgt  60
gagctgatac cgctcgaag                                              79

SEQ ID NO: 82          moltype = DNA  length = 79
FEATURE                Location/Qualifiers
misc_feature           1..79
                       note = Description of sequence: Primer # apc027;
                        AGA2-4-4-20 for insertion
source                 1..79
                       mol_type = other DNA
                       organism = synthetic construct
SEQUENCE: 82
gttattcctc gtatgcgaca cactaacaac gaatggttaa gtagccaggt gtccatcaca  60
tggcattacc accatatac                                              79
```

```
SEQ ID NO: 83           moltype = DNA  length = 79
FEATURE                 Location/Qualifiers
misc_feature            1..79
                        note = Description of sequence: Primer # apc028;
                         AGA2-4-4-20 for insertion
source                  1..79
                        mol_type = other DNA
                        organism = synthetic construct
SEQUENCE: 83
ctacagaaac gattttcaac agtatttacc tcgacacagg tcgcttggtc ctaattctct  60
taggattcga ttcacattc                                               79

SEQ ID NO: 84           moltype = DNA  length = 60
FEATURE                 Location/Qualifiers
misc_feature            1..60
                        note = Description of sequence: Primer # apc029; AGA2-4m5.3
                         Fragment 1 for pCT backbone
source                  1..60
                        mol_type = other DNA
                        organism = synthetic construct
SEQUENCE: 84
tacttcttat tcaaatgtaa taaaagatcg aattccctac ttcatacatt ttcaattaag  60

SEQ ID NO: 85           moltype = DNA  length = 25
FEATURE                 Location/Qualifiers
misc_feature            1..25
                        note = Description of sequence: Primer # apc030; AGA2-4m5.3
                         Fragment 1 for pCT backbone
source                  1..25
                        mol_type = other DNA
                        organism = synthetic construct
SEQUENCE: 85
ctagcagaac caccaccacc agaac                                        25

SEQ ID NO: 86           moltype = DNA  length = 35
FEATURE                 Location/Qualifiers
misc_feature            1..35
                        note = Description of sequence: Primer # apc031; AGA2-4m5.3
                         Fragment 2 for pCT backbone
source                  1..35
                        mol_type = other DNA
                        organism = synthetic construct
SEQUENCE: 86
ggtggtggtg gttctgctag cgacgtcgtt atgac                             35

SEQ ID NO: 87           moltype = DNA  length = 66
FEATURE                 Location/Qualifiers
misc_feature            1..66
                        note = Description of sequence: Primer # apc032; AGA2-4m5.3
                         Fragment 2 for pCT backbone
source                  1..66
                        mol_type = other DNA
                        organism = synthetic construct
SEQUENCE: 87
gttacatcta cactgttgtt atcagatctc gagctattac aagtcttctt cagaaataag  60
cttttg                                                             66

SEQ ID NO: 88           moltype = DNA  length = 44
FEATURE                 Location/Qualifiers
misc_feature            1..44
                        note = Description of sequence: Primer # apc033; wtGFP
                         Fragment 1 for EMY backbone
source                  1..44
                        mol_type = other DNA
                        organism = synthetic construct
SEQUENCE: 88
cagagcagat tgtactgggt ctcaaatggt gagcaagggc gagg                   44

SEQ ID NO: 89           moltype = DNA  length = 30
FEATURE                 Location/Qualifiers
misc_feature            1..30
                        note = Description of sequence: Primer # apc034; wtGFP
                         Fragment 1 for EMY backbone
source                  1..30
                        mol_type = other DNA
                        organism = synthetic construct
SEQUENCE: 89
cgccgtagct gaaggtggtc acgagggtgg                                   30
```

```
SEQ ID NO: 90          moltype = DNA  length = 33
FEATURE                Location/Qualifiers
misc_feature           1..33
                       note = Description of sequence: Primer # apc035; wtGFP
                        Fragment 2 for EMY backbone
source                 1..33
                       mol_type = other DNA
                       organism = synthetic construct
SEQUENCE: 90
gtgaccacct tcagctacgg cgtgcagtgc ttc                              33

SEQ ID NO: 91          moltype = DNA  length = 45
FEATURE                Location/Qualifiers
misc_feature           1..45
                       note = Description of sequence: Primer # apc036; wtGFP
                        Fragment 2 for EMY backbone
source                 1..45
                       mol_type = other DNA
                       organism = synthetic construct
SEQUENCE: 91
gagctgatac cgctcggtct cttttacttg tacagctcgt ccatg                 45

SEQ ID NO: 92          moltype = DNA  length = 51
FEATURE                Location/Qualifiers
misc_feature           1..51
                       note = Description of sequence: Primer # apc037;
                        AGA2-4-4-20 for EMY backbone
source                 1..51
                       mol_type = other DNA
                       organism = synthetic construct
SEQUENCE: 92
catcagagca gattgtactg ggtctcaaat gcagttactt cgctgttttt c          51

SEQ ID NO: 93          moltype = DNA  length = 55
FEATURE                Location/Qualifiers
misc_feature           1..55
                       note = Description of sequence: Primer # apc038;
                        AGA2-4-4-20 for EMY backbone
source                 1..55
                       mol_type = other DNA
                       organism = synthetic construct
SEQUENCE: 93
gtgagctgat accgctcggt ctcttttaca agtcttcttc agaaataagc ttttg      55

SEQ ID NO: 94          moltype = DNA  length = 42
FEATURE                Location/Qualifiers
misc_feature           1..42
                       note = Description of sequence: Primer # apc039;
                        AGA2-4-4-20 mutants for HR backbone
source                 1..42
                       mol_type = other DNA
                       organism = synthetic construct
SEQUENCE: 94
aaaggtctca gtgcacatgg cattaccacc atatacatat cc                    42

SEQ ID NO: 95          moltype = DNA  length = 44
FEATURE                Location/Qualifiers
misc_feature           1..44
                       note = Description of sequence: Primer # apc040;
                        AGA2-4-4-20 mutants for HR backbone
source                 1..44
                       mol_type = other DNA
                       organism = synthetic construct
SEQUENCE: 95
aaaggtctca gaggaattct cttaggattc gattcacatt catc                  44

SEQ ID NO: 96          moltype = DNA  length = 62
FEATURE                Location/Qualifiers
misc_feature           1..62
                       note = Description of sequence: Primer # apc041;
                        High-throughput sequencing of GFP
source                 1..62
                       mol_type = other DNA
                       organism = synthetic construct
SEQUENCE: 96
acactctttc cctacacgac gctcttccga tctatcacga atggtgagca agggcgagga  60
gc                                                                 62
```

```
SEQ ID NO: 97          moltype = DNA  length = 61
FEATURE                Location/Qualifiers
misc_feature           1..61
                       note = Description of sequence: Primer # apc042;
                        High-throughput sequencing of GFP
source                 1..61
                       mol_type = other DNA
                       organism = synthetic construct
SEQUENCE: 97
gactggagtt cagacgtgtg ctcttccgat ctcgatgttc agctcgatgc ggttcaccag  60
g                                                                  61

SEQ ID NO: 98          moltype = DNA  length = 62
FEATURE                Location/Qualifiers
misc_feature           1..62
                       note = Description of sequence: Primer # apc043; dCas9
                        Fragment 1 for EMY backbone
source                 1..62
                       mol_type = other DNA
                       organism = synthetic construct
SEQUENCE: 98
catcagagca gattgtactg ggtctcaaat ggataaaaag tatagtattg gtttagctat  60
tg                                                                 62

SEQ ID NO: 99          moltype = DNA  length = 45
FEATURE                Location/Qualifiers
misc_feature           1..45
                       note = Description of sequence: Primer # apc044; dCas9
                        Fragment 1 for EMY backbone
source                 1..45
                       mol_type = other DNA
                       organism = synthetic construct
SEQUENCE: 99
caagaaagat tgtggaacta tggcatctac atcataatct gaaag                  45

SEQ ID NO: 100         moltype = DNA  length = 45
FEATURE                Location/Qualifiers
misc_feature           1..45
                       note = Description of sequence: Primer # apc045; dCas9
                        Fragment 2 for EMY backbone
source                 1..45
                       mol_type = other DNA
                       organism = synthetic construct
SEQUENCE: 100
ctttcagatt atgatgtaga tgccatagtt ccacaatctt tcttg                  45

SEQ ID NO: 101         moltype = DNA  length = 53
FEATURE                Location/Qualifiers
misc_feature           1..53
                       note = Description of sequence: Primer # apc046; dCas9
                        Fragment 2 for EMY backbone
source                 1..53
                       mol_type = other DNA
                       organism = synthetic construct
SEQUENCE: 101
gagctgatac cgctcggtct cttttaaacc tttctctttt tcttaggatc cac         53

SEQ ID NO: 102         moltype = DNA  length = 57
FEATURE                Location/Qualifiers
misc_feature           1..57
                       note = Description of sequence: Primer # apc047; Nested PCR
                        to fust RFA3 to dCas9 for EMY backbone, reverse primer
source                 1..57
                       mol_type = other DNA
                       organism = synthetic construct
SEQUENCE: 102
gagctgatac cgctcggtct cttttagtat atttctgggt atttcttaca tagtctc     57

SEQ ID NO: 103         moltype = DNA  length = 69
FEATURE                Location/Qualifiers
misc_feature           1..69
                       note = Description of sequence: Primer # apc048; forward
                        primer 1
source                 1..69
                       mol_type = other DNA
                       organism = synthetic construct
SEQUENCE: 103
ctagcggatc cgagactcct gggacctcag agtctgctac acccgaaagt tcaggtggat  60
cttctggtg                                                          69
```

```
SEQ ID NO: 104          moltype = DNA  length = 69
FEATURE                 Location/Qualifiers
misc_feature            1..69
                        note = Description of sequence: Primer # apc049; forward
                         primer 2
source                  1..69
                        mol_type = other DNA
                        organism = synthetic construct
SEQUENCE: 104
ggtggatcct aagaaaaaga gaaaggtttc cggtggatct tctggtggtt ctagcggatc  60
cgagactcc                                                          69

SEQ ID NO: 105          moltype = DNA  length = 50
FEATURE                 Location/Qualifiers
misc_feature            1..50
                        note = Description of sequence: Primer # apc050; Nested PCR
                         to fuse AID731-delta- to dCas9 for EMY backbone, reverse
                         primer
source                  1..50
                        mol_type = other DNA
                        organism = synthetic construct
SEQUENCE: 105
gagctgatac cgctcggtct cttttatgtc ctgaatgcat cacgtaaatc             50

SEQ ID NO: 106          moltype = DNA  length = 59
FEATURE                 Location/Qualifiers
misc_feature            1..59
                        note = Description of sequence: Primer # apc051; forward
                         primer 1
source                  1..59
                        mol_type = other DNA
                        organism = synthetic construct
SEQUENCE: 106
ttcaggtgga ggcagtggag gtggtggatc tatggattca ctattaatga atagaagtg   59

SEQ ID NO: 107          moltype = DNA  length = 52
FEATURE                 Location/Qualifiers
misc_feature            1..52
                        note = Description of sequence: Primer # apc052; forward
                         primer 2
source                  1..52
                        mol_type = other DNA
                        organism = synthetic construct
SEQUENCE: 107
cgtaaggtgg atcctaagaa aaagagaaag gtttcaggtg gaggcagtgg ag          52

SEQ ID NO: 108          moltype = DNA  length = 55
FEATURE                 Location/Qualifiers
misc_feature            1..55
                        note = Description of sequence: Primer # apc053;
                         MCP-AID*-delta- for EMY backbone
source                  1..55
                        mol_type = other DNA
                        organism = synthetic construct
SEQUENCE: 108
catcagagca gattgtactg ggtctcaaat ggctagtaat tttactcaat tcgtg       55

SEQ ID NO: 109          moltype = DNA  length = 50
FEATURE                 Location/Qualifiers
misc_feature            1..50
                        note = Description of sequence: Primer # apc054;
                         MCP-AID*-delta- for EMY backbone
source                  1..50
                        mol_type = other DNA
                        organism = synthetic construct
SEQUENCE: 109
gagctgatac cgctcggtct cttttatgtc ctgaatgcat cacgtaaatc             50

SEQ ID NO: 110          moltype = DNA  length = 23
FEATURE                 Location/Qualifiers
misc_feature            1..23
                        note = Description of sequence: Primer # apc055;
                         MCP-AIDdead Fragment 1 (MCP) for EMY backbone
source                  1..23
                        mol_type = other DNA
                        organism = synthetic construct
SEQUENCE: 110
ctctttttct tagggcctga acc                                          23
```

```
SEQ ID NO: 111          moltype = DNA  length = 26
FEATURE                 Location/Qualifiers
misc_feature            1..26
                        note = Description of sequence: Primer # apc056;
                         MCP-AIDdead Fragment 2 (AIDdead) for EMY backbone
source                  1..26
                        mol_type = other DNA
                        organism = synthetic construct
SEQUENCE: 111
aggccctaag aaaaagagaa aagtgg                                        26

SEQ ID NO: 112          moltype = DNA  length = 26
FEATURE                 Location/Qualifiers
misc_feature            1..26
                        note = Description of sequence: Primer # apc057;
                         MCP-AIDmono Fragment 1 (MCP) for EMY backbone
source                  1..26
                        mol_type = other DNA
                        organism = synthetic construct
SEQUENCE: 112
atccatgccg gctgcggcca cttttc                                        26

SEQ ID NO: 113          moltype = DNA  length = 65
FEATURE                 Location/Qualifiers
misc_feature            1..65
                        note = Description of sequence: Primer # apc058;
                         MCP-AIDmono Fragment 2 for EMY backbone
source                  1..65
                        mol_type = other DNA
                        organism = synthetic construct
SEQUENCE: 113
gaaaagtggc cgcagccggc atggatccag ctacctttac gtaccaattt aagaacgtga  60
gatgg                                                               65

SEQ ID NO: 114          moltype = DNA  length = 39
FEATURE                 Location/Qualifiers
misc_feature            1..39
                        note = Description of sequence: Primer # apc059;
                         MCP-AIDmono Fragment 2 for EMY backbone
source                  1..39
                        mol_type = other DNA
                        organism = synthetic construct
SEQUENCE: 114
catggtgacc aagaggtaaa ccatgtaaca cgataacac                          39

SEQ ID NO: 115          moltype = DNA  length = 36
FEATURE                 Location/Qualifiers
misc_feature            1..36
                        note = Description of sequence: Primer # apc060;
                         MCP-AIDmono Fragment 3 for EMY backbone
source                  1..36
                        mol_type = other DNA
                        organism = synthetic construct
SEQUENCE: 115
gtgttacatg gtttacctct tggtcaccat gctatg                             36

SEQ ID NO: 116          moltype = DNA  length = 40
FEATURE                 Location/Qualifiers
misc_feature            1..40
                        note = Description of sequence: Primer # apc061;
                         MCP-AIDmono Fragment 3 for EMY backbone
source                  1..40
                        mol_type = other DNA
                        organism = synthetic construct
SEQUENCE: 116
ctgaactccg gcttcggcta atcttcttaa gccttcaggc                         40

SEQ ID NO: 117          moltype = DNA  length = 39
FEATURE                 Location/Qualifiers
misc_feature            1..39
                        note = Description of sequence: Primer # apc062;
                         MCP-AIDmono Fragment 4 for EMY backbone
source                  1..39
                        mol_type = other DNA
                        organism = synthetic construct
SEQUENCE: 117
aggcttaaga agattagccg aagccggagt tcagattgc                          39
```

```
SEQ ID NO: 118         moltype = DNA  length = 52
FEATURE                Location/Qualifiers
misc_feature           1..52
                       note = Description of sequence: Primer # apc063;
                        MCP-AIDmono Fragment 4 for EMY backbone
source                 1..52
                       mol_type = other DNA
                       organism = synthetic construct
SEQUENCE: 118
gagctgatac cgctcggtct cttttactgc aatattcttc ttaattgcct ac          52

SEQ ID NO: 119         moltype = DNA  length = 37
FEATURE                Location/Qualifiers
misc_feature           1..37
                       note = Description of sequence: Primer # apc064;
                        MCP-AID*mono Fragment 1 for EMY backbone
source                 1..37
                       mol_type = other DNA
                       organism = synthetic construct
SEQUENCE: 119
ggtgaccaag agataaacca tgtaacacga taacacc                           37

SEQ ID NO: 120         moltype = DNA  length = 37
FEATURE                Location/Qualifiers
misc_feature           1..37
                       note = Description of sequence: Primer # apc065;
                        MCP-AID*mono Fragment 2 for EMY backbone
source                 1..37
                       mol_type = other DNA
                       organism = synthetic construct
SEQUENCE: 120
cgtgttacat ggtttatctc ttggtcacca tgctatg                           37

SEQ ID NO: 121         moltype = DNA  length = 40
FEATURE                Location/Qualifiers
misc_feature           1..40
                       note = Description of sequence: Primer # apc066;
                        MCP-AID*mono Fragment 2 for EMY backbone
source                 1..40
                       mol_type = other DNA
                       organism = synthetic construct
SEQUENCE: 121
agctttgaag gttctaccat gattttcgac gaaggtattc                        40

SEQ ID NO: 122         moltype = DNA  length = 34
FEATURE                Location/Qualifiers
misc_feature           1..34
                       note = Description of sequence: Primer # apc067;
                        MCP-AID*mono Fragment 3 for EMY backbone
source                 1..34
                       mol_type = other DNA
                       organism = synthetic construct
SEQUENCE: 122
gtcgaaaatc atggtagaac cttcaaagct tggg                              34

SEQ ID NO: 123         moltype = DNA  length = 19
FEATURE                Location/Qualifiers
misc_feature           1..19
                       note = Description of sequence: Primer # apc068;
                        MCP-AID*mono Fragment 3 for EMY backbone
source                 1..19
                       mol_type = other DNA
                       organism = synthetic construct
SEQUENCE: 123
gagctgatac cgctcggtc                                               19

SEQ ID NO: 124         moltype = DNA  length = 44
FEATURE                Location/Qualifiers
misc_feature           1..44
                       note = Description of sequence: Primer # apc069;
                        AID731-delta- Fragment 1 for EMY backbone
source                 1..44
                       mol_type = other DNA
                       organism = synthetic construct
SEQUENCE: 124
ggtacaaaaa ttcacttcta ttcattaata gtgaatccat agag                   44

SEQ ID NO: 125         moltype = DNA  length = 52
FEATURE                Location/Qualifiers
```

```
misc_feature           1..52
                       note = Description of sequence: Primer # apc070;
                        AID731-delta- Fragment 2 for EMY backbone
source                 1..52
                       mol_type = other DNA
                       organism = synthetic construct
SEQUENCE: 125
ggattcacta ttaatgaata gaagtgaatt tttgtaccaa tttaagaacg tg          52

SEQ ID NO: 126         moltype = DNA  length = 53
FEATURE                Location/Qualifiers
misc_feature           1..53
                       note = Description of sequence: Primer # apc071;
                        AID731-delta- Fragment 2 for EMY backbone
source                 1..53
                       mol_type = other DNA
                       organism = synthetic construct
SEQUENCE: 126
acgagaaaag gaagttgctg agtcgcatct tttcactacg taacatagat aag         53

SEQ ID NO: 127         moltype = DNA  length = 55
FEATURE                Location/Qualifiers
misc_feature           1..55
                       note = Description of sequence: Primer # apc072;
                        AID731-delta- Fragment 3 for EMY backbone
source                 1..55
                       mol_type = other DNA
                       organism = synthetic construct
SEQUENCE: 127
tgcgactcag caacttcctt ttctcgtgat ttcggttact taagaaataa gaacg       55

SEQ ID NO: 128         moltype = DNA  length = 41
FEATURE                Location/Qualifiers
misc_feature           1..41
                       note = Description of sequence: Primer # apc073;
                        AID731-delta- Fragment 3 for EMY backbone
source                 1..41
                       mol_type = other DNA
                       organism = synthetic construct
SEQUENCE: 128
cagctactag tctggcacaa tcagagcatg gtgaccaaga g                      41

SEQ ID NO: 129         moltype = DNA  length = 44
FEATURE                Location/Qualifiers
misc_feature           1..44
                       note = Description of sequence: Primer # apc074;
                        AID731-delta- Fragment 4 for EMY backbone
source                 1..44
                       mol_type = other DNA
                       organism = synthetic construct
SEQUENCE: 129
gctctgattg tgccagacta gtagctgatt tcttacgtgg taac                   44

SEQ ID NO: 130         moltype = DNA  length = 44
FEATURE                Location/Qualifiers
misc_feature           1..44
                       note = Description of sequence: Primer # apc075;
                        AID731-delta- Fragment 4 for EMY backbone
source                 1..44
                       mol_type = other DNA
                       organism = synthetic construct
SEQUENCE: 130
cagcagtaaa agtaatcttc gaaagtcatt attgcaatct gaac                   44

SEQ ID NO: 131         moltype = DNA  length = 41
FEATURE                Location/Qualifiers
misc_feature           1..41
                       note = Description of sequence: Primer # apc076;
                        AID731-delta- Fragment 5 for EMY backbone
source                 1..41
                       mol_type = other DNA
                       organism = synthetic construct
SEQUENCE: 131
gcaataatga ctttcgaaga ttacttttac tgctggaata c                      41

SEQ ID NO: 132         moltype = DNA  length = 19
FEATURE                Location/Qualifiers
misc_feature           1..19
                       note = Description of sequence: Primer # apc077;
```

```
                         MCP-altcodon_AID*-delta- Fragment 1 (MCP) for EMY backbone
source                  1..19
                        mol_type = other DNA
                        organism = synthetic construct
SEQUENCE: 132
ggctgcggcc acttttctc                                              19

SEQ ID NO: 133          moltype = DNA  length = 29
FEATURE                 Location/Qualifiers
misc_feature            1..29
                        note = Description of sequence: Primer # apc078;
                         MCP-altcodon_AID*-delta- Fragment 2 (human or alt. yeast
                         codon optimized AID*-delta-) for EMY backbone
source                  1..29
                        mol_type = other DNA
                        organism = synthetic construct
SEQUENCE: 133
ctaagaaaaa gagaaaagtg gccgcagcc                                   29

SEQ ID NO: 134          moltype = DNA  length = 50
FEATURE                 Location/Qualifiers
misc_feature            1..50
                        note = Description of sequence: Primer # apc079;
                         MCPz-AID*-delta- Fragment 1 (pGal2) for HR1 backbone
source                  1..50
                        mol_type = other DNA
                        organism = synthetic construct
SEQUENCE: 134
gaatggttaa gtagccaggt gtccatcgtg cctaatccaa ggaggtttac            50

SEQ ID NO: 135          moltype = DNA  length = 55
FEATURE                 Location/Qualifiers
misc_feature            1..55
                        note = Description of sequence: Primer # apc080;
                         MCPz-AID*-delta- Fragment 1 (pGal2) for HR1 backbone
source                  1..55
                        mol_type = other DNA
                        organism = synthetic construct
SEQUENCE: 135
ggcatctcga gagacattat gaaagaatta ttttttttat tatgttaatc ttgtg       55

SEQ ID NO: 136          moltype = DNA  length = 41
FEATURE                 Location/Qualifiers
misc_feature            1..41
                        note = Description of sequence: Primer # apc081;
                         MCPz-AID*-delta- Fragment 2 (MCPz) for HR1 backbone
source                  1..41
                        mol_type = other DNA
                        organism = synthetic construct
SEQUENCE: 136
aaaataattc tttcataatg tctctcgaga tgcccaaaaa g                     41

SEQ ID NO: 137          moltype = DNA  length = 42
FEATURE                 Location/Qualifiers
misc_feature            1..42
                        note = Description of sequence: Primer # apc082;
                         MCPz-AID*-delta- Fragment 2 (MCPz) for HR1 backbone
source                  1..42
                        mol_type = other DNA
                        organism = synthetic construct
SEQUENCE: 137
cacctccaga tccacctcct ccgtagatgc cggagtttgc tg                    42

SEQ ID NO: 138          moltype = DNA  length = 53
FEATURE                 Location/Qualifiers
misc_feature            1..53
                        note = Description of sequence: Primer # apc083;
                         MCPz-AID*-delta- Fragment 3 (AID*-delta-) for HR1 backbone
source                  1..53
                        mol_type = other DNA
                        organism = synthetic construct
SEQUENCE: 138
ggaggaggtg gatctggagg tggaggctct atggattcac tattaatgaa tag         53

SEQ ID NO: 139          moltype = DNA  length = 38
FEATURE                 Location/Qualifiers
misc_feature            1..38
                        note = Description of sequence: Primer # apc084;
                         MCPz-AID*-delta- Fragment 3 (AID*-delta-) for HR1 backbone
```

```
source                  1..38
                        mol_type = other DNA
                        organism = synthetic construct
SEQUENCE: 139
cttcagcaac cgtcctttta tgtcctgaat gcatcacg                          38

SEQ ID NO: 140          moltype = DNA  length = 37
FEATURE                 Location/Qualifiers
misc_feature            1..37
                        note = Description of sequence: Primer # apc085;
                         MCPz-AID*-delta- Fragment 4 (Tvma2) for HR1 backbone
source                  1..37
                        mol_type = other DNA
                        organism = synthetic construct
SEQUENCE: 140
cattcaggac ataaaaggac ggttgctgaa gaaaaag                           37

SEQ ID NO: 141          moltype = DNA  length = 46
FEATURE                 Location/Qualifiers
misc_feature            1..46
                        note = Description of sequence: Primer # apc086;
                         MCPz-AID*-delta- Fragment 4 (Tvma2) for HR1 backbone
source                  1..46
                        mol_type = other DNA
                        organism = synthetic construct
SEQUENCE: 141
tcgacacagg tcgcttggtc ctgaggtgtg ttccttgatc tttttc                 46

SEQ ID NO: 142          moltype = DNA  length = 67
FEATURE                 Location/Qualifiers
misc_feature            1..67
                        note = Description of sequence: Primer # apc087;
                         MCP-AID*-delta--RFA3 Fragment 1 (Pgal2-MCP-AID*-delta-)
                         for HR1 backbone
source                  1..67
                        mol_type = other DNA
                        organism = synthetic construct
SEQUENCE: 142
ctgaacttcc gccgctagaa cctcctgaag aaccaccaga ttatgtcctg aatgcatcac  60
gtaaatc                                                            67

SEQ ID NO: 143          moltype = DNA  length = 64
FEATURE                 Location/Qualifiers
misc_feature            1..64
                        note = Description of sequence: Primer # apc088;
                         MCP-AID*-delta--RFA3 Fragment 2 (RFA3) for HR1 backbone
source                  1..64
                        mol_type = other DNA
                        organism = synthetic construct
SEQUENCE: 143
gaggttctag cggcggaagt tcaggtggat cttctggtgg atccatggcc agcgaaacac  60
caag                                                               64

SEQ ID NO: 144          moltype = DNA  length = 42
FEATURE                 Location/Qualifiers
misc_feature            1..42
                        note = Description of sequence: Primer # apc089;
                         MCP-AID*-delta--RFA3 Fragment 2 (RFA3) for HR1 backbone
source                  1..42
                        mol_type = other DNA
                        organism = synthetic construct
SEQUENCE: 144
gcaaccgtcc ttctagtata tttctgggta tttcttacat ag                     42

SEQ ID NO: 145          moltype = DNA  length = 40
FEATURE                 Location/Qualifiers
misc_feature            1..40
                        note = Description of sequence: Primer # apc090;
                         MCP-AID*-delta--RFA3 Fragment 3 (Tvma2) for HR1 backbone
source                  1..40
                        mol_type = other DNA
                        organism = synthetic construct
SEQUENCE: 145
acccagaaat atactagaag gacggttgct gaagaaaaag                        40

SEQ ID NO: 146          moltype = DNA  length = 62
FEATURE                 Location/Qualifiers
misc_feature            1..62
                        note = Description of sequence: Primer # apc091; pSNR52 for
```

```
                       pY120 backbone
source                1..62
                      mol_type = other DNA
                      organism = synthetic construct
SEQUENCE: 146
gagccagtga gttgattgga agacctggat cctctttgaa aagataatgt atgattatgc  60
tt                                                                 62

SEQ ID NO: 147        moltype = DNA  length = 40
FEATURE               Location/Qualifiers
misc_feature          1..40
                      note = Description of sequence: Primer # apc092; pSNR52 for
                       pY120 backbone
source                1..40
                      mol_type = other DNA
                      organism = synthetic construct
SEQUENCE: 147
aattccgtca gccagggtct cgatcattta tctttcactg                        40

SEQ ID NO: 148        moltype = DNA  length = 38
FEATURE               Location/Qualifiers
misc_feature          1..38
                      note = Description of sequence: Primer # apc093; Blank gap
                       for pY120 backbone
source                1..38
                      mol_type = other DNA
                      organism = synthetic construct
SEQUENCE: 148
gataaatgat cgagaccctg gctgacggaa tttatgcc                          38

SEQ ID NO: 149        moltype = DNA  length = 34
FEATURE               Location/Qualifiers
misc_feature          1..34
                      note = Description of sequence: Primer # apc094; Blank gap
                       for pY120 backbone
source                1..34
                      mol_type = other DNA
                      organism = synthetic construct
SEQUENCE: 149
ctagctctga aactgagacc gagaaaactc accg                              34

SEQ ID NO: 150        moltype = DNA  length = 57
FEATURE               Location/Qualifiers
misc_feature          1..57
                      note = Description of sequence: Primer # apc095; Nested PCR
                       M13 for pY120 backbone
source                1..57
                      mol_type = other DNA
                      organism = synthetic construct
SEQUENCE: 150
gagtgagctg ataccgctcg aagacggatc cagacataaa aaacaaaaaa agcaccg     57

SEQ ID NO: 151        moltype = DNA  length = 53
FEATURE               Location/Qualifiers
misc_feature          1..53
                      note = Description of sequence: Primer # apc096; forward
                       primer 1
source                1..53
                      mol_type = other DNA
                      organism = synthetic construct
SEQUENCE: 151
gtttcagagc taggccaaca tgaggatcac ccatgtctgc agggcctagc aag         53

SEQ ID NO: 152        moltype = DNA  length = 39
FEATURE               Location/Qualifiers
misc_feature          1..39
                      note = Description of sequence: Primer # apc097; forward
                       primer 2
source                1..39
                      mol_type = other DNA
                      organism = synthetic construct
SEQUENCE: 152
gagttttctc ggtctcagtt tcagagctag gccaacatg                         39

SEQ ID NO: 153        moltype = DNA  length = 41
FEATURE               Location/Qualifiers
misc_feature          1..41
                      note = Description of sequence: Primer # apc098; M4 or No
                       Ms2 for pY120 backbone
```

```
source                  1..41
                        mol_type = other DNA
                        organism = synthetic construct
SEQUENCE: 153
gttttctcgg tctcagtttc agagctagaa atagcaagtt g                    41

SEQ ID NO: 154          moltype = DNA  length = 22
FEATURE                 Location/Qualifiers
misc_feature            1..22
                        note = Description of sequence: Primer # apc099; Mtx2
                         Fragment 1 (gRNA scaffold) for pY120 backbone
source                  1..22
                        mol_type = other DNA
                        organism = synthetic construct
SEQUENCE: 154
tcccgcaccg actcggtgcc ac                                         22

SEQ ID NO: 155          moltype = DNA  length = 19
FEATURE                 Location/Qualifiers
misc_feature            1..19
                        note = Description of sequence: Primer # apc100; Mtx2
                         Fragment 2 (Mtx2) for pY120 backbone
source                  1..19
                        mol_type = other DNA
                        organism = synthetic construct
SEQUENCE: 155
aagtggcacc gagtcggtg                                             19

SEQ ID NO: 156          moltype = DNA  length = 22
FEATURE                 Location/Qualifiers
misc_feature            1..22
                        note = Description of sequence: Primer # apc101; Fragment 1
                         (pSNR52, blank gap, M1) for pY120 backbone
source                  1..22
                        mol_type = other DNA
                        organism = synthetic construct
SEQUENCE: 156
gagccagtga gttgattgga ag                                         22

SEQ ID NO: 157          moltype = DNA  length = 27
FEATURE                 Location/Qualifiers
misc_feature            1..27
                        note = Description of sequence: Primer # apc102; Fragment 1
                         (pSNR52, blank gap, M1) for pY120 backbone
source                  1..27
                        mol_type = other DNA
                        organism = synthetic construct
SEQUENCE: 157
aagttgataa cggactagcc ttatttc                                    27

SEQ ID NO: 158          moltype = DNA  length = 24
FEATURE                 Location/Qualifiers
misc_feature            1..24
                        note = Description of sequence: Primer # apc103; Fragment 2
                         (No MS2 or M4) for pY120 backbone
source                  1..24
                        mol_type = other DNA
                        organism = synthetic construct
SEQUENCE: 158
agcaagttga aataaggcta gtcc                                       24

SEQ ID NO: 159          moltype = DNA  length = 31
FEATURE                 Location/Qualifiers
misc_feature            1..31
                        note = Description of sequence: Primer # apc104; [Makes M1
                         or M14]
source                  1..31
                        mol_type = other DNA
                        organism = synthetic construct
SEQUENCE: 159
gagctgatac cgctcgaaga cctggatcca g                               31

SEQ ID NO: 160          moltype = DNA  length = 53
FEATURE                 Location/Qualifiers
misc_feature            1..53
                        note = Description of sequence: Primer # apc105;
                         pSNR52-blank gap-[Mt or M13t] Nested PCR for pY120g
                         backbone, reverse primer 1
source                  1..53
```

```
                        mol_type = other DNA
                        organism = synthetic construct
SEQUENCE: 160
aacaaaaaaa gcacatgggt gatcctcatg tgcgcgcacc gactcggtgc cac         53

SEQ ID NO: 161          moltype = DNA  length = 60
FEATURE                 Location/Qualifiers
misc_feature            1..60
                        note = Description of sequence: Primer # apc106;
                         pSNR52-blank gap-[Mt or M13t] Nested PCR for pY120g
                         backbone, reverse primer 2
source                  1..60
                        mol_type = other DNA
                        organism = synthetic construct
SEQUENCE: 161
gctgataccg ctcgaagacc tgcagagaca taaaaaacaa aaaaagcaca tgggtgatcc  60

SEQ ID NO: 162          moltype = DNA  length = 22
FEATURE                 Location/Qualifiers
misc_feature            1..22
                        note = Description of sequence: Primer # apc107; Fragment 1
                         (pSNR52, blank gap, M1 or M3 or M1,3) for pY120 backbone
source                  1..22
                        mol_type = other DNA
                        organism = synthetic construct
SEQUENCE: 162
tcccgcaccg actcggtgcc ac                                           22

SEQ ID NO: 163          moltype = DNA  length = 19
FEATURE                 Location/Qualifiers
misc_feature            1..19
                        note = Description of sequence: Primer # apc108; Fragment 2
                         (Mtx2) for pY120 backbone
source                  1..19
                        mol_type = other DNA
                        organism = synthetic construct
SEQUENCE: 163
aagtggcacc gagtcggtg                                               19

SEQ ID NO: 164          moltype = DNA  length = 68
FEATURE                 Location/Qualifiers
misc_feature            1..68
                        note = Description of sequence: Primer # apc109; Fragment 1
                         (pSNR52, blank gap, M3) for pY120 backbone
source                  1..68
                        mol_type = other DNA
                        organism = synthetic construct
SEQUENCE: 164
cctcggtgcc acttggccct gcagacatgg gtgatcctca tgttggccaa gttgataacg  60
gactagcc                                                           68

SEQ ID NO: 165          moltype = DNA  length = 27
FEATURE                 Location/Qualifiers
misc_feature            1..27
                        note = Description of sequence: Primer # apc110; Fragment 2
                         (M4) for pY120 backbone
source                  1..27
                        mol_type = other DNA
                        organism = synthetic construct
SEQUENCE: 165
gcagggccaa gtggcaccga ggccaac                                      27

SEQ ID NO: 166          moltype = DNA  length = 25
FEATURE                 Location/Qualifiers
misc_feature            1..25
                        note = Description of sequence: Primer # apc111; Anneal for
                         NT1
source                  1..25
                        mol_type = other DNA
                        organism = synthetic construct
SEQUENCE: 166
tgatccggcg tcgaagcctg taaag                                        25

SEQ ID NO: 167          moltype = DNA  length = 25
FEATURE                 Location/Qualifiers
misc_feature            1..25
                        note = Description of sequence: Primer # apc112; Anneal for
                         NT1
source                  1..25
```

```
                        mol_type = other DNA
                        organism = synthetic construct
SEQUENCE: 167
aaacctttac aggcttcgac gccgg                                            25

SEQ ID NO: 168          moltype = DNA  length = 25
FEATURE                 Location/Qualifiers
misc_feature            1..25
                        note = Description of sequence: Primer # apc113; Anneal for
                         wtGFP t74L
source                  1..25
                        mol_type = other DNA
                        organism = synthetic construct
SEQUENCE: 168
tgatcggcga gggcgatgcc accta                                            25

SEQ ID NO: 169          moltype = DNA  length = 25
FEATURE                 Location/Qualifiers
misc_feature            1..25
                        note = Description of sequence: Primer # apc114; Anneal for
                         wtGFP t74L
source                  1..25
                        mol_type = other DNA
                        organism = synthetic construct
SEQUENCE: 169
aaactaggtg gcatcgccct cgccg                                            25

SEQ ID NO: 170          moltype = DNA  length = 25
FEATURE                 Location/Qualifiers
misc_feature            1..25
                        note = Description of sequence: Primer # apc115; Anneal for
                         wtGFP t22L
source                  1..25
                        mol_type = other DNA
                        organism = synthetic construct
SEQUENCE: 170
tgatcccggc aagctgcccg tgccc                                            25

SEQ ID NO: 171          moltype = DNA  length = 25
FEATURE                 Location/Qualifiers
misc_feature            1..25
                        note = Description of sequence: Primer # apc116; Anneal for
                         wtGFP t22L
source                  1..25
                        mol_type = other DNA
                        organism = synthetic construct
SEQUENCE: 171
aaacgggcac gggcagcttg ccggg                                            25

SEQ ID NO: 172          moltype = DNA  length = 25
FEATURE                 Location/Qualifiers
misc_feature            1..25
                        note = Description of sequence: Primer # apc117; Anneal for
                         wtGFP 18L
source                  1..25
                        mol_type = other DNA
                        organism = synthetic construct
SEQUENCE: 172
tgatcgtagc tgaaggtggt cacga                                            25

SEQ ID NO: 173          moltype = DNA  length = 25
FEATURE                 Location/Qualifiers
misc_feature            1..25
                        note = Description of sequence: Primer # apc118; Anneal for
                         wtGFP 18L
source                  1..25
                        mol_type = other DNA
                        organism = synthetic construct
SEQUENCE: 173
aaactcgtga ccaccttcag ctacg                                            25

SEQ ID NO: 174          moltype = DNA  length = 25
FEATURE                 Location/Qualifiers
misc_feature            1..25
                        note = Description of sequence: Primer # apc119; Anneal for
                         wtGFP 6L
source                  1..25
                        mol_type = other DNA
                        organism = synthetic construct
```

```
SEQUENCE: 174
tgatcgcact gcacgccgta gctga                                       25

SEQ ID NO: 175         moltype = DNA  length = 25
FEATURE                Location/Qualifiers
misc_feature           1..25
                       note = Description of sequence: Primer # apc120; Anneal for
                        wtGFP 6L
source                 1..25
                       mol_type = other DNA
                       organism = synthetic construct
SEQUENCE: 175
aaactcagct acggcgtgca gtgcg                                       25

SEQ ID NO: 176         moltype = DNA  length = 25
FEATURE                Location/Qualifiers
misc_feature           1..25
                       note = Description of sequence: Primer # apc121; Anneal for
                        wtGFP 28L
source                 1..25
                       mol_type = other DNA
                       organism = synthetic construct
SEQUENCE: 176
tgatcgtggt cacgagggtg ggcca                                       25

SEQ ID NO: 177         moltype = DNA  length = 25
FEATURE                Location/Qualifiers
misc_feature           1..25
                       note = Description of sequence: Primer # apc122; Anneal for
                        wtGFP 28L
source                 1..25
                       mol_type = other DNA
                       organism = synthetic construct
SEQUENCE: 177
aaactggccc accctcgtga ccacg                                       25

SEQ ID NO: 178         moltype = DNA  length = 25
FEATURE                Location/Qualifiers
misc_feature           1..25
                       note = Description of sequence: Primer # apc123; Anneal for
                        wtGFP 29R
source                 1..25
                       mol_type = other DNA
                       organism = synthetic construct
SEQUENCE: 178
tgatcgtcgt gctgcttcat gtggt                                       25

SEQ ID NO: 179         moltype = DNA  length = 25
FEATURE                Location/Qualifiers
misc_feature           1..25
                       note = Description of sequence: Primer # apc124; Anneal for
                        wtGFP 29R
source                 1..25
                       mol_type = other DNA
                       organism = synthetic construct
SEQUENCE: 179
aaacaccaca tgaagcagca cgacg                                       25

SEQ ID NO: 180         moltype = DNA  length = 25
FEATURE                Location/Qualifiers
misc_feature           1..25
                       note = Description of sequence: Primer # apc125; Anneal for
                        wtGFP 48L
source                 1..25
                       mol_type = other DNA
                       organism = synthetic construct
SEQUENCE: 180
tgatcgggca cgggcagctt gccgg                                       25

SEQ ID NO: 181         moltype = DNA  length = 25
FEATURE                Location/Qualifiers
misc_feature           1..25
                       note = Description of sequence: Primer # apc126; Anneal for
                        wtGFP 48L
source                 1..25
                       mol_type = other DNA
                       organism = synthetic construct
SEQUENCE: 181
aaacccggca agctgcccgt gcccg                                       25
```

```
SEQ ID NO: 182         moltype = DNA  length = 25
FEATURE                Location/Qualifiers
misc_feature           1..25
                       note = Description of sequence: Primer # apc127; Anneal for
                        wtGFP 62R
source                 1..25
                       mol_type = other DNA
                       organism = synthetic construct
SEQUENCE: 182
tgatcgacgt agccttcggg catgg                                        25

SEQ ID NO: 183         moltype = DNA  length = 25
FEATURE                Location/Qualifiers
misc_feature           1..25
                       note = Description of sequence: Primer # apc128; Anneal for
                        wtGFP 62R
source                 1..25
                       mol_type = other DNA
                       organism = synthetic construct
SEQUENCE: 183
aaacccatgc ccgaaggcta cgtcg                                        25

SEQ ID NO: 184         moltype = DNA  length = 25
FEATURE                Location/Qualifiers
misc_feature           1..25
                       note = Description of sequence: Primer # apc129; Anneal for
                        wtGFP 81L
source                 1..25
                       mol_type = other DNA
                       organism = synthetic construct
SEQUENCE: 184
tgatccttca gggtcagctt gccgt                                        25

SEQ ID NO: 185         moltype = DNA  length = 25
FEATURE                Location/Qualifiers
misc_feature           1..25
                       note = Description of sequence: Primer # apc130; Anneal for
                        wtGFP 81L
source                 1..25
                       mol_type = other DNA
                       organism = synthetic construct
SEQUENCE: 185
aaacacggca agctgaccct gaagg                                        25

SEQ ID NO: 186         moltype = DNA  length = 25
FEATURE                Location/Qualifiers
misc_feature           1..25
                       note = Description of sequence: Primer # apc131; Anneal for
                        wtGFP 84R
source                 1..25
                       mol_type = other DNA
                       organism = synthetic construct
SEQUENCE: 186
tgatctgaag aagatggtgc gctcc                                        25

SEQ ID NO: 187         moltype = DNA  length = 25
FEATURE                Location/Qualifiers
misc_feature           1..25
                       note = Description of sequence: Primer # apc132; Anneal for
                        wtGFP 84R
source                 1..25
                       mol_type = other DNA
                       organism = synthetic construct
SEQUENCE: 187
aaacggagcg caccatcttc ttcag                                        25

SEQ ID NO: 188         moltype = DNA  length = 21
FEATURE                Location/Qualifiers
misc_feature           1..21
                       note = Description of sequence: Primer # apc133; gRNA-tRNA
                        Fragment 1 for pUC backbone (used for Mtx2 and M13)
source                 1..21
                       mol_type = other DNA
                       organism = synthetic construct
SEQUENCE: 188
gcgttggccg attcattaat g                                            21

SEQ ID NO: 189         moltype = DNA  length = 37
```

```
FEATURE               Location/Qualifiers
misc_feature          1..37
                      note = Description of sequence: Primer # apc134; gRNA-tRNA
                       Fragment 1 for pUC backbone (used for Mtx2 and M13)
source                1..37
                      mol_type = other DNA
                      organism = synthetic construct
SEQUENCE: 189
ctctgaaact gagaccgaag gagaaaactc accgagg                           37

SEQ ID NO: 190        moltype = DNA  length = 37
FEATURE               Location/Qualifiers
misc_feature          1..37
                      note = Description of sequence: Primer # apc135; Mtx2
                       gRNA-tRNA Fragment 2 (Mtx2) for pUC backbone
source                1..37
                      mol_type = other DNA
                      organism = synthetic construct
SEQUENCE: 190
ctccttcggt ctcagtttca gagctagaaa tagcaag                           37

SEQ ID NO: 191        moltype = DNA  length = 37
FEATURE               Location/Qualifiers
misc_feature          1..37
                      note = Description of sequence: Primer # apc136; Mtx2
                       gRNA-tRNA Fragment 2 (Mtx2) for pUC backbone
source                1..37
                      mol_type = other DNA
                      organism = synthetic construct
SEQUENCE: 191
aaccacttgc gcttgtttgg gaacacgagc gacatgg                           37

SEQ ID NO: 192        moltype = DNA  length = 37
FEATURE               Location/Qualifiers
misc_feature          1..37
                      note = Description of sequence: Primer # apc137; Mtx2
                       gRNA-tRNA Fragment 3 (tRNA-Gly) for pUC backbone
source                1..37
                      mol_type = other DNA
                      organism = synthetic construct
SEQUENCE: 192
gttcccaaac aagcgcaagt ggtttagtgg taaaatc                           37

SEQ ID NO: 193        moltype = DNA  length = 20
FEATURE               Location/Qualifiers
misc_feature          1..20
                      note = Description of sequence: Primer # apc138; Mtx2
                       gRNA-tRNA Fragment 3 (tRNA-Gly) for pUC backbone and
                       Primer # apc142; M13 gRNA-tRNA Fragment 3 (tRNA-Gly) for
                       pUC backbone
source                1..20
                      mol_type = other DNA
                      organism = synthetic construct
SEQUENCE: 193
ggcctcttcg ctattacgcc                                              20

SEQ ID NO: 194        moltype = DNA  length = 37
FEATURE               Location/Qualifiers
misc_feature          1..37
                      note = Description of sequence: Primer # apc139; M13
                       gRNA-tRNA Fragment 2 (M13) for pUC backbone
source                1..37
                      mol_type = other DNA
                      organism = synthetic construct
SEQUENCE: 194
ctccttcggt ctcagtttca gagctagaaa tagcaag                           37

SEQ ID NO: 195        moltype = DNA  length = 33
FEATURE               Location/Qualifiers
misc_feature          1..33
                      note = Description of sequence: Primer # apc140; M13
                       gRNA-tRNA Fragment 2 (M13) for pUC backbone
source                1..33
                      mol_type = other DNA
                      organism = synthetic construct
SEQUENCE: 195
cacttgcgct tgtttgcacc gactcggtgc cac                               33

SEQ ID NO: 196        moltype = DNA  length = 32
```

```
FEATURE                 Location/Qualifiers
misc_feature            1..32
                        note = Description of sequence: Primer # apc141; M13
                         gRNA-tRNA Fragment 3 (tRNA-Gly) for pUC backbone
source                  1..32
                        mol_type = other DNA
                        organism = synthetic construct
SEQUENCE: 196
gtcggtgcaa acaagcgcaa gtggtttagt gg                                  32

SEQ ID NO: 197          moltype = DNA  length = 61
FEATURE                 Location/Qualifiers
misc_feature            1..61
                        note = Description of sequence: Primer # apc143; mtx2
                         VH4420 3x cassette Fragment 1 for pY120 backbone
source                  1..61
                        mol_type = other DNA
                        organism = synthetic construct
SEQUENCE: 197
aaaggtctca tgatcctctt aagttgttca tttgcgtttc agagctagaa atagcaagtt  60
g                                                                    61

SEQ ID NO: 198          moltype = DNA  length = 39
FEATURE                 Location/Qualifiers
misc_feature            1..39
                        note = Description of sequence: Primer # apc144; mtx2
                         VH4420 3x cassette Fragment 1 for pY120 backbone
source                  1..39
                        mol_type = other DNA
                        organism = synthetic construct
SEQUENCE: 198
aaaggtctca atgaaactct ctgcgcaagc ccggaatcg                           39

SEQ ID NO: 199          moltype = DNA  length = 49
FEATURE                 Location/Qualifiers
misc_feature            1..49
                        note = Description of sequence: Primer # apc145; mtx2
                         VH4420 3x cassette Fragment 2 for pY120 backbone
source                  1..49
                        mol_type = other DNA
                        organism = synthetic construct
SEQUENCE: 199
aaaggtctca tcatgggcct cccgtttcag agctagaaat agcaagttg                49

SEQ ID NO: 200          moltype = DNA  length = 52
FEATURE                 Location/Qualifiers
misc_feature            1..52
                        note = Description of sequence: Primer # apc146; mtx2
                         VH4420 3x cassette Fragment 2 for pY120 backbone
source                  1..52
                        mol_type = other DNA
                        organism = synthetic construct
SEQUENCE: 200
aaaggtctca aaacgagaaa ggactggagt gggttgcgca agcccggaat cg            52

SEQ ID NO: 201          moltype = DNA  length = 57
FEATURE                 Location/Qualifiers
misc_feature            1..57
                        note = Description of sequence: Primer # apc147; m13 VH4420
                         3x cassette Fragment 1 for pY120 backbone
source                  1..57
                        mol_type = other DNA
                        organism = synthetic construct
SEQUENCE: 201
aaaggtctca tgatcgtcac taaaagtgaa tccaggtttc agagctaggc caacatg       57

SEQ ID NO: 202          moltype = DNA  length = 39
FEATURE                 Location/Qualifiers
misc_feature            1..39
                        note = Description of sequence: Primer # apc148; m13 VH4420
                         3x cassette Fragment 1 for pY120 backbone
source                  1..39
                        mol_type = other DNA
                        organism = synthetic construct
SEQUENCE: 202
aaaggtctca gaaacatatt atgcgcaagc ccggaatcg                           39

SEQ ID NO: 203          moltype = DNA  length = 45
FEATURE                 Location/Qualifiers
```

```
misc_feature          1..45
                      note = Description of sequence: Primer # apc149; m13 VH4420
                       3x cassette Fragment 2 for pY120 backbone
source                1..45
                      mol_type = other DNA
                      organism = synthetic construct
SEQUENCE: 203
aaaggtctca tttcataatt atagtttcag agctaggcca acatg                 45

SEQ ID NO: 204        moltype = DNA  length = 52
FEATURE               Location/Qualifiers
misc_feature          1..52
                      note = Description of sequence: Primer # apc150; m13 VH4420
                       3x cassette Fragment 2 for pY120 backbone
source                1..52
                      mol_type = other DNA
                      organism = synthetic construct
SEQUENCE: 204
aaaggtctca aaacgtacag taatagatac ccattgcgca agcccggaat cg         52

SEQ ID NO: 205        moltype = DNA  length = 65
FEATURE               Location/Qualifiers
misc_feature          1..65
                      note = Description of sequence: Primer #
                       apc151;High-throughput sequencing of 4-4-20
source                1..65
                      mol_type = other DNA
                      organism = synthetic construct
SEQUENCE: 205
acactctttc cctacacgac gctcttccga tctgcatcag atggtgacgt caaactggat  60
gagac                                                             65

SEQ ID NO: 206        moltype = DNA  length = 68
FEATURE               Location/Qualifiers
misc_feature          1..68
                      note = Description of sequence: Primer # apc152;
                       High-throughput sequencing of 4-4-20
source                1..68
                      mol_type = other DNA
                      organism = synthetic construct
SEQUENCE: 206
gactggagtt cagacgtgtg ctcttccgat cttgagacca tctacactgt tgttatcaga  60
tctcgagc                                                          68

SEQ ID NO: 207        moltype = DNA  length = 25
FEATURE               Location/Qualifiers
misc_feature          1..25
                      note = Description of sequence: Primer # apc153; Anneal for
                       wtGFP c78R
source                1..25
                      mol_type = other DNA
                      organism = synthetic construct
SEQUENCE: 207
tgatcttcaa gtccgccatg cccga                                       25

SEQ ID NO: 208        moltype = DNA  length = 25
FEATURE               Location/Qualifiers
misc_feature          1..25
                      note = Description of sequence: Primer # apc154; Anneal for
                       wtGFP c78R
source                1..25
                      mol_type = other DNA
                      organism = synthetic construct
SEQUENCE: 208
aaactcgggc atggcggact tgaag                                       25

SEQ ID NO: 209        moltype = RNA  length = 20
FEATURE               Location/Qualifiers
misc_feature          1..20
                      note = Description of sequence: t78R gRNA spacer
source                1..20
                      mol_type = other RNA
                      organism = synthetic construct
SEQUENCE: 209
ttcaagtccg ccatgcccga                                             20

SEQ ID NO: 210        moltype = RNA  length = 20
FEATURE               Location/Qualifiers
misc_feature          1..20
```

-continued

```
                         note = Description of sequence: m13, VHCDR1 gRNA spacer
source                   1..20
                         mol_type = other RNA
                         organism = synthetic construct
SEQUENCE: 210
gtcactaaaa gtgaatccag                                              20

SEQ ID NO: 211           moltype = RNA  length = 20
FEATURE                  Location/Qualifiers
misc_feature             1..20
                         note = Description of sequence: m13, VHCDR2 gRNA spacer
source                   1..20
                         mol_type = other RNA
                         organism = synthetic construct
SEQUENCE: 211
taatatgttt cataattata                                              20

SEQ ID NO: 212           moltype = RNA  length = 20
FEATURE                  Location/Qualifiers
misc_feature             1..20
                         note = Description of sequence: m13, VHCDR3 gRNA spacer
source                   1..20
                         mol_type = other RNA
                         organism = synthetic construct
SEQUENCE: 212
atgggtatct attactgtac                                              20
```